(12) United States Patent
Bentwich et al.

(10) Patent No.: US 7,943,754 B2
(45) Date of Patent: May 17, 2011

(54) BIOINFORMATICALLY DETECTABLE GROUP OF NOVEL REGULATORY BACTERIAL AND BACTERIAL ASSOCIATED OLIGONUCLEOTIDES AND USES THEREOF

(75) Inventors: Itzhak Bentwich, Kfar Daniel (IL); Amir Avniel, Rishon leZion (IL)

(73) Assignee: Rosetta-Genomics, Rehovot (IL)

( * ) Notice: Subject to any disclaimer, the term of this patent is extended or adjusted under 35 U.S.C. 154(b) by 1096 days.

(21) Appl. No.: 10/709,691

(22) Filed: May 24, 2004

(65) Prior Publication Data

US 2007/0031843 A1   Feb. 8, 2007

Related U.S. Application Data

(63) Continuation-in-part of application No. 10/708,951, filed on Apr. 2, 2004.

(60) Provisional application No. 60/521,433, filed on Apr. 26, 2004.

(51) Int. Cl.
*C07H 21/02* (2006.01)
*C07H 21/04* (2006.01)
*C12Q 1/68* (2006.01)

(52) U.S. Cl. .............. 536/24.5; 514/44 A; 536/23.1; 536/24.1; 435/320.1

(58) Field of Classification Search ............... None
See application file for complete search history.

(56) References Cited

U.S. PATENT DOCUMENTS

| | | | | |
|---|---|---|---|---|
| 5,541,308 | A * | 7/1996 | Hogan et al. ............... | 536/23.1 |
| 6,582,908 | B2 * | 6/2003 | Fodor et al. ............... | 435/6 |
| 6,812,339 | B1 * | 11/2004 | Venter et al. ............... | 536/24.31 |
| 7,232,806 | B2 * | 6/2007 | Tuschl et al. ............... | 514/44 |
| 7,250,289 | B2 * | 7/2007 | Zhou ............... | 435/287.2 |

OTHER PUBLICATIONS

New England Biolabs 1998/99 Catalog, cover page, p. 121 and 284.*
Bentwich (2005) FEBS Lett. 5904-5910.*
Krutzfeldt et al. (2006) Nature Genetics 38:514-519.*
Hagiwara et al., J Gene Med. Sep. 2003;5(9):784-94.*
Sunamoto et al., Lab Invest., 1998 78:967-72.*
Martin et al. (2007) J. Biosci. 32:1049-1052.*
Maziere et al. (2007) Drug Discovery Today 12:452-458.*
Smalheiser et al. (2006) Methods Mol. Biol. 342:115-127.*
Watanabe et al. (2007) "Computational Prediction of miRNA Targets" Methods Enzymology 427:65-86.*
Cullen (2004) "Derivation and function of small interfering RNAs and microRNAs" Viral Res. 102:3-9.*
Buck et al. (Biotechniques (1999) 27(3): 526-538).*
Bartel et al. (2004) Cell 116:281-297, pp. 285-288.*
Zamore et al. (2004) PLoS Biology 2(4):0465-0475.*
Dunn et al. GenBank Accession No. AZ593982, published online at NCBI on Dec. 13, 2000.*
Birren et al., GenBank Acc. No. AC015918 "*Homo sapiens* chromosome 17 clone CTD-3165O8 map 17", published online by NCBI on Mar. 27, 2003.*
Brown (1998) "In situ hybridization with riboprobes: An overview for veterinary pathologists" Vet. Pathol. 35:159-167.*
Lerat, E. From Gene Trees to Organismal Phylogeny in Prokaryotes: The Case of the gamma-Proteobacteria. PLoS Biology 2003;1(1):101-9.
Olsen, LC. Human uracil-DNA glycosylase complements *E.coli* ung mutants. Nucleic Acids Research 1991;19(16):4473-8.
Venkatesh, J. Importance of Uracil DNA Glycosylase in *Pseudomonas aeruginosa* and *Mycobacterium smegmatis*, G+C-rich Bacteria, in Mutation Prevention, Tolerance to Acidified Nitrite, and Endurance in Mouse Macrophages. The Journal of Biological Chemistry 2003; 278(27):24350-8.
Bartel, D.P., "MicroRNAs: Genomics, Biogenesis, Mechanism, and Function," Cell, 2004;116:281-97.
Zamore, P.D., et al., "RNAi: Double-Stranded RNA Directs the ATP-Dependent Cleavage of mRNA at 21 to 23 Nucleotide Intervals," Cell, 2000;101:25-33.
Elbashir, S.M. et al., "RNA interference is mediated by 21- and 22-nucleotide RNAs", Genes and Development, 2001;15:188-200.
Lim, L.P. et al., "The microRNAs of *Caenorhabditis elegans*," Genes & Dev., 2003;17:991-1008.
Morin, R.D. et al., "Application of massively parallel sequencing to microRNA profiling and discovery of human embryonic stem cells," Genome Res., 2008;18:610-21.
Doench JG and Sharp PA. Specificity of microRNA target selection in translational repression. Genes Dev, 2004;18(5):504-11.
Granovsky M et al. Suppression of tumor growth and metastasis in Mgat5-deficient mice. Nat Med 2000;6(3):306-12. (Abstract).
Partridge EA et al. Regulation of Cytokine Receptors by Golgi N-Glycan Processing and Endocytosis. Science 2004;306(5693):120-4.
Lai EC. Micro RNAs are complementary to 3' UTR sequence motifs that mediate negative post-transcription. Nature Genetics 2002;30:363-4.
Stark A. Identification of *Drosophila* MicroRNA Targets. PLoS Biology 2003;1(3):397-409.
Lai EC. Predicting and validating microRNA targets. Genome Biology 2004;5:115.

(Continued)

*Primary Examiner* — Sean R McGarry
(74) *Attorney, Agent, or Firm* — Teddy C. Scott, Jr.; Ron Galant; Polsinelli Shughart PC

(57) ABSTRACT

The present invention relates to a first group of novel bacterial and human associated oligonucleotides, here identified as "Genomic Address Messenger" or "GAM" oligonucleotide, and a second group of novel operon-like bacterial and human polynucleotides, here identified as "Genomic Record" or "GR" polynucleotide. GAM oligonucleotides selectively inhibit translation of known "target" genes, many of which are known to be involved in various bacterial infections. Nucleic acid molecules are provided respectively encoding 21,916 bacterial and 6,100 human GAM precursor oligonucleotides, and 6,056 bacterial and 430 human GR polynucleotides, as are vectors and probes both comprising the nucleic acid molecules, and methods and systems for detecting GAM oligonucleotides and GR polynucleotides and specific functions and utilities thereof, for detecting expression of GAM oligonucleotides and GR polynucleotides, and for selectively enhancing and selectively inhibiting translation of the respective target genes thereof.

6 Claims, 27 Drawing Sheets

OTHER PUBLICATIONS

Vella MC. Architecture of a Validated MicroRNA::Target Interaction. Chemistry & Biology 2004;11:1619-23.
Brennecke J. Principles of MicroRNA—Target Recognition. PLoS Biology 2005;3(3):e85.
Lewis BP. Prediction of Mammalian MicroRNA Targets. Cell 2003;115:787-98.
Enright AJ. MicroRNA targets in *Drosophila*. Genome Biology 2003;5:R1.

* cited by examiner

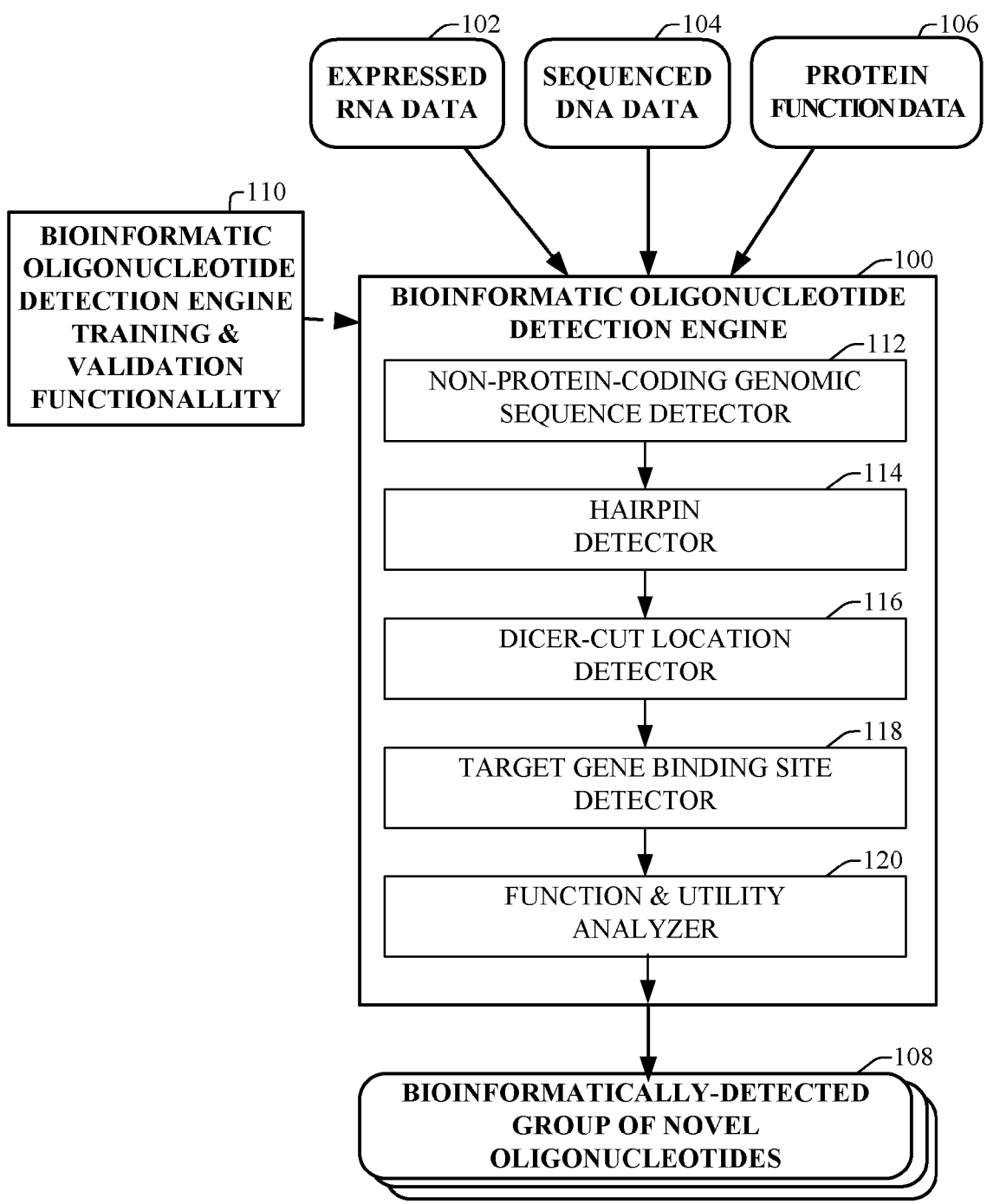

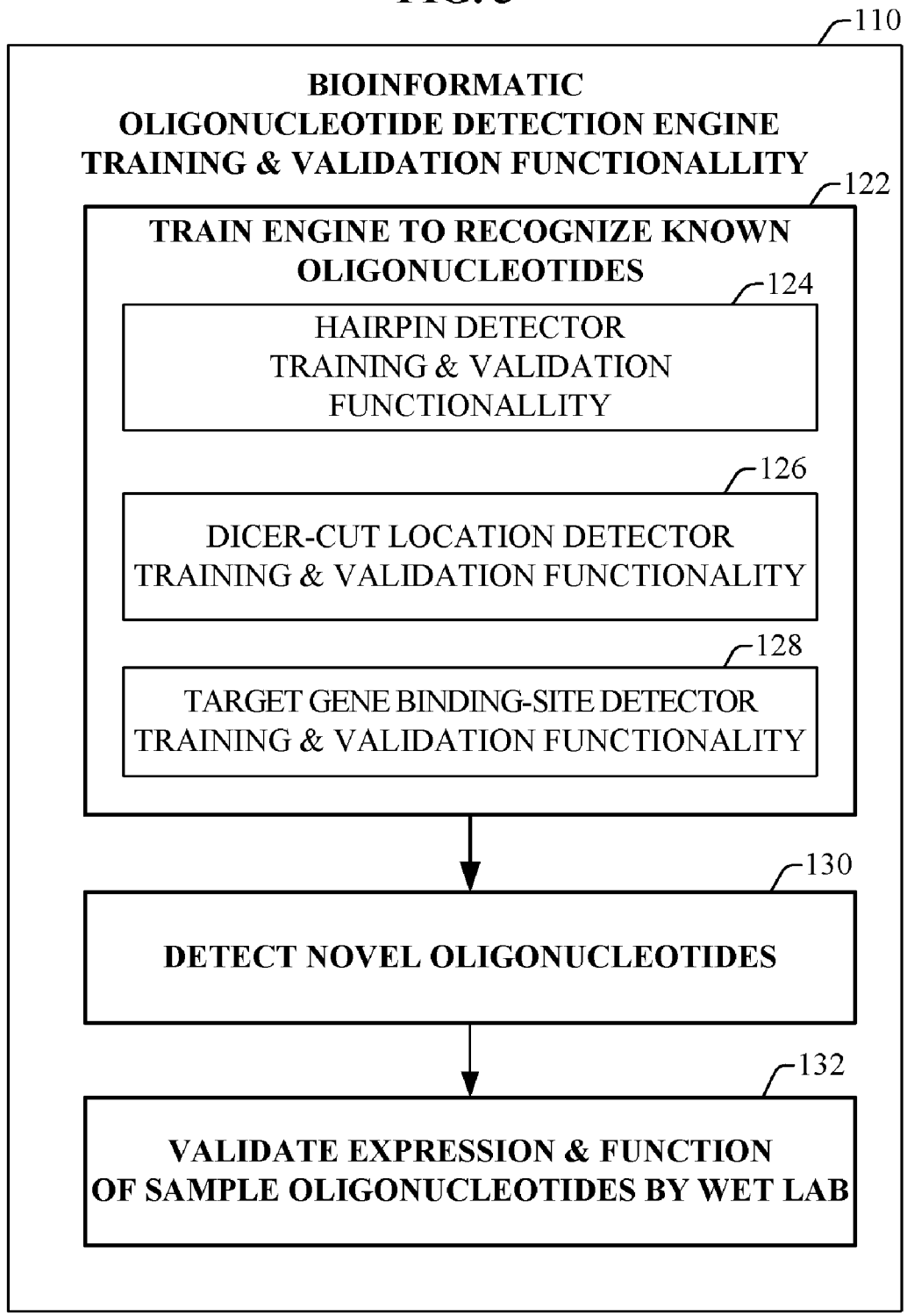

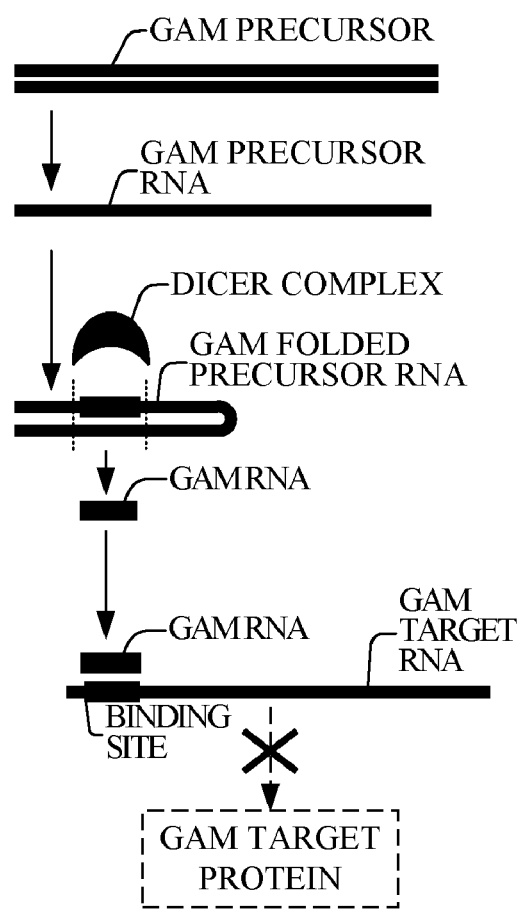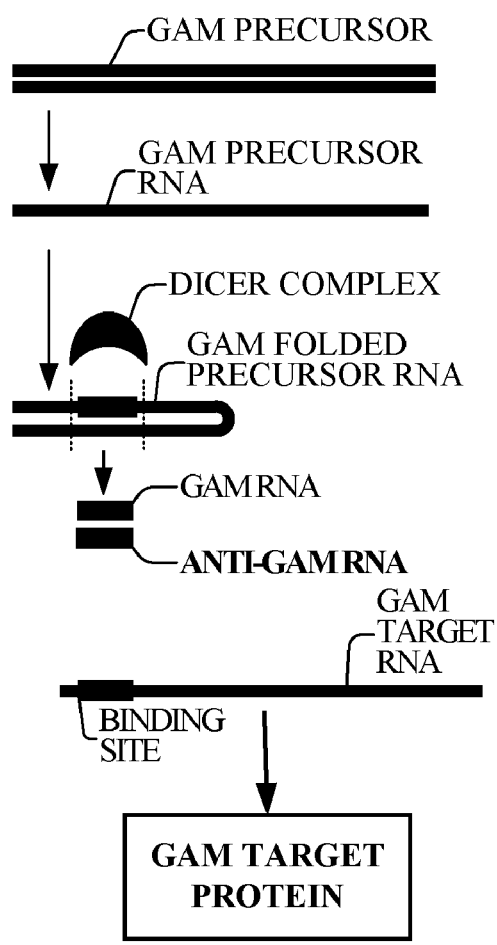

FIG. 13

| ROW | PRIMER SEQUENCE | SEQ ID NO | SEQUENCED SEQENCE | SEQ ID NO | PREDICTED GAM RNA | SEQ ID NO | DIST-ANCE | GAM NAME |
|---|---|---|---|---|---|---|---|---|
| 1* | AATTGCTTGAAC | 4254671 | CCAGGAAGTGGA | 4254700 | AATTGCTTGAACCCAGGAAGTGGA | 4254729 | 0 | 25-A |
| 2* | ACTGCACTCC | 4254672 | AGCCTGGGC | 4254701 | ACTGCACTCCAGCCTGGGCTAC | 4254730 | 0 | 351661-A |
| 3 | CACTGCACTC | 4254673 | CAGCCCGAGCAACA | 4254702 | CACTGCACTCCAGCCCGAGCAA | 4254731 | 0 | 351946-A |
| 4 | CTAGACTGAAG | 4254674 | CTCCTTGAGGAC | 4254703 | CTAGACTGAAGCTCCTTGAGGA | 4254732 | 0 | 352759-A |
| 5 | GAAGTTTGAAG | 4254675 | CCTGTGTTCA | 4254704 | GAAGTTTGAAGCCTGTGTTCA | 4254733 | 0 | 4426-A |
| 6 | TCACTGCAAC | 4254676 | CTCCACCA | 4254705 | (TCACTGCAACCTCCACCACGTG) (TCACTGCAACCTCCACCAGCCT) | 4254734, 4254735 | 0 | (357950-A), (352721-A) |
| 7* | TCTAAGAGAAAG | 4254677 | GAAGTTCAGA | 4254706 | TCTAAGAGAAAGGAAGTTCAGA | 4254736 | 0 | 337950-A |
| 8 | GGGCAGTGGA | 4254678 | GCTGGAA | 4254707 | GGGCGTGGAGCTGGAATGATGT | 4254737 | 1 | 351996-A |
| 9 | AATTGCTTGAAC | 4254679 | CCAAGAAGTGGA | 4254708 | AATCACTTGAACCCAAGAAGTG | 4254738 | 2 | 351874-A |
| 10 | AGCAGCCCA | 4254680 | GGGTTTTGT | 4254709 | AGCAAGACCAGGGTTTTGTGTT | 4254739 | 2 | 352083-A |
| 11 | AGGCAAGACG | 4254681 | GACCAGA | 4254710 | AGGCAGAGAGGACCAGAGACT | 4254740 | 2 | 351944-A |
| 12 | AGGGAAAGAAT | 4254682 | TAATGTAA | 4254711 | GGGAAATAATTAATGTGAAGTC | 4254741 | 2 | 353325-A |
| 13 | AGGGAAAGAAT | 4254683 | TAATGTGAG | 4254712 | AGGAAAAAATTAATGTGAGTC | 4254742 | 2 | 352649-A |
| 14 | ATTCAGTTG | 4254684 | CCCATGTTT | 4254713 | (ATTCATTGCCCATGTTTG), (TATTCATGCCCATGGTGA) | 4254743, 4254744 | 2 | (352957-A, 352960-A) |
| 15 | CTAGACTGAAG | 4254685 | CTCCTTGAGG | 4254714 | CTGGACTGAGCTCCTTGAGGCC | 4254745 | 2 | 352288-A |
| 16 | TTCAGAGTGGT | 4254686 | TAAGTTCTG | 4254715 | TTCTGATGGTTAAGTTCTGTCA | 4254746 | 2 | 353875-A |
| 17 | TTCAGAGTGGT | 4254687 | TAAGTTCTGC | 4254716 | TTCAAGTGTTTAAGTTCTGCTT | 4254747 | 2 | 351940-A |
| 18 | AGCAGCCCA | 4254688 | GAAGGAAGC | 4254717 | AGGCCAAGAAGGAAGCAGAGG | 4254748 | 3 | 352496-A |
| 19 | AGTTTGCCTTG | 4254689 | TAAGAAAAG | 4254718 | AGTTTGTGTAAGAAAAGC | 4254749 | 3 | 352518-A |
| 20 | ATCAGGGGTG | 4254690 | GGTGCTAA | 4254719 | ATTAGGAGAGTTGTCAGTATAG | 4254750 | 3 | 353484-A |
| 21 | ATGGTGGGAG | 4254691 | AGTTTGTCAGT | 4254720 | TGGAGGAGAGTTTGTCAGTATAG | 4254751 | 3 | 351990-A |
| 22 | CCCAGGAAG | 4254692 | TGGAGCCTGGGC | 4254721 | CCCGGGTGGAGCCTGGGCTGTG | 4254752 | 3 | 353880-A |
| 23 | GGGCAGTGGA | 4254693 | GGTCCGT | 4254722 | AGGGCAGGAGGTCCGTCCCCTTC | 4254753 | 3 | 352810-A |
| 24 | GGGCAGTGGA | 4254694 | TCTAGAC | 4254723 | GTGACAGTGAATCTAGACAGAC | 4254754 | 3 | 353184-A |
| 25 | TCAAGCTCATTC | 4254695 | CACTAAA | 4254724 | CTCAGCTCATCCACTAAATCCC | 4254755 | 3 | 353855-A |
| 26 | TGGAAAGTT | 4254696 | GGTTGTATGGTT | 4254725 | GGAATGGTGGTTGTATGGTTG | 4254756 | 3 | 353855-A |
| 27 | TGGAGAGTT | 4254697 | CCATATTTG | 4254726 | TGATAGATCCATATTTTGGTAA | 4254757 | 3 | 352004-A |
| 28 | TGGAGAGTT | 4254698 | GTTTGTACAGT | 4254727 | TGGGTTTTGTTTGTACAGTGTA | 4254758 | 3 | 353160-A |
| 29 | TCACTGCAAC | 4254699 | CTCCACC | 4254728 | TCACTGCAACCTCCACCTTCCG | 4254759 | 0 | 353856-A |

FIG. 15A

EST72223 (705 nt.)

EST72223 sequence:

CCCTTATTAGAGGATTCTGCTCATGCCAGGGTGAGGTAGTAAGTTGTATTG
TTGTGGGGTAGGGATATTAGGCCCCAATTAGAAGATAACTATACAACT MIR98
TACTACTTTCCCTGGTGTGTGGCATATTCACACTTAGTCTTAGCAGTGTTGCC
TCCATCAGACAAAGTTGTAGATGTTCCTTGGATAATTTGGACTGGAAGAAAAGA
GACATGGAAGGGGACAGATGGTGTTTAGGGTGAGGCAGATGTCATTATAAAGT
GACTTGTCTTTCATTAATTGGAGCATATAATTATTTTACCTTTGGGCATGAACTC
ATTTTGCTATTCTTCAACTGTGTAATGATTGCATTTTATTAGTAATAGAACAGGA
ATGTGTGCAAGGGAATGGAAAGCATACTTTAAGAATTTTGGGCCAGGCGCGGT
GGTTCATGCCTGTAATCCCAGCATTTTGGGAGGCCGAGGCGGGTGGATCAC
CTGAGGTCAGGAGTTCGAGACCAACCTGGCCAACACGGCGAAACCCCGCCTC
TACTCAAATACAAAAATTAGCCAGGCTTGGTGACACTCGCCTGTGGTCCCAGC
TACTCAGGAGGCTGAGGCAGGAGAATTGCTTGAACCCAGGAAGTGGAG
GCTTCAGTGAGCTGAGAACACGCCACTGCACTCCAGTCCTGGGCAAC GAM25
AGAGCAAGACTCTGTCTCAGGAAAAAAAAAG

FIG. 15B

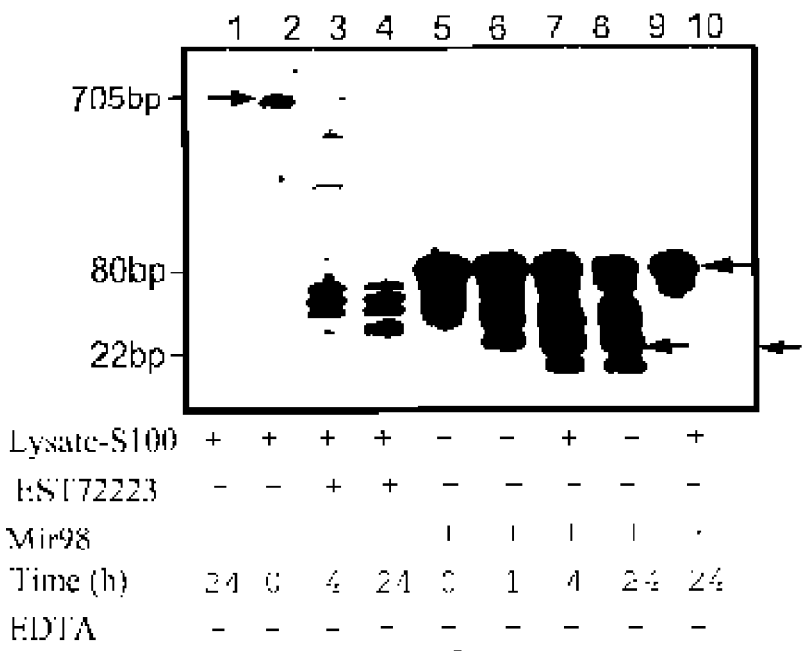

FIG. 18C

| MIRNA NAME | HELA | BRAIN | LIVER | THYMUS | TESTES | PLACENTA | REFERENCE |
|---|---|---|---|---|---|---|---|
| HSA-MIR-124A | 1879 | 65517 | 7025 | 3099 | 2672 | 2498 | 1,3 |
| HSA-MIR-9 | 642 | 42659 | 3504 | 4455 | 4485 | 2313 | 2,3 |
| HSA-MIR-128A | 2015 | 27701 | 4940 | 4876 | 5166 | 2495 | 3 |
| HSA-MIR-129 | 503 | 22573 | 1175 | 2213 | 5364 | 2017 | 3 |
| HSA-MIR-128B | 1168 | 21969 | 3954 | 4819 | 5383 | 2027 | |
| HSA-MIR-122A | 1051 | 447 | 65518 | 2644 | 617 | 570 | 1,3 |
| HSA-MIR-194 | 501 | 910 | 65518 | 4737 | 2342 | 7952 | 3 |
| HSA-MIR-148 | 413 | 620 | 38436 | 5250 | 6204 | 2711 | |
| HSA-MIR-192 | 452 | 606 | 20650 | 1628 | 1263 | 2607 | |
| HSA-MIR-96 | 887 | 3100 | 1477 | 44800 | 2266 | 5466 | |
| HSA-MIR-150 | 648 | 1463 | 5295 | 65518 | 29728 | 5280 | |
| HSA-MIR-205 | 551 | 615 | 1646 | 65518 | 2645 | 39072 | |
| HSA-MIR-182 | 662 | 1944 | 1091 | 25771 | 2034 | 3683 | |
| HSA-MIR-183 | 1026 | 1123 | 1286 | 8754 | 1681 | 2138 | |
| HSA-MIR-204 | 525 | 3898 | 1757 | 6535 | 64859 | 6233 | |
| HSA-MIR-10B | 410 | 433 | 477 | 3871 | 23083 | 738 | |
| HSA-MIR-154 | 438 | 733 | 1914 | 3309 | 14750 | 9637 | |
| HSA-MIR-134 | 448 | 617 | 698 | 763 | 2250 | 997 | |
| HSA-MIR-224 | 3233 | 11061 | 7684 | 32305 | 5377 | 65518 | |
| HSA-MIR-210 | 844 | 2280 | 10703 | 6864 | 15288 | 62452 | |
| HSA-MIR-221 | 625 | 9325 | 3520 | 20212 | 10608 | 54287 | |
| HSA-MIR-141 | 696 | 805 | 1220 | 4063 | 2000 | 46845 | |
| HSA-MIR-23A | 1312 | 3492 | 2990 | 6021 | 11173 | 40076 | |
| HSA-MIR-200C | 556 | 595 | 1027 | 10636 | 1478 | 33532 | |
| HSA-MIR-136 | 465 | 725 | 709 | 776 | 3100 | 8840 | |

1 LAGOS-QUINTANA ET AL., CURRENT BIOLOGY 12:735 (2002)
2 KRICHEVSKY ET AL., RNA 9:1274 (2003)
3 SEMPERE ET AL., GENOME BIOLOGY 5:R13 (2004)

BIOINFORMATICALLY DETECTABLE GROUP OF NOVEL REGULATORY BACTERIAL AND BACTERIAL ASSOCIATED OLIGONUCLEOTIDES AND USES THEREOF

CROSS REFERENCE TO RELATED APPLICATIONS

This application is a continuation in part of U.S. patent application Ser. No. 10/708,951, filed 2 Apr. 2004, entitled "Bioinformatically Detectable Group of Novel Regulatory Bacterial and Bacterial Associated Oligonucleotides and Uses Thereof", the disclosure of which is hereby incorporated by reference and claims priority therefrom; This application also is a continuation in part of U.S. Provisional Patent Application Ser. No. 60/521,433 filed 26 Apr. 2004, entitled "A Microarray for the Detection of MicroRNA Oligonucleotides", the disclosure of which is hereby incorporated by reference and claims priority therefrom.

REFERENCES CITED

Altschul, S. F., Gish, W., Miller, W., Myers, E. W., and Lipman, D. J. (1990). Basic local alignment search tool. J. Mol. Biol. 215, 403-410.

Dan Gusfield, Algorithms on strings, trees, and sequences: computer science and computational biology, Cambridge University Press, 1997.

Elbashir, S. M., Lendeckel, W., and Tuschl, T. (2001). RNA interference is mediated by 21- and 22-nucleotide RNAs. Genes Dev. 15, 188-200.

Gussow, D. and Clackson, T. (1989). Direct clone characterization from plaques and colonies by the polymerase chain reaction. Nucleic Acids Res. 17, 4000.

Hamosh A, Scott A F, Amberger J, Bocchini C, Valle D and McKusick V A. (2002). Online Mendelian Inheritance in Man (OMIM), a knowledgebase of human genes and genetic disorders. Nucleic Acids Res. 30: 52-55.

Jenuth, J. P. (2000). The NCBI. Publicly available tools and resources on the Web. Methods Mol. Biol. 132, 301-312.

Kirkness, E. F. and Kerlavage, A. R. (1997). The TIGR human cDNA database. Methods Mol. Biol. 69, 261-268.

Krichevsky, A. M., King, K. S., Donahue, C. P., Khrapko, K., and Kosik, K. S. (2003). A microRNA array reveals extensive regulation of microRNAs during brain development. RNA. 9, 1274-1281.

Lagos-Quintana, M., Rauhut, R., Lendeckel, W., and Tuschl, T. (2001). Identification of novel genes coding for small expressed RNAs. Science 294, 853-858.

Lau, N. C., Lim, L. P., Weinstein, E. G., and Bartel, D. P. (2001). An abundant class of tiny RNAs with probable regulatory roles in *Caenorhabditis elegans*. Science 294, 858-862.

Lockhart, D. J., Dong, H., Byrne, M. C., Follettie, M. T., Gallo, M. V., Chee, M. S., Mittmann, M., Wang, C., Kobayashi, M., Horton, H., and Brown, E. L. (1996). Expression monitoring by hybridization to high-density oligonucleotide arrays. Nat. Biotechnol. 14, 1675-1680.

Mathews, D. H., Sabina, J., Zuker, M., and Turner, D. H. (1999). Expanded sequence dependence of thermodynamic parameters improves prediction of RNA secondary structure. J. Mol. Biol. 288, 911-940.

Reinhart, B. J., Slack, F. J., Basson, M., Pasquinelli, A. E., Bettinger, J. C., Rougvie, A. E., Horvitz, H. R., and Ruvkun, G. (2000). The 21-nucleotide let-7 RNA regulates developmental timing in *Caenorhabditis elegans*. Nature 403, 901-906.

Southern, E. M. (1992). Detection of specific sequences among DNA fragments separated by gel electrophoresis. 1975. Biotechnology 24, 122-139.

Tom M. Mitchell, Machine Learning, McGraw Hill, 1997.

Wightman, B., Ha, I., and Ruvkun, G. (1993). Posttranscriptional regulation of the heterochronic gene lin-14 by lin-4 mediates temporal pattern formation in *C. elegans*. Cell 75, 855-862.

BACKGROUND OF THE INVENTION

1. Field of the Invention

The present invention relates to a group of bioinformatically detectable novel bacterial oligonucleotides and to a group of bioinformatically detectable novel human oligonucleotides associated with bacterial infections, both are identified here as "Genomic Address Messenger" (GAM) oligonucleotides.

All of abovementioned oligonucleotides are believed to be related to the microRNA (miRNA) group of oligonucleotides.

2. Description of Prior Art miRNA oligonucleotides are short ~22 nucleotide (nt)-long, non-coding, regulatory RNA oligonucleotides that are found in a wide range of species. miRNA oligonucleotides are believed to function as specific gene translation repressors and are sometimes involved in cell differentiation.

The ability to detect novel miRNA oligonucleotides is limited by the methodologies used to detect such oligonucleotides. All miRNA oligonucleotides identified so far either present a visibly discernable whole body phenotype, as do Lin-4 and Let-7 (Wightman, B., Ha, I., and Ruvkun, G., Cell 75: 855-862 (1993); Reinhart et al. Nature 403: 901-906 (2000)), or produce sufficient quantities of RNA so as to be detected by standard molecular biological techniques.

Ninety-three miRNA oligonucleotides have been discovered in several species (Lau et al., Science 294: 858-862 (2001), Lagos-Quintana et al., Science 294: 853-858 (2001)) by sequencing a limited number of clones (300 by Lau and 100 by Lagos-Quintana) of size-fractionated small segments of RNA. miRNAs that were detected in these studies therefore represent the more prevalent among the miRNA oligonucleotide family and cannot be much rarer than 1% of all small ~20 nt-long RNA oligonucleotides.

The aforementioned studies provide no basis for the detection of miRNA oligonucleotides which either do not present a visually discernable whole body phenotype, or are rare (e.g. rarer than 0.1% of all of the size-fractionated, ~20 nt-long RNA segments that were expressed in the tissues examined), and therefore do not produce large enough quantities of RNA to be detected by standard biological techniques.

To date, miRNA oligonucleotides have not been detected in bacteria.

The following U.S. Patents relate to bioinformatic detection of genes: U.S. patent application Ser. No. 10/348,935, entitled "Statistical algorithms for folding and target accessibility prediction and design of nucleic acids", U.S. Pat. No. 6,369,195, entitled "Prostate-specific gene for diagnosis, prognosis and management of prostate cancer", and U.S. Pat. No. 6,291,666 entitled "Spike tissue-specific promoter", each of which is hereby incorporated by reference herein.

BRIEF DESCRIPTION OF SEQUENCE LISTING, TABLES AND COMPUTER PROGRAM LISTING

Reference is made to the appendix submitted on the two compact discs, which contain a replacement sequence listing comprising 4,254,670 genomic sequences contained in files named SEQ LIST.0 (614,454 KB, 16 Feb. 2006) and SEQ LIST.1(105,842 KB, 16 Feb. 2006), and is hereby incorporated by reference herein.

Tables relating to genomic sequences are attached to the present application, appear in the following files (size, creation date) included on CD, incorporated herein: TABLE_1.txt (28.3 MB, 18 May 2004), TABLE_2.txt (350 MB, 18 May 2004), TABLE_3.txt (5.64 MB, 18 May 2004), TABLE_4.txt (17.1 MB, 18 May 2004), TABLE_5.txt (5.04 MB, 18 May 2004), TABLE_6.txt (536 MB, 18 May 2004), TABLE_7_A.txt (619 MB, 18 May 2004), TABLE_7_B.txt (340 MB, 18 May 2004), TABLE_8_A.txt (619 MB, 18 May 2004), TABLE_8_B.txt (619 MB, 18 May 2004), TABLE_8_C.txt (619 MB, 18 May 2004), TABLE_8_D.txt (457 MB, 18 May 2004), TABLE_9.txt (654 MB, 18 May 2004), TABLE_10.txt (49.1 MB, 18 May 2004), and TABLE_11.txt (79.8 MB, 18 May 2004), all of which are incorporated by reference herein. Further, additional tables relating to genomic sequences are attached to the present application, appear in the following files (size, creation date) attached to the application, incorporated herein: TABLE_12.txt (41.1 KB, 18 May 2004) and TABLE_13.txt (46.9 KB, 18 May 2004), are incorporated by reference herein.

host response mechanism, and therefore knowledge of this novel group of human oligonucleotides may be useful in preventing and treating bacterial diseases.

Furthermore, the present invention relates to a novel group of 24,160 bioinformatically detectable bacterial regulatory RNA oligonucleotides, which repress expression of bacterial target genes, by means of complementary hybridization to binding sites in untranslated regions of these bacterial target genes. It is believed that this novel group of bacterial oligonucleotides represents a pervasive novel internal bacterial regulation mechanism, and therefore knowledge of this novel group of bacterial oligonucleotides may be useful in preventing and treating bacterial diseases.

In addition, the present invention relates to a novel group of 6,100 bioinformatically detectable human regulatory RNA oligonucleotides, which repress expression of bacterial target genes, by means of complementary hybridization to binding sites in untranslated regions of these bacterial target genes. It is believed that this novel group of human oligonucleotides represents a pervasive novel antibacterial host defense mechanism, and therefore knowledge of this novel group of human oligonucleotides may be useful in preventing and treating bacterial diseases.

LENGTHY TABLES

The patent contains a lengthy table section. A copy of the table is available in electronic form from the USPTO web site (http://seqdata.uspto.gov/?pageRequest=docDetail&DocID=US07943754B2). An electronic copy of the table will also be available from the USPTO upon request and payment of the fee set forth in 37 CFR 1.19(b)(3).

A computer program listing constructed and operative in accordance with a preferred embodiment of the present invention is enclosed on an electronic medium in computer readable form, and is hereby incorporated by reference herein. The computer program listing is contained in 7 files, the name, sizes and creation date of which are as follows: AUXILARY_FILES.txt (117K, 14 Nov. 2003); EDIT_DISTANCE.txt (144K, 24 Nov. 2003); FIRST-K.txt (96K, 24 Nov. 2003); HAIRPIN_PREDICTION.txt (19K, 25 Mar. 2004); TWO_PHASED_SIDE_SELECTOR.txt (4K, 14 Nov. 2003); TWO_PHASED_PREDICTOR.txt (74K, 14 Nov. 2003), and BS_CODE.txt (118K, 11 May 2004).

SUMMARY OF THE INVENTION

The present invention relates to a novel group of 3,873 bioinformatically detectable bacterial regulatory RNA oligonucleotides, which repress expression of human target genes, by means of complementary hybridization to binding sites in untranslated regions of these target genes. It is believed that this novel group of bacterial oligonucleotides represents a pervasive bacterial mechanism of attacking a host, and therefore knowledge of this novel group of bacterial oligonucleotides may be useful in preventing and treating bacterial diseases.

Additionally, the present invention relates to a novel group of 4,363 bioinformatically detectable human regulatory RNA oligonucleotides, which repress expression of human target genes associated with the bacterial infection, by means of complementary hybridization to binding sites in untranslated regions of these target genes. It is believed that this novel group of human oligonucleotides represents a pervasive novel Also disclosed are 6,056 novel microRNA-cluster like bacterial polynucleotides and 430 novel microRNA-cluster like human polynucleotides, both referred to here as Genomic Record (GR) polynucleotides.

In various preferred embodiments, the present invention seeks to provide improved method and system for detection and prevention of bacterial diseases, which are mediated by this group of novel oligonucleotides.

Accordingly, the invention provides several substantially pure nucleic acids (e.g., genomic DNA, cDNA or synthetic DNA) each comprising a novel GAM oligonucleotide, vectors comprising the DNAs, probes comprising the DNAs, a method and system for selectively modulating translation of known target genes utilizing the vectors, and a method and system utilizing the GAM probes to modulate expression of GAM target genes.

The present invention represents a scientific breakthrough, disclosing novel miRNA-like oligonucleotides the number of which is dramatically larger than previously believed existed. Prior-art studies reporting miRNA oligonucleotides ((Lau et al., Science 294:858-862 (2001), Lagos-Quintana et al., Science 294: 853-858 (2001)) discovered 93 miRNA oligonucleotides in several species, including 21 in human, using conventional molecular biology methods, such as cloning and sequencing.

Molecular biology methodologies employed by these studies are limited in their ability to detect rare miRNA oligonucleotides, since these studies relied on sequencing of a limited number of clones (300 clones by Lau and 100 clones by Lagos-Quintana) of small segments (i.e. size-fractionated) of RNA. miRNA oligonucleotides detected in these studies therefore, represent the more prevalent among the miRNA oligonucleotide family, and are typically not be much rarer than 1% of all small ~20 nt-long RNA oligonucleotides present in the tissue from the RNA was extracted.

Recent studies state the number of miRNA oligonucleotides to be limited, and describe the limited sensitivity of available methods for detection of miRNA oligonucleotides: "The estimate of 255 human miRNA oligonucleotides is an upper bound implying that no more than 40 miRNA oligonucleotides remain to be identified in mammals" (Lim et al., Science, 299:1540 (2003)); "Estimates place the total number of vertebrate miRNA genes at about 200-250" (Ambros et al. Curr. Biol. 13:807-818 (2003)); and "Confirmation of very low abundance miRNAs awaits the application of detection methods more sensitive than Northern blots" (Ambros et al. Curr. Biol. 13:807-818 (2003)).

The oligonucleotides of the present invention represent a revolutionary new dimension of genomics and of biology: a dimension comprising a huge number of non-protein-coding oligonucleotides which modulate expression of thousands of proteins and are associated with numerous major diseases. This new dimension disclosed by the present invention dismantles a central dogma that has dominated life-sciences during the past 50 years, a dogma which has emphasized the importance of protein-coding regions of the genome, holding non-protein-coding regions to be of little consequence, often dubbing them "junk DNA".

Indeed, only in November, 2003 has this long held belief as to the low importance of non-protein-coding regions been vocally challenged. As an example, an article titled "The Unseen Genome-Gems in the Junk" (Gibbs, W. W. Sci. Am. 289:46-53 (2003)) asserts that the failure to recognize the importance of non-protein-coding regions "may well go down as one of the biggest mistakes in the history of molecular biology." Gibbs further asserts that "what was damned as junk because it was not understood, may in fact turn out to be the very basis of human complexity." The present invention provides a dramatic leap in understanding specific important roles of non-protein-coding regions.

An additional scientific breakthrough of the present invention is a novel conceptual model disclosed by the present invention, which conceptual model is preferably used to encode in a genome the determination of cell differentiation, utilizing oligonucleotides and polynucleotides of the present invention.

Using the bioinformatic engine of the present invention, 21,916 bacterial GAM oligonucleotides and their respective precursors and targets have been detected and 6,100 human GAM oligonucleotides and their respective precursors and targets have been detected. These bioinformatic predictions are supported by robust biological studies. Microarray experiments validated expression of 346 of the human GAM oligonucleotides of the present invention. Of these, 311 received an extremely high score: over six standard deviations higher than the background "noise" of the microarray, and over two standard deviations above their individual "mismatch" control probes and 33 received a high score: over four standard deviations higher than the background "noise" of the microarray. Further, 38 GAM oligonucleotides were sequenced.

In various preferred embodiments, the present invention seeks to provide an improved method and system for specific modulation of the expression of specific target genes involved in significant human diseases. It also provides an improved method and system for detection of the expression of novel oligonucleotides of the present invention, which modulate these target genes. In many cases, the target genes may be known and fully characterized, however in alternative embodiments of the present invention, unknown or less well characterized genes may be targeted.

A "Nucleic acid" is defined as a ribonucleic acid (RNA) molecule, or a deoxyribonucleic acid (DNA) molecule, or complementary deoxyribonucleic acid (cDNA), comprising either naturally occurring nucleotides or non-naturally occurring nucleotides.

"Substantially pure nucleic acid", "Isolated Nucleic Acid", "Isolated Oligoucleotide" and "Isolated Polynucleotide" are defined as a nucleic acid that is free of the genome of the organism from which the nucleic acid is derived, and include, for example, a recombinant nucleic acid which is incorporated into a vector, into an autonomously replicating plasmid or virus, or into the genomic nucleic acid of a prokaryote or eukaryote at a site other than its natural site; or which exists as a separate molecule (e.g., a cDNA or a genomic or cDNA fragment produced by PCR or restriction endonuclease digestion) independent of other nucleic acids.

An "Oligonucleotide" is defined as a nucleic acid comprising 2-139 nts, or preferably 16-120 nts. A "Polynucleotide" is defined as a nucleic acid comprising 140-5000 nts, or preferably 140-1000 nts.

A "Complementary" sequence is defined as a first nucleotide sequence which reverses complementary of a second nucleotide sequence: the first nucleotide sequence is reversed relative to a second nucleotide sequence, and wherein each nucleotide in the first nucleotide sequence is complementary to a corresponding nucleotide in the second nucleotide sequence (e.g. ATGGC is the complementary sequence of GCCAT).

"Hybridization", "Binding" and "Annealing" are defined as hybridization, under in vivo physiological conditions, of a first nucleic acid to a second nucleic acid, which second nucleic acid is at least partially complementary to the first nucleic acid.

A "Hairpin Structure" is defined as an oligonucleotide having a nucleotide sequence that is 50-140 nts in length, the first half of which nucleotide sequence is at least partially complementary to the second part thereof, thereby causing the nucleic acid to fold onto itself, forming a secondary hairpin structure.

A "Hairpin-Shaped Precursor" is defined as a Hairpin Structure which is processed by a Dicer enzyme complex, yielding an oligonucleotide which is about 19 to about 24 nts in length.

"Inhibiting translation" is defined as the ability to prevent synthesis of a specific protein encoded by a respective gene by means of inhibiting the translation of the mRNA of this gene. For example, inhibiting translation may include the following steps: (1) a DNA segment encodes an RNA, the first half of whose sequence is partially complementary to the second half thereof; (2) the precursor folds onto itself forming a hairpin-shaped precursor; (3) a Dicer enzyme complex cuts the hairpin-shaped precursor yielding an oligonucleotide that is approximately 22 nt in length; (4) the oligonucleotide binds complementarily to at least one binding site, having a nucleotide sequence that is at least partially complementary to the oligonucleotide, which binding site is located in the mRNA of a target gene, preferably in the untranslated region (UTR) of a target gene, such that the binding inhibits translation of the target protein.

A "Translation inhibitor site" is defined as the minimal nucleotide sequence sufficient to inhibit translation.

The present invention describes novel GAM oligonucleotides, detected using a bioinformatic engine described hereinabove. The ability of this detection engine has been demonstrated using stringent algorithmic criteria, showing that the engine has both high sensitivity, indicated by the high detection rate of published miRNA oligonucleotides and their targets, as well as high specificity, indicated by the low amount of "background" hairpin candidates passing its filters. Laboratory tests, based both on sequencing of predicted GAM oligonucleotides and on microarray experiments, validated 381 of the GAM oligonucleotides in the present invention. Further, almost all of the bacterial target genes (6,141 of the 7,351) and almost all of the human target genes (64 out of 76) described in the present invention are bound by one or more of the 381 human GAM oligonucleotides validated by the microarray experiments.

There is thus provided in accordance with a preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein the oligonucleotide has at least 80% sequence identity with a nucleotide sequence selected from the group consisting of SEQ ID NOs: 1-385 and 386-49787.

There is further provided in accordance with another preferred embodiment of the present invention a bioinformatically detectable isolated oligonucleotide having a nucleotide sequence selected from the group consisting of SEQ ID NOs: 1-385 and 386-49787.

There is still further provided in accordance with another preferred embodiment of the present invention a bioinformatically detectable first oligonucleotide which is a portion of a mRNA transcript of a target gene, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOs: 1-385 and 386-49787.

There is additionally provided in accordance with another preferred embodiment of the present invention a bioinformatically detectable oligonucleotide having a nucleotide sequence selected from the group consisting of SEQ ID NOs: 2337129-4223628.

There is additionally provided in accordance with another preferred embodiment of the present invention a method for treatment of a disease involving a tissue in which a protein is pathologically expressed to an undesirable extent, the protein having a messenger RNA, the method including: providing a material which modulates activity of a microRNA oligonucleotide which binds complementarily to a segment of the messenger RNA, and introducing the material into the tissue, causing modulation of the activity of the microRNA oligonucleotide and thereby modulating expression of the protein in a desired manner.

There is moreover provided in accordance with another preferred embodiment of the present invention a method for treatment of a disease involving tissue in which a protein is pathologically expressed to an undesirable extent, the protein having a messenger RNA, the method including: providing a material which at least partially binds a segment of the messenger RNA that is bound complementarily by a microRNA oligonucleotide, thereby modulating expression of the protein, and introducing the material into the tissue, thereby modulating expression of the protein.

There is further provided in accordance with another preferred embodiment of the present invention a method for treatment of a disease involving a tissue in which a protein is pathologically over-expressed, the protein having a messenger RNA, the method including: providing a microRNA oligonucleotide which binds complementarily to a segment of the messenger RNA, and introducing the microRNA oligonucleotide into the tissue, causing the microRNA oligonucleotide to bind complementarily to a segment of the messenger RNA and thereby inhibit expression of the protein.

There is still further provided in accordance with another preferred embodiment of the present invention a method for treatment of a disease involving a tissue in which a protein is pathologically over-expressed, the protein having a messenger RNA, the method including: providing a chemically-modified microRNA oligonucleotide which binds complementarily to a segment of the messenger RNA, and introducing the chemically-modified microRNA oligonucleotide into the tissue, causing the microRNA oligonucleotide to bind complementarily to a segment of the messenger RNA and thereby inhibit expression of the protein.

There is additionally provided in accordance with another preferred embodiment of the present invention a method for treatment of a disease involving a tissue in which a protein is pathologically under-expressed, the protein having a messenger RNA, the method including: providing an oligonucleotide that inhibits activity of a microRNA oligonucleotide which binds complementarily to a segment of the messenger RNA, and introducing the oligonucleotide into the tissue, causing inhibition of the activity of the microRNA oligonucleotide and thereby promotion of translation of the protein.

There is moreover provided in accordance with another preferred embodiment of the present invention a method for treatment of a disease involving a tissue in which a protein is pathologically under-expressed, the protein having a messenger RNA, the method including: providing a chemically-modified oligonucleotide that inhibits activity of a microRNA oligonucleotide which binds complementarily to a segment of the messenger RNA, and introducing the chemically-modified oligonucleotide into the tissue, causing inhibition of the activity of the microRNA oligonucleotide and thereby promotion of translation of the protein.

There is further provided in accordance with another preferred embodiment of the present invention a method for diagnosis of a disease involving a tissue in which a protein is expressed to abnormal extent, the protein having a messenger RNA, the method including: assaying a microRNA oligonucleotide which at least partially binds a segment of the messenger RNA and modulates expression of the protein, thereby providing an indication of at least one parameter of the disease.

There is still further provided in accordance with another preferred embodiment of the present invention a method for detection of expression of an oligonucleotide, the method including: determining a first nucleotide sequence of a first oligonucleotide, which first nucleotide sequence is not complementary to a genome of an organism, receiving a second nucleotide sequence of a second oligonucleotide whose expression is sought to be detected, designing a third nucleotide sequence that is complementary to the second nucleotide sequence of the second oligonucleotide, and a fourth nucleotide sequence that is complementary to a fifth nucleotide sequence which is different from the second nucleotide sequence of the second oligonucleotide by at least one nucleotide, synthesizing a first oligonucleotide probe having a sixth nucleotide sequence including the third nucleotide sequence followed by the first nucleotide sequence of the first oligonucleotide, and a second oligonucleotide probe having a seventh nucleotide sequence including the fourth nucleotide sequence followed by the first nucleotide sequence of the first oligonucleotide, locating the first oligonucleotide probe and the second oligonucleotide probe on a microarray platform, receiving an RNA test sample from at least one tissue of the organism, obtaining size-fractionated RNA from the RNA test sample, amplifying the size-fractionated RNA, hybridizing the adaptor-linked RNA with the first and second oligonucleotide probes on the microarray platform, and determining expression of the first oligonucleotide in the at least one tissue of the organism, based at least in part on the hybridizing.

There is additionally provided in accordance with another preferred embodiment of the present invention a bioinformatically detectable isolated polynucleotide which is endogenously processed into a plurality of hairpin-shaped precursor oligonucleotides, each of which is endogenously processed into a respective oligonucleotide, which in turn anneals to a portion of a mRNA transcript of a target gene, wherein binding of the oligonucleotide to the mRNA transcript represses expression of the target gene.

There is moreover provided in accordance with another preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein the target gene does not encode a protein.

There is further provided in accordance with another preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein a function of the oligonucleotide includes modulation of cell type.

There is still further provided in accordance with another preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein the oligonucleotide is maternally transferred by a cell to at least one daughter cell of the cell, and a function of the oligonucleotide includes modulation of cell type of the daughter cell.

There is additionally provided in accordance with another preferred embodiment of the present invention a method for bioinformatic detection of microRNA oligonucleotides, the method including: bioinformatically detecting a hairpin-shaped precursor oligonucleotide, bioinformatically detecting an oligonucleotide which is endogenously processed from the hairpin-shaped precursor oligonucleotide, and bioinformatically detecting a target gene of the oligonucleotide wherein the oligonucleotide anneals to at least one portion of a mRNA transcript of the target gene, and wherein the binding represses expression of the target gene, and the target gene is associated with a disease.

BRIEF DESCRIPTION OF DRAWINGS

FIG. 2 is a simplified block diagram illustrating a bioinformatic oligonucleotide detection system capable of detecting oligonucleotides of the novel group of oligonucleotides of the present invention, which system is constructed and operative in accordance with a preferred embodiment of the present invention;

FIG. 3 is a simplified flowchart illustrating operation of a mechanism for training of a computer system to recognize the novel oligonucleotides of the present invention, which mechanism is constructed and operative in accordance with a preferred embodiment of the present invention;

FIGS. 11A and 11B are simplified diagrams which, when taken together, illustrate a mode of oligonucleotide therapy applicable to novel oligonucleotides of the present invention;

FIG. 13 is a summary table of laboratory results validating expression of novel human oligonucleotides detected by a bioinformatic oligonucleotide detection engine constructed and operative in accordance with a preferred embodiment of the present invention, thereby validating its efficacy;

FIG. 15A is an annotated sequence of EST72223 (SEQ ID NO: 4254771) comprising known human microRNA oligonucleotide MIR98 and novel human oligonucleotide GAM25 PRECURSOR detected by the oligonucleotide detection system of the present invention. Additionally annotated in EST72223 are the miRNA-98 hairpin in bold (SEQ ID NO: 4254772), the sequence of the mature miRNA-98 in bold and underline (SEQ ID NO: 4254773), the sequence of the GAM25 hairpin in bold (SEQ ID NO: 4254774), and the sequence of the mature miRNA of GAM25 in bold and underline (SEQ ID NO: 4254775).

FIGS. 15B, 15C and 15D are pictures of laboratory results demonstrating laboratory confirmation of expression of known human oligonucleotide MIR98 and of novel bioinformatically-detected human GAM25 RNA respectively, both of FIG. 15A, thus validating the bioinformatic oligonucleotide detection system of the present invention;

FIG. 18C is a summary table demonstrating detection of known microRNA oligonucleotides using a microarray constructed and operative in accordance with a preferred embodiment of the present invention.

BRIEF DESCRIPTION OF SEQUENCES

A Sequence Listing of genomic sequences of the present invention designated SEQ ID NO:1 through SEQ ID: 4,254,670 is attached to this application, and is hereby incorporated herein. The genomic listing comprises the following nucleotide sequences: nucleotide sequences of 21,916 bacterial and 6,100 human GAM precursors of respective novel oligonucleotides of the present invention; nucleotide sequences of 32,713 bacterial and 11,428 human GAM RNA oligonucleotides of respective novel oligonucleotides of the present invention; and nucleotide sequences of 1,507,219 target gene binding sites of respective novel oligonucleotides of the present invention.

DETAILED DESCRIPTION

Figure 1:
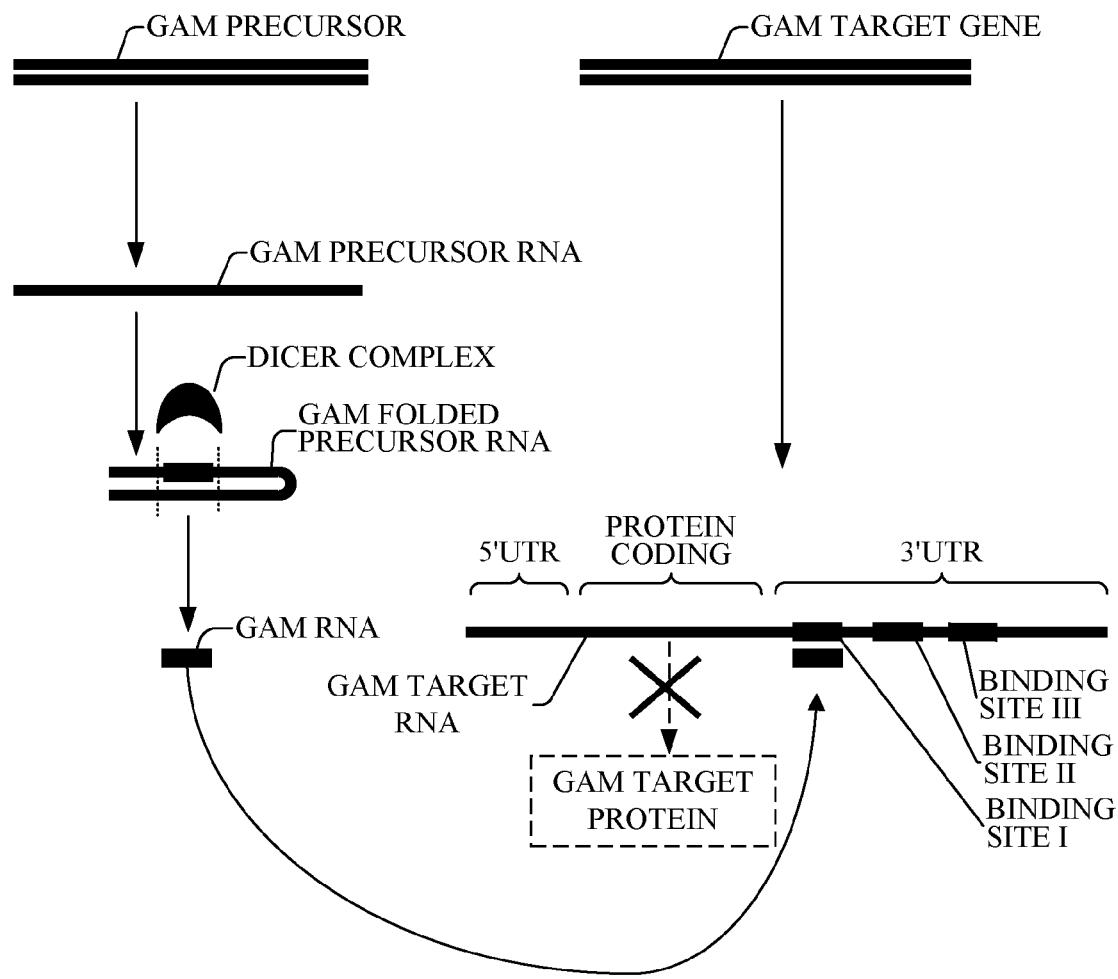
FIG. 1 is a simplified diagram illustrating a mode by which an oligonucleotide of a novel group of oligonucleotides of the present invention modulates expression of known target genes.

Reference is now made to FIG. 1, which is a simplified diagram describing a plurality of novel bioinformatically-detected oligonucleotide of the present invention referred to here as the Genomic Address Messenger (GAM) oligonucleotide, which modulates expression of respective target genes whose function and utility are known in the art.

GAM is a novel bioinformatically detectable regulatory, non-protein-coding, miRNA-like oligonucleotide. The method by which GAM is detected is described with additional reference to FIGS. 1-8.

The GAM PRECURSOR is preferably encoded by a bacterial genome. Alternatively or additionally, the GAM PRECURSOR is preferably encoded by the human genome. The GAM TARGET GENE is a gene encoded by the human genome. Alternatively or additionally, the GAM TARGET GENE is a gene encoded by a bacterial genome.

The GAM PRECURSOR encodes a GAM PRECURSOR RNA. Similar to other miRNA oligonucleotides, the GAM PRECURSOR RNA does not encode a protein.

GAM PRECURSOR RNA folds onto itself, forming GAM FOLDED PRECURSOR RNA, which has a two-dimensional "hairpin" structure. GAM PRECURSOR RNA folds onto itself, forming GAM FOLDED PRECURSOR RNA, which has a two-dimensional "hairpin structure". As is well-known in the art, this "hairpin structure" is typical of RNA encoded by known miRNA precursor oligonucleotides and is due to the full or partial complementarity of the nucleotide sequence of the first half of an miRNA precursor to the RNA that is encoded by a miRNA oligonucleotide to the nucleotide sequence of the second half thereof.

A complementary sequence is a sequence which is reversed and wherein each nucleotide is replaced by a complementary nucleotide, as is well known in the art (e.g. ATGGC is the complementary sequence of GCCAT).

An enzyme complex designated DICER COMPLEX, an enzyme complex composed of Dicer RNaseIII together with other necessary proteins, cuts the GAM FOLDED PRECURSOR RNA yielding a single-stranded ~22 nt-long RNA segment designated GAM RNA.

GAM TARGET GENE encodes a corresponding messenger RNA, designated GAM TARGET RNA. As is typical of mRNA of a protein-coding gene, each GAM TARGET RNAs of the present invention comprises three regions, as is typical of mRNA of a protein-coding gene: a 5' untranslated region, a protein-coding region and a 3' untranslated region, designated 5'UTR, PROTEIN-CODING and 3'UTR, respectively.

GAM RNA binds complementarily to one or more target binding sites located in the untranslated regions of each of the GAM TARGET RNAs of the present invention. This complementary binding is due to the partial or full complementarity between the nucleotide sequence of GAM RNA and the nucleotide sequence of each of the target binding sites. As an illustration, FIG. 1 shows three such target binding sites, designated BINDING SITE I, BINDING SITE II and BINDING SITE III, respectively. It is appreciated that the number of target binding sites shown in FIG. 1 is only illustrative and that any suitable number of target binding sites may be present. It is further appreciated that although FIG. 1 shows target binding sites only in the 3'UTR region, these target binding sites may instead be located in the 5'UTR region or in both the 3'UTR and 5'UTR regions.

The complementary binding of GAM RNA to target binding sites on GAM TARGET RNA, such as BINDING SITE I, BINDING SITE II and BINDING SITE III, inhibits the translation of each of the GAM TARGET RNAs of the present invention into respective GAM TARGET PROTEIN, shown surrounded by a broken line.

It is appreciated that the GAM TARGET GENE in fact represents a plurality of GAM target genes. The mRNA of each one of this plurality of GAM target genes comprises one or more target binding sites, each having a nucleotide sequence which is at least partly complementary to GAM RNA and which when bound by GAM RNA causes inhibition of translation of the GAM target mRNA into a corresponding GAM target protein.

The mechanism of the translational inhibition that is exerted by GAM RNA on one or more GAM TARGET GENEs may be similar or identical to the known mechanism of translational inhibition exerted by known miRNA oligonucleotides.

The nucleotide sequences of each of a plurality of GAM oligonucleotides that are described by FIG. 1 and their respective genomic sources and genomic locations are set forth in Tables 1-3, hereby incorporated herein. Specifically, in Table 1, line 778 describes GAM RNA (miRNA) as set forth in SEQ ID NO: 348 is shown as predicted from human.

TABLE 1

| GAM SEQ-ID | GAM NAME | GAM RNA SEQUENCE | GAM ORGANISM | GAM POS |
|---|---|---|---|---|
| 348 | GAM353678 | CAGCAGCACACTGTGGTTTGTA | Human | A |

In Table 2, lines 42112-42207, describes GAM PRECURSOR RNA (hairpin) as set forth in SEQ ID NO: 4233864 and as it relates to FIGS. 1-8.

TABLE 2

| GAM NAME | GAM ORGA-NISM | PRECUR SEQ-ID | PRECURSOR SEQUENCE | GAM DESCRIPTION |
|---|---|---|---|---|
| GAM 353678 | Human | 4233864 | CCTGCTCCCG CCCCAGCAGC ACACTGTGGT TTGTACGGCA CTGTGGCCAC GTCCAAACCA CACTGTGGTG TTAGAGCGAG GGTGGGGGAGG | FIG. 1 further provides a conceptual description of another novel bioinformatically-detected human oligonucleotide of the present invention referred to here as the Genomic Address Messenger 353678 (GAM353678) oligonucleotide, which modulates expression of respective target genes whose function and utility are known in the art. GAM353678 is a novel bioinformatically detectable regulatory, non-protein-coding, miRNA-like oligonucleotide. The method by which GAM353678 is detected is described with additional reference to FIGS. 1-8. The GAM353678 precursor, herein designated GAM PRECURSOR, is encoded by the Human genome. GAM353678 target gene, herein designated GAM TARGET GENE, is a target gene encoded by the target organism as specified in Tables 6-7. The GAM353678 precursor, herein designated GAM PRECURSOR, encodes a GAM353678 precursor RNA, herein designated GAM PRECURSOR RNA. Similar to other miRNA oligonucleotides, the GAM353678 precursor RNA does not encode a protein. GAM353678 precursor RNA folds onto itself, forming GAM353678 folded precursor RNA, |

TABLE 2-continued

| GAM NAME | GAM ORGA- NISM | PRECUR SEQ- ID | PRECURSOR SEQUENCE | GAM DESCRIPTION |
|---|---|---|---|---|
| | | | | herein designated GAM FOLDED PRECURSOR RNA, which has a two-dimensional "hairpin" structure. GAM PRECURSOR RNA folds onto itself, forming GAM FOLDED PRECURSOR RNA, which has a two-dimensional "hairpin structure". As is well-known in the art, this "hairpin structure" is typical of RNA encoded by known miRNA precursor oligonucleotides and is due to the full or partial complementarity of the nucleotide sequence of the first half of an miRNA precursor to the RNA that is encoded by a miRNA oligonucleotide to the nucleotide sequence of the second half thereof. A nucleotide sequence that is identical or highly similar to the nucleotide sequence of the GAM353678 precursor RNA is designated SEQ ID NO: 4233864, and is provided hereinbelow with reference to the sequence listing section. The nucleotide sequence designated SEQ ID NO: 4233864 is located from position 7121806 to position 7121896 relative to chromosome 17 on the "-" strand, and overlaps an intergenic region (UCSC.h16.refGene database). Furthermore, the nucleotide sequence designated SEQ ID NO: 4233864 is positioned in a region that is conserved between human, mouse and rat (UCSC.hg16.humorMm3Rn3). A schematic representation of a predicted secondary folding of GAM353678 folded precursor RNA, herein designated GAM FOLDED PRECURSOR RNA is set forth in Table 4 incorporated herein. An enzyme complex designated DICER COMPLEX, an enzyme complex composed of Dicer RNaseIII together with other necessary proteins, cuts the GAM353678 folded precursor RNA yielding a single-stranded ~22 nt-long RNA segment designated GAM353678 RNA, herein designated GAM RNA. Table 5 provides a nucleotide sequence that is highly likely to be identical or extremely similar to the nucleotide sequence of GAM353678 RNA, hereby incorporated herein. GAM353678 target gene, herein designated GAM TARGET GENE, encodes a corresponding messenger RNA, designated GAM353678 target RNA, herein designated GAM TARGET RNA. As is typical of mRNA of a protein-coding gene, GAM353678 target RNA comprises three regions, as is typical of mRNA of a protein-coding gene: a 5' untranslated region, a protein-coding region and a 3' |

TABLE 2-continued

| GAM NAME | GAM ORGA- NISM | PRECUR SEQ- ID | PRECURSOR SEQUENCE | GAM DESCRIPTION |
|---|---|---|---|---|
| | | | | untranslated region, designated 5'UTR, PROTEIN-CODING and 3'UTR, respectively. GAM353678 RNA, herein designated GAM RNA, binds complementarily to one or more target binding sites located in the untranslated regions of GAM353678 target RNA. This complementary binding is due to the partial or full complementarity between the nucleotide sequence of GAM353678 RNA and the nucleotide sequence of each of the target binding sites. As an illustration, FIG. 1 shows three such target binding sites, designated BINDING SITE I, BINDING SITE II and BINDING SITE III, respectively. It is appreciated that the number of target binding sites shown in FIG. 1 is only illustrative and that any suitable number of target binding sites may be present. It is further appreciated that although FIG. 1 shows target binding sites only in the 3'UTR region, these target binding sites may instead be located in the 5'UTR region or in both the 3'UTR and 5'UTR regions. The complementary binding of GAM353678 RNA, herein designated GAM RNA, to target binding sites on GAM353678 target RNA, herein designated GAM TARGET RNA, such as BINDING SITE I, BINDING SITE II and BINDING SITE III, inhibits the translation of GAM353678 target RNA into respective GAM353678 target protein, herein designated GAM TARGET PROTEIN, shown surrounded by a broken line. It is appreciated that the GAM353678 target gene, herein designated GAM TARGET GENE, in fact represents a plurality of GAM353678 target genes. The mRNA of each one of this plurality of GAM353678 target genes comprises one or more target binding sites, each having a nucleotide sequence which is at least partly complementary to GAM353678 RNA, herein designated GAM RNA, and which when bound by GAM353678 RNA causes inhibition of translation of the GAM353678 target mRNA into a corresponding GAM353678 target protein. The mechanism of the translational inhibition that is exerted by GAM353678 RNA, herein designated GAM RNA, on one or more GAM353678 target genes, herein collectively designated GAM TARGET GENE, may be similar or identical to the known mechanism of translational inhibition exerted by known miRNA |

TABLE 2-continued

| GAM NAME | GAM ORGA-NISM | PRECUR SEQ-ID | PRECURSOR SEQUENCE | GAM DESCRIPTION |
|---|---|---|---|---|
| | | | | oligonucleotides. The nucleotide sequence of GAM353678 precursor RNA, herein designated GAM PRECURSOR RNA, its respective genomic source and genomic location and a schematic representation of a predicted secondary folding of GAM353678 folded precursor RNA, herein designated GAM FOLDED PRECURSOR RNA are set forth in Tables 3-4, hereby incorporated herein. The nucleotide sequences of a "diced" GAM353678 RNA, herein designated GAM RNA, from GAM353678 folded precursor RNA are set forth in Table 5, hereby incorporated herein. The nucleotide sequences of target binding sites, such as BINDING SITE I, BINDING SITE II and BINDING SITE III of FIG. 1, found on GAM353678 target RNA, herein designated GAM TARGET RNA, and a schematic representation of the complementarity of each of these target binding sites to GAM353678 RNA, herein designated GAM RNA, are set forth in Tables 6-7, hereby incorporated herein. It is appreciated that the specific functions and accordingly the utilities of GAM353678 RNA are correlated with and may be deduced from the identity of the GAM353678 target gene inhibited thereby, and whose functions are set forth in Table 8, hereby incorporated herein. |

Table 3, lines 1279-1280, shows data relating to the source and location of the GAM oligonucleotide, specificaly the GAM PRECRSOR (hairpin) and its position in the genomic sequence of human.

TABLE 3

| GAM NAME | PRECURSOR SEQ-ID | GAM ORGANISM | SOURCE | STR AND | SRC-START OFFSET | SRC-END OFFSET |
|---|---|---|---|---|---|---|
| GAM353678 | 4233864 | Human | 17 | | 7121806 | 7121896 |

The nucleotide sequences of GAM PRECURSOR RNAs, and a schematic representation of a predicted secondary folding of GAM FOLDED PRECURSOR RNAs, of each of a plurality of GAM oligonucleotides described by FIG. 1 are set forth in Table 4, hereby incorporated herein. Table 4 lines 2384-2388, shows a schematic representation of the GAM folder precursor as set forth in SEQ ID NO:348, beginning at the 5' end (beginning of upper row) to the 3' end (beginning of lower row), where the hairpin loop is positioned at the right part of the drawing.

TABLE 4

| GAM NAME | PRE CUR SEQ-ID | GAM ORGANISM | GAM PRECURSOR SEQUENCE | GAM FOLDED PRECURSOR RNA | | | | | |
|---|---|---|---|---|---|---|---|---|---|
| GAM 353 678 | 423 386 4 | Human | CCTGCTCCCGCCCAGCAGC ACACTGTGGTTTGTACGGCACCT CTGTGGCCACGTCCAAACCAGGA CACTGTGGTGTTAGAGCGAG GGTGGGGGAGG | G CTCCCGCCC GTTTG AC GGGGGTGGG CAAAC TG - C | C------ AGCA GGC T CCG G CA | G CACA TTGT AGCGAGA GT | C TGTG- GTGT G | T -- ACAC- C- | AC |

The nucleotide sequences of "diced" GAM RNAs of each of a plurality of GAM oligonucleotides described by FIG. 1 are set forth in Table 5, hereby incorporated herein. Table 5, line 1276 shows the mature GAM RNA as set forth in SEQ ID NO: 348 as sliced by DICER from the GAM PRECURSOR sequence (hairpin) as set forth in SEQ ID NO: 4233864.

GAM RNAs that are described by FIG. 1 are set forth in Tables 6-7, hereby incorporated herein. Table 6 shows data relating to the SEQ ID NO of the GAM target binding site sequence of the target gene name as bound by the GAM RNA as set forth in SEQ ID NO: 348. Table 6, lines 3688165, 767082, 762322 and 763042 related to target binding site SEQ ID NO: 1810388, 673420, 671402 respectively.

| GAM NAME | GAM ORGAN-ISM | GAM RNA SEQUENCE | PRECUR SEQ-ID | GAM POS |
|---|---|---|---|---|
| GAM353678 | Human | CAGCAGCACACTGTG-GTTTGTA | 4233864 | A |

The nucleotide sequences of target binding sites, such as BINDING SITE I, BINDING SITE II and BINDING SITE III that are found on GAM TARGET RNAs of each of a plurality of GAM oligonucleotides that are described by FIG. 1, and a schematic representation of the complementarity of each of these Target binding sites to each of a plurality of

TABLE 6

| TARGET BINDING SITE SEQ-ID | TARGET ORGANISM | TARGET | TARGET BINDING SITE SEQUENCE |
|---|---|---|---|
| 1810388 | Human | MGAT5 | CACCATGCTGCTG |
| 673420 | Human | SERPINH1 | AAACTAGGTGCTGCAG |
| 671402 | Human | SERPINH1 | ATACCATGATGCTG |
| 671042 | Human | SERPINH1 | CTATAAAACTAGGTGCTGCAG |

Table 7, lines 312839-313773 shows data relating to target genes and binding site of GAM oligonucleotides.

TABLE 7

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | | | | | GAM POS |
|---|---|---|---|---|---|---|---|---|---|---|---|---|
| GAM35 3678 | Human | CAGCAGCA CACTGTGG TTTGTA | AAACCAAA CTTATGCA GCTG | nup C | NC_004431 from 2795390 2796631 (+) | Escherichia  coli CFT073 | 3 --- AAACCA TTTGGT ATG | A T T G | A TGC A C C- | A ACG A | A GCTG CGAC | A |
| GAM35 3678 | Human | CAGCAGCA CACTGTGG TTTGTA | AAACCAAA CTTATGCA GCTG | nup C | NC_004741 from 2494019 2495221 (+) | Shingella  flexneri 2a str. 2457T | 3 --- AAACCA TTTGGT ATG | A T T G | A TGC A C C- | A ACG A | A GCTG CGAC | A |
| GAM35 3678 | Human | CAGCAGCA CACTGTGG TTTGTA | AAACCCTG CTGCG | rel A | NC_000962 from 2907824 2910196 (-) | Mycobacterium  tuberculos is H37Rv | 3 --- AAACC TTTGG ATG | C TGCTAC | ----- TGCTGC ACGACG TGTCAC | - G C A | A | |
| GAM35 3673 | Human | CAGCAGCA CACTGTGG TTTGTA | AAACCCTG CTGCG | rel A | NC_002945 from 2875274 2877646 (-) | Mycobacterium  bovis subs p bovis AF21 22/97 | 3 --- AAACC TTTGG ATG | C TGTCAC | ----- TGCTGC ACGACG | - G C | A A | |
| GAM35 3678 | Human | CAGCAGCA CACTGTGG TTTGTA | AAACCCTT TCTGCTGC TT | yab O | NC_004431 from 61489 to 62148 (-) | Escherichia  coli CFT073 | 3 --- AAACC TTTGG ATG | C T G T | TTC- TGCT TCAC TCAC | GCT GCA C | T A | |
| GAM35 3678 | Human | CAGCAGCA CACTGTGG TTTGTA | AAACCGAT GCAGTGCG GCTG | amt B | NC_004337 from 408059 to 409345 (+) | Shigella  flexneri 2a str. 301 | 3 --- AAACCG TTTGGT ATG | AT G GT | CAG TGC AC- | G CGT A A | A CGAC | A |
| GAM35 3678 | Human | CAGCAGCA CACTGTGG TTTGTA | AAACCGAT GCAGTGCG | amt B | NC_004741 from 407860 to | Shigella  flexneri | 3 --- AAACCG | AT G | CAG TGC | G CGT | A CTG | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| | | | TTTGTA | GCTG | 409146 (+) | 2a str. 2457T | TTTGGT  C   ACG CGAC<br>ATG    GT AC-   A | |
| GAM35 3678 | Human | CAGCAGCA CACTGTGG TTTGTA | AAACCGAT GCCGTGCG GCTG | amt B | NC_004431 from 547616 to 548902 (+) | Escherichia coli CFT073 | 3 ---  AT CCG   G    A<br>AAACCG  G   TGC GCTG<br>TTTGGT  C   ACG CGAC<br>ATG    GT AC-   A | 3 |
| GAM35 3678 | Human | CAGCAGCA CACTGTGG TTTGTA | AAACCGCC CCCAGTCT GCTG | dsd A | NC_003197 from 4004453 to 40057 (+) T2 | Salmonella typhimurium LT2 | 3 ---  CCCCAG -    A<br>AAACCGC   T<br>CTGCTG    TTTGGTG<br>  A GACGAC ATG<br>     TCAC - C | 3 |
| GAM35 3678 | Human | CAGCAGCA CACTGTGG TTTGTA | AAACCGGC CTTGCCGC TG | gad | NC_002947 from 4871625 to 4872929 (+) | Pseudomonas putida KT244 0 | 3 ---    GCC -   C    A<br>AAACCG  T TGC GCTG<br>TTTGGT  A ACG CGAC<br>ATG    GTC C   A | 3 |
| GAM35 3678 | Human | CAGCAGCA CACTGTGG TTTGTA | AAACGAAT TGAATCAT GCCGCTG | aro A | NC_003116 from 1557502 to 1558803 (+) | Neisseria meningitidis Z 2491 | 3 --- G ATTGAATCA   C A<br>AAAC A           TGC<br>GCTG    TTTG T<br>    ACG CGAC ATG<br>  G GTCAC----   A | 3 |
| GAM35 3678 | Human | CAGCAGCA CACTGTGG TTTGTA | AAACGACG GGCTGCTG | ruv B | NC_003143 from 2336449 to 2337453 (+) | Yersinia pestis | 3 --- G ---G    AAAC A<br>ACG   GCTGCTG    TTTG<br>TGT  CGACGAC ATG    G<br>CACA | 3 |
| GAM35 3678 | Human | CAGCAGCA CACTGTGG TTTGTA | AAACGACG GGCTGCTG | ruv B | NC_004088 from 2482031 to 2433035 (-) | Yersinia pestis KIM | 3 --- G ---G    AAAC A<br>ACG   GCTGCTG    TTTG<br>TGT  CGACGAC ATG    G<br>CACA | 3 |
| GAM35 3678 | Human | CAGCAGCA CACTGTGG TTTGTA | AAACGATA TCCTGCTG | yci E | NC_004431 from 1558641 to 1559147 (-) | Escherichia coli CFT073 | 3 ---  G   --- C   A<br>AAAC ATA    T CTGCTG<br>TTTG TGT    A GACGAC<br>ATG    G   CAC C | 3 |
| GAM35 3678 | Human | CAGCAGCA CACTGTGG TTTGTA | AAACGCAT GTTCATGC GCTG | van B | NC_002516 from 5504120 to 5505073 (+) | Pseudomonas aeruginosa PA01 | 3 --- G  T CA  -    A<br>AAAC CATG T TGC<br>GCTG    TTTG GTGT A<br>  ACG CGAC ATG   -   C<br>C-    A | 3 |
| GAM35 3678 | Human | CAGCAGCA CACTGTGG TTTGTA | AAACGCTC CGTATACT GCTGCTA | fts Y | NC_000922 from 1115427 to 1116299 (-) | Chlamydophila pneumoniae CWL029 | 3 --- GC CCGTATAC    A<br>  A      AAAC T<br>TGCTGCT    TTTG<br>G    ACGA ATG<br>GT TCAC----   C | 3 |
| GAM35 3678 | Human | CAGCAGCA CACTGTGG TTTGTA | AAACGCTC CGTATACT GCTGCTA | fts Y | NC_002491 from 1113127 to 1113999 (-) | Chlamydophila pneumoniae J138 | 3 --- GC CCGTATAC    A<br>  A      AAAC T<br>TGCTGCT    TTTG<br>G    ACGACGA ATG<br>GT TCAC----   C | 3 |
| GAM35 3678 | Human | CAGCAGCA CACTGTGG TTTGTA | AAACTAAT CGACAGTT GCTGCG | rbs R | NC_004337 from 3947708 to 3948700 (+) | Shigella flexneri 2a str. 301 | 3 ---   ATCGACAGT    A<br>  -     AAACTA<br>    TGCTGC G<br>    TTTGGT<br>  ACGACG C ATG<br>    GTCAC----    A | 3 |
| GAM35 3678 | Human | CAGCAGCA CACTGTGG TTTGTA | AAACTAAT CGACAGTT GCTGCG | rbs R | NC_004741 from 3824594 to 3825577 (-) | Shigella flexneri 2a str. 2457T | 3 ---   ATCGACAGT    A<br>  -     AAACTA<br>    TGCTGC G<br>    TTTGGT<br>  ACGACG C ATG<br>    GTCAC----    A | 3 |
| GAM35 3678 | Human | CAGCAGCA CACTGTGG TTTGTA | AAACTAGG TGCTGCAG | SER PIN H 1 | NM_001235 | Human | 3 ---  G  ---    A   A<br>AAACTA G  TGCTGC G<br>TTTGGT T  ACGACG C<br>ATG    G  CAC    A | 3 |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| GAM35 3678 | Human | CAGCAGCA ACTGTGG TTTGTA | AAACTCAG GCTGGCAA GCTGCTG | aro H | NC_004337 from 1557527 1558573 (-) | Shigella flexneri 2a str. 301 | 3 ---     T  G C  GCAA    A<br>AAAC CA G TG<br>GCTGCTG    TTTG GT T<br>AC  CGACGAC ATG   -<br>G C   ---A | 3 |
| GAM35 3678 | Human | CAGCAGCA CACTGTGG TTTGTA | AAAGCTGC TGCTT | zra P | NC_003197 from 4387727 4338182 (-) | Salmonella typhimurium LT2 | 3 ---    G ------    T A<br>AAA C    TGCTGCT<br>TTT G    ACGACGA<br>ATG   G TGTCAC   C | 3 |
| GAM35 3678 | Human | CAGCAGCA CACTGTGG TTTGTA | AAATCAGT TGTACTTG TTGCTG | cys M | NC_003197 from 2551651 2552562 (-) | Salmonella typhimurium LT2 | 3 ---   GTTGTACT  T    A<br>AAATCA    TG<br>TGCTG   TTTGGT<br>AC ACGAC ATG<br>GTCAC---  G | 3 |
| GAM35 3678 | Human | CAGCAGCA CACTGTGG TTTGTA | AACATTGC TGCTG | rbs R | NC_004431 from 4439260 4440252 (+) | Escherichia coli CFT073 | 3 --- - ----   AA C A<br>AT   TGCTGCTG  TT G<br>TG  ACGACGAC ATG T G<br>TCAC | 3 |
| GAM35 3678 | Human | CAGCAGCA CACTGTGG TTTGTA | AACTGCTG CTC | oxy R | NC_003197 from 4343080 4343997 (+) | Salmonella typhimurium | 3 --- - -------   C A<br>AA C     TGCTGCT<br>TT G    ACGACGA<br>ATG  T GTGTCAC   C | 3 |
| GAM35 3678 | Human | CAGCAGCA CACTGTGG TTTGTA | AACT- GCTG CTC | oxy R | NC_003198 from 3607204 3608121 (-) | Salmonella enterica serovar Typhi | 3 --- - -------   C A<br>AA C     TGCTGCT<br>TT G    ACGACGA<br>ATG  T GTGTCAC   C | 3 |
| GAM35 3678 | Human | CAGCAGCA CACTGTGG TTTGTA | AACT- GCTG CTC | oxy R | NC_004631 from 3592864 3593781 (-) | Salmonella enterica enterica serovar Typhi Ty2 | 3 --- - -------   C A<br>AA C     TGCTGCT<br>TT G    ACGACGA<br>ATG  T GTGTCAC   C | 3 |
| GAM35 3678 | Human | CAGCAGCA CACTGTGG TTTGTA | AAGCCGGT TGCGGTGC TGCTG | aro A | NC_003116 from 1557502 1558803 (+) | Neisseria meningitidis Z 2491 | 3 ---     GTTGCGG    A<br>AAGCCG<br>TGCTGCTG<br>TTTGGT<br>ACGACGAC ATG<br>GTCAC-- | 3 |
| GAM35 3678 | Human | CAGCAGCA CACTGTGG TTTGTA | AATCCACT CCGTGTTG CTG | gig P | NC_003193 from 4144568 4147015 (+) | Salmonella enterica enterica serovar Typhi | 3 --- T  TCC  T    AAA<br>CCAG  GTG TGCTG   TT<br>GGTG  CAC ACGAC ATG  T<br>TCA   G | 3 |
| GAM35 3678 | Human | CAGCAGCA CACTGTGG TTTGTA | AATCCACT CCGTGTTG CTG | gig P | NC_004631 from 4129215 4131662 (+) | Salmonella enterica enterica serovar Typhi Ty2 | 3 --- T  TCC  T    AAA<br>CCAG  GTG TGCTG   TT<br>GGTG  CAC ACGAC ATG  T<br>TCA   G | 3 |
| GAM35 3678 | Human | CAGCAGCA CACTGTGG TTTGTA | ACATGCTG CTT | nup C | NC_004431 from 2795390 2796631 (+) | Escherichia coli CFT073 | 3 --- -- - -----    T A<br>A   C A    TGCTGCT<br>T  G T    ACGACGA<br>ATG TT G GTCAC   C | 3 |
| GAM35 3678 | Human | CAGCAGCA CACTGTGG TTTGTA | ACATGCTG CTT | nup C | NC_004741 from 2494019 2495221 (+) | Shigella flexneri 2a str. 2457T | 3 --- -- - -----    T A<br>A   C A    TGCTGCT<br>T  G T    ACGACGA<br>ATG TT G GTCAC   C | 3 |
| GAM35 3678 | Human | CAGCAGCA CACTGTGG TTTGTA | ACGATGGT GTACTGCT GCTT | pho Y2 | NC_000962 from 913556 to 914197 (-) | Mycobacterium tuberculosis H37Rv | 3 --- -- G     TAC    A<br>T  A   C ATGGTG<br>TGCTGCT   T  G<br>TGTCAC   ACGACGA ATG TT<br>G    ---    C | 3 |
| GAM35 3678 | Human | CAGCAGCA CACTGTGG TTTGTA | ACGATGGT GTACTGCT GCTT | pho Y2 | NC_002945 from 914388 to 915029 (-) | Mycobacterium bovis subs p bovis AF21 | 3 --- -- G     TAC    A<br>T  A   C ATGGTG<br>TGCTGCT   T  G | 3 |

TABLE 7-continued

| GAM NAME | GAM ORGANISM | GAM RNA SEQUENCE | TARGET BS-SEQ TARGET | TARG REF-ID | TARGET ORGANISM | BINDING SITE DRAW (UPPER:TARGET;LOWER:GAM) | GAM POS |
|---|---|---|---|---|---|---|---|
| | | | | 22/97 | | TGTCAC  ACGACGA ATG TT<br>G         ---         C | |
| GAM35 3678 | Human | CAGCAGCA CACTGTGG TTTGTA | ACTGCTGC TC | glg P<br>NC_003193<br>from 4144568 to 4147015 (+) | Salmonella enterica enterica serovar Typhi | 3 --- -- -------    C A<br>     A  C    TGCTGCT<br>     T  G    ACGACGA<br>ATG TT GTGTCAC    C | |
| GAM35 3678 | Human | CAGCAGCA CACTGTGG TTTGTA | ACTGCTGC TC | glg P<br>NC_004631<br>from 4129215 to 4131662 (+) | Salmonella enterica enterica serovar Typhi Ty2 | 3 --- -- -------    C A<br>     A  C    TGCTGCT<br>     T  G    ACGACGA<br>ATG TT GTGTCAC    C | |
| GAM35 3678 | Human | CAGCAGCA CACTGTGG TTTGTA | AGAATGTT GTTAGTGC TGCTG | rec G<br>NC_00677<br>from 2014723 to 2016954 (-) | Mycobacterium leprae | 3 ---    -- T TTAG    A<br>      AGA ATG TG<br>   TGCTGCTG  TTT  TGT<br>AC   ACGACGAC ATG  GG<br>C    ---- | |
| GAM35 3678 | Human | CAGCAGCA CACTGTGG TTTGTA | AGACCATG AAGAACTG GCTGCTG | rel A<br>NC_000962<br>from 2907824 to 2910196 (-) | Mycobacterium tuberculosis is H37Rv | 3 ---      AA AACTG     A<br>      AGACCATG  G<br>       GCTGCTG    TTTGGTGT<br>C      CGACGAC ATG<br>         CA ----A | |
| GAM35 3678 | Human | CAGCAGCA CACTGTGG TTTGTA | AGACCATG AAGAACTG GCTGCTG<br>46 (-) | rel A<br>NC_002945<br>from 2875274 to 2877646 (-) | Mycobacterium bovis subs p bovis AF21 22/97 | 3 ---      AA AACTG     A<br>      AGACCATG  G<br>       GCTGCTG    TTTGGTGT<br>C      CGACGAC ATG<br>         CA ----A | |
| GAM35 3678 | Human | CAGCAGCA CACTGTGG TTTGTA | AGCTTGCT GCTG | glp C<br>NC_003143<br>from 4289650 to 4290897 (-) | Yersinia pestis | 3 ---   -  ------    AG CTA<br>         TGCTGCTG    T-<br>T GG<br>         ACGACGAC ATG T<br>   TGTCAC | |
| GAM35 3678 | Human | CAGCAGCA CACTGTGG TTTGTA | AGCTTGCT GCTG | glp C<br>NC_004088<br>from 454677 to 456047 (+) | Yersinia pestis KIM | 3 ---   -  ------    AG CTA<br>         TGCTGCTG    T-<br>T GG<br>         ACGACGAC ATG T<br>   TGTCAC | |
| GAM35 3678 | Human | CAGCAGCA CACTGTGG TTTCTA | ATACCAAG GCTGCTG | fts Y<br>NC_000922<br>from 1115427 to 1116299 (-) | Chlamydophila pneumoniae CWL029 | 3 --- T  A----G    A    A<br>   ACCA    GCTGCTG    T<br>   TGGT    CGACGAC ATG T<br>          GTCACA | |
| GAM35 3678 | Human | CAGCAGCA CACTGTGG TTTCTA | ATACCAAG GCTGCTG | fts Y<br>NC_002491<br>from 1113127 to 1113999 (-) | Chlamydophila pneumoniae J138 | 3 --- T  A----G    A    A<br>   ACCA    GCTGCTG    T<br>   TGGT    CGACGAC ATG T<br>          GTCACA | |
| GAM35 3678 | Human | CAGCAGCA CACTGTGG TTTGTA | ATACCATG ATGCTG | SER PIN H 1<br>NM_001235 | Human | 3 --- T  -----  A    A A<br>   ACCA    TG TGCTG    T<br>   TGGT    AC ACGAC ATG T<br>          GTCAC  G | |
| GAM35 3678 | Human | CAGCAGCA CACTGTGG TTTGTA | ATTTCTGC TGCTT | aro D<br>NC_004342<br>from 48128 to 48832 (-) | Leptospira interrogans serovarlai str. 56601 | 3 --- TT ------    T A<br>     A TC    TGCTGCT<br>     T GG    ACGACGA<br>ATG TT TGTCAC    C | |
| GAM35 3678 | Human | CAGCAGCA CACTGTGG TTTGTA | CAAAAACG GTCTGCCG CTG | acc C<br>NC_002929<br>from 926407 to 927777 (+) | Bordetella pertussis | 3 -- A-   C    C     A<br>   CAAA  ACGGT TGC GCTG<br>   GTTT  TGTCA ACG CGAC<br>   AT    GG    C    A | |
| GAM35 3678 | Human | CAGCAGCA CACTGTGG TTTGTA | CAAAAGCT TTTCGCTT GCGGCTG | zra P<br>NC_003197<br>from 4387727 to 4388182 (-) | Salmonella typhimurium LT2 | 3 --   -- GCT TTCGCT   GA<br>   CAAA A  T          TGC<br>   GCTG GTTT T       A<br>      ACG CGAC AT    GG<br>      GTC C----- A | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| GAM35 3678 | Human | CAGCAGCA CACTGTGG TTTGTA | CAAAAGTC GTCCTGTG CGGCTG | glp D | NC_004310 from 210763 to 212274 (+) | *Brucella suis* 1330 | 3 --    -- GTCGTCCTG  G   A<br>     CAAA   A            TGC<br>     GCTG   GTTT    T<br>        ACG CGAC   AT<br>     GG GTCAC----    A | |
| GAM35 3678 | Human | CAGCAGCA CACTGTGG TTTGTA | CAAACAGG CTGCTGCT G | avt A | NC_004337 from 3721175 to 3722533 (+) | *Shigella flexneri* 2a str. 301 | 3 --      - G C--      CAAAC A<br>     A G     TGCTGCTG     GTTTG<br>     T T     ACGACGAC AT       G<br>     G CAC | |
| GAM35 3678 | Human | CAGCAGCA CACTGTGG TTTGTA | CAAACAGG CTGCTGCT G | avt A | NC_004741 from 4052685 to 4053938 (-) | *Shigella flexneri* 2a str. 2457T | 3 --      - G C--      CAAAC A<br>     A G     TGCTGCTG     GTTTG<br>     T T     ACGACGAC AT       G<br>     G CAC | |
| GAM35 3678 | Human | CAGCAGCA CACTGTGG TTTGTA | CAAACATC ATGGTTGC | mia A | NC_000117 from 899276 to 900295 (+) | *Chlamydia trachomatis* | 3 --      - CA GT    T  A<br>     TG    GTTTG TG   AC<br>     ACGAC AC AT   G  TC<br>     --    G | |
| GAM35 3678 | Human | CAGCAGCA CACTGTGG TTTGTA | CAAACCAG CGGTCTGC TG | sel B | NC_002947 from 582133 to 584055 (+) | *Pseudomonas putida* KT2440 | 3 --         GC G- -         A<br>     CAAACCA    G   T CTGCTG<br>     GTTTGGT    C   A GACGAC<br>     AT        GT AC C | |
| GAM35 3678 | Human | CAGCAGCA CACTGTGG TTTGTA | CAAACCAT GATGCTG | mia A | NC_000117 from 899276 to 900295 (+) | *Chlamydia trachomatis* | 3 --      ----- A       A<br>     CAAACCA      TG TGCTG<br>     GTTTGG       AC ACGAC<br>     AT        GTCAC G | |
| GAM35 3678 | Human | CAGCAGCA CACTGTGG TTTGTA | CAAACCGA CCCTGCTG CTG | min E | NC_002947 from 1932680 to 1932934 (-) | *Pseudomonas putida* KT2440 | 3 --       ACCC-         A<br>     CAAACCA      TGCTGCTG<br>     GTTTGGT      ACGACGAC<br>     AT        GTCAC | |
| GAM35 3678 | Human | CAGCAGCA CACTGTGG TTTGTA | CAAACCGC AGTACTGG TGCTG | dna E | NC_002677 from 1423014 to 1426547 (+) | *Mycobacterium leptae* | 3 --         AC  G        A<br>     CAAACCGCAGT  TG TGCTG<br>     GTTTGGTGTCA  AC ACGAC<br>     AT        C- G | |
| GAM35 3678 | Human | CAGCAGCA CACTGTGG TTTGTA | CAAACTCT TTTTCTTC TGCTG | aro D | NC_004342 from 48128 to 48832 (-) | *Leptospira interrogans serovarlai* str. 56601 | 3 --     C TT TC T     A<br>     CAAACT T  T  T CTGCTG<br>     GTTTGG G  A  A GACGAC<br>     AT      T TC C- C | |
| GAM35 3678 | Human | CAGCAGCA CACTGTGG TTTGTA | CAAAGCAC TGCTGCTG | pts H | NC_003198 from 2505403 to 2505660 (+) | *Salmonella enterica enterica serovar* Typhi | 3 --     G ----     CAAA  A<br>     CAC    TGCTGCTG    GTTT<br>     GTG    ACGACGAC AT    G<br>     TCAC | |
| GAM35 3678 | Human | CAGCAGCA CACTGTGG TTTGTA | CAAAGCCG CGTGCGCT G | amt B | NC_004337 from 408059 to 409345 (+) | *Shigella flexneri* 2a str. 301 | 3 --      G CGC --    -       A<br>     CAAA  C     G   TGC GCTG<br>     GTTT  G     C   ACG CGAC<br>     AT    G TGT AC    A | |
| GAM35 3678 | Human | CAGCAGCA CACTGTGG TTTGTA | CAAAGCCG CGTGCGCT G | amt B | NC_004431 from 547616 to 548902 (+) | *Escherichia coli* CFT073 | 3 --      G CGC --    -       A<br>     CAAA  C     G   TGC GCTG<br>     GTTT  G     C   ACG CGAC<br>     AT    G TGT AC    A | |
| GAM35 3678 | Human | CAGCAGCA CACTGTGG TTTGTA | CAAAGCCG CGTGCGCT G | amt B | NC_004741 from 407860 to 409146 (+) | *Shigella flexneri* 2a str. 2457T | 3 --      G CGC --    -       A<br>     CAAA  C     G   TGC GCTG<br>     GTTT  G     C   ACG CGAC<br>     AT    G TGT AC    A | |
| GAM35 3678 | Human | CAGCAGCA CACTGTGG TTTGTA | CAAAGCCT TTTTTCGG GCTGCTG | pil T | NC_002947 from 5816934 to 5817944 (-) | *Pseudomonas putida* KT2440 | 3 --     G C TT TTCGG      A<br>     CAAA  C T    T<br>         GCTGCTG    GTTT G G<br>     A     CGACGAC AT      G<br>     T TC C---A | |
| GAM35 3678 | Human | CAGCAGCA CACTGTGG TTTGTA | CAAAGCGT CATGTAAT GCTTGCTG | cys M | NC_003197 from 2551651 to 2552562 (-) | *Salmonella typhimurium* LT2 | 3 --     G  CA TAA     T A<br>     CAAA  CGT TG    TGCT<br>     GCTG     GTTT GTG   AC<br>     ACGA CGAC  AT      G<br>     TC  ---     - | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET; LOWER:GAM) | GAM POS |
|---|---|---|---|---|---|---|---|---|
| GAM35 3678 | Human | CAGCAGCACACTGTGGTTTGTA | CAAATCCCCAGTTGTGCTG | glc C | NC_004431 from 3542871 to 3543695 (+) | Escherichia coli CFT073 | 3 -- C CAGT - A<br>CAAATC C TG TGCTG<br>GTTTGG G AC ACGAC<br>AT T TCAC G | 3 |
| GAM35 3678 | Human | CAGCAGCACACTGTGGTTTGTA | CAACACATTACTGCTTGCTCTG | aro H | NC_004337 from 1557527 to 1558573 (-) | Shigella flexneri 2a str. 301 | 3 -- CA TACTGCT - A<br>CAA CAT TGCT<br>CTG GTT GTG<br>ACGA GAC AT TG<br>TCAC--- C | 3 |
| GAM35 3678 | Human | CAGCAGCACACTGTGGTTTGTA | CAACACTTTGCGCTG | spe D | NC_003197 from 194201 to 194995 (-) | Salmonella typhimurium LT2 | 3 -- - TT-- - A<br>CAA C AC TGC GCTG<br>GTT G TG ACG CGAC<br>AT T G TCAC A | 3 |
| GAM35 3678 | Human | CAGCAGCACACTGTGGTTTGTA | CAACACTTTGCGCTG | spe D | NC_003198 from 196389 to 197183 (-) | Salmonella enterica enterica serovar Typhi | 3 -- - TT-- - A<br>CAA C AC TGC GCTG<br>GTT G TG ACG CGAC<br>AT T G TCAC A | 3 |
| GAM35 3678 | Human | CAGCAGCACACTGTGGTTTGTA | CAACACTTTGCGCTG | spe D | NC_004631 from 196380 to 197174 (-) | Salmonella enterica enterica serovar Typhi Ty2 | 3 -- - TT-- - A<br>CAA C AC TGC GCTG<br>GTT G TG ACG CGAC<br>AT T G TCAC A | 3 |
| GAM35 3678 | Human | CAGCAGCACACTGTGGTTTGTA | CAACAGCAGTTGCTGCTG | ace K | NC_002947 from 5184742 to 5186457 (-) | Pseudomonas putida KT2440 | 3 -- - GCAGT CAA C A<br>A TGCTGCTG GTT G<br>T ACGACGAC AT T G<br>GTCAC | 3 |
| GAM35 3678 | Human | CAGCAGCACACTGTGGTTTGTA | CAACAGTTTCTTGGTC (mrp)TGCTG | fmt B | NC_002745 from 2218145 to 2225590 (-) | Staphylococcus aureus u bsp. aureus N315 | 3 -- - GTT CTTGG - A<br>CAA C A T T<br>CTGCTG GTT G T A<br>A GACGAC AT T G<br>GTC C---- C | 3 |
| GAM35 3678 | Human | CAGCAGCACACTGTGGTTTGTA | CAACAGTTTCTTGGTC (mrp)TGCTG | fmt B | NC_002758 from 2287935 to 2295380 (-) | Staphylococcus aureus u bsp. aureus Mu50 | 3 -- - GTT CTTGG - A<br>CAA C A T T<br>CTGCTG GTT G T A<br>A GACGAC AT T G<br>GTC C---- C | 3 |
| GAM35 3678 | Human | CAGCAGCACACTGTGGTTTGTA | CAACAGTTTCTTGGTCTGCTG | tru ncated fmt | NC_003923 from 2238083 to 2240143 (-) | Staphylococcus aureus u bsp. aureus MW2 | 3 -- - GTT CTTGG - A<br>CAA C A T T<br>CTGCTG GTT G T A<br>A GACGAC AT T G<br>GTC C---- C | 3 |
| GAM35 3678 | Human | CAGCAGCACACTGTGGTTTGTA | CAACCCACCAGCACTGCTGCG | cys Q | NC_002947 from 315184 to 315984 (+) | Pseudomonas putida KT2440 | 3 -- C CAGCAC -A<br>CAA CCAC TGCTGC<br>G GTT GGTG<br>ACGACG C AT T<br>TCAC-- A | 3 |
| GAM35 3678 | Human | CAGCAGCACACTGTGGTTTGTA | CAACCGCTGCTGCTG | pho Y2 | NC_000962 from 913556 to 914197 (-) | Mycobacterium tuberculosis H37Rv | 3 -- - ---- CAA A<br>CCGC TGCTGCTG GTT<br>GGTG ACGACGAC AT T<br>TCAC | 3 |
| GAM35 3678 | Human | CAGCAGCACACTGTGGTTTGTA | CAACCGCTGCTGCTG | pho Y2 | NC_002945 from 914388 to 915029 (-) | Mycobacterium bovis subs p bovis AF21 22/97 | 3 -- - ---- CAA A<br>CCGC TGCTGCTG GTT<br>GGTG ACGACGAC AT T<br>TCAC | 3 |
| GAM35 3678 | Human | CAGCAGCACACTGTGGTTTGTA | CAACCGGTGCTGCTG | dad X | NC_004431 from 1476306 to 1477376 (+) | Escherichia coli CFT073 | 3 -- - G---- - A<br>CAA CCG TGCTGC G<br>GTT GGT ACGACG C<br>AT T GTCAC A | 3 |
| GAM35 3678 | Human | CAGCAGCACACTGTGGTTTGTA | CAACCGTCGGTGATGCTCTG | fha L | NC_002929 from 3085865 to 3098455 (+) | Bordetella pertussis | 3 -- - C GTGA - A<br>CAA CCGT G TGCT<br>CTG GTT GGTG C<br>ACGA GAC AT T T<br>AC-- C | 3 |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| GAM35 3678 | Human | CAGCAGCA CACTGTGG TTTGTA | CAACCTGC GCTG | speD | NC_003197 from 194201 to 194995 (-) | Salmonella typhimurium LT2 | 3 -- - ------ - A<br>CAA CC TGC GCTG<br>GTT GG ACG CGAC<br>AT T TGTCAC A | |
| GAM35 3678 | Human | CAGCAGCA CACTGTGG TTTGTA | CAACCTGC GCTG | speD | NC_003198 from 196389 to 197183 (-) | Salmonella enterica enterica serovar Typhi | 3 -- - ------ - A<br>CAA CC TGC GCTG<br>GTT GG ACG CGAC<br>AT T TGTCAC A | |
| GAM35 3678 | Human | CAGCAGCA CACTGTGG TTTGTA | CAACCTGC GCTG | speD | NC_004631 from 196380 to 197174 (-) | Salmonella enterica enterica serovar Typhi Ty2 | 3 -- - ------ - A<br>CAA CC TGC GCTG<br>GTT GG ACG CGAC<br>AT T TGTCAC A | |
| GAM35 3678 | Human | CAGCAGCA CACTGTGG TTTGTA | CAACGCCA AGCTGCTG | flhB | NC_002929 from 1441767 to 1442921 (+) | Bordetella pertussis | 3 -- CG -----A CAA A<br>CCA GCTGCTG GTT<br>GGT CGACGAC AT<br>T- GTCACA | |
| GAM35 3678 | Human | CAGCAGCA CACTGTGG TTTGTA | CAAGCCAA TCTGCTG | sseB | NC_004431 from 2922456 to 2923241 (-) | Escherichia coli CFT073 | 3 -- A---- - A<br>CAAGCCA T CTGCTG<br>GTTTGGT A GACGAC<br>AT GTCAC C | |
| GAM35 3678 | Human | CAGCAGCA CACTGTGG TTTGTA | CAAGCCCG CTTGCTGT G | aer-2 | NC_002947 from 2406996 to 2408561 (-) | Pseudomonas putida KT2440 | 3 -- CGCT-- - A<br>CAAGCC TGCTG TG<br>GTTTGG ACGAC AC<br>AT TGTCAC G | |
| GAM35 3678 | Human | CAGCAGCA CACTGTGG TTTGTA | CAAGCCTG CGCTG | lppI | NC_000962 from 2291267 to 2291923 (+) | Mycobacterium tuberculosis H37Rv | 3 -- ------ - A<br>CAAGCC TGC GCTG<br>GTTTGG ACG CGAC<br>AT TGTCAC A | |
| GAM35 3678 | Human | CAGCAGCA CACTGTGG TTTCTA | CAAGCCTG CGCTG | lppI | NC_002945 from 2275182 to 2275838 (+) | Mycobacterium bovis subs p bovis AF21 22/97 | 3 -- ------ - A<br>CAAGCC TGC GCTG<br>GTTTGG ACG CGAC<br>AT TGTCAC A | |
| GAM35 3678 | Human | CAGCAGCA CACTGTGG TTTGTA | CAAGCTGC TGCTG | risA | NC_002929 from 3765257 to 3765991 (-) | Bordetella pertussis | 3 CAAGC A<br>TGCTGCTG GTTTG<br>ACGACGAC AT<br>GTGTCAC | |
| GAM35 3678 | Human | CAGCAGCA CACTGTGG TTTGTA | CAAGGACC ATGCGCTG | accC | NC_002929 from 926407 to 927777 (+) | Bordetella pertussis | 3 -- GG ----- - A<br>CAA ACCA TGC<br>GCTG GTT TGGT<br>ACG CGAC AT --<br>GTCAC A | |
| GAM35 3678 | Human | CAGCAGCA CACTGTGG TTTGTA | CAAGGCAA AGGTCTGC TG | rpsT | NC_002947 from 707068 to 707346 (-) | Pseudomonas putida KT2440 | 3 -- G A G- - CAAGA<br>CA AG T CTGCTG GTTT<br>GT TC A GACGAC AT G<br>G AC C | |
| GAM35 3678 | Human | CAGCAGCA CACTGTGG TTTGTA | CAATAACA ATGCAGCT G | fmtB (mrp) | NC_002745 from 2218145 to 2225590 (-) | Staphylococcus aureussu bsp. aureus N315 | 3 -- T A A---- A A<br>CAA A CA TGC GCTG<br>GTT T GT ACG CGAC<br>AT - G GTCAC A | |
| GAM35 3678 | Human | CAGCAGCA CACTGTGG TTTGTA | CAATAACA ATGCAGCT G | fmtB (mrp) | NC_002758 from 2287935 to 2295380 (-) | Staphylococcus aureussu bsp. aureus Mu50 | 3 -- T A A---- A A<br>CAA A CA TGC GCTG<br>GTT T GT ACG CGAC<br>AT - G GTCAC A | |
| GAM35 3678 | Human | CAGCAGCA CACTGTGG TTTGTA | CAATAACA ATGCAGCT G | truncated fmtB | NC_003923 from 2238083 to 2240143 (-) | Staphylococcus aureussu bsp. aureus MW2 | 3 -- T A A---- A A<br>CAA A CA TGC GCTG<br>GTT T GT ACG CGAC<br>AT - G GTCAC A | |
| GAM35 3678 | Human | CAGCAGCA CACTGTGG TTTGTA | CAATAGCG CCTGCTGC TG | nupC | NC_004337 from 2515842 to 2517083 (+) | Shigella flexneri 2a str. 301 | 3 -- T-- GC CC CAA A<br>A G TGCTGCTG GTT<br>T C ACGACGAC AT<br>TGG GT AC | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| GAM35 3678 | Human | CAGCAGCA CACTGTGG TTTGTA | CAATAGCG CCTGCTGC TG | nupC | NC_004431 from 2795390 to 2796631 (+) | Escherichia coli CFT073 | ``` 3 --    T-- GC CC    CAA   A      A  G   TGCTGCTG   GTT      T  C   ACGACGAC   AT    TGG      GT      AC ``` | |
| GAM35 3678 | Human | CAGCAGCA CACTGTGG TTTGTA | CAATAGCG CCTGCTGC TG | nupC | NC_004741 from 2494019 to 2495221 (+) | Shigella flexneri 2a str. 2457T | ``` 3 --    T-- GC CC    CAA   A      A  G   TGCTGCTG   GTT      T  C   ACGACGAC   AT    TGG      GT      AC ``` | |
| GAM35 3678 | Human | CAGCAGCA CACTGTGG TTTCTA | CAATATAG AAGCTGCT GCTA | def | NC_000922 from 1221735 to 1222295 (+) | Chlamydophila pneumoniae CWL029 | ``` 3 --    TA  G AGC     A  A    CAA   TA A    TGCTGCT    GTT   GT T    ACGACGA     AT    TG  G   CAC          C ``` | |
| GAM35 3678 | Human | CAGCAGCA CACTGTGG TTTCTA | CAATATAG AAGCTGCT CCTA | def | NC_002491 from 1218069 to 1218629 (+) | Chlamydophila pneumoniae J138 | ``` 3 --    TA  G AGC     A  A    CAA   TA A    TGCTGCT    GTT   GT T    ACGACGA     AT    TG  G   CAC          C ``` | |
| GAM35 3678 | Human | CAGCAGCA CACTGTGG TTTGTA | CAATCACC GGGCCGAT GCGGCTG | glcC | NC_004431 from 3542871 to 3543695 (+) | Escherichia coli CFT073 | ``` 3 --    T - C G CCGA   G A    CAA C AC G G      TGC   GCTG   GTT G TG C  C     ACG   CGAC AT    T G  T    A ----         A ``` | |
| GAM35 3678 | Human | CAGCAGCA CACTGTGG TTTGTA | CAATCAGG GATACTGC TG | pta | NC_002947 from 891625 to 893712 (-) | Pseudomonas putida KT2440 | ``` 3 --    T - G A- A   CAA A    C A GG  T  CTGCTG   GTT    G T TC  A  GACGAC AT   T    G G   AC          C ``` | |
| GAM35 3678 | Human | CAGCAGCA CACTGTGG TTTGTA | CAATCCCC GCTTCCTG CTG | tcfA | NC_002929 from 1264436 to 1266379 (+) | Bordetella pertussis | ``` 3 --    T  C  C - C    CAA A    CC CG T  T  CTGCTG   GTT    GG GT A  A  GACGAC AT    T     T  C  C  C ``` | |
| GAM35 3678 | Human | CAGCAGCA CACTGTGG TTTGTA | CAATCCCG GCCATTTG CTCTG | ruvB | NC_003142 from 2336449 to 2337453 (+) | Yersinia pestis | ``` 3 --    T CG CCATT    - A    CAA CC  G        TGCT   CTG    GTT GG  T       ACGA    GAC AT    T   TG    CAC--             C ``` | |
| GAM35 3678 | Human | CAGCAGCA CACTGTGG TTTGTA | CAATCCCG GCCATTTG CTCTG | ruvB | NC_004088 from 2482031 to 2483035 (-) | Yersinia pestis KIM | ``` 3 --    T CG CCATT    - A    CAA CC  G        TGCT   CTG    GTT GG  T       ACGA    GAC AT    T   TG    CAC--             C ``` | |
| GAM35 3678 | Human | CAGCAGCA CACTGTGG TTTGTA | CAATCGCA GCACTGGT GCTG | nupC | NC_004337 from 2515842 to 2517083 (+) | Shigella flexneri 2a str. 301 | ``` 3 --    T G GCAC-  G    A    CAA  C CA    TG TGCTG    GTT  G GT    AC ACGAC     AT    T -     GTCAC  G ``` | |
| GAM35 3678 | Human | CAGCAGCA CACTGTGG TTTGTA | CAATCGCA CTTTCTGC GCTG | rpsT | NC_002947 from 707068 to 707346 (-) | Pseudomonas putida KT2440 | ``` 3 --    T T TT C   -      A    CAA C CAC  T TGC GCTG    GTT G GTG  A ACG CGAC     AT    T - TC C       A ``` | |
| GAM35 3678 | Human | CAGCAGCA CACTGTGG TTTGTA | CACACAGG TCATCCTT GCGCTG | prcA | NC_002677 from 1576553 to 1577350 (+) | Mycobacterium leprae | ``` 3 --    C  - G TCATCCT    - A    CA AC A G         TGC   GCTG   GT TG T  T     ACG   CGAC AT    T  G    G CAC----         A ``` | |
| GAM35 3678 | Human | CAGCAGCA CACTGTGG TTTGTA | CACATGTT GTACATGC TGCTT | nupC | NC_004337 from 2515842 to 2517083 (+) | Shingella flexneri 2a str. 301 | ``` 3 --    -- -   T TACA      A      T  CA  C ATG TG    TGCTGCT    GT  G TGT    AC    ACGACGA  AT TT  G     C ----             C ``` | |
| GAM35 3678 | Human | CAGCAGCA CACTGTGG TTTGTA | CACCAATG CTCCTG | lppI | NC_000962 from 2291267 to 2291923 (+) | Mycobacterium tuberculosis H37Rv | ``` 3 --    -- A---- C    A    CA  CCA    TGCT CTG    GT  GGT    ACGA GAC    AT TT    GTCAC    C ``` | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| GAM35 3678 | Human | CAGCAGCA CACTGTGG TTTGTA | CACCAATG CTCCTG | lpp I | NC_002945 from 2275182 to 2275838 (+) | Mycobacterium bovis subsp bovis AF21 22/97 | 3 -- -- A---- C A<br>CA CCA TGCT CTG<br>GT GGT ACGA GAC<br>AT TT GTCAC C | |
| GAM35 3678 | Human | CAGCAGCA CACTGTGG TTTGTA | CACCACCG CTAACTGC TGCG | omp G | NC_004431 from 1624577 to 1625533 (+) | Escherichia coli CFT073 | 3 -- -- C CTAAC A<br>- CA CCAC G<br>TGCTGC G GT GGTG<br>C ACGACG C AT TT<br>T AC--- A | |
| GAM35 3678 | Human | CAGCAGCA CACTGTGG TTTGTA | CACCACCT CCTGCTG | phn V | NC_003198 from 471575 to 472366 (-) | Salmonella enterica enterica serovar Typhi | 3 -- -- C--- C CA A<br>CCAC T CTGCTG GT<br>GGTG A GACGAC AT<br>TT TCAC C | |
| GAM35 3678 | Human | CAGCAGCA CACTGTGG TTTGTA | CACCACCT CCTGCTG | phn V | NC_004631 from 2508735 to 2509526 (-) | Salmonella enterica serovar Typhi Ty2 | 3 -- -- C--- C CA A<br>CCAC T CTGCTG GT<br>GGTG A GACGAC AT<br>TT TCAC C | |
| GAM35 3678 | Human | CAGCAGCA CACTGTGG TTTGTA | CACCACGT AGTGCTTC TG | pil T | NC_002947 from 5816934 to 5817944 (-) | Pseudomonas putida KT2440 | 3 -- -- TA T A<br>CA CCACG GTGCT CTG<br>GT GGTGT CACGA GAC<br>AT TT CA C | |
| GAM35 3678 | Human | CAGCAGCA CACTGTGG TTTGTA | CACCAGCG CCTGCGCT G | oxy R | NC_003197 from 4343080 to 4343997 (+) | Salmonella typhimurium LT2 | 3 -- -- GC CC - CAA<br>CCA G TGC GCTG GT<br>GGT C ACG CGAC AT<br>TT GT AC A | |
| GAM35 3678 | Human | CAGCAGCA CACTGTGG TTTGTA | CACCAGCG CCTGCGCT G | oxy R | NC_003198 from 3607204 to 3608121 (-) | Salmonella enterica enterica serovar Typhi | 3 -- -- GC CC - CAA<br>CCA G TGC GCTG GT<br>GGT C ACG CGAC AT<br>TT GT AC A | |
| GAM35 3678 | Human | CAGCAGCA CACTGTGG TTTGTA | CACCAGCG CCTGCGCT G | oxy R | NC_004631 from 3592864 to 3593781 (-) | Salmonella enterica serovar Typhi Ty2 | 3 -- -- GC CC - CAA<br>CCA G TGC GCTG GT<br>GGT C ACG CGAC AT<br>TT GT AC A | |
| GAM35 3678 | Human | CAGCAGCA CACTGTGG TTTGTA | CACCATGC TGCTG | MGA T5 | NM_002410 | Human | 3 -- -- ----- CA A<br>CCA TGCTGCTG GT<br>GGT ACGACGAC AT<br>TT GTCAC | |
| GAM35 3678 | Human | CAGCAGCA CACTGTGG TTTGTA | CACCATTG CTGCCG | ipa H_5 | NC_004741 from 2023205 to 2024848 (+) | Shingella flexneri 2a str. 2457T | 3 -- -- ---- C A<br>CA CCAT TGCTGC G<br>GT GGTG ACGACG C<br>AT TT TCAC A | |
| GAM35 3678 | Human | CAGCAGCA CACTGTGG TTTGTA | CACCATTG CTGCCG | ipa H9.8 | NC_004337 from 1422064 to 1423779 (-) | Shingella flexneri 2a str. 301 | 3 -- -- ---- C A<br>CA CCAT TGCTGC G<br>GT GGTG ACGACG C<br>AT TT TCAC A | |
| GAM35 3678 | Human | CAGCAGCA CACTGTGG TTTGTA | CACCATTG CTGCCG | sit D | NC_004337 from 1405360 to 1406217 (-) | Shingella flexneri 2a str. 301 | 3 -- -- ---- C A<br>CA CCAT TGCTGC G<br>GT GGTG ACGACG C<br>AT TT TCAC A | |
| GAM35 3678 | Human | CAGCAGCA CACTGTGG TTTGTA | CACCATTG CTGCCG | sit D | NC_004741 from 1904666 to 1905523 (+) | Shingella flexneri 2a str. 2457T | 3 -- -- ---- C A<br>CA CCAT TGCTGC G<br>GT GGTG ACGACG C<br>AT TT TCAC A | |
| GAM35 3678 | Human | CAGCAGCA CACTGTGG TTTGTA | CACCATTT CTGCCGCT G | dna E | NC_002677 from 1423014 to 1426547 (+) | Mycobacterium leprae | 3 -- -- TTC- C CA A<br>CCAT TGC GCTG GT<br>GGTG ACG CGAC AT<br>TT TCAC A | |
| GAM35 3678 | Human | CAGCAGCA CACTGTGG TTTGTA | CACCATTT CTGCCGCT G | pcn A | NC_002677 from 3248268 to 3249728 (-) | Mycobacterium leprae | 3 -- -- TTC- C CA A<br>CCAT TGC GCTG GT<br>GGTG ACG CGAC AT<br>TT TCAC A | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| GAM35 3678 | Human | CAGCAGCA CACTGTGG TTTGTA | CACCATTT CTGCCGCT G | pol A | NC_002677 from 1648220 1650955 (-) | Mycobacterium leprae | 3 -- -- TTC- C CA A<br>  CCAT  TGC GCTG  GT<br>  GGTG  ACG CGAC AT<br>  TT   TCAC  A | |
| GAM35 3678 | Human | CAGCAGCA CACTGTGG TTTGTA | CACCATTT CTGCCGCT G | tru A | NC_002677 from 2343329 2344078 (-) | Mycobacterium leprae | 3 -- -- TTC- C CA A<br>  CCAT  TGC GCTG  GT<br>  GGTG  ACG CGAC AT<br>  TT   TCAC  A | |
| GAM35 3678 | Human | CAGCAGCA CACTGTGG TTTGTA | CACCCAGC GTTTGCTG CTT | dad X | NC_004431 from 1476306 1477376 (+) | Escherichia coli CFT073 | 3 -- C- GC T  T A<br>  CA CCA GT TGCTGCT<br>  GT GGT CA ACGACGA<br>  AT TT  GT C   C | |
| GAM35 3678 | Human | CAGCAGCA CACTGTGG TTTGTA | CACCCAGG TGTCGCTG CTG | nic T | NC_000962 from 3166681 3167799 (+) | Mycobacterium tuberculosis H37Rv | 3 -- C- G TGTC CA A<br>  CCA G  GCTGCTG  GT<br>  GGT T  CGACGAC AT<br>  TT  G CACA | |
| GAM35 3678 | Human | CAGCAGCA CACTGTGG TTTGTA | CACCCAGG TGTCGCTG CTG | nic T | NC_002945 from 3123200 3124318 (+) | Mycobacterium bovis subs p bovis AF21 22/97 | 3 -- C- G TGTC CA A<br>  CCA G  GCTGCTG  GT<br>  GGT T  CGACGAC AT<br>  TT  G CACA | |
| GAM35 3678 | Human | CAGCAGCA CACTGTGG TTTGTA | CACCTTTC TGCTGCTC | ris A | NC_002929 from 3765257 3765991 (-) | Bordetella pertussis | 3 -- -- T TC-- C A<br>  CA  CC T  TGCTGCT<br>  GT  GG G  ACGACGA<br>  AT  TT  T TCAC   C | |
| GAM35 3678 | Human | CAGCAGCA CACTGTGG TTTGTA | CACGCCAT ATGTGTTT GTGCTG | ipa H_5 | NC_004741 from 2023205 2024848 (+) | Shingella flexneri 2a str. 2457T | 3 -- C  TGTGTT - A<br>  CA GCCATA   TG<br>  TGCTG  GT TGGTGT<br>  AC ACGAC AT  T<br>  CAC--- G | |
| GAM35 3678 | Human | CAGCAGCA CACTGTGG TTTGTA | CACGCCAT ATGTGTTT GTGCTG | ipa H9.8 | NC_004337 from 1422064 1423779 (-) | Shingella flexneri 2a str. 301 | 3 -- C  TGTGTT - A<br>  CA GCCATA   TG<br>  TGCTG  GT TGGTGT<br>  AC ACGAC AT  T<br>  CAC--- G | |
| GAM35 3678 | Human | CAGCAGCA CACTGTGG TTTGTA | CACGCCAT ATGTGTTT GTGCTG | sit D | NC_004337 from 1405360 1406217 (-) | Shingella flexneri 2a str. 301 | 3 -- C  TGTGTT - A<br>  CA GCCATA   TG<br>  TGCTG  GT TGGTGT<br>  AC ACGAC AT  T<br>  CAC--- G | |
| GAM35 3678 | Human | CAGCAGCA CACTGTGG TTTGTA | CACGCCAT ATGTGTTT GTGCTG | sit D | NC_004741 from 1904666 1905523 (+) | Shingella flexneri 2a str. 2457T | 3 -- C  TGTGTT - A<br>  CA GCCATA   TG<br>  TGCTG  GT TGGTGT<br>  AC ACGAC AT  T<br>  CAC--- G | |
| GAM35 3678 | Human | CAGCAGCA CACTGTGG TTTGTA | CACGCCAT ATGTGTTT CTGCTG | rbs R | NC_004337 from 3947708 3948700 (+) | Shingella flexneri 2a str. 301 | 3 --  A  T TACC  A<br>  CAGA CAC GT<br>    GCTGCTG  GTTT GTG<br>  CA  CGACGAC AT   G<br>  T  C--A | |
| GAM35 3678 | Human | CAGCAGCA CACTGTGG TTTGTA | CACGCCAT ATGTGTTT CTGCTG | rbs R | NC_004431 from 4439260 4440252 (+) | Escherichia coli CFT073 | 3 --  A  T TACC  A<br>  CAGA CAC GT<br>    GCTGCTG  GTTT GTG<br>  CA  CGACGAC AT   G<br>  T  C--A | |
| GAM35 3678 | Human | CAGCAGCA CACTGTGG TTTGTA | CACGCCAT ATGTGTTT CTGCTG | rbs R | NC_004741 from 3824594 3825577 (-) | Shingella flexneri 2a str. 2457T | 3 --  A  T TACC  A<br>  CAGA CAC GT<br>    GCTGCTG  GTTT GTG<br>  CA  CGACGAC AT   G<br>  T  C--A | |
| GAM35 3678 | Human | CAGCAGCA CACTGTGG TTTGTA | CAGAAGCA TGAACATT GCTGCTG | rbs R | NC_004337 from 3947708 3948700 (+) | Shingella flexneri 2a str. 301 | 3 --  G G  AACAT  CA A<br>  AA CATG   TGCTGCTG<br>  GT TT  GTGT<br>  ACGACGAC AT - G<br>  CAC-- | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET; LOWER:GAM) | GAM POS |
|---|---|---|---|---|---|---|---|---|
| GAM35 3678 | Human | CAGCAGCA CACTGTGG TTTGTA | CAGAAGCA TGAACATT GCTGCTG | rbs R | NC_004741 from 3824594 to 3825577 (-) | Shingella flexneri 2a str. 2457T | 3 -- G G AACAT CA A<br>AA CATG TGCTGCTG<br>GT TT GTGT<br>ACGACGAC AT - G<br>CAC-- | |
| GAM35 3678 | Human | CAGCAGCA CACTGTGG TTTGTA | CAGACGAT CTCCTGCT G | fep C | NC_002516 from 4653508 to 4654305 (-) | Pseudomonas aeruginosa PA01 | 3 -- G C--- C A<br>CAGAC AT T CTGCTG<br>GTTTG TG A GACGAC<br>AT G TCAC C | |
| GAM35 3678 | Human | CAGCAGCA CACTGTGG TTTGTA | CAGACTCA GCTGCTGC TC | pil T | NC_002947 from 5816934 to 5817944 (-) | Pseudomonas putida KT2440 | 3 -- T GC--- CA<br>CAGAC CA TGCTGCT<br>GTTTG GT ACGACGA<br>AT - GTCAC C | |
| GAM35 3678 | Human | CAGCAGCA CACTGTGG TTTGTA | CAGCAGGC TTTGCTGC TG | cII | NC_003198 from 4537312 to 4537533 (+) | Salmonella enterica enterica serovar Typhi | 3 -- - G C T CAG C A<br>A G T TGCTGCTG GTT G<br>T T A ACGACGAC AT T G<br>G C C | |
| GAM35 3678 | Human | CAGCAGCA CACTGTGG TTTGTA | CAGCAGGC TTTGCTGC TG | cII | NC_004631 from 4520121 to 4520342 (+) | Salmonella enterica enterica serovar Typhi Ty2 | 3 -- - G C T CAG C A<br>A G T TGCTGCTG GTT G<br>T T A ACGACGAC AT T G<br>G C C | |
| GAM35 3678 | Human | CAGCAGCA CACTGTGG TTTGTA | CAGCCACA GCTGCTG | gad | NC_002947 from 4871625 to 4872929 (+) | Pseudomonas putida KT2440 | 3 -- - ----A CAG A<br>GGTG CGACGAC AT T<br>TCACA | |
| GAM35 3678 | Human | CAGCAGCA CACTGTGG TTTGTA | CAGCCAGG TTTTGCTC TG | phn V | NC_003198 from 471575 to 472366 (-) | Salmonella enterica serovar Typhi | 3 -- - G T T - A<br>CAG CCA G T TGCT CTG<br>GTT GGT T A ACGA GAC<br>AT T G CC C | |
| GAM35 3678 | Human | CAGCAGCA CACTGTGG TTTGTA | CAGCCAGG TTTTGCTC TG | phn V | NC_004631 from 2508735 to 2509526 (+) | Salmonella enterica serovar Typhi Ty2 | 3 -- - G T T - A<br>CAG CCA G T TGCT CTG<br>GTT GGT T A ACGA GAC<br>AT T G CC C | |
| GAM35 3678 | Human | CAGCAGCA CACTGTGG TTTGTA | CAGCGAGG CCTCGTGC TGCTG | tcf A | NC_002929 from 1264436 to 1266379 (+) | Bordetella pertussis | 3 -- - G G CCTCG CAG A<br>C A G TGCTGCTG<br>GTT G T T<br>ACGACGAC AT T G G<br>CAC-- | |
| GAM35 3678 | Human | CAGCAGCA CACTGTGG TTTGTA | CAGCGCTT GGTGATGC TGCTG | uhp A | NC_003143 from 4522790 to 4523380 (-) | Yersinia pestis | 3 -- CG T A CAG A<br>C TGGTG TGCTGCTG GTT<br>G GTCAC ACGACGAC AT<br>TG T - | |
| GAM35 3678 | Human | CAGCAGCA CACTGTGG TTTGTA | CAGCGCTT GGTGATGC TGCTG | cys Q | NC_002947 from 315184 to 315984 (+) | Pseudomonas putida KT2440 | 3 -- G G CAGGC CA A<br>GGTGTGCTGCTG GTTTG GT<br>TCACACGACGAC AT -<br>G | |
| GAM35 3678 | Human | CAGCAGCA CACTGTGG TTTGTA | CATACCTC CCGCACTG CTGCCG | pbp G | NC_002947 from 4323707 to 4324633 (+) | Pseudomonas putida KT2440 | 3 -- T T CCGCAC CA<br>CA ACC C TGCTGC<br>G GT TGG G<br>ACGACG C AT T T<br>TCAC-- A | |
| GAM35 3678 | Human | CAGCAGCA CACTGTGG TTTGTA | CATATCTG CTGCTG | ung | NC_000907 from 18676 to 19335 (+) | Haemophilus influenzae R d | 3 -- T ------ CA ATCA<br>TGCTGCTG GT TGG<br>ACGACGAC AT T<br>TGTCAC | |
| GAM35 3678 | Human | CAGCAGCA CACTGTGG TTTGTA | CATCCACA CGCTGCTG | ssb | NC_002947 from 571027 to 571572 (+) | Pseudomonas putida KT2440 | 3 -- T- ---C CA A<br>CCACA GCTGCTG GT<br>GGTGT CGACGAC AT<br>TT CACA | |
| GAM35 3678 | Human | CAGCAGCA CACTGTGG TTTGTA | CATCCATA TCGCCATT | rbs R | NC_004431 from 4439260 to | Escherichia coli CFT073 | 3 -- T- TC CCAT A<br>G CA CCATA G | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| | | | TTTGTA | GCTGGTG | 4440252 (+) | | TGCTG TG GT GGTGT<br>ACGAC AC AT TT<br>CA ---- G | |
| GAM35 3678 | Human | CAGCAGCA CACTGTGG TTTGTA | CATCGCGG GCGCGCTG CTGCTC | glp C | NC_003143 from 4289650 to 4290897 (-) | Yersinia pestis | 3 -- TCG G CGCGC A<br>C CA CG G<br>TGCTGCT GT GT T<br>ACGACGA AT TTG G<br>CAC-- C | |
| GAM35 3678 | Human | CAGCAGCA CACTGTGG TTTGTA | CATCGCGG GCGCGCTG CTGCTC | glp C | NC_004088 from 454677 to 456047 (+) | Yersinia pestis KIM | 3 -- TCG G CGCGC A<br>C CA CG G<br>TGCTGCT GT GT T<br>ACGACGA AT TTG G<br>CAC-- C | |
| GAM35 3678 | Human | CAGCAGCA CACTGTGG TTTGTA | CATCGCGG TGGTGGAT GCTGCTT | dna E | NC_002677 from 1423014 to 1426547 (-) | Yersinia pestis | 3 -- T GT GTGGA A<br>T CA GTCG G<br>TGCTGCT GT TGGT<br>C ACGACGA AT T<br>GT AC--- C | |
| GAM35 3678 | Human | CAGCAGCA CACTGTGG TTTGTA | CATCGCGG TGGTGGAT GCTGCTT | pcn A | NC_002677 from 3248268 to 3249728 (-) | Mycobacterium leprae | 3 -- T GT GTGGA A<br>T CA GTCG G<br>TGCTGCT GT TGGT<br>C ACGACGA AT T<br>GT AC--- C | |
| GAM35 3678 | Human | CAGCAGCA CACTGTGG TTTGTA | CATCGCGG TGGTGGAT GCTGCTT | pol A | NC_002677 from 1648220 to 1650955 (-) | Mycobacterium leprae | 3 -- T GT GTGGA A<br>T CA GTCG G<br>TGCTGCT GT TGGT<br>C ACGACGA AT T<br>GT AC--- C | |
| GAM35 3678 | Human | CAGCAGCA CACTGTGG TTTGTA | CATCGCGG TGGTGGAT GCTGCTT | tru A | NC_002677 from 2343329 to 2344078 (-) | Mycobacterium leprae | 3 -- T GT GTGGA A<br>T CA GTCG G<br>TGCTGCT GT TGGT<br>C ACGACGA AT T<br>GT AC--- C | |
| GAM35 3678 | Human | CAGCAGCA CACTGTGG TTTGTA | CCCGTGCT GCTT | omp G | NC_004431 from 1624577 to 1625533 (+) | Escherichia coli CFT073 | 3 --- ----- T A<br>C CCG TGCTGCT<br>G GGT ACGACGA<br>AT TTT GTCAC C | |
| GAM35 3678 | Human | CAGCAGCA CACTGTGG TTTGTA | CCCTCGGT GCTGCTG | flh B | NC_002929 from 1441767 to 1442921 (+) | Bordetella pertussis | 3 --- T -- C CCA<br>CGG TGCTGCTG G GG<br>GTC ACGACGAC AT TTT T<br>AC | |
| GAM35 3678 | Human | CAGCAGCA CACTGTGG TTTGTA | CGAACCAC CGATGCTG TG | aer-2 | NC_002947 from 2406996 to 2408561 (-) | Pseudomonas putida KT2440 | 3 -- C A- - A<br>CGAACCAC G TGCTG TG<br>GTTTGGTG C ACGAC AC<br>AT T AC G | |
| GAM35 3678 | Human | CAGCAGCA CACTGTGG TTTGTA | CGAACGTG CTGCTG | prc A | NC_002677 from 1576553 to 1577350 (+) | Mycobacterium leprae | 3 -- G------ CGAAC A<br>TGCTGCTG GTTTG<br>ACGACGAC AT<br>GTGTCAC | |
| GAM35 3678 | Human | CAGCAGCA CACTGTGG TTTGTA | CGACCACC GCGTGGTG CTG | van B | NC_002516 from 5504120 to 5505073 (+) | Pseudomonas aeruginosa PA01 | 3 -- - C C G CGAA<br>CCAC G GTG TGCTG GTT<br>GGTG C CAC ACGAC AT T<br>T A G | |
| GAM35 3678 | Human | CAGCAGCA CACTGTGG TTTGTA | CGACTGCT GCTG | pch A | NC_002516 from 4745120 to 4746550 (+) | Pseudomonas aeruginosa PA01 | 3 -- - ------- CGA C A<br>TGCTGCTG GTT G<br>ACGACGAC AT T<br>GTGTCAC | |
| GAM35 3678 | Human | CAGCAGCA CACTGTGG TTTGTA | CGAGCGAT GCTGCTT | dsd A | NC_003197 from 4004453 to 4005775 (+) | Salmonella typhimurium LT2 | 3 -- G ----- T A<br>CGAGC A TGCTGCT<br>GTTTG T ACGACGA<br>AT G GTCAC C | |
| GAM35 3678 | Human | CAGCAGCA CACTGTGG TTTGTA | CGAGGGAT GTAGTGCT | nic T | NC_000962 from 3166681 to | Mycobacterium tuberculosis | 3 -- GG TA C A<br>CGAG ATG GTGCTGCT | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET; LOWER:GAM) | GAM POS |
|---|---|---|---|---|---|---|---|---|
| | | TTTGTA | GCTC | | 3167799 (+) | H37Rv | `     GTTT   TGT  CACGACGA`<br>`   AT       GG   CA         C` | |
| GAM35 3678 | Human | CAGCAGCA CACTGTGG TTTGTA | CGAGGGAT GTAGTGCT GCTC | nic T | NC_002945 from 3123200 to 3124318 (+) | Mycobacterium bovis subs p bovis AF21 22/97 | `3 --   GG  TA     C  A`<br>`  CGAG  ATG  GTGCTGCT`<br>`  GTTT  TGT  CACGACGA`<br>`  AT       GG   CA        C` | |
| GAM35 3678 | Human | CAGCAGCA CACTGTGG TTTGTA | CGCCAGAT TGCTGCTG | yab O | NC_004431 from 61489 to 62148 (-) | Escherichia coli CFT073 | `3 --   --    G T--    CG      A`<br>`  CCA A    TGCTGCTG   GT`<br>`  GGT  T   ACGACGAC   AT`<br>`  TT    G CAC` | |
| GAM35 3678 | Human | CAGCAGCA CACTGTGG TTTGTA | CGCCGGTT GCTGCTG | pch A | NC_002516 from 4745120 to 4746550 (+) | Pseudomonas aeruginosa PA01 | `3 --   --   GT---   CG     A`<br>`  CCG        TGCTGCTG   GT`<br>`  GGT        ACGACGAC   AT`<br>`  TT     GTCAC` | |
| GAM35 3678 | Human | CAGCAGCA CACTGTGG TTTGTA | CGCCGGTT GCTGCTT | fep C | NC_002516 from 4653508 to 4654305 (-) | Pseudomonas aeruginosa PA01 | `3 --   --   GT---         T A`<br>`  CG    CCG       TGCTGCT`<br>`  GT    GGT       ACGACGA`<br>`  AT    TT    GTCAC          C` | |
| GAM35 3678 | Human | CAGCAGCA CACTGTGG TTTGTA | CGCTGCTG CTG | liv H | NC_002929 from 1144729 to 1145607 (+) | Bordetella pertussis | `3 --   --   -------   CG   C A`<br>`              TGCTGCTG   GT  G`<br>`              ACGACGAC   AT  TT`<br>`  GTGTCAC` | |
| GAM35 3678 | Human | CAGCAGCA CACTGTGG TTTGTA | CGGAATTT GCTGCTG | yci E | NC_004431 from 1558641 to 1559147 (-) | Escherichia coli CFT073 | `3 --    --  T---   CGGA      A`<br>`  AT         TGCTGCTG   GTTT`<br>`  TG         ACGACGAC   AT`<br>`      GG   TCAC` | |
| GAM35 3678 | Human | CAGCAGCA CACTGTGG TTTGTA | CGTCCACG CGGGTGGT GCTGCTC | flh B | NC_002929 from 1441767 to 1442921 (+) | Bordetella pertussis | `3 --   T-         CG  GTGG     A`<br>`       C    CG   CCACG  G`<br>`           TGCTGCT   GT  GGTGT`<br>`  C      ACGACGA   AT   TT`<br>`      CA  ----            C` | |
| GAM35 3678 | Human | CAGCAGCA CACTGTGG TTTGTA | CGTCCATC TTGCTGCT C | pbp G | NC_002947 from 4323707 to 4324633 (+) | Pseudomonas putida KT2440 | `3 --   T-   CT--         C A`<br>`  CG    CCAT       TGCTGCT`<br>`  GT    GGTG       ACGACGA`<br>`  AT    TT    TCAC            C` | |
| GAM35 3678 | Human | CAGCAGCA CACTGTGG TTTGTA | CGTCCTGC TGCTG | aco R | NC_002516 from 4639501 to 4641378 (-) | Pseudomonas aeruginosa PA01 | `3 --   T-   ------    CG  CCA`<br>`              TGCTGCTG   GT  GG`<br>`              ACGACGAC   AT  TT`<br>`  TGTCAC` | |
| GAM35 3678 | Human | CAGCAGCA CACTGTGG TTTGTA | CGTGCCTG CTGCTC | ace K | NC_002947 from 5184742 to 5186457 (-) | Pseudomonas putida KT2440 | `3 --   T    ------         C A`<br>`  CG    GCC       TGCTGCT`<br>`  GT    TGG       ACGACGA`<br>`  AT    T    TGTCAC           C` | |
| GAM35 3678 | Human | CAGCAGCA CACTGTGG TTTGTA | CTAAAGTG CTGCTG | rec G | NC_002677 from 2014723 to 2016954 (-) | Mycobacterium leprae | `3 --   T  --  G----     C AA  A`<br>`  A           TGCTGCTG   G TT`<br>`  T           ACGACGAC   AT T`<br>`  GG  GTCAC` | |
| GAM35 3678 | Human | CAGCAGCA CACTGTGG TTTGTA | CTAACACG CGCTGCTC TG | ung | NC_000907 from 18676 to 19335 (+) | Haemophilus influenzae R d | `3 --   T   -   CGC     -     CA`<br>`  AAC  ACG       TGCT  CTG    G`<br>`  TTG  TGT       ACGA  GAC    AT  T`<br>`     G  CAC             C` | |
| GAM35 3678 | Human | CAGCAGCA CACTGTGG TTTGTA | CAGCAGCA CACTGTGG TTTGTA | cII G | NC_003198 from 4537312 to 4537533 (+) | Salmonella enterica enterica serovar Typhi | `3 --    T    TGTA-- -    C    A`<br>`  AACC       T       CTGCTG    G`<br>`  TTGG       A       GACGAC    AT T`<br>`  TGTCAC  C` | |
| GAM35 3678 | Human | CAGCAGCA CACTGTGG TTTGTA | CAGCAGCA TATCTGCT G | cII G | NC_004631 from 4520121 to 4520342 (+) | Salmonella enterica enterica serovar Typhi Ty2 | `3 --    T    TGTA-- -    C    A`<br>`  AACC       T       CTGCTG    G`<br>`  TTGG       A       GACGAC    AT T`<br>`  TGTCAC  C` | |
| GAM35 3678 | Human | CAGCAGCA CACTGTGG TTTGTA | CTACCTGC CTGCTGCT | uhp A | NC_003143 from 4522790 to | Yersinia pestis | `3 --    T  -  TGCC--        C A CCA`<br>`              TGCTGCTG        G T GG` | |

TABLE 7-continued

| GAM NAME | GAM ORGANISM | GAM RNA SEQUENCE | TARGET BS-SEQ | TARGET | TARG REF-ID | TARGET ORGANISM | BINDING SITE DRAW (UPPER:TARGET;LOWER:GAM) | GAM POS |
|---|---|---|---|---|---|---|---|---|
| | | | TTTGTA | G | 4523380 (−) | | ACGACGAC AT T T<br>TGTCAC | |
| GAM35 3678 | Human | CAGCAGCA CACTGTGG TTTGTA | CTAGCCCT GCTGCTC | aco R | NC_002516 from 4639501 to 4641378 (−) | Pseudomonas aeruginosa PA01 | 3 -- T  C----- C A<br>  C AGCC     TGCTGCT<br>  G TTGG     ACGACGA<br>  AT T   TGTCAC    C | |
| GAM35 3678 | Human | CAGCAGCA CACTGTGG TTTGTA | CTCCTGCT GCTG | ssb | NC_002947 from 571027 to 571572 (+) | Pseudomonas putida KT2440 | 3 -- T--  ------  C  CCA<br>       TGCTGCTG   G   GG<br>       ACGACGAC AT TTT<br>       TGTCAC | |
| GAM35 3678 | Human | CAGCAGCA CACTGTGG TTTGTA | CTCGGGTT TCTTGCTG CTG | fha L | NC_002929 from 3085865 to 3098455 (+) | Bordetella pertussis | 3 -- T-- G GTT CT  C   CA<br>  G   T   TGCTGCTG  G   G<br>  T   A   ACGACGAC AT TTT<br>  G GTC C- | |
| GAM35 3678 | Human | CAGCAGCA CACTGTGG TTTGTA | CTGACCTT GCTGCTC | pta | NC_002947 from 891625 to 893712 (−) | Pseudomonas putida KT2440 | 3 -- T   T-----  C A<br>  C GACC     TGCTGCT<br>  G TTGG     ACGACGA<br>  AT T   TGTCAC    C | |
| GAM35 3678 | Human | CAGCAGCA CACTGTGG TTTGTA | CTGCCTGC TGCTC | orn | NC_003143 from 378331 to 378876 (+) | Yersinia pestis | 3 -- T -  ------  C A<br>  C G CC     TGCTGCT<br>  G T  GG     ACGACGA<br>  AT T T  TGTCAC    C | |
| GAM35 3678 | Human | CAGCAGCA CACTGTGG TTTGTA | CTGCGTGC TGCTT | glp D | NC_004310 from 210763 to 212274 (+) | Brucella suis 1330 | 3 -- T - G------  T A<br>  C G C      TGCTGCT<br>  G T G      ACGACGA<br>  AT T T  GTGTCAC    C | |
| GAM35 3678 | Human | CAGCAGCA CACTGTGG TTTGTA | CTTACTTG CTGCTC | sse B | NC_004431 from 2922456 to 2923241 (−) | Escherichia coli CFT073 | 3 -- TT  ------  C A<br>  C ACT     TGCTGCT<br>  G TGG     ACGACGA<br>  AT TT  TGTCAC    C | |
| GAM35 3678 | Human | CAGCAGCA CACTGTGG TTTGTA | CTTCCTGC TGCTT | def | NC_000922 from 1221735 to 1222295 (+) | Chlamydophila pneumoniae CWL029 | 3 -- TT-  ------  T A<br>  C  CC     TGCTGCT<br>  G  GG     ACGACGA<br>  AT TTT  TGTCAC    C | |
| GAM35 3678 | Human | CAGCAGCA CACTGTGG TTTGTA | CTTCCTGC TGCTT | def | NC_002491 from 1218069 to 1218629 (+) | Chlamydophila pneumoniae J138 | 3 -- TT-  ------  T A<br>  C  CC     TGCTGCT<br>  G  GG     ACGACGA<br>  AT TTT  TGTCAC    C | |

It is appreciated that the specific functions and accordingly the utilities of each of a plurality of GAM oligonucleotides that are described by FIG. 1 are correlated with and may be deduced from the identity of the GAM TARGET GENES inhibited thereby, and whose functions are set forth in Table 8, hereby incorporated herein. Table 8, lines 685695-687709 shows data relating to the function and utilities of GAM RNA as set forth in SEQ ID NO: 348.

TABLE 8

| GAM NAME | GAM RNA SEQUENCE | GAM ORGANISM | TARGET | TARGET ORGANISM | GAM GAM FUNCTION | POS |
|---|---|---|---|---|---|---|
| GAM35 3678 | CAGCAGCA CACTGTGG TTTGTA | Human | ac cC | Bordetella pertussis | GAM353678 is a human miRNA-like oligonucleotide, which targets biotin carboxylase (accC, NC_002929 from 926407 to 927777 (+)), a bacterial target gene encoded by the Bordetella pertussis genome, as part of an anti-bacterial host defense mechanism. accC BINDING SITE 1 and accC BINDING SITE 2 are bacterial target binding sites that are found in the untranslated regions of mRNA encoded by the accC gene, corresponding to target binding sites such as BINDING SITE I, BINDING SITE II or BINDING SITE III of FIG. 1. The nucleotide sequences of accC BINDING SITE 1 and accC BINDING SITE 2, | A |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | and the complementary secondary structure to the nucleotide sequence of GAM353678 RNA are set forth in Tables 6-7, hereby incorporated herein. A function of GAM353678 is to inhibit accC, a GAM353678 bacterial target gene which is associated with *Bordetella pertussis* infection, as part of an anti-bacterial host defense mechanism. Accordingly, the utilities of GAM353678 include the diagnosis, prevention and treatment of *Bordetella pertussis* infection and associated clinical conditions | |
| GAM353678 | CAGCAGCACACTGTGGTTTGTA | Human | aceK | *Pseudomonas putida* KT2440 | GAM353678 is a human miRNA-like oligonucleotide, which targets isocitrate dehydrogenase kinase/phosphatase (aceK, NC_002947 from 5184742 to 5186457 (−)), a bacterial target gene encoded by the *Pseudomonas putida* KT2440 genome, as part of an anti-bacterial host defense mechanism. aceK BINDING SITE 1 and aceK BINDING SITE 2 are bacterial target binding sites that are found in the untranslated regions of mRNA encoded by the aceK gene, corresponding to target binding sites such as BINDING SITE I, BINDING SITE II or BINDING SITE III of FIG. 1. The nucleotide sequences of aceK BINDING SITE 1 and aceK BINDING SITE 2, and the complementary secondary structure to the nucleotide sequence of GAM353678 RNA are set forth in Tables 6-7, hereby incorporated herein. Another function of GAM353678 is to inhibit aceK, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | A |
| GAM353678 | CAGCAGCACACTGTGGTTTGTA | Human | acoR | *Pseudomonas aeruginosa* PA01 | GAM353678 is a human miRNA-like oligonucleotide, which targets transcriptional regulator AcoR (acoR, NC_002516 from 4639501 to 4641378 (−)), a bacterial target gene encoded by the *Pseudomonas aeruginosa* PA01 genome, as part of an anti-bacterial host defense mechanism. acoR BINDING SITE 1 and acoR BINDING SITE 2 are bacterial target binding sites that are found in the untranslated regions of mRNA encoded by the acoR gene, corresponding to target binding sites such as BINDING SITE I, BINDING SITE II or BINDING SITE III of FIG. 1. The nucleotide sequences of acoR BINDING SITE 1 and acoR BINDING SITE 2, and the complementary secondary structure to the nucleotide sequence of GAM353678 RNA are set forth in Tables 6-7, hereby incorporated herein. Another function of GAM353678 is to inhibit acoR, a GAM353678 bacterial target gene which is associated with *Pseudomonas aeruginosa* PA01 infection, as part of an anti-bacterial host defense mechanism. Accordingly, the utilities of GAM353678 include the diagnosis, prevention and treatment of *Pseudomonas aeruginosa* PA01 infection and associated clinical conditions | A |
| GAM353678 | CAGCAGCACACTGTGGTTTGTA | Human | aer-2 | *Pseudomonas putida* KT2440 | GAM353678 is a human miRNA-like oligonucleotide, which targets aerotaxis receptor Aer-2 (aer-2, NC_002947 from 2406996 to 2408561 (−)), a bacterial target gene encoded by the *Pseudomonas* | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | *putida* KT2440 genome, as part of an anti-bacterial host defense mechanism. aer-2 BINDING SITE 1 and aer-2 BINDING SITE 2 are bacterial target binding sites that are found in the untranslated regions of mRNA encoded by the aer-2 gene, corresponding to target binding sites such as BINDING SITE I, BINDING SITE II or BINDING SITE III of FIG. 1. The nucleotide sequences of aer-2 BINDING SITE 1 and aer-2 BINDING SITE 2, and the complementary secondary structure to the nucleotide sequence of GAM353678 RNA are set forth in Tables 6-7, hereby incorporated herein. Another function of GAM353678 is to inhibit aer-2, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | |
| GAM35 3678 | CAGCAGCA CACTGTGG TTTGTA | Human | amtB | *Shigella flexneri* 2a str. 3 01 | GAM353678 is a human miRNA-like oligonucleotide, which targets probable ammonium transporter (amtB, NC_004337 from 408059 to 409345 (+)), a bacterial target gene encoded by the *Shigella flexneri* 2a str. 301 genome, as part of an anti-bacteria 1 host defense mechanism. amtB BINDING SITE 1 and amtB BINDING SITE 2 are bacterial target binding sites that are found in the untranslated regions of mRNA encoded by the amtB gene, corresponding to target binding sites such as BINDING SITE I, BINDING SITE II or BINDING SITE III of FIG. 1. The nucleotide sequences of amtB BINDING SITE 1 and amtB BINDING SITE 2, and the complementary secondary structure to the nucleotide sequence of GAM353678 RNA are set forth in Tables 6-7, hereby incorporated herein. Another function of GAM353678 is to inhibit amtB, a GAM353678 bacterial target gene which is associated with *Shigella flexneri* 2a str. 301 infection, as part of an anti-bacterial host defense mechanism. Accordingly, the utilities of GAM353678 include the diagnosis, prevention and treatment of *Shigella flexneri* 2a str. 301 infection and associated clinical conditions | A |
| GAM35 3678 | CAGCAGCA CACTGTGG TTTGTA | Human | amtB | *Escherichia coli* C FT073 | GAM353678 is a human miRNA-like oligonucleotide, which targets Probable ammonium transporter (amtB, NC_004431 from 547616 to 548902 (+)), a bacterial target gene encoded by the *Escherichia coli* CFT073 genome, as part of an anti-bacterial host defense mechanism. amtB BINDING SITE 1 and amtB BINDING SITE 2 are bacterial target binding sites that are found in the untranslated regions of mRNA encoded by the amtB gene, corresponding to target binding sites such as BINDING SITE I, BINDING SITE II or BINDING SITE III of FIG. 1. The nucleotide sequences of amtB BINDING SITE 1 and amtB BINDING SITE 2, and the complementary secondary structure to the nucleotide sequence of GAM353678 RNA are set forth in Tables 6-7, hereby incorporated herein. Another function of GAM353678 is to inhibit amtB, a GAM353678 bacterial target gene which is associated with *Escherichia coli* CFT073 infection, as part of an anti-bacterial host defense | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | mechanism. Accordingly, the utilities of GAM353678 include the diagnosis, prevention and treatment of *Escherichia coli* CFT07 3 infection and associated clinical conditions | |
| GAM35 3678 | CAGCAGCA CACTGTGG TTTGTA | Human | amtB | *Shigella flexneri* 2a str. 2 457T | GAM353678 is a human miRNA-like oligonucleotide, which targets probable ammonium transporter (amtB, NC_004741 from 407860 to 409146 (+)), a bacterial target gene encoded by the *Shigella flexneri* 2a str. 2457T genome, as part of an anti-bacterial host defense mechanism. amtB BINDING SITE 1 and amtB BINDING SITE 2 are bacterial target binding sites that are found in the untranslated regions of mRNA encoded by the amtB gene, corresponding to target binding sites such as BINDING SITE I, BINDING SITE II or BINDING SITE III of FIG. 1. The nucleotide sequences of amtB BINDING SITE 1 and amtB BINDING SITE 2, and the complementary secondary structure to the nucleotide sequence of GAM353678 RNA are set forth in Tables 6-7, hereby incorporated herein. Another function of GAM353678 is to inhibit amtB, a GAM353678 bacterial target gene which is associated with *Shigella flexneri* 2a str. 2457T infection, as part of an anti-bacterial host defense mechanism. Accordingly, the utilities of GAM353678 inc lude the diagnosis, prevention and treatment of *Shigella flexneri* 2a str. 2457T infection and associated clinical conditions | A |
| GAM35 3678 | CAGCAGCA CACTGTGG TTTGTA | Human | aroA | *Neisseria meningitidis* Z49 1 | GAM353678 is a human miRNA-like oligonucleotide, which targets 5- enolpyruvoylshikimate-3-phosphate synthase (aroA, NC_003116 from 1557502 to 1558803 (+)), a bacterial target gene encoded by the *Neisseria meningitidis* Z2491 genome, as part of an anti- bacterial host defense mechanism. aroA BINDING SITE 1 and aroA BINDING SITE 2 are bacterial target binding sites that are found in the untranslated regions of mRNA encoded by the aroA gene, corresponding to target binding sites such as BINDING SITE I, BINDING SITE II or BINDING SITE III of FIG. 1. The nucleotide sequences of aroA BINDING SITE 1 and aroA BINDING SITE 2, and the complementary secondary structure to the nucleotide sequence of GAM353678 RNA are set forth in Tables 6-7, hereby incorporated herein. Another function of GAM353678 is to inhibit aroA, a GAM353678 bacterial target gene which is associated with *Neisseria meningitidis* Z2491 infection, as part of an anti-bacterial host defense mechanism. Accordingly, the utilities of GAM353678 include the diagnosis, prevention and treatment of *Neisseria meningitidis* Z2491 infection and associated clinical conditions | A |
| GAM35 3678 | CAGCAGCA CACTGTGG TTTGTA | Human | aroD | *Leptospira interrogans serovar lai* str. 56601 | GAM353678 is a human miRNA-like oligonucleotide, which targets 3- dehydroquinate dehydratase (aroD, NC_004342 from 48128 to 48832 (−)), a bacterial target gene encoded by the *Leptospira interrogans serovar lai* str. 56601 genome, as part of an anti- bacterial host defense mechanism. aroD BINDING SITE 1 and aroD BINDING SITE 2 are bacterial target binding sites that are found in the untranslated regions of mRNA encoded by the aroD gene, corresponding to target binding sites such as BINDING SITE | A |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | I, BINDING SITE II or BINDING SITE III of FIG. 1. The nucleotide sequences of aroD BINDING SITE 1 and aroD BINDING SITE 2, and the complementary secondary structure to the nucleotide sequence of GAM353678 RNA are set forth in Tables 6-7, hereby incorporated herein. Another function of GAM353678 is to inhibit aroD, a GAM353678 bacterial target gene which is associated with *Leptospira interrogans serovar lai* str. 56601 infection, as part of an anti-b acterial host defense mechanism. Accordingly, the utilities of GAM353678 include the diagnosis, prevention and treatment of *Leptospira interrogans serovar lai* str. 56601 infection and associated clinical conditions | |
| GAM35 3678 | CAGCAGCA CACTGTGG TTTGTA | Human | aroH | *Shigella flexneri* 2a str. 3 01 | GAM353678 is a human miRNA-like oligonucleotide, which targets 3-deoxy-D-arabinoheptulosonate-7-phosphate synthase (DAHP synthetase, tryptophan repressible) (aroH, NC_004337 from 1557527 to 1558573 (−)), a bacterial target gene encoded by the *Shigella flexneri* 2a str. 301 genome, as part of an anti-bacterial host defense mechanism. aroH BINDING SITE 1 and aroH BINDING SITE 2 are bacterial target binding sites that are found in the untranslated regions of mRNA encoded by the aroH gene, corresponding to target binding sites such as BINDING SITE I, BINDING SITE II or BINDING SITE III of FIG. 1. The nucleotide sequences of aroH BINDING SITE 1 and aroH BINDING SITE 2, and the complementary secondary structure to the nucleotide sequence of GAM353678 RNA are set forth in Tables 6-7, hereby incorporated herein. Another function of GAM353678 is to inhibit aroH, a GAM353678 bacterial target gene which is associated with *Shigella flexneri* 2a str. 301 infection, as part of an anti-bacterial host defense mechanism. Accordingly, the utilities of GAM353678 include the diagnosis, prevention and treatment of *Shigella flexneri* 2a str. 301 infection and associated clinical conditions | A |
| GAM35 3678 | CAGCAGCA CACTGTGG TTTGTA | Human | avtA | *Shigella flexneri* 2a str. 3 01 | GAM353678 is a human miRNA-like oligonucleotide, which targets alanine-alpha-ketoisovalerate (or valine-pyruvate) transaminase, transaminase C (avtA, NC_004337 from 3721175 to 3722533 (+)), a bacterial target gene encoded by the *Shigella flexneri* 2a str. 301 genome, as part of an anti-bacterial host defense mechanism. avtA BINDING SITE is a bacterial target binding site that is a found in the the 3' untranslated region of mRNA encoded by the avtA gene, corresponding to a target binding site such as BINDING SITE I, BINDING SITE II or BINDING SITE III of FIG. 1. The nucleotide sequences of avtA BINDING SITE, and the complementary secondary structure to the nucleotide sequence of GAM353678 RNA are set forth in Tables 6-7, hereby incorporated herein. Another function of GAM353678 is to inhibit avtA, a GAM353678 bacterial target gene which is associated with *Shigella flexneri* 2a str. 301 infection, as part of an anti-bacterial host defense mechanism. Accordingly, the utilities of GAM353678 include the diagnosis, prevention and treatment of *Shigella flexneri* 2a str. 301 infection and associated clinical conditions | A |

TABLE 8-continued

| GAM NAME | GAM RNA SEQUENCE | GAM ORGANISM | TARGET | TARGET ORGANISM | GAM GAM FUNCTION | POS |
|---|---|---|---|---|---|---|
| GAM35 3678 | CAGCAGCA CACTGTGG TTTGTA | Human | avtA | Shigella flexneri 2a str. 2 457T | GAM353678 is a human miRNA-like oligonucleotide, which targets alanine-alpha-ketoisovalerate/valine-pyruvate transaminase C (avtA, NC_004741 from 4052685 to 4053938 (−)), a bacterial target gene encoded by the Shigella flexneri 2a str. 2457T genome, as part of an anti-bacterial host defense mechanism. avtA BINDING SITE is a bacterial target binding site that is a found in the the 3' untranslated region of mRNA encoded by the avtA gene, corresponding to a target binding site such as BINDING SITE I, BINDING SITE II or BINDING SITE III of FIG. 1. The nucleotide sequences of avtA BINDING SITE, and the complementary secondary structure to the nucleotide sequence of GAM353678 RNA are set forth in Tables 6-7, hereby incorporated herein. Another function of GAM353678 is to inhibit avtA, a GAM353678 bacterial target gene which is associated with Shigella flexneri 2a str. 2457T infection, as part of an anti-bacterial host defense mechanism. Accordingly, the utilities of GAM353678 include the diagnosis, prevention and treatment of Shigella flexneri 2a str. 2457T infection and associated clinical conditions | A |
| GAM35 3678 | CAGCAGCA CACTGTGG TTTGTA | Human | cII | Salmonella enterica enterica serovar Typhi Ty2 | GAM353678 is a human miRNA-like oligonucleotide, which targets transcriptional regulatory protein (cII, NC_004631 from 4520121 to 4520342 (+)), a bacterial target gene encoded by the Salmonella enterica enterica serovar Typhi Ty2 genome, as part of an anti-bacterial host defense mechanism. cII BINDING SITE 1 and cII BINDING SITE 2 are bacterial target binding sites that are found in the untranslated regions of m RNA encoded by the cII gene, corresponding to target binding sites such as BINDING SITE I, BINDING SITE II or BINDING SITE III of FIG. 1. The nucleotide sequences of cII BINDING SITE 1 and cII BINDING SITE 2, and the complementary secondary structure to the nucleotide sequence of GAM353678 RNA are set forth in Tables 6-7, hereby incorporated herein. Another function of GAM353678 is to inhibit cII, a GAM353678 bacterial target gene which is associated with Salmonella enterica enterica serovar Typhi Ty2 infection, as part of an anti-bacterial host defense mechanism. Accordingly, the utilities of GAM353678 include the diagnosis, prevention and treatment of Salmonella enterica enterica serovar Typhi Ty2 infection and associated clinical conditions | A |
| GAM35 3678 | CAGCAGCA CACTGTGG TTTGTA | Human | cII | Salmonella enterica enterica serovar Typhi | GAM353678 is a human miRNA-like oligonucleotide, which targets transcriptional regulatory protein (cII, NC_003198 from 4537312 to 4537533 (+)), a bacterial target gene encoded by the Salmonella enterica enterica serovar Typhi genome, as part of an anti-bacterial host defense mechanism. cII BINDING SITE 1 and cII BINDING SITE 2 are bacterial target binding sites that are found in the untranslated regions of m RNA encoded by the cII gene, corresponding to target binding sites such as BINDING SITE I, BINDING SITE II or BINDING SITE III of FIG. 1. The nucleotide sequences of cII BINDING SITE 1 and cII BINDING SITE 2, and the complementary secondary structure | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | to the nucleotide sequence of GAM353678 RNA are set forth in Tables 6-7, hereby incorporated herein. Another function of GAM353678 is to inhibit cII, a GAM353678 bacterial target gene which is associated with *Salmonella enterica enterica serovar Typhi* infection, as part of an anti- bacterial host defense mechanism. Accordingly, the utilities of GAM 353678 include the diagnosis, prevention and treatment of *Salmonella enterica enterica serovar Typhi* infection and associated clinical conditions | |
| GAM35 3678 | CAGCAGCA CACTGTGG TTTGTA | Human | cysM | *Salmonella typhimurium* LT2 | GAM353678 is a human miRNA-like oligonucleotide, which targets cysteine synthase B (cysM, NC_003197 from 2551651 to 2552562 (−)), a bacterial target gene encoded by the *Salmonella typhimurium* LT2 genome, as part of an anti- bacterial host defense mechanism. cysM BINDING SITE 1 and cysM BINDING SITE 2 are bacterial target binding sites that are found in the untranslated regions of mRNA encoded by the cysM gene, corresponding to target binding sites such as BINDING SITE I, BINDING SITE II or BINDING SITE III of FIG. 1. The nucleotide sequences of cysM BINDING SITE 1 and cysM BINDING SITE 2, and the complementary secondary structure to the nucleotide sequence of GAM353678 RNA are set forth in Tables 6-7, hereby incorporated herein. Another function of GAM353678 is to inhibit cysM, a GAM353678 bacterial target gene which is associated with *Salmonella typhimurium* LT2 infection, as part of an anti-bacterial host defense mechanism. Accordingly, the utilities of GAM353678 include the diagnosis, prevention and treatment of *Salmonella typhimurium* LT2 infection and associated clinical conditions | A |
| GAM35 3678 | CAGCAGCA CACTGTGG TTTGTA | Human | cysQ | *Pseudomonas putida* KT2440 | GAM353678 is a human miRNA-like oligonucleotide, which targets 3'(2'), 5'- bisphosphate nucleotidase (cysQ, NC_002947 from 315184 to 315984 (+)), a bacterial target gene encoded by the *Pseudomonas putida* KT2440 genome, as part of an anti- bacterial host defense mechanism. cysQ BINDING SITE 1 and cysQ BINDING SITE 2 are bacterial target binding sites that are found in the untranslated regions of mRNA encoded by the cysQ gene, corresponding to target binding sites such as BINDING SITE I, BINDING SITE II or BINDING SITE III of FIG. 1. The nucleotide sequences of cysQ BINDING SITE 1 and cysQ BINDING SITE 2, and the complementary secondary structure to the nucleotide sequence of GAM353678 RNA are set forth in Tables 6-7, hereby incorporated herein. Another function of GAM353678 is to inhibit cysQ, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | A |
| GAM35 3678 | CAGCAGCA CACTGTGG TTTGTA | Human | dadX | *Escherichia coli* C FT073 | GAM353678 is a human miRNA-like oligonucleotide, which targets Alanine racemase, catabolic (dadX, NC_004431 from 1476306 to 1477376 (+)), a bacterial target gene encoded by the *Escherichia coli* CFT073 genome, as part of an anti- bacterial host defense mechanism. dadX | A |

TABLE 8-continued

| GAM NAME | GAM RNA SEQUENCE | GAM ORGA-NISM | TAR-GET | TARGET ORGANISM | GAM FUNCTION | POS |
|---|---|---|---|---|---|---|
| | | | | | BINDING SITE 1 and dadX BINDING SITE 2 are bacterial target binding sites that are found in the untranslated regions of mRNA encoded by the dadX gene, corresponding to target binding sites such as BINDING SITE I, BINDING SITE II or BINDING SITE III of FIG. 1. The nucleotide sequences of dadX BINDING SITE 1 and dadX BINDING SITE 2, and the complementary secondary structure to the nucleotide sequence of GAM353678 RNA are set forth in Tables 6-7, hereby incorporated herein. Another function of GAM353678 is to inhibit dadX, a GAM353678 bacterial target gene which is associated with *Escherichia coli* CFT073 infection, as part of an anti-bacterial host defense mechanism. Accordingly, the utilities of GAM353678 include the diagnosis, prevention and treatment of *Escherichia coli* CFT073 infection and associated clinical conditions | |
| GAM35 3678 | CAGCAGCA CACTGTGG TTTGTA | Human | def | *Chlamydophila pneumoniae* CWL029 | GAM353678 is a human miRNA-like oligonucleotide, which targets Polypeptide Deformylase (def, NC_000922 from 1221735 to 1222295 (+)), a bacterial target gene encoded by the *Chlamydophila pneumoniae* CWL029 genome, as part of an anti-bacterial host defense mechanism. def BINDING SITE 1 and def BINDING SITE 2 are bacterial target binding sites that are found in the untranslated regions of mRNA encoded by the def gene, corresponding to target binding sites such as BINDING SITE I, BINDING SITE II or BINDING SITE III of FIG. 1. The nucleotide sequences of def BINDING SITE 1 and def BINDING SITE 2, and the complementary secondary structure to the nucleotide sequence of GAM353678 RNA are set forth in Tables 6-7, hereby incorporated herein. Another function of GAM353678 is to inhibit def, a GAM353678 bacterial target gene which is associated with *Chlamydophila pneumoniae* CWL029 infection, as part of an anti-bacterial host defense mechanism. Accordingly, the utilities of GAM353678 include the diagnosis, prevention and treatment of *Chlamydophila pneumoniae* CWL029 infection and associated clinical conditions. | A |
| GAM35 3678 | CAGCAGCA CACTGTGG TTTGTA | Human | def | *Chlamydophila pneumoniae* J138 | GAM353678 is a human miRNA-like oligonucleotide, which targets polypeptide deformylase (def, NC_002491 from 1218069 to 1218629 (+)), a bacterial target gene encoded by the *Chlamydophila pneumoniae* J138 genome, as part of an anti-bacterial host defense mechanism. def BINDING SITE 1 and def BINDING SITE 2 are bacterial target binding sites that are found in the untranslated regions of m RNA encoded by the def gene, corresponding to target binding sites such as BINDING SITE I, BINDING SITE II or BINDING SITE III of FIG. 1. The nucleotide sequences of def BINDING SITE 1 and def BINDING SITE 2, and the complementary secondary structure to the nucleotide sequence of GAM353678 RNA are set forth in Tables 6-7, hereby incorporated herein. Another function of GAM353678 is to inhibit def, a GAM353678 bacterial target gene which is associated with *Chlamydophila pneumoniae* J138 infection, as part of an anti-bacterial host defense mechanism. Accordingly, the utilities of GAM353678 include the | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | diagnosis, prevention and treatment of *Chlamydophila pneumoniae* J138 infection and associated clinical conditions | |
| GAM35 3678 | CAGCAGCA CACTGTGG TTTGTA | Human | dnaE | *Mycobacterium leprae* | GAM353678 is a human miRNA-like oligonucleotide, which targets DNA polymerase III, [alpha] subunit (dnaE, NC_002677 from 1423014 to 1426547 (+)), a bacterial target gene encoded by the *Mycobacterium leprae* genome, as part of an anti-bacterial host defense mechanism. dnaE BINDING SITE 1 through dnaE BINDING SITE 3 are bacterial target binding sites that are found in the untranslated regions of mRNA encoded by the dnaE gene, corresponding to target binding sites such as BINDING SITE I, BINDING SITE II or BINDING SITE III of FIG. 1. The nucleotide sequences of dnaE BINDING SITE 1 through dnaE BINDING SITE 3, and the complementary secondary structure to the nucleotide sequence of GAM353678 RNA are set forth in Tables 6-7, hereby incorporated herein. Another function of GAM353678 is to inhibit dnaE, a GAM353678 bacterial target gene which is associated with *Mycobacterium leprae* infection, as part of an anti-bacterial host defense mechanism. Accordingly, the utilities of GAM353678 include the diagnosis, prevention and treatment of *Mycobacterium leprae* infection and associated clinical conditions | A |
| GAM35 3678 | CAGCAGCA CACTGTGG TTTGTA | Human | dsdA | *Salmonella typhimurium* LT2 | GAM353678 is a human miRNA-like oligonucleotide, which targets D-serine deaminase (dsdA, NC_003197 from 4004453 to 4005775 (+)), a bacterial target gene encoded by the *Salmonella typhimurium* LT2 genome, as part of an anti-bacterial host defense mechanism. dsdA BINDING SITE 1 and dsdA BINDING SITE 2 are bacterial target binding sites that are found in the untranslated regions of mRNA encoded by the dsdA gene, corresponding to target binding sites such as BINDING SITE I, BINDING SITE II or BINDING SITE III of FIG. 1. The nucleotide sequences of dsdA BINDING SITE 1 and dsdA BINDING SITE 2, and the complementary secondary structure to the nucleotide sequence of GAM353678 RNA are set forth in Tables 6-7, hereby incorporated herein. Another function of GAM353678 is to inhibit dsdA, a GAM353678 bacterial target gene which is associated with *Salmonella typhimurium* LT2 infection, as part of an anti-bacterial host defense mechanism. Accordingly, the utilities of GAM353678 include the diagnosis, prevention and treatment of *Salmonella typhimurium* LT2 infection and associated clinical conditions | A |
| GAM35 3678 | CAGCAGCA CACTGTGG TTTGTA | Human | fepC | *Pseudomonas aeruginosa* PA01 | GAM353678 is a human miRNA-like oligonucleotide, which targets ferric enterobactin transport protein FepC (fepC, NC_002516 f rom 4653508 to 4654305 (−)), a bacterial target gene encoded by the *Pseudomonas aeruginosa* PA01 genome, as part of an anti-bacterial host defense mechanism. fepC BINDING SITE 1 and fepC BINDING SITE 2 are bacterial target binding sites that are found in the untranslated regions of mRNA encoded by the fepC gene, corresponding to target binding sites such as BINDING SITE I, BINDING SITE II or BINDING SITE III of FIG. 1. The nucleotide sequences of fepC BINDING SITE 1 and fepC BINDING SITE 2, | A |

TABLE 8-continued

| GAM NAME | GAM RNA SEQUENCE | GAM ORGANISM | TARGET | TARGET ORGANISM | GAM GAM FUNCTION | POS |
|---|---|---|---|---|---|---|
| | | | | | and the complementary secondary structure to the nucleotide sequence of GAM353678 RNA are set forth in Tables 6-7, hereby incorporated herein. Another function of GAM353678 is to inhibit fepC, a GAM353678 bacterial target gene which is associated with *Pseudomonas aeruginosa* PA01 infection, as part of an anti-bacterial host defense mechanism. Accordingly, the utilities of GAM353678 include the diagnosis, prevention and treatment of *Pseudomonas aeruginosa* PA01 infection and associated clinical conditions | |
| GAM35 3678 | CAGCAGCA CACTGTGG TTTGTA | Human | fhaL | *Bordetella pertussis* | GAM353678 is a human miRNA-like oligonucleotide, which targets adhesin (fhaL, NC_002929 from 3085865 to 3098455 (+)), a bacterial target gene encoded by the *Bordetella pertussis* genome, as part of an anti-bacterial host defense mechanism. fhaL BINDING SITE 1 and fhaL BINDING SITE 2 are bacterial target binding sites that are found in the untranslated regions of mRNA encoded by the fhaL gene, corresponding to target binding sites such as BINDING SITE I, BINDING SITE II or BINDING SITE III of FIG. 1. The nucleotide sequences of fhaL BINDING SITE 1 and fhaL BINDING SITE 2, and the complementary secondary structure to the nucleotide sequence of GAM353678 RNA are set forth in Tables 6-7, hereby incorporated herein. Another function of GAM353678 is to inhibit fhaL, a GAM353678 bacterial target gene which is associated with *Bordetella pertussis* infection, as part of an anti-bacterial host defense mechanism. Accordingly, the utilities of GAM353678 include the diagnosis, prevention and treatment of *Bordetella pertussis* infection and associated clinical conditions | A |
| GAM35 3678 | CAGCAGCA CACTGTGG TTTGTA | Human | flhB | *Bordetella pertussis* | GAM353678 is a human miRNA-like oligonucleotide, which targets flagellar biosynthetic protein FlhB (flhB, NC_002929 from 1441767 to 1442921 (+)), a bacterial target gene encoded by the *Bordetella pertussis* genome, as part of an anti-bacterial host defense mechanism. flhB BINDING SITE 1 through flhB BINDING SITE 3 are bacterial target binding sites that are found in the untranslated regions of mRNA encoded by the flhB gene, corresponding to target binding sites such as BINDING SITE I, BINDING SITE II or BINDING SITE III of FIG. 1. The nucleotide sequences of flhB BINDING SITE 1 through flhB BINDING SITE 3, and the complementary secondary structure to the nucleotide sequence of GAM353678 RNA are set forth in Tables 6-7, hereby incorporated herein. Another function of GAM353678 is to inhibit flhB, a GAM353678 bacterial target gene which is associated with *Bordetella pertussis* infection, as part of an anti-bacterial host defense mechanism. Accordingly, the utilities of GAM353678 include the diagnosis, prevention and treatment of *Bordetella pertussis* infection and associated clinical conditions | A |
| GAM35 3678 | CAGCAGCA CACTGTGG TTTGTA | Human | fmtB mr p | (*Staphylococcus*) *aureus* subsp. *aureus* N315 | GAM353678 is a human miRNA-like oligonucleotide, which targets FmtB protein (fmtB(mrp), NC_002745 from 2218145 to 2225590 (−)), a bacterial target gene encoded by the *Staphylococcus aureus* subsp. *aureus* N315 genome, as part | A |

TABLE 8-continued

| GAM NAME | GAM RNA SEQUENCE | GAM ORGANISM | TARGET | TARGET ORGANISM | GAM FUNCTION | POS |
|---|---|---|---|---|---|---|
| | | | | | of an anti-bacterial host defense mechanism. fmtB(mrp) BINDING SITE 1 and fmtB(mrp) BINDING SITE 2 are bacterial target binding sites that are found in the untranslated regions of mRNA encoded by the fmtB(mrp) gene, corresponding to target binding sites such as BINDING SITE I, BINDING SITE II or BINDING SITE III of FIG. 1. The nucleotide sequences of fm tB(mrp) BINDING SITE 1 and fmtB(mrp) BINDING SITE 2, and the complementary secondary structure to the nucleotide sequence of GAM353678 RNA are set forth in Tables 6-7, hereby incorporated herein. Another function of GAM353678 is to inhibit fmtB(mrp), a GAM35 3678 bacterial target gene which is associated with *Staphylococcus aureus* subsp. *aureus* N315 infection, as part of an anti-bacterial host defense mechanism. Accordingly, the utilities of GAM353678 include the diagnosis, prevention and treatment of *Staphylococcus aureus* subsp. *aureus* N315 infection and associated clinical conditions | |
| GAM35 3678 | CAGCAGCA CACTGTGG TTTGTA | Human | fmtB (mr p) | (*Staphylococcus aureus* subsp. *aureus* Mu50 | GAM353678 is a human miRNA-like oligonucleotide, which targets FmtB protein (fmtB(mrp), NC_002758 from 2287935 to 2295380 (−)), a bacterial target gene encoded by the *Staphylococcus aureus* subsp. *aureus* Mu50 genome, as part of an anti-bacterial host defense mechanism. fmtB(mrp) BINDING SITE 1 and fmtB(mrp) BINDING SITE 2 are bacterial target binding sites that are found in the untranslated regions of mRNA encoded by the fmtB(mrp) gene, corresponding to target binding sites such as BINDING SITE I, BINDING SITE II or BINDING SITE III of FIG. 1. The nucleotide sequences of fmtB (mrp) BINDING SITE 1 and fmtB(mrp) BINDING SITE 2, and the complementary secondary structure to the nucleotide sequence of GAM353678 RNA are set forth in Tables 6-7, hereby incorporated herein. Another function of GAM353678 is to inhibit fmtB(mrp), a GAM353678 bacterial target gene which is associated with *Staphylococcus aureus* subsp. *aureus* Mu50 infection, as part of an anti-bacterial host defense mechanism. Accordingly, the utilities of GAM353678 include the diagnosis, prevention and treatment of *Staphylococcus aureus* subsp. *aureus Mu50 infection and associated clinical conditions* | A |
| GAM35 3678 | CAGCAGCA CACTGTGG TTTGTA | Human | ftsY | *Chlamydophila pneumoniae* J1 38 | GAM353678 is a human miRNA-like oligonucleotide, which targets cell division protein ftsY (ftsY, NC_002491 from 1113127 to 1113999 (−)), a bacterial target gene encoded by the *Chlamydophila pneumoniae* J138 genome, as part of an anti-bacterial host defense mechanism. ftsY BINDING SITE 1 and ftsY BINDING SITE 2 are bacterial target binding sites that are found in the untranslated regions of mRNA encoded by the ftsY gene, corresponding to target binding sites such as BINDING SITE I, BINDING SITE II or BINDING SITE III of FIG. 1. The nucleotide sequences of ftsY BINDING SITE 1 and ftsY BINDING SITE 2, and the complementary secondary structure to the nucleotide sequence of GAM353678 RNA are set forth in Tables 6-7, hereby incorporated herein. Another function of | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | GAM353678 is to inhibit ftsY, a GAM353678 bacterial target gene which is associated with *Chlamydophila pneumoniae* J138 infection, as part of an anti-bacterial host defense mechanism. Accordingly, the utilities of GAM353678 include the diagnosis, prevention and treatment of *Chlamydophila pneumoniae* J138 infection and associated clinical conditions | |
| GAM35 3678 | CAGCAGCA CACTGTGG TTTGTA | Human | ftsY | *Chlamydophila pneumoniae* CW L029 | GAM353678 is a human miRNA-like oligonucleotide, which targets Cell Division Protein FtsY (ftsY, NC_000922 from 1115427 to 1116299 (−)), a bacterial target gene encoded by the *Chlamydophila pneumoniae* CWL029 genome, as part of an anti-bacterial host defense mechanism. ftsY BINDING SITE 1 and ftsY BINDING SITE 2 are bacterial target binding sites that are found in the untranslated regions of mRNA encoded by the ftsY gene, corresponding to target binding sites such as BINDING SITE I, BINDING SITE II or BINDING SITE III of FIG. 1. The nucleotide sequences of ftsY BINDING SITE 1 and ftsY BINDING SITE 2, and the complementary secondary structure to the nucleotide sequence of GAM353678 RNA are set forth in Tables 6-7, hereby incorporated herein. Another function of GAM353678 is to inhibit ftsY, a GAM353678 bacterial target gene which is associated with *Chlamydophila pneumoniae* CWL029 infection, as part of an anti-bacterial host defense mechanism. Accordingly, the utilities of GAM353678 include the diagnosis, prevention and treatment of *Chlamydophila pneumoniae* CWL029 infection and associated clinical conditions | A |
| GAM35 3678 | CAGCAGCA CACTGTGG TTTGTA | Human | gad | *Pseudomonas putida* KT2440 | GAM353678 is a human miRNA-like oligonucleotide, which targets guanine aminohydrolase (gad, NC_002947 from 4871625 to 4872929 (+)), a bacterial target gene encoded by the *Pseudomonas putida* KT2440 genome, as part of an anti-bacterial host defense mechanism. gad BINDING SITE 1 and gad BINDING SITE 2 are bacterial target binding sites that are found in the untranslated regions of m RNA encoded by the gad gene, corresponding to target binding sites such as BINDING SITE I, BINDING SITE II or BINDING SITE III of FIG. 1. The nucleotide sequences of gad BINDING SITE 1 and gad BINDING SITE 2, and the complementary secondary structure to the nucleotide sequence of GAM353678 RNA are set forth in Tables 6-7, hereby incorporated herein. Another function of GAM353678 is to inhibit gad, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT 2440 infection and associated clinical conditions | A |
| GAM35 3678 | CAGCAGCA CACTGTGG TTTGTA | Human | glcC | *Escherichis coli* CFT073 | GAM353678 is a human miRNA-like oligonucleotide, which targets Glc operon transcriptional activator (glcC, NC_004431 from 3542871 to 3543695 (+)), a bacterial target gene encoded by the *Escherichia coli* CFT073 genome, as part of an anti-bacterial host defense mechanism. glcC BINDING SITE 1 and glcC BINDING SITE 2 are bacterial target binding sites that are found in the untranslated regions of | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | mRNA encoded by the glcC gene, corresponding to target binding sites such as BINDING SITE I, BINDING SITE II or BINDING SITE III of FIG. 1. The nucleotide sequences of glcC BINDING SITE 1 and glcC BINDING SITE 2, and the complementary secondary structure to the nucleotide sequence of GAM353678 RNA are set forth in Tables 6-7, hereby incorporated herein. Another function of GAM353678 is to inhibit glcC, a GAM353678 bacterial target gene which is associated with *Escherichia coli* CFT073 infection, as part of an anti-bacterial host defense mechanism. Accordingly, the utilities of GAM353678 include the diagnosis, prevention and treatment of *Escherichia coli* CFT073 infection and associated clinical conditions | |
| GAM35 3678 | CAGCAGCA CACTGTGG TTTGTA | Human | glgP | *Salmonella enterica enterica serovar Typhi* Ty 2 | GAM353678 is a human miRNA-like oligonucleotide, which targets glycogen phosphorylase (glgP, NC_004631 from 4129215 to 4131662 (+)), a bacterial target gene encoded by the *Salmonella enterica enterica serovar Typhi* Ty2 genome, as part of an anti-bacterial host defense mechanism. glgP BINDING SITE 1 and glgP BINDING SITE 2 are bacterial target binding sites that are found in the untranslated regions of mRNA encoded by the glgP gene, corresponding to target binding sites such as BINDING SITE I, BINDING SITE II or BINDING SITE III of FIG. 1. The nucleotide sequences of glgP BINDING SITE 1 and glgP BINDING SITE 2, and the complementary secondary structure to the nucleotide sequence of GAM353678 RNA are set forth in Tables 6-7, hereby incorporated herein. Another function of GAM353678 is to inhibit glgP, a GAM353678 bacterial target gene which is associated with *Salmonella enterica enterica serovar Typhi* Ty2 infection, as part of an anti-bacterial host defense mechanism. Accordingly, the utilities of GAM353678 include the diagnosis, prevention and treatment of *Salmonella enterica enterica serovar Typhi* Ty2 infection and associated clinical conditions | A |
| GAM35 3678 | CAGCAGCA CACTGTGG TTTGTA | Human | glgP | *Salmonella enterica enterica serovar Typhi* | GAM353678 is a human miRNA-like oligonucleotide, which targets glycogen phosphorylase (glgP, NC_003198 from 4144568 to 414 7015 (+)), a bacterial target gene encoded by the *Salmonella enterica enterica serovar Typhi* genome, as part of an anti-bacterial host defense mechanism. glgP BINDING SITE 1 and glgP BINDING SITE 2 are bacterial target binding sites that are found in the untranslated regions of mRNA encoded by the glgP gene, corresponding to target binding sites such as BINDING SITE I, BINDING SITE II or BINDING SITE III of FIG. 1. The nucleotide sequences of glgP BINDING SITE 1 and glgP BINDING SITE 2, and the complementary secondary structure to the nucleotide sequence of GAM353678 RNA are set forth in Tables 6-7, hereby incorporated herein. Another function of GAM353678 is to inhibit glgP, a GAM353678 bacterial target gene which is associated with *Salmonella enterica enterica serovar Typhi* infection, as part of an anti-bacterial host defense mechanism. Accordingly, the utilities of GAM353678 include the diagnosis, prevention and treatment of | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | *Salmonella enterica enterica* serovar *Typhi* infection and associated clinical conditions | |
| GAM35 3678 | CAGCAGCA CACTGTGG TTTGTA | Human | glpC | *Yersinia pestis* KIM | GAM353678 is a human miRNA-like oligonucleotide, which targets sn-glycerol-3-phosphate dehydrogenase (anaerobic), K-small subunit (glpC, NC_004088 from 454677 to 456047 (+)), a bacterial target gene encoded by the *Yersinia pestis* KIM genome, as part of an anti-bacterial host defense mechanism. glpC BINDING SITE 1 and glpC BINDING SITE 2 are bacterial target binding sites that are found in the untranslated regions of mRNA encoded by the glpC gene, corresponding to target binding sites such as BINDING SITE I, BINDING SITE II or BINDING SITE III of FIG. 1. The nucleotide sequences of glpC BINDING SITE 1 and glpC BINDING SITE 2, and the complementary secondary structure to the nucleotide sequence of GAM353678 RNA are set forth in Tables 6-7, hereby incorporated herein. Another function of GAM353678 is to inhibit glpC, a GAM353678 bacterial target gene which is associated with *Yersinia pestis* KIM infection, as part of an anti-bacterial host defense mechanism. Accordingly, the utilities of GAM353678 include the diagnosis, prevention and treatment of *Yersinia pestis* KIM infection and associated clinical conditions | A |
| GAM35 3678 | CAGCAGCA CACTGTGG TTTGTA | Human | glpC | *Yersinia pestis* | GAM353678 is a human miRNA-like oligonucleotide, which targets anaerobic glycerol-3-phosphate dehydrogenase subunit C (glpC, NC_003143 from 4289650 to 4290897 (−)), a bacterial target gene encoded by the *Yersinia pestis* genome, as part of an anti-bacterial host defense mechanism. glpC BINDING SITE 1 and glpC BINDING SITE 2 are bacterial target binding sites that are found in the untranslated regions of mRNA encoded by the glpC gene, corresponding to target binding sites such as BINDING SITE I, BINDING SITE II or BINDING SITE III of FIG. 1. The nucleotide sequences of glpC BINDING SITE 1 and glpC BINDING SITE 2, and the complementary secondary structure to the nucleotide sequence of GAM353678 RNA are set forth in Tables 6-7, hereby incorporated herein. Another function of GAM353678 is to inhibit glpC, a GAM353678 bacterial target gene which is associated with *Yersinia pestis* infection, as part of an anti-bacterial host defense mechanism. Accordingly, the utilities of GAM353678 include the diagnosis, prevention and treatment of *Yersinia pestis* infection and associated clinical conditions | A |
| GAM35 3678 | CAGCAGCA CACTGTGG TTTGTA | Human | glpD | *Brucella suis* 1330 | GAM353678 is a human miRNA-like oligonucleotide, which targets glycerol-3-phosphate dehydrogenase (glpD, NC_004310 from 210763 to 212274 (+)), a bacterial target gene encoded by the *Brucella suis* 1330 genome, as part of an anti-bacterial host defense mechanism. glpD BINDING SITE 1 and glpD BINDING SITE 2 are bacterial target binding sites that are found in the untranslated regions of mRNA encoded by the glpD gene, corresponding to target binding sites such as BINDING SITE I, BINDING SITE II or BINDING SITE III of FIG. 1. The nucleotide sequences of glpD BINDING SITE | A |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | 1 and glpD BINDING SITE 2, and the complementary secondary structure to the nucleotide sequence of GAM353678 RNA are set forth in Tables 6-7, hereby incorporated herein. Another function of GAM353678 is to inhibit glpD, a GAM353678 bacterial target gene which is associated with *Brucella suis* 1330 infection, as part of an anti-bacterial host defense mechanism. Accordingly, the utilities of GAM353678 include the diagnosis, prevention and treatment of *Brucella suis* 1330 infection and associated clinical conditions | |
| GAM353678 | CAGCAGCACACTGTGGTTTGTA | Human | ipaH_5 | *Shigella flexneri* 2a str. 2457T | GAM353678 is a human miRNA-like oligonucleotide, which targets invasion plasmid antigen (ipaH_5, NC_004741 from 2023205 to 2024848 (+)), a bacterial target gene encoded by the *Shigella flexneri* 2a str. 2457T genome, as part of an anti-bacterial host defense mechanism. ipaH_5 BINDING SITE 1 and ipaH_5 BINDING SITE 2 are bacterial target binding sites that are found in the untranslated regions of mRNA encoded by the ipaH_5 gene, corresponding to target binding sites such as BINDING SITE I, BINDING SITE II or BINDING SITE III of FIG. 1. The nucleotide sequences of ipaH_5 BINDING SITE 1 and ipaH_5 BINDING SITE 2, and the complementary secondary structure to the nucleotide sequence of GAM353678 RNA are set forth in Tables 6-7, hereby incorporated herein. Another function of GAM353678 is to inhibit ipaH_5, a GAM353678 bacterial target gene which is associated with *Shigella flexneri* 2a str. 2457T infection, as part of an anti-bacterial host defense mechanism. Accordingly, the utilities of GAM353678 include the diagnosis, prevention and treatment of *Shigella flexneri* 2a str. 2457T infection and associated clinical conditions | A |
| GAM353678 | CAGCAGCACACTGTGGTTTGTA | Human | ipaH9.8 | *Shigella flexneri* 2a str. 301 | GAM353678 is a human miRNA-like oligonucleotide, which targets invasion plasmid antigen (ipaH9.8, NC_004337 from 1422064 to 1423779 (−)), a bacterial target gene encoded by the *Shigella flexneri* 2a str. 301 genome, as part of an anti-bacterial host defense mechanism. ipaH9.8 BINDING SITE 1 and ipaH9.8 BINDING SITE 2 are bacterial target binding sites that are found in the untranslated regions of mRNA encoded by the ipaH9.8 gene, corresponding to target binding sites such as BINDING SITE I, BINDING SITE II or BINDING SITE III of FIG. 1. The nucleotide sequences of ipaH9.8 BINDING SITE 1 and ipaH9.8 BINDING SITE 2, and the complementary secondary structure to the nucleotide sequence of GAM353678 RNA are set forth in Tables 6-7, hereby incorporated herein. Another function of GAM353678 is to inhibit ipaH9.8, a GAM353678 bacterial target gene which is associated with *Shigella flexneri* 2a str. 301 infection, as part of an anti-bacterial host defense mechanism. Accordingly, the utilities of GAM353678 include the diagnosis, prevention and treatment of *Shigella flexneri* 2a str. 301 infection and associated clinical conditions. | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| GAM35 3678 | CAGCAGCA CACTGTGG TTTGTA | Human | lives | *Bordetella pertussis* | GAM353678 is a human miRNA-like oligonucleotide, which targets high- affinity branched-chain amino acid transport system permease protein (livH, NC_002929 from 1144729 to 1145607 (+)), a bacterial target gene encoded by the *Bordetella pertussis* genome, as part of an anti-bacterial host defense mechanism. lives BINDING SITE is a bacterial target binding site that is a found in the the 3' untranslated region of mRNA encoded by the livH gene, corresponding to a target binding site such as BINDING SITE I, BINDING SITE II or BINDING SITE III of FIG. 1. The nucleotide sequences of livH BINDING SITE, and the complementary secondary structure to the nucleotide sequence of GAM353678 RNA are set forth in Tables 6-7, hereby incorporated herein. Another function of GAM353678 is to inhibit lives, a GAM353678 bacterial target gene which is associated with *Bordetella pertussis* infection, as part of an anti- bacterial host defense mechanism. Accordingly, the utilities of GAM353678 include the diagnosis, prevention and treatment of *Bordetella pertussis* infection and associated clinical conditions | A |
| GAM35 3678 | CAGCAGCA CACTGTGG TTTGTA | Human | lppI | *Mycobacterium tuberculosis* H37Rv | GAM353678 is a human miRNA-like oligonucleotide, which targets lppI (lppI, NC_000962 from 2291267 to 2291923 (+)), a bacterial target gene encoded by the *Mycobacterium tuberculosis* H37Rv genome, as part of an anti-bacterial host defense mechanism. lppI BINDING SITE 1 and lppI BINDING SITE 2 are bacterial target binding sites that are found in the untranslated regions of mRNA encoded by the lppI gene, corresponding to target binding sites such as BINDING SITE I, BINDING SITE II or BINDING SITE III of FIG. 1. The nucleotide sequences of lppI BINDING SITE 1 and lppI BINDING SITE 2, and the complementary secondary structure to the nucleotide sequence of GAM353678 RNA are set forth in Tables 6-7, hereby incorporated herein. Another function of GAM353678 is to inhibit lppI, a GAM353678 bacterial target gene which is associated with *Mycobacterium tuberculosis* H37Rv infection, as part of an anti-bacterial host defense mechanism. Accordingly, the utilities of GAM353678 include the diagnosis, prevention and treatment of *Mycobacterium tuberculosis* H37Rv infection and associated clinical conditions | A |
| GAM35 3678 | CAGCAGCA CACTGTGG TTTGTA | Human | lppI | *Mycobacterium bovis* subsp *bovis* AF21 22/97 | GAM353678 is a human miRNA-like oligonucleotide, which targets Probable lipoprotein lppI (lppI, NC_002945 from 2275182 to 2275838 (+)), a bacterial target gene encoded by the *Mycobacterium bovis* subsp *bovis* AF2122/97 genome, as part of an anti-bacterial host defense mechanism. lppI BINDING SITE 1 and lppI BINDING SITE 2 are bacterial target binding sites that are found in the untranslated regions of mRNA encoded by the lppI gene, corresponding to target binding sites such as BINDING SITE I, BINDING SITE II or BINDING SITE III of FIG. 1. The nucleotide sequences of lppI BINDING SITE 1 and lppI BINDING SITE 2, and the complementary secondary structure to the nucleotide sequence of GAM353678 RNA are set forth in Tables 6-7, hereby incorporated herein. Another function of | A |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | GAM353678 is to inhibit lppI, a GAM353678 bacterial target gene which is associated with *Mycobacterium bovis* subsp *bovis* AF2122/97 infection, as part of an anti-bacterial host defense mechanism. Accordingly, the utilities of GAM 353678 include the diagnosis, prevention and treatment of *Mycobacterium bovis* subsp *bovis* AF2122/97 infection and associated clinical conditions | |
| GAM35 3678 | CAGCAGCA CACTGTGG TTTGTA | Human | MGAT5 | Human | GAM353678 is a human miRNA-like oligonucleotide, which targets a human mannosyl (alpha-1,6-)-glycoprotein beta-1,6-N-acetyl-glucosaminyltransferase (MGAT5, Accession number: NM_002410) as part of a host response mechanism associated with a *Salmonella typhimurium* LT2 infection. MGAT5 BINDING SITE is a human target binding site that is a found in the the 3' untranslated region of mRNA encoded by the MGAT5 gene, corresponding to a target binding site such as BINDING SITE I, BINDING SITE II or BINDING SITE III of FIG. 1. Additionally, using the binding site prediction system of the present invention GAM353678-A binds to sequences on orthologous UTR of rat(NM_023095). The nucleotide sequences of MGAT5 BINDING SITE, and the complementary secondary structure to the nucleotide sequence of GAM353678 RNA are set forth in Tables 6-7, hereby incorporated herein. Another function of GAM353678 is to inhibit MGAT5, a GAM353678 human target gene which encodes an enzyme that catalyzes beta 1-6 branching on N-linked carbohydrates. MGAT5 is associated with *Salmonella typhimurium* LT2 infection, and therefore GAM353678 is associated with the abovementioned infection, as part of a host response mechanism. Accordingly, the utilities of GAM353678 include the diagnosis, prevention and treatment of *Salmonella typhimurium* LT2 infection and associated clinical conditions. The function of MGAT5 and its association with various diseases and clinical conditions has been established by previous studies, as described hereinabove with reference to GAM3451. | A |
| GAM35 3678 | CAGCAGCA CACTGTGG TTTGTA | Human | miaA | *Chlamydia trachomatis* | GAM353678 is a human miRNA-like oligonucleotide, which targets tRNA isopentenylpyrophosphate transferase (miaA, NC_000117 from 899276 to 900295 (+)), a bacterial target gene encoded by the *Chlamydia trachomatis* genome, as part of an anti-bacterial host defense mechanism. miaA BINDING SITE 1 and miaA BINDING SITE 2 are bacterial target binding sites that are found in the untranslated regions of mRNA encoded by the miaA gene, corresponding to target binding sites such as BINDING SITE I, BINDING SITE II or BINDING SITE III of FIG. 1. The nucleotide sequences of miaA BINDING SITE 1 and miaA BINDING SITE 2, and the complementary secondary structure to the nucleotide sequence of GAM353678 RNA are set forth in Tables 6-7, hereby incorporated herein. Another function of GAM353678 is to inhibit miaA, a GAM353678 bacterial target gene which is associated with *Chlamydia trachomatis* infection, as part of an anti-bacterial host defense mechanism. Accordingly, the utilities of GAM353678 include the diagnosis, | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | prevention and treatment of *Chlamydia trachomatis* infection and associated clinical conditions | |
| GAM35 3678 | CAGCAGCA CACTGTGG TTTGTA | Human | minE | *Pseudomonas putida* KT2440 | GAM353678 is a human miRNA-like oligonucleotide, which targets cell division topological specificity factor MinE (minE, NC_002947 from 1932680 to 1932934 (−)), a bacterial target gene encoded by the *Pseudomonas putida* KT2440 genome, as part of an anti-bacterial host defense mechanism. minE BINDING SITE is a bacterial target binding site that is a found in the the 3' untranslated region of mRNA encoded by the minE gene, corresponding to a target binding site such as BINDING SITE I, BINDING SITE II or BINDING SITE III of FIG. 1. The nucleotide sequences of minE BINDING SITE, and the complementary secondary structure to the nucleotide sequence of GAM353678 RNA are set forth in Tables 6-7, hereby incorporated herein. Another function of GAM353678 is to inhibit minE, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | A |
| GAM35 3678 | CAGCAGCA CACTGTGG TTTGTA | Human | nicT | *Mycobacterium tuberculosis* H37Rv | GAM353678 is a human miRNA-like oligonucleotide, which targets nicT (nicT, NC_000962 from 3166681 to 3167799 (+)), a bacterial target gene encoded by the *Mycobacterium tuberculosis* H37Rv genome, as part of an anti-bacterial host defense mechanism. nicT BINDING SITE 1 and nicT BINDING SITE 2 are bacterial target binding sites that are found in the untranslated regions of mRNA encoded by the nicT gene, corresponding to target binding sites such as BINDING SITE I, BINDING SITE II or BINDING SITE III of FIG. 1. The nucleotide sequences of nicT BINDING SITE 1 and nicT BINDING SITE 2, and the complementary secondary structure to the nucleotide sequence of GAM353678 RNA are set forth in Tables 6-7, hereby incorporated herein. Another function of GAM353678 is to inhibit nicT, a GAM353678 bacterial target gene which is associated with *Mycobacterium tuberculosis* H37Rv infection, as part of an anti-bacterial host defense mechanism. Accordingly, the utilities of GAM353678 include the diagnosis, prevention and treatment of *Mycobacterium tuberculosis* H37Rv infection and associated clinical conditions | A |
| GAM35 3678 | CAGCAGCA CACTGTGG TTTGTA | Human | nicT | *Mycobacterium bovis* subsp *bovis* AF21 22/97 | GAM353678 is a human miRNA-like oligonucleotide, which targets POSSIBLE NICKEL-TRANSPORT INTEGRAL MEMBRANE PROTEIN NICT (nic T, NC_002945 from 3123200 to 3124318 (+)), a bacterial target gene encoded by the *Mycobacterium bovis* subsp *bovis* AF2122/97 genome, as part of an anti-bacterial host defense mechanism. nicT BINDING SITE 1 and nicT BINDING SITE 2 are bacterial target binding sites that are found in the untranslated regions of mRNA encoded by the nicT gene, corresponding to target binding sites such as BINDING SITE I, BINDING SITE II or BINDING SITE III of FIG. 1. The nucleotide sequences of nicT BINDING SITE 1 and nicT BINDING SITE 2, and the | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | complementary secondary structure to the nucleotide sequence of GAM353678 RNA are set forth in Tables 6-7, hereby incorporated herein. Another function of GAM353678 is to inhibit nicT, a GAM353678 bacterial target gene which is associated with *Mycobacterium bovis* subsp *bovis* AF2122/97 infection, as part of an anti-bacterial host defense mechanism. Accordingly, the utilities of GAM353678 include the diagnosis, prevention and treatment of *Mycobacterium bovis* subsp *bovis* AF2122/97 infection and associated clinical conditions | |
| GAM35 3678 | CAGCAGCA CACTGTGG TTTGTA | Human | nupC | *Shigella flexneri* 2a str. 3 01 | GAM353678 is a human miRNA-like oligonucleotide, which targets permease of transport system for 3 nucleosides (nupC, NC_004337 from 2515842 to 2517083 (+)), a bacterial target gene encoded by the *Shigella flexneri* 2a str. 301 genome, as part of an anti-bacterial host defense mechanism. nupC BINDING SITE 1 through nupC BINDING SITE 3 are bacterial target binding sites that are found in the untranslated regions of mRNA encoded by the nupC gene, corresponding to target binding sites such as BINDING SITE I, BINDING SITE II or BINDING SITE III of FIG. 1. The nucleotide sequences of nupC BINDING SITE 1 through nupC BINDING SITE 3, and the complementary secondary structure to the nucleotide sequence of GAM353678 RNA are set forth in Tables 6-7, hereby incorporated herein. Another function of GAM353678 is to inhibit nupC, a GAM353678 bacterial target gene which is associated with *Shigella flexneri* 2a str. 301 infection, as part of an anti-bacterial host defense mechanism. Accordingly, the utilities of GAM353678 include the diagnosis, prevention and treatment of *Shigella flexneri* 2a str. 301 infection and associated clinical conditions | A |
| GAM35 3678 | CAGCAGCA CACTGTGG TTTGTA | Human | nupC | *Escherichia coli* CFT073 | GAM353678 is a human miRNA-like oligonucleotide, which targets Nucleoside permease nupC (nupC, NC_004431 from 2795390 to 2796631 (+)), a bacterial target gene encoded by the *Escherichia coli* CFT073 genome, as part of an anti-bacterial host defense mechanism. nupC BINDING SITE 1 through nupC BINDING SITE 3 are bacterial target binding sites that are found in the untranslated regions of mRNA encoded by the nupC gene, corresponding to target binding sites such as BINDING SITE I, BINDING SITE II or BINDING SITE III of FIG. 1. The nucleotide sequences of nupC BINDING SITE 1 through nupC BINDING SITE 3, and the complementary secondary structure to the nucleotide sequence of GAM353678 RNA are set forth in Tables 6-7, hereby incorporated herein. Another function of GAM353678 is to inhibit nupC, a GAM353678 bacterial target gene which is associated with *Escherichia coli* CFT073 infection, as part of an anti-bacterial host defense mechanism. Accordingly, the utilities of GAM353678 include the diagnosis, prevention and treatment of *Escherichia coli* CFT073 infection and associated clinical conditions | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| GAM35 3678 | CAGCAGCA CACTGTGG TTTGTA | Human | nupC | *Shigella flexneri* 2a str. 2 457T | GAM353678 is a human miRNA-like oligonucleotide, which targets permease of transport system for 3 nucleosides (nupC, NC_004741 from 2494019 to 2495221 (+)), a bacterial target gene encoded by the *Shigella flexneri* 2a str. 2457T genome, as part of an anti-bacterial host defense mechanism. nupC BINDING SITE 1 through nupC BINDING SITE 3 are bacterial target binding sites that are found in the untranslated regions of mRNA encoded by the nupC gene, corresponding to target binding sites such as BINDING SITE I, BINDING SITE II or BINDING SITE III of FIG. 1. The nucleotide sequences of nupC BINDING SITE 1 through nupC BINDING SITE 3, and the complementary secondary structure to the nucleotide sequence of GAM353678 RNA are set forth in Tables 6-7, hereby incorporated herein. Another function of GAM353678 is to inhibit nupC, a GAM353678 bacterial target gene which is associated with *Shigella flexneri* 2a str. 2457T infection, as part of an anti- bacterial host defense mechanism. Accordingly, the utilities of GAM353678 include the diagnosis, prevention and treatment of *Shigella flexneri* 2a str. 2457T infection and associated clinical conditions | A |
| GAM35 3678 | CAGCAGCA CACTGTGG TTTGTA | Human | ompG | *Escherichia coli* CFT073 | GAM353678 is a human miRNA-like oligonucleotide, which targets Outer membrane protein G precursor (ompG, NC_004431 from 1624577 to 1625533 (+)), a bacterial target gene encoded by the *Escherichia coli* CFT073 genome, as part of an anti-bacterial host defense mechanism. ompG BINDING SITE 1 and ompG BINDING SITE 2 are bacterial target binding sites that are found in the untranslated regions of mRNA encoded by the ompG gene, corresponding to target binding sites such as BINDING SITE I, BINDING SITE II or BINDING SITE III of FIG. 1. The nucleotide sequences of ompG BINDING SITE 1 and ompG BINDING SITE 2, and the complementary secondary structure to the nucleotide sequence of GAM353678 RNA are set forth in Tables 6-7, hereby incorporated herein. Another function of GAM353678 is to inhibit ompG, a GAM353678 bacterial target gene which is associated with *Escherichia coli* CFT073 infection, as part of an anti-bacterial host defense mechanism. Accordingly, the utilities of GAM353678 include the diagnosis, prevention and treatment of *Escherichia coli* CFT073 infection and associated clinical conditions | A |
| GAM35 3678 | CAGCAGCA CACTGTGG TTTGTA | Human | orn | *Yersinia pestis* | GAM353678 is a human miRNA-like oligonucleotide, which targets oligoribonuclease (orn, NC_003143 from 378331 to 378876 (+)), a bacterial target gene encoded by the *Yersinia pestis* genome, as part of an anti-bacterial host defense mechanism. orn BINDING SITE is a bacterial target binding site that is a found in the the 3' untranslated region of mRNA encoded by the orn gene, corresponding to a target binding site such as BINDING SITE I, BINDING SITE II or BINDING SITE III of FIG. 1. The nucleotide sequences of orn BINDING SITE, and the complementary secondary structure to the nucleotide sequence of GAM353678 RNA are set forth in Tables 6-7, hereby | A |

TABLE 8-continued

| GAM NAME | GAM RNA SEQUENCE | GAM ORGANISM | TARGET | TARGET ORGANISM | GAM GAM FUNCTION | POS |
|---|---|---|---|---|---|---|
| | | | | | incorporated herein. Another function of GAM353678 is to inhibitorn, a GAM353678 bacterial target gene which is associated with *Yersinia pestis* infection, as part of an anti-bacterial host defense mechanism. Accordingly, the utilities of GAM353678 include the diagnosis, prevention and treatment of *Yersinia pestis* infection and associated clinical conditions | |
| GAM353678 | CAGCAGCACACTGTGGTTTGTA | Human | oxyR | *Salmonella enterica enterica serovar Typhi* | GAM353678 is a human miRNA-like oligonucleotide, which targets hydrogen peroxide-inducible regulon activator (oxyR, NC_003198 from 3607204 to 3608121 (−)), a bacterial target gene encoded by the *Salmonella enterica enterica serovar Typhi* genome, as part of an anti-bacterial host defense mechanism. oxyR BINDING SITE 1 and oxyR BINDING SITE 2 are bacterial target binding sites that are found in the untranslated regions of mRNA encoded by the oxyR gene, corresponding to target binding sites such as BINDING SITE I, BINDING SITE II or BINDING SITE III of FIG. 1. The nucleotide sequences of oxyR BINDING SITE 1 and oxyR BINDING SITE 2, and the complementary secondary structure to the nucleotide sequence of GAM353678 RNA are set forth in Tables 6-7, hereby incorporated herein. Another function of GAM353678 is to inhibit oxyR, a GAM353678 bacterial target gene which is associated with *Salmonella enterica enterica serovar Typhi* infection, as part of an anti-bacterial host defense mechanism. Accordingly, the utilities of GAM353678 include the diagnosis, prevention and treatment of *Salmonella enterica enterica serovar Typhi* infection and associated clinical conditions | A |
| GAM353678 | CAGCAGCACACTGTGGTTTGTA | Human | oxyR | *Salmonella typhimurium* LT2 | GAM353678 is a human miRNA-like oligonucleotide, which targets oxidative stress regulatory protein (oxyR, NC_003197 from 4343080 to 4343997 (+)), a bacterial target gene encoded by the *Salmonella typhimurium* LT2 genome, as part of an anti-bacterial host defense mechanism. oxyR BINDING SITE 1 and oxyR BINDING SITE 2 are bacterial targ et binding sites that are found in the untranslated regions of mRNA encoded by the oxyR gene, corresponding to target binding sites such as BINDING SITE I, BINDING SITE II or BINDING SITE III of FIG.1. The nucleotide sequences of oxyR BINDING SITE 1 and oxyR BINDING SITE 2, and the complementary secondary structure to the nucleotide sequence of GAM353678 RNA are set forth in Tables 6-7, hereby incorporated herein. Another function of GAM353678 is to inhibit oxyR, a GAM353678 bacterial target gene which is associated with *Salmonella typhimurium* LT2 infection, as part of an anti-bacterial host defense mechanism. Accordingly, the utilities of GAM353678 include the diagnosis, prevention and treatment of *Salmonella typhimurium* LT2 infection and associated clinical conditions | A |
| GAM353678 | CAGCAGCACACTGTGGTTTGTA | Human | oxyR | *Salmonella enterica enterica serovar Typhi* Ty 2 | GAM353678 is a human miRNA-like oligonucleotide, which targets hydrogen peroxide-inducible regulon activator (oxyR, NC_004631 from 3592864 to 3593781 (−)), a bacterial target gene encoded by the *Salmonella enterica enterica serovar Typhi* Ty2 genome, as part of an anti-bacterial host defense mechanism. | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | oxyR BINDING SITE 1 and oxyR BINDING SITE 2 are bacterial target binding sites that are found in the untranslated regions of mRNA encoded by the oxyR gene, corresponding to target binding sites such as BINDING SITE I, BINDING SITE II or BINDING SITE III of FIG. 1. The nucleotide sequences of oxyR BINDING SITE 1 and oxyR BINDING SITE 2, and the complementary secondary structure to the nucleotide sequence of GAM353678 RNA are set forth in Tables 6-7, hereby incorporated herein. Another function of GAM353678 is to inhibit oxyR, a GAM353678 bacterial target gene which is associated with *Salmonella enterica enterica serovar Typhi* Ty2 infection, as part of an anti-bacterial host defense mechanism. Accordingly, the utilities of GAM353678 include the diagnosis, prevention and treatment of *Salmonella enterica enterica serovar Typhi* Ty2 infection and associated clinical conditions | |
| GAM35 3678 | CAGCAGCA CACTGTGG TTTGTA | Human | pbpG | *Pseudomonas putida* KT2440 | GAM353678 is a human miRNA-like oligonucleotide, which targets D-alanyl-D-alanine-endopeptidase (pbpG, NC_002947 from 4323707 to 4324633 (+)), a bacterial target gene encoded by the *Pseudomonas putida* KT2440 genome, as part of an anti-bacterial host defense mechanism. pbpG BINDING SITE 1 and pbpG BINDING SITE 2 are bacterial target binding sites that are found in the untranslated regions of mRNA encoded by the pbpG gene, corresponding to target binding sites such as BINDING SITE I, BINDING SITE II or BINDING SITE III of FIG. 1. The nucleotide sequences of pbpG BINDING SITE 1 and pbpG BINDING SITE 2, and the complementary secondary structure to the nucleotide sequence of GAM353678 RNA are set forth in Tables 6-7, hereby incorporated herein. Another function of GAM353678 is to inhibit pbpG, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | A |
| GAM35 3678 | CAGCAGCA CACTGTGG TTTGTA | Human | pchA | *Pseudomonas aeruginosa* PA01 | GAM353678 is a human miRNA-like oligonucleotide, which targets salicylate biosynthesis isochorismate synthase (pchA, NC_002516 from 4745120 to 4746550 (+)), a bacterial target gene encoded by the *Pseudomonas aeruginosa* PA01 genome, as part of an anti-bacterial host defense mechanism. pchA BINDING SITE 1 and pchA BINDING SITE 2 are bacterial target binding sites that are found in the untranslated regions of mRNA encoded by the pchA gene, corresponding to target binding sites such as BINDING SITE I, BINDING SITE II or BINDING SITE III of FIG. 1. The nucleotide sequences of pchA BINDING SITE 1 and pchA BINDING SITE 2, and the complementary secondary structure to the nucleotide sequence of GAM353678 RNA are set forth in Tables 6-7, hereby incorporated herein. Another function of GAM353678 is to inhibit pchA, a GAM353678 bacterial target gene which is associated with *Pseudomonas aeruginosa* PA01 infection, as part of an anti-bacterial | A |

TABLE 8-continued

| GAM NAME | GAM RNA SEQUENCE | GAM ORGA- NISM | TAR- GET | TARGET ORGANISM | GAM FUNCTION | POS |
|---|---|---|---|---|---|---|
| | | | | | host defense mechanism. Accordingly, the utilities of GAM353678 include the diagnosis, prevention and treatment of *Pseudomonas aeruginosa* PA01 infection and associated clinical conditions | |
| GAM35 3678 | CAGCAGCA CACTGTGG TTTGTA | Human | pcnA | *Mycobacterium leprae* | GAM353678 is a human miRNA-like oligonucleotide, which targets pcnA (pcnA, NC_002677 from 3248268 to 3249728 (−)), a bacterial target gene encoded by the *Mycobacterium leprae* genome, as part of an anti-bacterial host defense mechanism. pcnA BINDING SITE 1 and pcnA BINDING SITE 2 are bacterial target binding sites that are found in the untranslated regions of mRNA encoded by the pcnA gene, corresponding to target binding sites such as BINDING SITE I, BINDING SITE II or BINDING SITE III of FIG. 1. The nucleotide sequences of pcnA BINDING SITE 1 and pcnA BINDING SITE 2, and the complementary secondary structure to the nucleotide sequence of GAM353678 RNA are set forth in Tables 6-7, hereby incorporated herein. Another function of GAM353678 is to inhibit pcnA, a GAM353678 bacterial target gene which is associated with *Mycobacterium leprae* infection, as part of an anti-bacterial host defense mechanism. Accordingly, the utilities of GAM353678 include the diagnosis, prevention and treatment of *Mycobacterium leprae* infection and associated clinical conditions | A |
| GAM35 3678 | CAGCAGCA CACTGTGG TTTGTA | Human | phnV | *Salmonella enterica enterica serovar Typhi* | GAM353678 is a human miRNA-like oligonucleotide, which targets probable membrane component of 2-aminoethylphosphonate transp orter (phnV, NC_003198 from 471575 to 472366 (−)), a bacterial target gene encoded by the *Salmonella enterica enterica serovar Typhi* genome, as part of an anti-bacterial host defense mechanism. phnV BINDING SITE 1 and phnV BINDING SITE 2 are bacterial target binding sites that are found in the untranslated regions of mRNA encoded by the phnV gene, corresponding to target binding sites such as BINDING SITE I, BINDING SITE II or BINDING SITE III of FIG. 1. The nucleotide sequences of phnV BINDING SITE 1 and phnV BINDING SITE 2, and the complementary secondary structure to the nucleotide sequence of GAM353678 RNA are set forth in Tables 6-7, hereby incorporated herein. Another function of GAM353678 is to inhibit phnV, a GAM353678 bacterial target gene which is associated with *Salmonella enterica enterica serovar Typhi* infection, as part of an anti-bacterial host defense mechanism. Accordingly, the utilities of GAM353678 include the diagnosis, prevention and treatment of *Salmonella enterica enterica serovar Typhi* infection and associated clinical conditions | A |
| GAM35 3678 | CAGCAGCA CACTGTGG TTGTA | Human | phnV | *Salmonella enterica enterica serovar Typhi* Ty 2 | GAM353678 is a human miRNA-like oligonucleotide, which targets probable membrane component of 2-aminoethylphosphonate transporter (phnV, NC_004631 from 2508735 to 2509526 (+)), a bacterial target gene encoded by the *Salmonella enterica enterica serovar Typhi* Ty2 genome, as part of an anti-bacterial host defense mechanism. phnV BINDING SITE 1 and phnV BINDING SITE 2 are bacterial target binding sites that are found in the untranslated regions of mRNA | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | encoded by the phnV gene, corresponding to target binding sites such as BINDING SITE I, BINDING SITE II or BINDING SITE III of FIG. 1. The nucleotide sequences of phnV BINDING SITE 1 and phnV BINDING SITE 2, and the complementary secondary structure to the nucleotide sequence of GAM353678 RNA are set forth in Tables 6-7, hereby incorporated herein. Another function of GAM353678 is to inhibit phnV, a GAM353678 bacterial target gene which is associated with *Salmonella enterica enterica serovar Typhi* Ty2 infection, as part of an anti- bacterial host defense mechanism. Accordingly, the utilities of GAM353678 include the diagnosis, prevention and treatment of *Salmonella enterica enterica serovar Typhi* Ty2 infection and associated clinical conditions | |
| GAM35 3678 | CAGCAGCA CACTGTGG TTTGTA | Human | phoY2 | *Mycobacterium bovis* subsp *bovis* AF21 22/97 | GAM353678 is a human miRNA-like oligonucleotide, which targets PROBABLE PHOSPHATE-TRANSPORT SYSTEM TRANSCRIPTIONAL REGULATORY PROTEIN PHOY2 (phoY2, NC_002945 from 914388 to 915029 (−)), a bacterial target gene encoded by the *Mycobacterium bovis* subsp *bovis* AF2122/97 genome, as part of an anti-bacterial host defense mechanism. phoY2 BINDING SITE 1 and phoY2 BINDING SITE 2 are bacterial target binding sites that are found in the untranslated regions of mRNA encoded by the phoY2 gene, corresponding to target binding sites such as BINDING SITE I, BINDING SITE II or BINDING SITE III of FIG. 1. The nucleotide sequences of phoY2 BINDING SITE 1 and phoY2 BINDING SITE 2, and the complementary secondary structure to the nucleotide sequence of GAM353678 RNA are set forth in Tables 6-7, hereby incorporated herein. Another function of GAM353678 is to inhibit phoY2, a GAM353678 bacterial target gene which is associated with *Mycobacterium bovis* subsp *bovis* AF2122/97 infection, as part of an anti- bacterial host defense mechanism. Accordingly, the utilities of GAM353678 include the diagnosis, prevention and treatment of *Mycobacterium bovis* subsp *bovis* AF2122/97 infection and associated clinical conditions | A |
| GAM35 3678 | CAGCAGCA CACTGTGG TTTGTA | Human | phoY2 | *Mycobacterium tubrculosis* H37Rv | GAM353678 is a human miRNA-like oligonucleotide, which targets phoY2 (phoY2, NC_000962 from 913556 to 914197 (−)), a bacterial target gene encoded by the *Mycobacterium tuberculosis* H37Rv genome, as part of an anti-bacterial host defense mechanism. phoY2 BINDING SITE 1 and phoY2 BINDING SITE 2 are bacterial target binding sites that are found in the untranslated regions of mRNA encoded by the phoY2 gene, corresponding to target binding sites such as BINDING SITE I, BINDING SITE II or BINDING SITE III of FIG. 1. The nucleotide sequences of phoY2 BINDING SITE 1 and phoY2 BINDING SITE 2, and the complementary secondary structure to the nucleotide sequence of GAM353678 RNA are set forth in Tables 6-7, hereby incorporated herein. Another function of GAM353678 is to inhibit phoY2, a GAM353678 bacterial target gene which is associated with *Mycobacterium tuberculosis* H37Rv infection, as part of an anti-bacterial host defense mechanism. Accordingly, the utilities of GAM353678 include the diagnosis, prevention and treatment of | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| GAM35 3678 | CAGCAGCA CACTGTGG TTTGTA | Human | pilT | *Pseudomonas putida* KT2440 | *Mycobacterium tuberculosis* H37Rv infection and associated clinical conditions GAM353678 is a human miRNA-like oligonucleotide, which targets type IV pili twitching motility protein PilT (pilT, NC_002947 from 5816934 to 5817944 (−)), a bacterial target gene encoded by the *Pseudomonas putida* KT2440 genome, as part of an anti-bacterial host defense mechanism. pilT BINDING SITE 1 through pilT BINDING SITE 3 are bacterial target binding sites that are found in the untranslated regions of mRNA encoded by the pilT gene, corresponding to target binding sites such as BINDING SITE I, BINDING SITE II or BINDING SITE III of FIG. 1. The nucleotide sequences of pilT BINDING SITE 1 through pilT BINDING SITE 3, and the complementary secondary structure to the nucleotide sequence of GAM353678 RNA are set forth in Tables 6-7, hereby incorporated herein. Another function of GAM353678 is to inhibit pilT, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | A |
| GAM35 3678 | CAGCAGCA CACTGTGG TTTGTA | Human | polA | *Mycobacterium leprae* | GAM353678 is a human miRNA-like oligonucleotide, which targets DNA polymerase I (polA, NC_002677 from 1648220 to 1650955 (−)), a bacterial target gene encoded by the *Mycobacterium leprae* genome, as part of an anti-bacterial host defense mechanism. polA BINDING SITE 1 and polA BINDING SITE 2 are bacterial target binding sites that are found in the untranslated regions of mRNA encoded by the polA gene, corresponding to target binding sites such as BINDING SITE I, BINDING SITE II or BINDING SITE III of FIG. 1. The nucleotide sequences of polA BINDING SITE 1 and polA BINDING SITE 2, and the complementary secondary structure to the nucleotide sequence of GAM353678 RNA are set forth in Tables 6-7, hereby incorporated herein. Another function of GAM353678 is to inhibit polA, a GAM353678 bacterial target gene which is associated with *Mycobacterium leprae* infection, as part of an anti-bacterial host defense mechanism. Accordingly, the utilities of GAM353678 include the diagnosis, prevention and treatment of *Mycobacterium leprae* infection and associated clinical conditions | A |
| GAM35 3678 | CAGCAGCA CACTGTGG TTTGTA | Human | prcA | *Mycobacterium leprae* | GAM353678 is a human miRNA-like oligonucleotide, which targets proteasome [alpha]-type subunit 1 (prcA, NC_002677 from 1576553 to 1577350 (+)), a bacterial target gene encoded by the *Mycobacterium leprae* genome, as part of an anti-bacterial host defense mechanism. prcA BINDING SITE 1 and prcA BINDING SITE 2 are bacterial target binding sites that are found in the untranslated regions of mRNA encoded by the prcA gene, corresponding to target binding sites such as BINDING SITE I, BINDING SITE II or BINDING SITE III of FIG. 1. The nucleotide sequences of prcA BINDING SITE 1 and prcA BINDING SITE 2, and the complementary secondary structure to the | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | nucleotide sequence of GAM353678 RNA are set forth in Tables 6-7, hereby incorporated herein. Another function of GAM353678 is to inhibit prcA, a GAM353678 bacterial target gene which is associated with *Mycobacterium leprae* infection, as part of an anti-bacterial host defense mechanism. Accordingly, the utilities of GAM353678 include the diagnosis, prevention and treatment of *Mycobacterium leprae* infection and associated clinical conditions | |
| GAM35 3678 | CAGCAGCA CACTGTGG TTTGTA | Human | pta | *Pseudomonas putida* KT2440 | GAM353678 is a human miRNA-like oligonucleotide, which targets phosphate acetyltransferase (pta, NC_002947 from 891625 to 893712 (−)), a bacterial target gene encoded by the *Pseudomonas putida* KT2440 genome, as part of an anti-bacterial host defense mechanism. pta BINDING SITE 1 and pta BINDING SITE 2 are bacterial target binding sites that are found in the untranslated regions of mRNA encoded by the pta gene, corresponding to target binding sites such as BINDING SITE I, BINDING SITE II or BINDING SITE III of FIG. 1. The nucleotide sequences of pta BINDING SITE 1 and pta BINDING SITE 2, and the complementary secondary structure to the nucleotide sequence of GAM353678 RNA are set forth i n Tables 6-7, hereby incorporated herein. Another function of GAM353678 is to inhibit pta, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | A |
| GAM35 3678 | CAGCAGCA CACTGTGG TTTGTA | Human | ptsH | *Salmonella enterica enterica serovar Typhi* | GAM353678 is a human miRNA-like oligonucleotide, which targets phosphocarrier protein HPr (ptsH, NC_003198 from 2505403 to 2505660 (+)), a bacterial target gene encoded by the *Salmonella enterica enterica serovar Typhi* genome, as part of an anti-bacterial host defense mechanism. ptsH BINDING SITE is a bacterial target binding site that is a found in the the 3' untranslated region of mRNA encoded by the ptsH gene, corresponding to a target binding site such as BINDING SITE I, BINDING SITE II or BINDING SITE III of FIG. 1. The nucleotide sequences of ptsH BINDING SITE, and the complementary secondary structure to the nucleotide sequence of GAM353678 RNA are set forth in Tables 6-7, hereby incorporated herein. Another function of GAM353678 is to inhibit ptsH, a GAM353678 bacterial target gene which is associated with *Salmonella enterica enterica serovar Typhi* infection, as part of an anti-bacterial host defense mechanism. Accordingly, the utilities of GAM353678 include the diagnosis, prevention and treatment of *Salmonella enterica enterica serovar Typhi* infection and associated clinical conditions | A |
| GAM35 3678 | CAGCAGCA CACTGTGG TTTGTA | Human | rbsR | *Shigella flexneri* 2a str. 3 01 | GAM353678 is a human miRNA-like oligonucleotide, which targets regulator for rbs operon (rbsR, NC_004337 from 3947708 to 3 948700 (+)), a bacterial target gene encoded by the *Shigella flexneri* 2a str. 301 genome, as part of an anti-bacterial host defense mechanism. | A |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | rbsR BINDING SITE 1 through rbsR BINDING SITE 3 are bacterial target binding sites that are found in the untranslated regions of mRNA encoded by the rbsR gene, corresponding to target binding sites such as BINDING SITE I, BINDING SITE II or BINDING SITE III of FIG. 1. The nucleotide sequences of rbsR BINDING SITE 1 through rbsR BINDING SITE 3, and the complementary secondary structure to the nucleotide sequence of GAM353678 RNA are set forth in Tables 6-7, hereby incorporated herein. Another function of GAM353678 is to inhibit rbsR, a GAM353678 bacterial target gene which is associated with *Shigella flexneri* 2a str. 301 infection, as part of an anti-bacterial host defense mechanism. Accordingly, the utilities of GAM353678 include the diagnosis, prevention and treatment of *Shigella flexneri* 2a str. 301 infection and associated clinical conditions | |
| GAM353678 | CAGCAGCACACTGTGGTTTGTA | Human | rbsR | *Shigella flexneri* 2a str. 2457T | GAM353678 is a human miRNA-like oligonucleotide, which targets regulator for rbs operon (rbsR, NC_004741 from 3824594 to 3825577 (−)), a bacterial target gene encoded by the *Shigella flexneri* 2a str. 2457T genome, as part of an anti-bacterial host defense mechanism. rbsR BINDING SITE 1 through rbsR BINDING SITE 3 are bacterial target binding sites that are found in the untranslated regions of mRNA encoded by the rbsR gene, corresponding to target binding sites such as BINDING SITE I, BINDING SITE II or BINDING SITE III of FIG. 1. The nucleotide sequences of rbsR BINDING SITE 1 through rbsR BINDING SITE 3, and the complementary secondary structure to the nucleotide sequence of GAM353678 RNA are set forth in Tables 6-7, hereby incorporated herein. Another function of GAM353678 is to inhibit rbsR, a GAM353678 bacterial target gene which is associated with *Shigella flexneri* 2a str. 2457T infection, as part of an anti-bacterial host defense mechanism. Accordingly, the utilities of GAM353678 include the diagnosis, prevention and treatment of *Shigella flexneri* 2a str. 2457T infection and associated clinical conditions | A |
| GAM353678 | CAGCAGCACACTGTGGTTTGTA | Human | rbsR | *Escherichia coli* CFT073 | GAM353678 is a human miRNA-like oligonucleotide, which targets Ribose operon repressor (rbsR, NC_004431 from 4439260 to 4440252 (+)), a bacterial target gene encoded by the *Escherichia coli* CFT073 genome, as part of an anti-bacterial host defense mechanism. rbsR BINDING SITE 1 through rbsR BINDING SITE 3 are bacterial target binding sites that are found in the untranslated regions of mRNA encoded by the rbsR gene, corresponding to target binding sites such as BINDING SITE I, BINDING SITE II or BINDING SITE III of FIG.l. The nucleotide sequences of rbsR BINDING SITE 1 through rbsR BINDING SITE 3, and the complementary secondary structure to the nucleotide sequence of GAM353678 RNA are set forth in Tables 6-7, hereby incorporated herein. Another function of GAM353678 is to inhibit rbsR, a GAM353678 bacterial target gene which is associated with *Escherichia coli* CFT073 infection, as part of an anti-bacterial host defense mechanism. Accordingly, the utilities of GAM353678 | |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | include the diagnosis, prevention and treatment of *Escherichia coli* CFT073 infection and associated clinical conditions | |
| GAM35 3678 | CAGCAGCA CACTGTGG TTTGTA | Human | recG | *Mycobacterium leprae* | GAM353678 is a human miRNA-like oligonucleotide, which targets ATP-dependent DNA helicase (recG, NC_002677 from 2014723 to 2016954 (−)), a bacterial target gene encoded by the *Mycobacterium leprae* genome, as part of an anti-bacterial host defense mechanism. recG BINDING SITE 1 and recG BINDING SITE 2 are bacterial target binding sites that are found in the untranslated regions of mRNA encoded by the recG gene, corresponding to target binding sites such as BINDING SITE I, BINDING SITE II or BINDING SITE III of FIG. 1. The nucleotide sequences of recG BINDING SITE 1 and recG BINDING SITE 2, and the complementary secondary structure to the nucleotide sequence of GAM353678 RNA are set forth in Tables 6-7, hereby incorporated herein. Another function of GAM353678 is to inhibit recG, a GAM353678 bacterial target gene which is associated with *Mycobacterium leprae* infection, as part of an anti-bacterial host defense mechanism. Accordingly, the utilities of GAM353678 include the diagnosis, prevention and treatment of *Mycobacterium leprae* infection and associated clinical conditions | A |
| GAM35 3678 | CAGCAGCA CACTGTGG TTTGTA | Human | relA | *Mycobacterium bovis* subsp *bovis* AF21 22/97 | GAM353678 is a human miRNA-like oligonucleotide, which targets PROBABLE GTP PYROPHOSPHOKINASE RELA (ATP:GTP 3'-PYROPHOSPHOTR ANSFERASE) (PPGPP SYNTHETASE I) ((P)PPGPP SYNTHETASE) (GTP DIPHOSPHOKINASE) (relA, NC_002945 from 2875274 to 2877646 (−) ), a bacterial target gene encoded by the *Mycobacterium bovis* subsp *bovis* AF2122/97 genome, as part of an anti-bacterial host defense mechanism. relA BINDING SITE 1 and relA BINDING SITE 2 are bacterial target binding sites that are found in the untranslated regions of mRNA encoded by the relA gene, corresponding to target binding sites such as BINDING SITE I, BINDING SITE II or BINDING SITE III of FIG. 1. The nucleotide sequences of relA BINDING SITE 1 and relA BINDING SITE 2, and the complementary secondary structure to the nucleotide sequence of GAM353678 RNA are set forth in Tables 6-7, hereby incorporated herein. Another function of GAM353678 is to inhibit relA, a GAM353678 bacterial target gene which is associated with *Mycobacterium bovis* subsp *bovis* AF2122/97 infection, as part of an anti-bacterial host defense mechanism. Accordingly, the utilities of GAM353678 include the diagnosis, prevention and treatment of *Mycobacterium bovis* subsp *bovis* AF2122/97 infection and associated clinical conditions | A |
| GAM35 3678 | CAGCAGCA CACTGTGG TTTGTA | Human | relA | *Mycobacterium tuberculosis* H37Rv | GAM353678 is a human miRNA-like oligonucleotide, which targets relA (relA, NC_000962 from 2907824 to 2910196 (−)), a bacterial target gene encoded by the *Mycobacterium tuberculosis* H37Rv genome, as part of an anti-bacterial host defense mechanism. relA BINDING SITE 1 and relA BINDING SITE 2 are bacterial target binding sites that are found in the untranslated regions of mRNA encoded by | A |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | the relA gene, corresponding to target binding sites such as BINDING SITE I, BINDING SITE II or BINDING SITE III of FIG. 1. The nucleotide sequences of relA BINDING SITE 1 and relA BINDING SITE 2, and the complementary secondary structure to the nucleotide sequence of GAM353678 RNA are set forth in Tables 6-7, hereby incorporated herein. Another function of GAM353678 is to inhibit relA, a GAM353678 bacterial target gene which is associated with *Mycobacterium tuberculosis* H37Rv infection, as part of an anti-bacterial host defense mechanism. Accordingly, the utilities of GAM353678 in clude the diagnosis, prevention and treatment of *Mycobacterium tuberculosis* H37Rv infection and associated clinical conditions | |
| GAM35 3678 | CAGCAGCA CACTGTGG TTTGTA | Human | risA | *Bordetella pertussis* | GAM353678 is a human miRNA-like oligonucleotide, which targets tresponse regulator protein (risA, NC_002929 from 3765257 to 3765991 (−)), a bacterial target gene encoded by the *Bordetella pertussis* genome, as part of an anti-bacterial host defense mechanism. risA BINDING SITE 1 and risA BINDING SITE 2 are bacterial target binding sites that are found in the untranslated regions of mRNA encoded by the risA gene, corresponding to target binding sites such as BINDING SITE I, BINDING SITE II or BINDING SITE III of FIG. 1. The nucleotide sequences of risA BINDING SITE 1 and risA BINDING SITE 2, and the complementary secondary structure to the nucleotide sequence of GAM353678 RNA are set forth in Tables 6-7, hereby incorporated herein. Another function of GAM353678 is to inhibit risA, a GAM353678 bacterial target gene which is associated with *Bordetella pertussis* infection, as part of an anti-bacterial host defense mechanism. Accordingly, the utilities of GAM353678 include the diagnosis, prevention and treatment of *Bordetella pertussis* infection and associated clinical conditions | A |
| GAM35 3678 | CAGCAGCA CACTGTGG TTTGTA | Human | rpsT | *Pseudomonas putida* KT2440 | GAM353678 is a human miRNA-like oligonucleotide, which targets ribosomal protein S20 (rpsT, NC_002947 from 707068 to 707346 (−)), a bacterial target gene encoded by the *Pseudomonas putida* KT2440 genome, as part of an anti-bacterial host defense mechanism. rpsT BINDING SITE 1 and rpsT BINDING SITE 2 are bacterial target binding sites that are found in the untranslated regions of mRNA encoded by the rpsT gene, corresponding to target binding sites such as BINDING SITE I, BINDING SITE II or BINDING SITE III of FIG. 1. The nucleotide sequences of rpsT BINDING SITE 1 and rpsT BINDING SITE 2, and the complementary secondary structure to the nucleotide sequence of GAM353678 RNA are set forth in Tables 6-7, hereby incorporated herein. Another function of GAM353678 is to inhibit rpsT, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | A |

TABLE 8-continued

| GAM NAME | GAM RNA SEQUENCE | GAM ORGANISM | TARGET | TARGET ORGANISM | GAM FUNCTION | POS |
|---|---|---|---|---|---|---|
| GAM35 3678 | CAGCAGCA CACTGTGG TTTGTA | Human | ruvB | *Yersinia pestis* | GAM353678 is a human miRNA-like oligonucleotide, which targets Holliday Junction DNA helicase (ruvB, NC_003143 from 2336449 to 2337453 (+)), a bacterial target gene enc

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | inhibit selB, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | |
| GAM35 3678 | CAGCAGCA CACTGTGG TTTGTA | Human | SERPI NH1 | Human | GAM353678 is a human miRNA-like oligonucleotide, which targets a human Serine proteinase inhibitor clade H (heat shock protein 47) member 1; (SERPINH1, Accession number: NM_001235) as part of a host response mechanism associated with a *Escherichia coli* CFT073, *Streptococcus pneumoniae* R6, *Streptococcus pneumoniae* TIGR4, *Streptococcus pyogenes* M1 GAS, *Streptococcus pyogenes* MGAS315, *Streptococcus pyogenes* MGAS8232 and *Streptococcus pyogenes* SSI-1 infections. SERPINH1 BINDING SITE 1 and SERPINH1 BINDING SITE 2 are human target binding sites that are found in the untranslated regions of mRNA encoded by the SERPINH1 gene, corresponding to target binding sites such as BINDING SITE I, BINDING SITE II or BINDING SITE III of FIG. 1. Additionally, using the binding site prediction system of the present invention GAM353678-A binds to sequences on orthologous UTR of rat(NM_017173). The nucleotide sequences of SERPINH1 BINDING SITE 1 and SERPINH1 BINDING SITE 2, and the complementary secondary structure to the nucleotide sequence of GAM353678 RNA are set forth in Tables 6-7, hereby incorporated herein. Another function of GAM353678 is to inhibit SERPINH1, a GAM353678 human target gene which encodes a heat shock protein and serpin, that may function as a chaperone for procollagen in the ER. SERPINH1 is associated with *Escherichia coli* CFT073, *Streptococcus pneumoniae* R6, *Streptococcus pneumoniae* TIGR4, *Streptococcus pyogenes* M1 GAS, *Streptococcus pyogenes* MGAS315, *Streptococcus pyogenes* MGAS8232 and *Streptococcus pyogenes* SSI-1 infections, and therefore GAM353678 is associated with the above mentioned infections, as part of a host response mechanism. Accordingly, the utilities of GAM353678 include the diagnosis, prevention and treatment of *Escherichia coli* CFT073, *Streptocoecus pneumoniae* R6, *Streptococcus pneumoniae* TIGR4, *Streptococcus pyogenes* M1 GAS, *Streptococcus pyogenes* MGAS315, *Streptocoecus pyogenes* MGAS8232 and *Streptococcus pyogenes* SSI-1 infections and associated clinical conditions. The function of SERPINH1 and its association with various diseases and clinical conditions has been established by previous studies, as described hereinabove with reference to GAM839. | A |
| GAM35 3678 | CAGCAGCA CACTGTGG TTTGTA | Human | sitD | *Shigella flexneri* 2a str. 301 | GAM353678 is a human miRNA-like oligonucleotide, which targets Iron transport protein, inner membrane component (sitD, NC_004337 from 1405360 to 1406217 (−)), a bacterial target gene encoded by the *Shigella flexneri* 2a str. 301 genome, as part of an anti-bacterial host defense mechanism. sitD BINDING SITE 1 and sitD BINDING SITE 2 are bacterial target binding sites that are found in | A |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | the untranslated regions of mRNA encoded by the sitD gene, corresponding to target binding sites such as BINDING SITE I, BINDING SITE II or BINDING SITE III of FIG. 1. The nucleotide sequences of sitD BINDING SITE 1 and sitD BINDING SITE 2, and the complementary secondary structure to the nucleotide sequence of GAM353678 RNA are set forth in Tables 6-7, hereby incorporated herein. Another function of GAM353678 is to inhibit sitD, a GAM353678 bacterial target gene which is associated with *Shigella flexneri* 2a str. 301 infection, as part of an anti-bacterial host defense mechanism. Accordingly, the utilities of GAM353678 include the diagnosis, prevention and treatment of *Shigella flexneri* 2a str. 301 infection and associated clinical conditions | |
| GAM353678 | CAGCAGCACACTGTGGTTTGTA | Human | sitD | *Shigella flexneri* 2a str. 2457T | GAM353678 is a human miRNA-like oligonucleotide, which targets Iron transport protein, inner membrane component (sitD, NC_004741 from 1904666 to 1905523 (+)), a bacterial target gene encoded by the *Shigella flexneri* 2a str. 2457T genome, as part of an anti-bacterial host defense mechanism. sitD BINDING SITE 1 and sitD BINDING SITE 2 are bacterial target binding sites that are found in the untranslated regions of mRNA encoded by the sitD gene, corresponding to target binding sites such as BINDING SITE I, BINDING SITE II or BINDING SITE III of FIG. 1. The nucleotide sequences of sitD BINDING SITE 1 and sitD BINDING SITE 2, and the complementary secondary structure to the nucleotide sequence of GAM353678 RNA are set forth in Tables 6-7, hereby incorporated herein. Another function of GAM353678 is to inhibit sitD, a GAM353678 bacterial target gene which is associated with *Shigella flexneri* 2a str. 2457T infection, as part of an anti-bacterial host defense mechanism. Accordingly, the utilities of GAM353678 include the diagnosis, prevention and treatment of *Shigella flexneri* 2a str. 2457T infection and associated clinical conditions | A |
| GAM353678 | CAGCAGCACACTGTGGTTTGTA | Human | speD | *Salmonella enterica enterica serovar Typhi* Ty2 | GAM353678 is a human miRNA-like oligonucleotide, which targets S-adenosylmethionine decarboxylase proenzyme (speD, NC_004631 from 196380 to 197174 (−)), a bacterial target gene encoded by the *Salmonella enterica enterica serovar Typhi* Ty2 genome, as part of an anti-bacterial host defense mechanism. speD BINDING SITE 1 and speD BINDING SITE 2 are bacterial target binding sites that are found in the untranslated regions of mRNA encoded by the speD gene, corresponding to target binding sites such as BINDING SITE I, BINDING SITE II or BINDING SITE III of FIG. 1. The nucleotide sequences of speD BINDING SITE 1 and speD BINDING SITE 2, and the complementary secondary structure to the nucleotide sequence of GAM353678 RNA are set forth in Tables 6-7, hereby incorporated herein. Another function of GAM353678 is to inhibit speD, a GAM353678 bacterial target gene which is associated withi Salmonella enterica enterica serovar *Typhi* Ty2 infection, as part of an anti-bacterial host defense mechanism. Accordingly, the utilities of GAM353678 include the diagnosis, prevention and treatment of *Salmonella enterica enterica* | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | *serovar Typhi* Ty2 infection and associated clinical conditions | |
| GAM35 3678 | CAGCAGCA CACTGTGG TTTGTA | Human | speD | *Salmonella enterica enterica serovar Typhi* | GAM353678 is a human miRNA-like oligonucleotide, which targets S-adenosylmethionine decarboxylase proenzyme (speD, NC_003198 from 196389 to 197183 (−)), a bacterial target gene encoded by the *Salmonella enterica enterica serovar Typhi* genome, as part of an anti-bacterial host defense mechanism. speD BINDING SITE 1 and speD BINDING SITE 2 are bacterial target binding sites that are found in the untranslated regions of mRNA encoded by the speD gene, corresponding to target binding sites such as BINDING SITE I, BINDING SITE II or BINDING SITE III of FIG. 1. The nucleotide sequences of speD BINDING SITE 1 and speD BINDING SITE 2, and the complementary secondary structure to the nucleotide sequence of GAM353678 RNA are set forth in Tables 6-7, hereby incorporated herein. Another function of GAM353678 is to inhibit speD, a GAM353678 bacterial target gene which is associated with *Salmonella enterica enterica serovar Typhi* infection, as part of an anti-bacterial host defense mechanism. Accordingly, the utilities of GAM353678 include the diagnosis, prevention and treatment of *Salmonella enterica enterica serovar Typhi* infection and associated clinical conditions | A |
| GAM35 3678 | CAGCAGCA CACTGTGG TTTGTA | Human | speD | *Salmonella typhimurium* LT2 | GAM353678 is a human miRNA-like oligonucleotide, which targets S-adenosylmethionine decarboxylase (speD, NC_003197 from 194201 to 194995 (−)), a bacterial target gene encoded by the *Salmonella typhimurium* LT2 genome, as part of an anti-bacterial host defense mechanism. speD BINDING SITE 1 and speD BINDING SITE 2 are bacterial target binding sites that are found in the untranslated regions of mRNA encoded by the speD gene, corresponding to target binding sites such as BINDING SITE I, BINDING SITE II or BINDING SITE III of FIG. 1. The nucleotide sequences of speD BINDING SITE 1 and speD BINDING SITE 2, and the complementary secondary structure to the nucleotide sequence of GAM353678 RNA are set forth in Tables 6-7, hereby incorporated herein. Another function of GAM353678 is to inhibit speD, a GAM353678 bacterial target gene which is associated with *Salmonella typhimurium* LT2 infection, as part of an anti-bacterial host defense mechanism. Accordingly, the utilities of GAM353678 include the diagnosis, prevention and treatment of *Salmonella typhimurium* LT2 infection and associated clinical conditions | A |
| GAM35 3678 | CAGCAGCA CACTGTGG TTTGTA | Human | ssb | *Pseudomonas putida* KT2440 | GAM353678 is a human miRNA-like oligonucleotide, which targets single-stranded DNA-binding protein (ssb, NC_002947 from 571027 to 571572 (+)), a bacterial target gene encoded by the *Pseudomonas putida* KT2440 genome, as part of an anti-bacterial host defense mechanism. ssb BINDING SITE 1 and ssb BINDING SITE 2 are bacterial target binding sites that are found in the untranslated regions of m RNA encoded by the ssb gene, corresponding to target binding sites such as BINDING SITE I, BINDING SITE II or BINDING SITE III of FIG. 1. The nucleotide sequences of ssb | A |

TABLE 8-continued

| GAM NAME | GAM RNA SEQUENCE | GAM ORGA-NISM | TAR-GET | TARGET ORGANISM | GAM GAM FUNCTION | POS |
|---|---|---|---|---|---|---|
| | | | | | BINDING SITE 1 and ssb BINDING SITE 2, and the complementary secondary structure to the nucleotide sequence of GAM353678 RNA are set forth in Tables 6-7, hereby incorporated herein. Another function of GAM353678 is to inhibit ssb, a GAM353678 bacterial target gene which is associated with *Pseudomonas putida* KT2440 infection, as part of an anti-bacterial host defense mechanism. Accordingly, the utilities of GAM353678 include the diagnosis, prevention and treatment of *Pseudomonas putida* KT2440 infection and associated clinical conditions | |
| GAM35 3678 | CAGCAGCA CACTGTGG TTTGTA | Human | sseB | *Escherichia coli* CFT073 | GAM353678 is a human miRNA-like oligonucleotide, which targets Protein sseB (sseB, NC_004431 from 2922456 to 2923241 (−) ), a bacterial target gene encoded by the *Escherichia coli* CFT073 genome, as part of an anti-bacterial host defense mechanism. sseB BINDING SITE 1 and sseB BINDING SITE 2 are bacterial target binding sites that are found in the untranslated regions of mRNA encoded by the sseB gene, corresponding to target binding sites such as BINDING SITE I, BINDING SITE II or BINDING SITE III of FIG. 1. The nucleotide sequences of sseB BINDING SITE 1 and sseB BINDING SITE 2, and the complementary secondary structure to the nucleotide sequence of GAM353678 RNA are set forth in Tables 6-7, hereby incorporated herein. Another function of GAM353678 is to inhibit sseB, a GAM353678 bacterial target gene which is associated with *Escherichia coli* CFT073 infection, as part of an anti-bacterial host defense mechanism. Accordingly, the utilities of GAM353678 include the diagnosis, prevention and treatment of *Escherichia coli* CFT073 infection and associated clinical conditions | A |
| GAM35 3678 | CAGCAGCA CACTGTGG TTTGTA | Human | tcfA | *Bordetella pertussis* | GAM353678 is a human miRNA-like oligonucleotide, which targets tracheal colonization factor precursor (tcfA, NC_002929 from 1264436 to 1266379 (+)), a bacterial target gene encoded by the *Bordetella pertussis* genome, as part of an anti-bacterial host defense mechanism. tcfA BINDING SITE 1 and tcfA BINDING SITE 2 are bacterial target binding sites that are found in the untranslated regions of mRNA encoded by the tcfA gene, corresponding to target binding sites such as BINDING SITE I, BINDING SITE II or BINDING SITE III of FIG. 1. The nucleotide sequences of tcfA BINDING SITE 1 and tcfA BINDING SITE 2, and the complementary secondary structure to the nucleotide sequence of GAM353678 RNA are set forth in Tables 6-7, hereby incorporated herein. Another function of GAM353678 is to inhibit tcfA, a GAM353678 bacterial target gene which is associated with *Bordetella pertussis* infection, as part of an anti-bacterial host defense mechanism. Accordingly, the utilities of GAM353678 include the diagnosis, prevention and treatment of *Bordetella pertussis* infection and associated clinical conditions | A |
| GAM35 3678 | CAGCAGCA CACTGTGG TTTGTA | Human | truA | *Mycobacterium leprae* | GAM353678 is a human miRNA-like oligonucleotide, which targets probable pseudouridylate synthase (truA, NC_002677 from 2343329 to 2344078 (−)), a bacterial target gene encoded by the | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | *Mycobacterium leprae* genome, as part of an anti-bacterial host defense mechanism. truA BINDING SITE 1 and truA BINDING SITE 2 are bacterial target binding sites that are found in the untranslated regions of mRNA encoded by the truA gene, corresponding to target binding sites such as BINDING SITE I, BINDING SITE II or BINDING SITE III of FIG. 1. The nucleotide sequences of truA BINDING SITE 1 and truA BINDING SITE 2, and the complementary secondary structure to the nucleotide sequence of GAM353678 RNA are set forth in Tables 6-7, hereby incorporated herein. Another function of GAM353678 is to inhibit truA, a GAM353678 bacterial target gene which is associated with *Mycobacterium leprae* infection, as part of an anti-bacterial host defense mechanism. Accordingly, the utilities of GAM353678 include the diagnosis, prevention and treatment of *Mycobacterium leprae* infection and associated clinical conditions | |
| GAM35 3678 | CAGCAGCA CACTGTGG TTTGTA | Human | trunc ated fmtB | *Staphylococcus aureus* subsp. MW2 | GAM353678 is a human miRNA-like oligonucleotide, which targets truncated FmtB protein (truncated fmtB, NC_003923 *aureus* from 2238083 to 2240143 (−)), a bacterial target gene encoded by the *Staphylococcus aureus* subsp. *aureus* MW2 genome, as part of an anti-bacterial host defense mechanism. truncated fmtB BINDING SITE 1 and truncated fmtB BINDING SITE 2 are bacterial target binding sites that are found in the untranslated regions of mRNA encoded by the truncated fmtB gene, corresponding to target binding sites such as BINDING SITE I, BINDING SITE II or BINDING SITE III of FIG. 1. The nucleotide sequences of truncated fmtB BINDING SITE 1 and truncated fmtB BINDING SITE 2, and the complementary secondary structure to the nucleotide sequence of GAM353678 RNA are set forth in Table s 6-7, hereby incorporated herein. Another function of GAM353678 is to inhibit truncated fmtB, a GAM353678 bacterial target gene which is associated with *Staphylococcus aureus* subsp. *aureus* MW2 infection, as part of an anti-bacterial host defense mechanism. Accordingly, the utilities of GAM353678 include the diagnosis, prevention and treatment of *Staphylococcus aureus* subsp. *aureus* MW2 infection and associated clinical conditions | A |
| GAM35 3678 | CAGCAGCA CACTGTGG TTTGTA | Human | uhpA | *Yersinia pestis* | GAM353678 is a human miRNA-like oligonucleotide, which targets two- component system response regulator (uhpA, NC_003143 from 4522790 to 4523380 (−)), a bacterial target gene encoded by the *Yersinia pestis* genome, as part of an anti-bacterial host defense mechanism. uhpA BINDING SITE 1 and uhpA BINDING SITE 2 are bacterial target binding sites that are found in the untranslated regions of mRNA encoded by the uhpA gene, corresponding to target binding sites such as BINDING SITE I, BINDING SITE II or BINDING SITE III of FIG. 1. The nucleotide sequences of uhpA BINDING SITE 1 and uhpA BINDING SITE 2, and the complementary secondary structure to the nucleotide sequence of GAM353678 RNA are set forth in Tables 6-7, hereby incorporated herein. Another function of GAM353678 is to inhibit uhpA, a GAM353678 | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| | | | | | bacterial target gene which is associated with *Yersinia pestis* infection, as part of an anti-bacterial host defense mechanism. Accordingly, the utilities of GAM353678 include the diagnosis, prevention and treatment of *Yersinia pestis* infection and associated clinical conditions | |
| GAM35 3678 | CAGCAGCA CACTGTGG TTTGTA | Human | ung | *Haemophilus influenzae* Rd | GAM353678 is a human miRNA-like oligonucleotide, which targets uracil DNA glycosylase (ung, NC_000907 from 18676 to 19335 (+)), a bacterial target gene encoded by the *Haemophilus influenzae* Rd genome, as part of an anti-bacterial host defense mechanism. ung BINDING SITE 1 and ung BINDING SITE 2 are bacterial target binding sites that are found in the untranslated regions of mRNA encoded by the ung gene, corresponding to target binding sites such as BINDING SITE I, BINDING SITE II or BINDING SITE III of FIG. 1. The nucleotide sequences of ung BINDING SITE 1 and ung BINDING SITE 2, and the complementary secondary structure to the nucleotide sequence of GAM353678 RNA are set forth in Tables 6-7, hereby incorporated herein. Another function of GAM353678 is to inhibit ung, a GAM353678 bacterial target gene which is associated with *Haemophilus influenzae* Rd infection, as part of an anti-bacterial host defense mechanism. Accordingly, the utilities of GAM353678 include the diagnosis, prevention and treatment of *Haemophilus influenzae* Rd infection and associated clinical conditions | A |
| GAM35 3678 | CAGCAGCA CACTGTGG TTTGTA | Human | vanB | *Pseudomonas aeruginosa* PA01 | GAM353678 is a human miRNA-like oligonucleotide, which targets vanillate O-demethylase oxidoreductase (vanB, NC_002516 from 5504120 to 5505073 (+)), a bacterial target gene encoded by the *Pseudomonas aeruginosa* PA01 genome, as part of an anti-bacterial host defense mechanism. vanB BINDING SITE 1 and vanB BINDING SITE 2 are bacterial target binding sites that are found in the untranslated regions of mRNA encoded by the vanB gene, corresponding to target binding sites such as BINDING SITE I, BINDING SITE II or BINDING SITE III of FIG. 1. The nucleotide sequences of vanB BINDING SITE 1 and vanB BINDING SITE 2, and the complementary secondary structure to the nucleotide sequence of GAM353678 RNA are set forth in Tables 6-7, hereby incorporated herein. Another function of GAM353678 is to inhibit vanB, a GAM353678 bacterial target gene which is associated with *Pseudomonas aeruginosa* PA01 infection, as part of an anti-bacterial host defense mechanism. Accordingly, the utilities of GAM353678 include the diagnosis, prevention and treatment of *Pseudomonas aeruginosa* PA01 infection and associated clinical conditions | A |
| GAM35 3678 | CAGCAGCA CACTGTGG TTTGTA | Human | yabO | *Escherichia coli* CFT073 | GAM353678 is a human miRNA-like oligonucleotide, which targets Ribosomal large subunit pseudouridine synthase A (yabO, NC_004431 from 61489 to 62148 (−)), a bacterial target gene encoded by the *Escherichia coli* CFT073 genome, as part of an anti-bacterial host defense mechanism. yabO BINDING SITE 1 and yabO BINDING SITE 2 are bacterial target binding sites that are found in the untranslated regions of mRNA encoded by the yabO gene, corresponding to target | A |

TABLE 8-continued

| GAM NAME | GAM RNA SEQUENCE | GAM ORGA- NISM | TAR- GET | TARGET ORGANISM | GAM GAM FUNCTION | POS |
|---|---|---|---|---|---|---|
| GAM35 3678 | CAGCAGCA CACTGTGG TTTGTA | Human | yciE | Escherichia coli CFT073 | binding sites such as BINDING SITE I, BINDING SITE II or BINDING SITE III of FIG. 1. The nucleotide sequences of yabO BINDING SITE 1 and yabO BINDING SITE 2, and the complementary secondary structure to the nucleotide sequence of GAM353678 RNA are set forth in Tables 6-7, hereby incorporated herein. Another function of GAM353678 is to inhibit yabO, a GAM353678 bacterial target gene which is associated with *Escherichia coli* CFT073 infection, as part of an anti-bacterial host defense mechanism. Accordingly, the utilities of GAM353678 include the diagnosis, prevention and treatment of *Escherichia coli* CFT073 infection and associated clinical conditions GAM353678 is a human miRNA-like oligonucleotide, which targets Protein yciE (yciE, NC_004431 from 1558641 to 1559147 (−)), a bacterial target gene encoded by the *Escherichia coli* CFT073 genome, as part of an anti-bacterial host defense mechanism. yciE BINDING SITE 1 and yciE BINDING SITE 2 are bacterial target binding sites that are found in the untranslated regions of mRNA encoded by the yciE gene, corresponding to target binding sites such as BINDING SITE I, BINDING SITE II or BINDING SITE III of FIG. 1. The nucleotide sequences of yciE BINDING SITE 1 and yciE BINDING SITE 2, and the complementary secondary structure to the nucleotide sequence of GAM353678 RNA are set forth in Tables 6-7, hereby incorporated herein. Another function of GAM353678 is to inhibit yciE, a GAM353678 bacterial target gene which is associated with *Escherichia coli* CFT073 infection, as part of an anti-bacterial host defense mechanism. Accordingly, the utilities of GAM353678 include the diagnosis, prevention and treatment of *Escherichia coli* CFT073 infectionand associated clinical conditions | A |

Studies documenting the well known correlations between each of a plurality of GAM TARGET GENEs that are described by FIG. 1 and the known gene functions and related diseases are listed in Table 9, hereby incorporated herein. Specifically, in Table 9, lines 6046-6059 describes references of GAM target genes, as set forth in SEQ ID NO:348 in Table 8.

TABLE 9

| TARGET | TARGET ORGANISM | REFERENCES |
|---|---|---|
| MGAT5 | Human | Demetriou, M.; Granovsky, M.; Quaggin, S.; Dennis, J. W.: Negative regulation of T-cell activation and autoimmunity by Mgat5 N-glycosylation. Nature 409: 733-739, 2001. |
| MGAT5 | Human | Granovsky, M.; Fata, J.; Pawling, J.; Muller, W. J.; Khokha, R.; Dennis, J. W.: Suppression of tumor growth and metastasis in Mgat5-deficient mice. Nature Med.6: 306-12, 2000. |
| MGAT5 | Human | Saito, H.; Nishikawa, A.; Gu, J.; Ihara, Y.; Soejima, H.; Wada, Y.; Sekiya, C.; Niikawa, N.; Taniguchi, N.: cDNA cloning and chromosomal mapping of human N-acetyl glucosaminyltransferase V+. Biochem. Biophys. Res. Commun. 198: 318-327, 1994. |

Table 11, lines 275482-275565, shows data of GAM RNA SEQ ID NO:348 printed on microarray chip probes, as described in detail in FIG. 17.

TABLE 11

| PROBE SEQUENCE | PROBE TYPE | GAM RNA SEQ ID/GAM MIR NAME | RNA/MIR SEQUENCE | LIBRARY | SIGNAL | BACK-GROUND Z-SCORE | MIS-MATCH Z-SCORE |
|---|---|---|---|---|---|---|---|
| CCCAGCAGCAC ACTGTGGTTTG TACGCGATCCG TTATCGTTCGG TATCGAACGTA ACGAT | Predicted | 348 | CAGCAGCACACTGTG-GTTTGTA | A2 | 638 | 4.2 | 3.2 |
| CCCAGCAGCAC ACTGTGGTTTG TACGCGATCCG TTATCGTTCGG TATCGAACGTA ACGAT | Predicted | 348 | CAGCAGCACACTGTG-GTTTGTA | D2 | 9435 | 16.6 | 20.9 |
| CCCAGCAGCAC ACTGTGGTTTG TACGCGATCCG TTATCGTTCGG TATCGAACGTA ACGAT | Predicted | 348 | CAGCAGCACACTGTG-GTTTGTA | E1 | 25910 | 14.8 | 27.5 |
| CCCAGCAGCAC ACTGTGGTTTG TACGCGATCCG TTATCGTTCGG TATCGAACGTA ACGAT | Predicted | 348 | CAGCAGCACACTGTG-GTTTGTA | F1 | 65518 | 12.0 | 30.2 |
| CCCAGCAGCAC ACTGTGGTTTG TACGCGATCCG TTATCGTTCGG TATCGAACGTA ACGAT | Predicted | 348 | CAGCAGCACACTGTG-GTTTGTA | G1 | 65518 | 10.1 | 29.3 |
| CCCAGCAGCAC ACTGTGGTTTG TACGCGATCCG TTATCGTTCGG TATCGAACGTA ACGAT | Predicted | 348 | CAGCAGCACACTGTG-GTTTGTA | H1 | 37067 | 9.9 | 28.2 |
| CCCAGCAGCAC ACTGTGGTTTG TACGGATCGTT ATAACGATCCG GTATCGAACGT AACGA | Predicted | 348 | CAGCAGCACACTGTG-GTTTGTA | A2 | 606 | 3.7 | 3.2 |
| CCCAGCAGCAC ACTGTGGTTTG TACGGATCGTT ATAACGATCCG GTATCGAACGT AACGA | Predicted | 348 | CAGCAGCACACTGTG-GTTTGTA | D2 | 7549 | 15.4 | 19.5 |
| CCCAGCAGCAC ACTGTGGTTTG TACGGATCGTT ATAACGATCCG GTATCGAACGT AACGA | Predicted | 348 | CAGCAGCACACTGTG-GTTTGTA | E1 | 20239 | 13.8 | 25.3 |

TABLE 11-continued

| PROBE SEQUENCE | PROBE TYPE | GAM RNA SEQ ID/GAM MIR NAMERNA/MIR SEQUENCE | | LIBRARY | SIGNAL | BACK-GROUND Z-SCORE | MIS-MATCH Z-SCORE |
|---|---|---|---|---|---|---|---|
| CCCAGCAGCAC ACTGTGGTTTG TACGGATCGTT ATAACGATCCG GTATCGAACGT AACGA | Predicted | 348 | CAGCAGCACACTGTG-GTTTGTA | F1 | 65518 | 12.0 | 29.3 |
| CCCAGCAGCAC ACTGTGGTTTG TACGGATCGTT ATAACGATCCG GTATCGAACGT AACGA | Predicted | 348 | CAGCAGCACACTGTG-GTTTGTA | G1 | 65518 | 10.1 | 28.0 |
| CCCAGCAGCAC ACTGTGGTTTG TACGGATCGTT ATAACGATCCG GTATCGAACGT AACGA | Predicted | 348 | CAGCAGCACACTGTG-GTTTGTA | H1 | 27597 | 9.2 | 25.8 |

Table 12, line 177, shows data relating to GAM RNA SEQ ID NO:348 that were validated by means of Wet Laboratory.

TABLE 12

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| CAGCAGCACACTGTG-GTTTGTA | Chip strong | 65518 | 16.623587 | 30.172779 | 348 |

Table 13, lines 3-42, 47-69, 84-121, 143-179, 187-207, 210-256, 264-478 shows sequence data of GAMs associated with different bacterial infections.

TABLE 13

| ROW # | INFECTION NAME | SEQ ID NOs OF GAMS ASSOCIATED WITH INFECTION |
|---|---|---|
| 2 | Bordetella pertussis | 1, 6, 10, 11, 12, 13, 16, 18, 19, 20, 21, 22, 23, 24, 25, 26, 27, 28, 29, 33, 34, 37, 41, 42, 43, 44, 47, 48, 49, 50, 52, 53, 54, 55, 57, 58, 59, 60, 63, 65, 66, 67, 68, 69, 70, 71, 75, 76, 77, 79, 84, 86, 87, 88, 89, 91, 94, 96, 97, 99, 100, 101, 102, 103, 104, 105, 106, 107, 108, 109, 110, 111, 112, 113, 114, 115, 117, 119, 120, 121, 122, 123, 125, 126, 127, 130, 131, 132, 133, 137, 138, 139, 140, 141, 142, 145, 147, 149, 150, 151, 154, 155, 156, 157, 158, 160, 161, 162, 164, 165, 166, 167, 168, 170, 171, 172, 173, 174, 175, 176, 177, 179, 180, 181, 183, 184, 185, 188, 191, 195, 196, 197, 204, 205, 211, 212, 214, 215, 216, 219, 220, 222, 225, 228, 230, 231, 233, 237, 239, 241, 242, 243, 244, 250, 251, 253, 262, 264, 265, 266, 268, 271, 272, 274, 276, 277, 280, 281, 282, 284, 285, 287, 288, 289, 290, 293, 294, 296, 297, 299, 300, 301, 302, 304, 306, 308, 310, 312, 317, 318, 321, 322, 324, 326, 327, 329, 330, 332, 333, 334, 335, 336, 339, 340, 342, 343, 345, 348, 349, 350, 351, 352, 353, 355, 356, 357, 358, 360, 361, 362, 364, 365, 366, 367, 368, 369, 370, 371, 372, 373, 374, 375, 376, 378, 380, 381, 382, 383, 384, 385 and 49788-55666. |
| 3 | Brucella 1330 suis | 1, 6, 10, 11, 12, 13, 14, 16, 18, 19, 21, 23, 27, 32, 35, 37, 39, 40, 42, 47, 48, 49, 50, 52, 53, 58, 62, 63, 65, 68, 70, 71, 77, 79, 80, 85, 86, 89, 90, 98, 102, 105, 107, 108, 109, 111, 112, 114, 115, 119, 120, 124, 125, 121, 122, 123, 126, 132, 138, 141, 142, 143, 150, 151, 152, 154, 155, 156, 157, 158, 160, 161, 162, 164, 166, 168, 171, 172, 173, 175, 176, 177, 180, 181, 183, 185, 186, 190, 195, 198, 199, 200, 201, 205, 207, 211, 212, 214, 215, 217, 218, 219, 220, 221, 222, 225, 229, 230, 231, 233, 236, 237, 240, 241, 243, 244, 250, 251, 256, 258, 263, 264, 265, 266, 270, 277, 279, 280, 281, 282, 285, 287, 289, 290, 293, 294, 295, 297, 300, 302, 303, 306, 308, 310, 312, 315, 318, 319, 320, 321, 330, 331, 333, 334, 335, 342, 343, 347, 348, 349, 353, 354, 356, 357, 360, 361, 364, 365, 366, 368, 369, 370, 371, 373, 374, 375, 377, 381, 382, 384 and 55667-60259. |
| 4 | Chlamydia Trachomatis | 2, 3, 4, 6, 7, 8, 9, 10, 13, 14, 16, 18, 19, 20, 21, 22, 25, 26, 27, 30, 31, 32, 33, 36, 37, 38, 40, 45, 46, 47, 48, 49, 51, 52, 55, 62, 63, 64, 67, 73, 74, 75, 78, 81, 82, 84, 85, 86, 87, 88, 91, 94, 95, 98, 99, 104, 105, 106, 111, 113, 116, 122, 124, 126, 128, 132, 133, 136, 138, 146, 148, 149, 152, 154, 155, 156, 157, 160, 164, 166, 167, 177, 179, 180, 181, 187, 188, 190, 192, 194, 198, 199, 200, 205, 207, 208, 209, 210, 211, 213, 214, 217, 218, 222, 224, 225, 226, 229, 232, 233, 235, 236, 239, 241, 242, 243, 244, 245, 248, 251, 252, 253, 254, 256, 257, 259, 262, 264, 265, 269, 270, 271, 272, 273, 274, |

TABLE 13-continued

| ROW # | INFECTION NAME | SEQ ID NOs OF GAMS ASSOCIATED WITH INFECTION |
|---|---|---|
| | | 278, 279, 287, 288, 289, 293, 295, 296, 297, 298, 299, 302, 303, 305, 306, 309, 311, 312, 316, 318, 319, 320, 322, 323, 324, 325, 326, 327, 328, 330, 332, 333, 335, 338, 340, 341, 343, 344, 345, 348, 349, 350, 353, 354, 356, 363, 373, 384 and 60260-67437. |
| 6 | Chlamydophila pneumoniae CWL029 | 3, 5, 6, 8, 9, 10, 13, 17, 20, 21, 22, 23, 25, 27, 28, 31, 32, 33, 37, 39, 45, 46, 47, 48, 50, 52, 55, 62, 63, 64, 66, 67, 69, 73, 74, 82, 84, 85, 88, 89, 90, 91, 92, 95, 101, 102, 104, 105, 111, 114, 124148, 125, 126, 128, 143, 146, 152, 159, 160, 161, 164, 165, 166, 168, 175180, 181, 187, 176, 177, 178, 179, 189, 190, 192, 194, 201, 203, 205, 207, 208, 209, 212, 213, 214, 217, 218, 221, 223, 224, 227, 232, 233, 234, 236, 238, 239, 241, 242, 243, 244, 245, 247, 248, 252, 257, 258, 259, 260, 262, 263, 271, 272, 274, 275, 279, 281, 282, 283, 286, 289, 295, 297, 298, 299, 302, 305, 306, 309, 311, 312, 314, 319, 323, 324, 325, 326, 327, 330, 333, 338, 340, 343, 344, 345, 346, 348, 349, 350, 352, 353, 354, 356, 363, 377, 382, 383, 384 and 68148-75439. |
| 7 | Chlamydophila pneumoniae J138 | 3, 5, 6, 8, 9, 10, 17, 20, 21, 22, 23, 25, 27, 31, 32, 33, 37, 39, 45, 46, 47, 50, 52, 55, 62, 63, 64, 66, 67, 69, 73, 74, 8290, 92, 95, 101, 84, 85, 88, 89, 102, 104, 105, 111, 114, 125, 126, 128, 148, 152, 159, 160, 161, 143, 146, 164, 165, 166, 168, 175, 176, 177, 178, 179, 187, 189, 190, 192, 194, 201, 203, 205, 207, 208, 209, 212, 180, 181, 213, 214, 217, 218, 221, 223, 224, 227, 232, 233, 234, 236, 238, 239, 241, 242, 243, 244, 245, 247, 248, 252, 257, 259, 260, 262, 263, 271, 272, 274, 275, 279, 281, 282, 283, 286, 289, 295, 297, 298, 299, 302, 305, 306, 309, 311, 312, 314, 319, 323, 325, 326, 327, 330, 333, 338, 340, 343, 344, 345, 346, 348, 349, 350, 352, 353, 354, 356, 363, 377, 382, 383, 384 and 75440-82241. |
| 10 | Escherichia coli CFT 073 | 1, 2, 4, 5, 6, 7, 8, 9, 10, 11, 12, 13, 14, 16, 17, 18, 19, 21, 22, 23, 25, 26, 27, 28, 30, 31, 33, 34, 35, 36, 37, 39, 40, 42, 43, 45, 46, 47, 48, 49, 50, 51, 52, 53, 55, 56, 57, 58, 59, 62, 63, 64, 65, 66, 67, 68, 69, 70, 71, 72, 73, 75, 76, 78, 79, 80, 81, 82, 83, 84, 85, 86, 87, 88, 89, 90, 91, 92, 93, 94, 95, 96, 97, 99, 100, 101, 102, 103, 105, 106, 107, 108, 109, 110, 111, 112, 113, 114, 115, 116, 119, 120, 121, 122, 123, 124, 125, 126, 129, 131, 132, 133, 135, 136, 137, 138, 140, 141, 142, 143, 145, 146, 147, 148, 152, 154, 155, 156, 157, 158, 160, 161, 162, 163, 164, 165, 166, 167, 168, 171, 173, 174, 175, 176, 177, 179, 180, 181, 182, 184, 185, 186, 190, 191, 192, 193, 195, 196, 197, 203, 204, 205, 206, 207, 208, 209, 210, 211, 212, 213, 214, 215, 216, 217, 218, 220, 221, 222, 223, 224, 225, 229, 230, 231, 232, 233, 234, 235, 236, 237, 238, 239, 241, 242, 243, 244, 245, 246, 247, 248, 249, 250, 251, 252, 253, 254, 255, 256, 257, 258, 260, 261, 262, 265, 266, 267, 268, 270, 271, 272, 274, 276, 277, 278, 279, 280, 281, 282, 283, 284, 285, 287, 288, 289, 290, 291, 292, 293, 294, 295, 296, 297, 299, 300, 301, 302, 303, 305, 306, 307, 308, 309, 310, 311, 312, 314, 315, 316, 317, 318, 321, 322, 323, 324, 325, 326, 327, 329, 331, 332, 333, 334, 335, 336, 337, 338, 339, 340, 343, 344, 345, 347, 348, 349, 350, 351, 352, 353, 354, 355, 356, 357, 358, 359, 360, 361, 364, 365, 367, 368, 369, 370, 372, 373, 374, 375, 376, 378, 380, 381, 382, 383, 384 and 90623-103607. |
| 11 | Haemophilus influenzae Rd | 2, 3, 5, 6, 7, 8, 9, 10, 13, 15, 19, 20, 21, 22, 25, 26, 27, 30, 31, 32, 33, 34, 37, 38, 40, 41, 45, 46, 48, 49, 50, 51, 52, 66, 67, 68, 73, 53, 55, 62, 63, 64, 78, 81, 83, 84, 85, 88, 90, 91, 92, 98, 101, 105, 106, 111, 116, 117, 119, 122, 123, 124, 125, 126, 134, 138, 144, 146, 149, 151, 152, 155, 156, 160, 161, 164, 165, 166, 169, 171, 172, 174, 176, 177, 179, 180, 183, 190, 197, 198, 199, 200, 201, 203, 205, 207, 208, 211, 213, 214, 218, 221, 223, 226, 228, 229, 234, 236, 239, 240, 242, 244, 247, 248, 251, 254, 255, 256, 259, 262, 263, 264, 271, 272, 274, 277, 279, 281, 282, 283, 295, 296, 299, 302, 305, 306, 308, 311, 312, 313, 316, 317, 318, 319, 322, 323, 324, 325, 326, 327, 329, 333, 335, 338, 339, 340, 343, 344, 345, 348, 351, 353, 354, 356, 365, 368, 371, 375, 377, 379, 380, 385 and 103608-111433. |
| 12 | Leptospira interrogans serovar lai str. 56601 | 1, 3, 5, 7, 8, 10, 13, 19, 22, 25, 32, 38, 39, 41, 48, 49, 52, 67, 71, 73, 84, 85, 90, 91, 93, 95, 117, 124, 128, 164, 174, 192, 193, 203, 178, 179, 187, 190, 207, 225, 226, 227, 229, 238, 244, 258, 259, 262, 272, 279, 193, 203, 256, 257, 295, 298, 299, 303, 306, 307, 316, 324, 327, 333, 338, 340, 344, 348, 376, 379, 384 and 111434-116384. |
| 15 | Mycobacterium bovis AF2122/9 subsp bovis 7 | 1, 3, 4, 5, 6, 7, 11, 12, 13, 14, 15, 16, 17, 18, 19, 20, 21, 22, 23, 24, 25, 26, 27, 28, 29, 31, 32, 33, 36, 37, 39, 41, 42, 52, 43, 45, 46, 47, 48, 50, 51, 53, 54, 55, 57, 58, 59, 73, 75, 76, 60, 61, 62, 71, 64, 65, 66, 67, 68, 69, 70, 77, 78, 79, 80, 83, 84, 86, 87, 88, 89, 100, 101, 102, 90, 91, 93, 96, 97, 99, 103, 104, 105, 106, 107, 108, 109, 110, 111, 112, 113, 114, 115, 116, 117, 118, 119, 120, 121, 122, 123, 125, 127, 130, 131, 132, 133, 134, 135, 137, 138, 139, 141, 142, 143, 144, 145, 146, 147, 148, 149, 150, 151, 152, 154, 155, 156, 157, 158, 159, 160, 161, 162, 163, 165, 166, 167, 168, 170, 171, 172, 173, 174, 175, 176, 177, 178, 179, 180, 181, 183, 184, 185, 188, 189, 190, 191, 193, 194, 195, 196, 197, 198, 199, 200, 201, 202, 203, 204, 205, 206, 207, 208, 210, 211, 212, 213, 214, 215, 216, 218, 219, 220, 222, 225, 230, 231, 233, 236, 237, 239, 240, 241, 242, 243, 244, 245, 246, 250, 251, 252, 253, 254, 255, 256, 257, 261, 262, 263, 264, 265, 266, 267, 268, 270, 271, 273, 276, 277, 278, 280, 281, 282, 283, 285, 286, 287, 288, 289, 290, 291, 292, 293, 294, 296, 297, 299, 300, 302, 303, 304, 305, 306, 308, 310, 312, 313, 314, 315, 318, 320, 321, 322, 323, 324, 325, 326, 327, 329, 330, 331, 332, 333, 334, 335, 336, 337, 341, 342, 345, 346, 347, 348, 349, 350, 351, 352, 353, 355, 356, 357, 358, 360, 361, 362, 364, 365, 366, 367, 369, 370, 371, 372, 373, 374, 375, 376, 378, 380, 381, 382, 383, 384, 385 and 127919-137561. |
| 16 | Mycobacterium leprae | 3, 4, 5, 6, 7, 12, 13, 14, 15, 18, 19, 21, 22, 23, 24, 26, 29, 31, 32, 33, 36, 37, 39, 41, 42, 43, 45, 46, 47, 48, 49, 50, 53, 54, 68, 69, 70, 57, 59, 62, 65, 71, 73, 74, 75, 76, 78, 81, 83, 84, 86, 90, 94, 96, 98, 101, 103, 106, 107, 109, 110, 111, 112, 113, 114, 115, 116, 118, 119, 120, 121, 123, 131, 133, 134, 135, 137, 142, 143, 144, 145, 146, 147, 149, 154, 156, 157, 158, 159, 161, 162, 163, 165, 166, 167, 171, 172, 173, 174, 175, 176, 179, 183, 184, 185, 187, 188, 189, 190, 193, 196, 197, 198, 199, 200, 201, 202, 204, 205, 206, 211, 212, 214, 215, 216, 218, 219, 220, 221, 223, 224, 225, 228, 230, 231, 232, 233, 234, 235, 236, 237, 241, 242, 243, 245, 249, 250, 251, 253, 254, 256, 258, 261, 263, 265, 267, 268, 269, 271, 274, 276, 277, 280, 281, 284, 288, 289, 290, 291, 293, 294, 295, 296, 297, 299, 300, 301, 302, 303, 305, 306, 307, 309, 310, 311, 312, 313, 314, 315, 318, 320, 321, 323, 324, 327, 329, 330, 331, 332, 333, 334, 335, 336, 337, 338, 339, 340, 341, 343, 345, 346, 347, 348, 349, 353, 355, 356, 357, 358, 360, 361, 364, 365, 368, 369, 370, 371, 372, 374, 375, 376, 377, 378, 380, 381, 382, 383 and 137562-144598. |
| 18 | Mycobacterium tuberculosis H37Rv | 1, 3, 4, 5, 6, 7, 10, 11, 12, 13, 14, 15, 16, 17, 18, 19, 20, 21, 22, 23, 24, 25, 26, 27, 28, 29, 31, 32, 33, 37, 39, 41, 42, 43, 50, 51, 52, 45, 46, 47, 48, 53, 54, 55, 57, 58, 59, 60, 61, 62, 63, 64, 65, 66, 67, 68, 69, 70, 71, 73, 75, 76, 77, 78, 79, 80, 83, 84, 86, 87, 88, 89, 90, 91, 93, 94, 96, 97, 99, 100, 101, 102, 103, 104, |

TABLE 13-continued

| ROW # | INFECTION NAME | SEQ ID NOs OF GAMS ASSOCIATED WITH INFECTION |
|---|---|---|
| | | 105, 107, 108, 109, 110, 111, 112, 113, 114, 115, 116, 117, 118, 119, 120, 121, 122, 123, 125, 127, 130, 131, 132, 133, 134, 135, 137, 138, 139, 141, 142, 143, 144, 145, 146, 147, 148, 149, 150, 151, 152, 153, 154, 155, 156, 157, 158, 159, 160, 161, 162, 163, 165, 166, 167, 168, 170, 171, 172, 173, 174, 175, 176, 177, 178, 179, 180, 181, 183, 184, 185, 188, 189, 190, 191, 194, 195, 196, 197, 198, 199, 200, 201, 202, 203, 204, 205, 206, 207, 208, 210, 211, 212, 213, 214, 215, 216, 218, 219, 220, 222, 225, 230, 231, 233, 234, 236, 237, 239, 240, 241, 242, 243, 244, 245, 246, 250, 251, 252, 253, 254, 255, 256, 257, 261, 262, 263, 264, 265, 266, 267, 268, 270, 271, 272, 273, 274, 276, 277, 278, 280, 281, 282, 283, 284, 285, 286, 287, 288, 289, 290, 291, 292, 293, 294, 296, 297, 298, 299, 300, 302, 303, 304, 305, 306, 308, 310, 312, 313, 314, 315, 318, 320, 321, 323, 324, 325, 326, 327, 329, 330, 331, 332, 333, 334, 335, 336, 337, 341, 342, 345, 346, 347, 348, 349, 350, 351, 352, 353, 355, 356, 357, 358, 360, 361, 362, 364, 365, 366, 367, 368, 369, 370, 371, 372, 373, 374, 375, 376, 378, 380, 381, 382, 383, 384, 385 and 146807-155497. |
| 20 | *Neisseria meningitidis* Z2491 | 1, 6, 7, 8, 10, 12, 15, 17, 21, 22, 26, 28, 30, 37, 39, 40, 45, 49, 52, 56, 58, 60, 62, 63, 67, 70, 76, 86, 89, 90, 91, 96, 98, 102, 103, 105, 107, 108, 109, 111, 112, 113, 114, 115, 122, 123, 124, 125, 126, 127, 133, 138, 141, 142, 143,145, 147, 148, 149, 152, 157, 158, 164, 165, 166, 170, 171, 175, 176, 178, 181, 183, 187, 189, 197, 203, 217, 218, 219, 220, 221, 222, 225, 229, 230, 231, 237, 239, 243, 245, 247, 248, 251, 253, 254, 256, 257, 258, 259, 264, 265, 268, 273, 281, 282, 283, 285, 287, 289, 290, 293, 294, 295, 297, 300, 302, 306, 308, 314, 315, 316, 319, 321, 322, 325, 327, 329, 332, 333, 334, 338, 340, 341, 344, 346, 348, 349, 350, 351, 354, 355, 356, 365, 371, 372, 375, 376, 380, 381, 382, 384 and 155834-160603. |
| 21 | *Pseudomonas aeruginosa* PA01 | 1, 2, 6, 10, 11, 12, 13, 14, 16, 17, 18, 19, 20, 21, 22, 23, 24, 25, 26, 27, 28, 29, 30, 31, 33, 34, 35, 36, 37, 41, 42, 56, 43, 45, 46, 48, 49, 50, 52, 54, 55, 57, 56, 59, 60, 62, 63, 64, 76, 77, 78, 79, 81, 65, 66, 67, 68, 69, 70, 71, 73, 82, 83, 84, 86, 87, 88, 89, 90, 91, 94, 95, 96, 97, 99, 100, 101, 102, 103, 105, 106, 107, 108, 109, 110, 111, 112, 113, 114, 115, 116, 118, 119, 120, 121, 122, 123, 124, 125, 126, 127, 130, 131, 134, 137, 138, 139, 140, 141, 142, 144, 147, 149, 150, 151, 152, 154, 155, 156, 157, 158, 160, 161, 162, 163, 164, 165, 166, 167, 168, 169, 170, 171, 172, 173, 174, 175, 176, 177, 179, 180, 181, 183, 184, 185, 188, 190, 192, 193, 194, 195, 196, 197, 202, 204, 205, 208, 210, 211, 212, 213, 214, 215, 216, 218, 220, 222, 225, 228, 229, 230, 231, 232, 233, 236, 237, 241, 242, 243, 244, 250, 251, 253, 258, 262, 264, 265, 266, 267, 268, 270, 271, 272, 273, 274, 276, 277, 280, 281, 282, 283, 285, 286, 287, 288, 289, 290, 291, 292, 293, 294, 296, 297, 296, 299, 300, 301, 302, 306, 312, 314, 318, 319, 320, 321, 323, 324, 325, 327, 329, 330, 331, 333, 334, 335, 336, 339, 340, 341, 342, 343, 345, 347, 348, 349, 350, 351, 352, 353, 355, 356, 357, 358, 360, 361, 362, 364, 365, 366, 367, 368, 369, 370, 371, 372, 373, 374, 375, 376, 378, 380, 381, 382, 383, 384 and 160604-170274. |
| 22 | *Pseudomonas K putida* T2440 | 1, 5, 7, 9, 10, 11, 12, 13, 14, 16, 18, 19, 23, 24, 25, 26, 27, 28, 29, 31, 33, 34, 36, 37, 38, 39, 41, 42, 43, 44, 45, 46, 47, 49, 50, 51, 52, 53, 54, 55, 57, 58, 59, 61, 64, 65, 66, 68, 69, 70, 71, 73, 76, 84, 85, 86, 88, 89, 91, 94, 98, 99, 101, 102, 103, 105, 106, 107, 108, 109, 110, 111, 112, 113, 114, 115, 117, 118, 119, 120, 121, 122, 123, 125, 126, 131, 132, 133, 134, 135, 137, 138, 140, 141, 142, 143, 144, 145, 146, 147, 148, 149, 150, 151, 152, 153, 154, 155, 156, 157, 158, 159, 160, 161, 162, 163, 164, 166, 167, 168, 171, 172, 173, 174, 175, 176, 177, 179, 180, 181, 183, 184, 185, 187, 190, 191, 193, 195, 196, 197, 202, 204, 205, 207, 211, 212, 214, 215, 216, 220, 221, 222, 225, 228, 229, 230, 231, 232, 233, 234, 236, 237, 239, 240, 241, 242, 243, 244, 248, 250, 251, 253, 255, 258, 264, 265, 266, 267, 270, 271, 272, 274, 276, 277, 280, 281, 282, 283, 284, 285, 287, 288, 289, 290, 291, 292, 293, 294, 295, 296, 299, 300, 301, 302, 303, 304, 305, 306, 308, 310, 312, 313, 314, 316, 317, 318, 320, 321, 322, 323, 324, 327, 329, 333, 334, 335, 336, 337, 342, 343, 345, 346, 347, 348, 349, 350, 351, 352, 353, 354, 355, 356, 357, 358, 360, 361, 364, 365, 366, 367, 368, 369, 370, 371, 373, 374, 375, 376, 377, 378, 380, 381, 382, 383, 384, 385 and 170275-178543. |
| 24 | *Salmonella enterica enterica serovar Typhi* | 1, 3, 4, 6, 7, 8, 9, 10, 11, 12, 13, 16, 17, 18, 19, 20, 21, 22, 23, 25, 26, 27, 28, 30, 31, 32, 33, 35, 37, 38, 39, 51, 40, 42, 43, 45, 46, 47, 48, 49, 50, 52, 55, 56, 57, 58, 59, 60, 62, 63, 64, 65, 66, 67, 68, 69, 70, 71, 72, 73, 75, 7, 79, 80, 81, 83, 84, 86, 88, 89, 90, 91, 92, 94, 95, 98, 99, 100, 101, 102, 105, 106, 107, 108, 109, 111, 112, 113, 114, 115, 119, 120, 121, 122, 123, 124, 125, 126, 127, 129, 131, 132, 133, 135, 136, 137, 138, 142, 143, 144, 145, 146, 147, 148, 150, 152, 153, 154, 155, 156, 157, 158, 160, 161, 162, 163, 164, 165, 166, 167, 171, 172, 173, 174, 175, 176, 177, 179, 180, 181, 182, 183, 185, 187, 188, 189, 190, 191, 192, 193, 194, 195, 196, 197, 198, 199, 200, 201, 202, 203, 204, 205, 206, 208, 212, 213, 214, 215, 216, 217, 218, 219, 220, 221, 222, 223, 225, 226, 229, 230, 231, 232, 233, 234, 235, 236, 237, 238, 239, 240, 241, 242, 243, 244, 245, 247, 248, 250, 251, 252, 253, 254, 255, 256, 257, 260, 261, 262, 263, 265, 266, 269, 270, 271, 272, 274, 276, 277, 278, 280, 281, 282, 283, 284, 285, 287, 288, 289, 290, 291, 292, 293, 294, 295, 296, 297, 298, 299, 300, 301, 302, 303, 304, 305, 306, 311, 312, 314, 315, 318, 319, 323, 324, 325, 327, 328, 329, 330, 331, 332, 333, 334, 335, 336, 337, 339, 340, 341, 342, 343, 344, 345, 346, 347, 348, 349, 351, 352, 353, 354, 355, 356, 357, 358, 360, 361, 364, 365, 366, 367, 369, 370, 371, 373, 374, 375, 376, 378, 379, 380, 381, 382, 383, 384, 385 and 179915-190940. |
| 25 | *Salmonella enterica enterica serovar Typhi Ty2* | 1, 2, 3, 4, 6, 7, 8, 9, 10, 11, 12, 13, 14, 16, 17, 18, 19, 20, 21, 22, 23, 25, 26, 27, 28, 30, 31, 32, 33, 35, 37, 38, 50, 39, 40, 42, 43, 45, 46, 47, 48, 49, 51, 52, 55, 56, 57, 58, 59, 69, 70, 71, 72, 73, 60, 62, 63, 64, 65, 66, 67, 68, 75, 77, 79, 80, 81, 83, 84, 85, 86, 88, 89, 90, 91, 94, 95, 98, 99, 100, 101, 102, 105, 106, 107, 108, 109, 111, 112, 113,114, 115, 116, 119, 120, 121, 122, 123, 124, 125, 126, 127, 129, 131, 132, 133, 135, 136, 137, 138, 142, 143, 144, 145, 146, 147, 148, 150, 152, 153, 154, 155, 156, 157, 158, 160, 161, 162, 163, 164, 165, 166, 167, 171, 172, 173, 174, 175, 176, 177, 179, 180, 181, 182, 183, 185, 187, 188, 189, 190, 191, 192, 193, 194, 195, 196, 197, 198, 199, 200, 201, 202, 203, 204, 205, 206, 208, 212, 213, 214, 215, 216, 217, 218, 219, 220, 221, 222, 223, 225, 229, 230, 231, 232, 233, 234, 235, 236, 237, 238, 239, 240, 241, 242, 243, 244, 245, 247, 248, 250, 251, 252, 253, 254, 255, 256, 257, 260, 261, 262, 263, 265, 266, 269, 270, 271, 272, 274, 276, 277, 278, 280, 281, 282, 283, 284, 285, 287, 288, 289, |

TABLE 13-continued

| ROW # | INFECTION NAME | SEQ ID NOs OF GAMS ASSOCIATED WITH INFECTION |
|---|---|---|
| | | 290, 291, 292, 293, 294, 295, 296, 297, 298, 299, 300, 301, 302, 303, 304, 305, 306, 308, 311, 312, 314, 315, 318, 319, 323, 324, 325, 327, 328, 329, 330, 331, 332, 333, 334, 335, 336, 337, 338, 339, 340, 341, 342, 343, 344, 345, 346, 347, 348, 349, 351, 352, 353, 354, 355, 356, 357, 358, 360, 361, 364, 365, 366, 367, 369, 370, 371, 373, 374, 375, 376, 378, 379, 380, 381, 382, 383, 384, 385 and 190941-201927. |
| 26 | Salmonella typhimurium LT2 | 1, 2, 3, 5, 6, 7, 8, 9, 10, 11, 12, 13, 14, 16, 17, 18, 19, 20, 21, 22, 23, 24, 25, 26, 27, 28, 29, 30, 31, 32, 33, 48, 49, 36, 37, 38, 39, 42, 43, 45, 46, 47, 50, 51, 52, 54, 55, 56, 57, 58, 59, 60, 62, 63, 64, 65, 66, 67, 68, 69, 70, 71, 72, 73, 75, 77, 79, 82, 83, 84, 86, 88, 89, 90, 91, 94, 95, 96, 100, 101, 102, 103, 104, 105, 107, 108, 109, 111, 112, 113, 114, 115, 116, 119, 120, 121, 122, 123, 124, 125, 126, 127, 129, 131, 132, 133, 135, 137, 138, 142, 143, 144, 145, 146, 147, 148, 149, 150, 151, 152, 154, 155, 156, 157, 158, 160, 161, 162, 163, 164, 165, 166, 167, 168, 170, 171, 172, 173, 174, 175, 176, 177, 179, 180, 181, 182, 183, 185, 187, 188, 189, 190, 192, 193, 194, 195, 196, 197, 198, 199, 200, 201, 202, 203, 204, 205, 206, 207, 208, 211, 212, 213, 214, 215, 216, 217, 218, 219, 220, 221, 222, 225, 226, 227, 228, 229, 230, 231, 232, 233, 234, 235, 236, 237, 238, 239, 240, 241, 242, 243, 244, 245, 247, 248, 249, 250, 251, 252, 253, 255, 256, 257, 258, 260, 261, 262, 263, 266, 267, 268, 270, 271, 272, 273, 274, 275, 276, 279, 280, 281, 282, 285, 287, 288, 289, 290, 291, 292, 293, 294, 296, 297, 298, 299, 300, 302, 303, 306, 307, 308, 309, 310, 311, 312, 314, 315, 317, 318, 319, 323, 324, 325, 326, 327, 328, 329, 330, 331, 332, 333, 334, 335, 336, 337, 338, 340, 341, 342, 343, 344, 345, 347, 348, 349, 350, 351, 352, 353, 354, 355, 356, 357, 358, 359, 360, 361, 362, 363, 364, 365, 366, 368, 369, 370, 371, 373, 374, 375, 376, 379, 380, 381, 382, 383, 384, 385 and 201928-215605. |
| 27 | Shigella 2a flexneri str. 2457T | 1, 2, 5, 6, 9, 10, 11, 12, 13, 14, 16, 17, 18, 19, 21, 22, 23, 24, 25, 26, 27, 28, 29, 30, 32, 33, 35, 36, 37, 50, 51, 38, 39, 40, 41, 42, 43, 46, 47, 48, 49, 52, 54, 55, 56, 57, 58, 59, 62, 63, 65, 66, 67, 68, 69, 70, 71, 73, 76, 78, 80, 83, 84, 85, 86, 87, 88, 89, 90, 91, 93, 94, 95, 97, 99, 101, 102, 103, 104, 105, 107, 108, 109, 110, 111, 112, 113, 114, 115, 116, 117, 119, 120, 121, 122, 123, 124, 125, 126, 129, 131, 132, 133, 134, 135, 136, 137, 138, 139, 141, 142, 143, 145, 146, 147, 148, 149, 150, 151, 152, 154, 155, 156, 157, 158, 160, 161, 162, 163, 164, 165, 166, 167, 171, 172, 173, 174, 175, 176, 177, 179, 180, 181, 182, 184, 185, 187, 190, 191, 195, 196, 197, 198, 199, 200, 201, 202, 203, 204, 205, 207, 208, 212, 213, 214, 216, 218, 220, 221, 222, 223, 224, 225, 229, 230, 231, 232, 233, 234, 236, 237, 238, 239, 240, 241, 242, 243, 244, 245, 247, 248, 250, 251, 252, 253, 254, 255, 256, 257, 260, 261, 262, 263, 265, 268, 270, 271, 272, 274, 276, 277, 278, 279, 280, 281, 282, 283, 284, 285, 287, 288, 289, 290, 291, 292, 293, 295, 3296, 297, 298, 299, 300, 01, 302, 304, 306, 307, 308, 309, 310, 311, 312, 314, 315, 316, 317, 318, 320, 321, 322, 323, 324, 325, 327, 328, 329, 331, 332, 333, 334, 335, 336, 337, 338, 339, 340, 341, 343, 344, 345, 346, 347, 348, 349, 350, 351, 352, 353, 354, 356, 357, 358, 359, 360, 361, 362, 364, 365, 366, 367, 368, 369, 371, 373, 374, 375, 376, 379, 380, 381, 382, 383, 384, 385 and 215606-226197. |
| 28 | Shigella 2a flexneri str. 301 | 1, 2, 5, 6, 9, 10, 11, 12, 13, 14, 16, 17, 18, 19, 21, 22, 23, 24, 25, 26, 27, 28, 29, 30, 32, 33, 35, 36, 37, 52, 39, 40, 41, 42, 43, 46, 47, 48, 49, 50, 51, 54, 55, 56, 57, 58, 59, 62, 63, 64, 65, 66, 67, 68, 69, 70, 71, 73, 76, 77, 78, 80, 83, 84, 85, 86, 87, 88, 89, 90, 91, 92, 93, 94, 95, 97, 99, 101, 102, 103, 104, 105, 107, 108, 109, 110, 111, 112, 113, 114, 115, 116, 119, 120, 121, 122, 123, 124, 125, 126, 129, 132, 133, 134, 135, 136, 137, 138, 141, 142, 143, 144, 145, 146, 147, 148, 149, 150, 151, 152, 154, 155, 156, 157, 158, 159, 160, 161, 162, 163, 164, 165, 166, 167, 168, 171, 172, 173, 174, 175, 176, 177, 179, 180, 181, 182, 184, 185, 187, 190, 191, 195, 196, 197, 198, 199, 200, 201, 202, 203, 205, 207, 208, 210, 212, 213, 214, 216, 217, 218, 220, 221, 222, 223, 224, 225, 229, 230, 231, 232, 233, 234, 236, 237, 238, 239, 240, 241, 242, 243, 244, 245, 247, 248, 250, 251, 252, 253, 254, 255, 256, 257, 260, 262, 263, 264, 265, 266, 268, 269, 270, 271, 272, 274, 276, 277, 278, 279, 280, 281, 282, 283, 284, 285, 287, 288, 289, 290, 291, 292, 293, 295, 296, 297, 298, 299, 300, 301, 302, 304, 306, 308, 309, 311, 312, 314, 315, 316, 317, 318, 320, 321, 323, 324, 325, 327, 328, 329, 331, 333, 334, 335, 336, 337, 338, 339, 340, 341, 343, 344, 345, 346, 347, 348, 349, 350, 351, 352, 353, 354, 356, 357, 358, 359, 360, 361, 362, 364, 365, 366, 367, 368, 369, 371, 373, 374, 375, 376, 378, 379, 380, 381, 382, 383, 384, 385 and 226198-237003. |
| 29 | Staphylococcus Aureus subsp. aureus Mu50 | 2, 5, 7, 8, 9, 10, 13, 16, 19, 22, 25, 27, 31, 32, 33, 35, 36, 38, 39, 40, 41, 45, 46, 47, 48, 50, 51, 52, 55, 62, 63, 67, 71, 73, 81, 83, 84, 85, 90, 91, 92, 93, 95, 98, 100, 101, 105, 106, 111, 113, 116, 119, 120, 124, 131, 133, 138, 139, 146, 147, 149, 152, 153, 156, 160, 161, 162, 165, 166, 169, 171, 172, 174, 177, 179, 180, 181, 190, 192, 203, 204, 205, 207, 208, 213, 214, 217, 218, 222, 228, 231, 232, 236, 238, 240, 242, 244, 245, 247, 248, 252, 254, 256, 259, 261, 262, 270, 271, 272, 274, 275, 287, 293, 294, 299, 301, 302, 305, 306, 308, 309, 311, 316, 317, 323, 324, 325, 326, 327, 332, 333, 334, 335, 337, 339, 340, 342, 343, 344, 345, 346, 348, 349, 351, 353, 354, 356, 363, 365, 368, 371, 375, 379, 381 and 237004-244310. |
| 30 | Staphylococcus subsp. aureus MW2 | 2, 5, 7, 8, 10, 13, 16, 19, 22, 25, 27, 30, 31, 32, 33, 38, 39, 40, 41, 45, 46, 47, 48, 50, 51, 52, 55, 62, 63, 67, 71, 72, 73, 78, 81, 83, 84, 90, 91, 92, 93, 95, 98, 100, 101, 105, 106, 109, 111, 113, 117, 119, 120, 124, 126, 128, 130, 131, 133, 134, 138, 139, 143, 149, 152, 153, 156, 160, 161, 162, 166, 169, 171, 172, 174, 177, 179, 180, 181, 182, 190, 192, 203, 204, 205, 207, 208, 213, 214, 217, 218, 222, 228, 231, 232, 236, 238, 242, 244, 247, 248, 252, 254, 256, 257, 259, 261, 262, 271, 272, 274, 279, 287, 293, 294, 295, 299, 301, 302, 306, 307, 308, 309, 315, 316, 323, 324, 325, 326, 327, 332, 333, 334, 335, 337, 338, 339, 342, 343, 344, 345, 346, 348, 350, 351, 353, 356, 363, 365, 368, 371, 375, 379, 381 and 244311-250683. |
| 31 | Staphylococcus aureus subsp. aureus N315 | 2, 5, 7, 8, 9, 10, 13, 16, 19, 22, 25, 27, 31, 32, 33, 35, 36, 38, 39, 40, 41, 45, 46, 47, 48, 50, 51, 52, 55, 62, 63, 67, 71, 73, 81, 83, 84, 85, 90, 91, 92, 93, 95, 98, 100, 101, 105, 106, 111, 113, 117, 119, 120, 124, 131, 133, 134, 138, 139, 143, 146, 147, 149, 152, 153, 156, 160, 161, 162, 166, 169, 171, 172, 174, 177, 179, 180, 181, 190, 192, 203, 204, 205, 207, 208, 213, 214, 217, 218, 222, 226, 228, 231, 232, 236, 238, 240, 242, 244, 245, 247, 248, 252, 254, 256, 259, 260, 261, 262, 270, 271, 272, 274, 275, 279, 287, 293, 294, 299, 301, 302, 305, 306, 307, 308, 309, 311, 316, 317, 323, 324, 325, 326, 327, 332, 333, 334, 335, 337, 339, 340, 342, 343, 344, 345, 346, 348, 349, 351, 353, 354, 356, 363, 365, 368, 371, 375, 379, 381 and 250684-257140. |
| 32 | Streptococcus Pneumoniae R6 | 2, 3, 5, 6, 10, 13, 14, 17, 20, 21, 22, 23, 25, 26, 27, 30, 31, 32, 33, 35, 36, 37, 38, 39, 40, 41, 46, 47, 48, 49, 50, 52, 55, 56, 62, 63, 67, 73, 77, 81, 83, 84, |

TABLE 13-continued

| ROW # | INFECTION NAME | SEQ ID NOs OF GAMS ASSOCIATED WITH INFECTION |
|---|---|---|
| | | 85, 87, 90, 91, 92, 94, 95, 100, 101, 102, 105, 106, 111, 112, 114, 115, 116, 117, 119, 123, 124, 126, 133, 136, 138, 143, 145, 146, 147, 149, 152, 156, 160, 161, 164, 166, 168, 169, 171, 172, 174, 175, 176, 177, 179, 180, 190, 192, 203, 204, 205, 208, 209, 213, 214, 217, 218, 223, 226, 228, 229, 232, 233, 235, 236, 238, 239, 242, 244, 245, 246, 247, 248, 249, 252, 255, 256, 257, 258, 259, 260, 261, 262, 264, 268, 271, 274, 279, 282, 284, 287, 295, 296, 297, 298, 299, 300, 302, 303, 305, 306, 307, 309, 311, 312, 314, 315, 316, 320, 321, 323, 324, 325, 326, 327, 329, 333, 335, 338, 340, 341, 344, 345, 348, 350, 351, 352, 353, 356, 357, 359, 365, 368, 371, 372, 373, 375, 377, 379, 380, 382, 384, 385 and 257141-265301. |
| 33 | Streptococcus pneumoniae TIGR4 | 2, 10, 13, 25, 27, 33, 46, 48, 50, 52, 55, 62, 63, 67, 73, 81, 84, 91, 101, 105, 106, 111, 119, 149, 152, 160, 161, 176, 177, 164, 166, 168, 169, 171, 172, 175, 179, 180, 190, 205, 208, 213, 214, 218, 228, 236, 242, 244, 246, 262, 268, 271, 272, 274, 297, 299, 306, 321, 323, 324, 325, 327, 329, 333, 340, 345, 348, 351, 353, 356, 359, 365, 368, 371, 372, 375, 380 and 265302-266788. |
| 34 | Streptococcus pyogenes M1 GAS | 3, 5, 8, 10, 21, 22, 25, 27, 32, 37, 38, 39, 40, 43, 49, 90, 95, 96, 106, 116, 126, 129, 138, 163, 164, 168, 175, 261, 262, 176, 180, 226, 232, 244, 246, 259, 268, 283, 295, 296, 297, 299, 306, 309, 316, 321, 329, 330, 333, 348, 349, 359, 372, 379, 380 and 266789-269521. |
| 35 | Streptococcus pyogenes MGAS315 | 3, 8, 10, 13, 20, 22, 25, 27, 31, 32, 33, 37, 38, 40, 46, 48, 52, 55, 62, 67, 73, 84, 90, 91, 105, 106, 113, 116, 175, 176, 129, 138, 152, 160, 164, 166, 168, 177, 179, 180, 186, 190, 192, 208, 211, 213, 214, 218, 226, 229, 232, 236, 242, 244, 246, 262, 268, 271, 272, 274, 282, 283, 295, 296, 297, 299, 306, 309, 312, 321, 323, 324, 325, 327, 329, 333, 340, 345, 348, 349, 353, 356, 359, 372, 379, 380, 381 and 269522-272357. |
| 36 | Streptococcus pyogenes MGAS8232 | 3, 4, 8, 10, 13, 21, 22, 25, 27, 31, 33, 37, 38, 39, 40, 46, 48, 52, 55, 62, 67, 73, 84, 90, 91, 95, 105, 106, 113, 116, 129, 138, 168, 152, 160, 163, 164, 166, 175, 176, 177, 179, 180, 190, 205, 208, 213, 214, 218, 226, 232, 236, 242, 244, 246, 247, 259, 260, 261, 262, 268, 271, 272, 274, 295, 296, 297, 299, 306, 307, 309, 316, 321, 323, 324, 325, 327, 329, 330, 333, 337, 340, 344, 345, 348, 349, 353, 356, 359, 363, 372, 379, 380, 381 and 272358-275553. |
| 37 | Streptococcus pyogenes SSI-1 | 10, 13, 25, 27, 31, 33, 46, 48, 52, 55, 62, 67, 73, 84, 91, 164, 166, 168, 175, 176, 177, 179, 180, 190, 205, 208, 213, 214, 242, 218, 236, 244, 246, 262, 268, 271, 272, 274, 297, 299, 306, 324, 325, 327, 329, 321, 323, 105, 113, 152, 160, 333, 340, 345, 348, 353, 356, 359, 372, 380, 381 and 275554-276703. |
| 38 | Treponema subsp. pallidum str. Nichols | 3, 10, 13, 48, 52, 57, 59, 67, 81, 84, 86, 90, 91, 121, 131, 134, 174, 175, 176, 184, 218, 228, 231, 235, 236, 243, 261, 262, 269, 272 306, 289, 291, 295, 299, 312, 324, 329, 332, 333, 340 345, 356, 358 and 276704-277654. |
| 39 | Yersinia pestis | 1, 2, 3, 4, 5, 6, 7, 8, 9, 10, 12, 13, 16, 18, 19, 21, 22, 25, 26, 27, 28, 29, 30, 31, 32, 33, 34, 36, 37, 39, 40, 41, 54, 42, 43, 45, 46, 47, 48, 51, 52, 53, 55, 57, 58, 61, 62, 63, 67, 68, 70, 71, 73, 75, 76, 78, 82, 84, 85, 87, 88, 89, 90, 91, 93, 94, 95, 98, 99, 101, 102, 103, 105, 106, 107, 108, 111, 112, 113, 114, 115, 116, 117, 120, 121, 122, 123, 124, 125, 126, 129, 130, 131, 132, 133, 134, 135, 136, 138, 140, 141, 142, 143, 146, 148, 149, 151, 152, 153, 154, 155, 156, 160, 164, 165, 166, 167, 169, 171, 172, 174, 175, 176, 177, 178, 179, 180, 182, 184, 186, 187, 188, 190, 191, 192, 193, 196, 197, 198, 199, 200, 201, 202, 203, 205, 206, 208, 209, 211, 213, 214, 215, 217, 218, 219, 220, 221, 222, 224, 225, 226, 227, 229, 230, 232, 233, 234, 236, 237, 238, 239, 240, 241, 242, 243, 244, 245, 250, 251, 252, 253, 255, 256, 257, 258, 259, 260, 262, 263, 264, 270, 271, 272, 274, 276, 279, 280, 281, 282, 283, 286, 287, 289, 291, 292, 293, 295, 296, 298, 299, 300, 301, 302, 304, 306, 307, 308, 309, 311, 314, 315, 317, 319, 321, 322, 323, 324, 325, 326, 327, 329, 330, 331, 333, 334, 335, 336, 337, 340, 341, 342, 343, 344, 345, 346, 348, 349, 350, 351, 352, 353, 354, 355, 356, 357, 358, 359, 363, 364, 365, 367, 368, 370, 372, 373, 374, 376, 377, 378, 379, 380, 381, 382, 383, 384 and 277655-287825. |
| 40 | Yersinia pestis KIM | 1, 2, 3, 4, 5, 6, 7, 8, 9, 10, 12, 13, 16, 18, 19, 20, 21, 22, 25, 26, 27, 28, 29, 31, 32, 33, 34, 36, 37, 39, 40, 41, 53, 54, 42, 43, 45, 46, 47, 48, 51, 52, 55, 57, 58, 61, 62, 63, 65, 67, 68, 70, 71, 72, 73, 75, 76, 78, 84, 85, 87, 88, 89, 90, 91, 93, 94, 95, 97, 99, 101, 102, 103, 105, 106, 107, 108, 111, 112, 113, 114, 115, 117, 118, 120, 121, 122, 123, 124, 125, 126, 129, 130, 131, 132, 133, 134, 135, 136, 138, 140, 142, 143, 146, 147, 148, 149, 151, 152, 153, 154, 156, 158, 160, 164, 165, 166, 169, 171, 172, 174, 175, 176, 177, 178, 179, 180, 182, 186, 187, 188, 190, 191, 192, 193, 196, 197, 198, 199, 200, 201, 202, 203, 205, 206, 207, 208, 209, 211, 213, 214, 215, 217, 218, 220, 221, 222, 224, 225, 226, 227, 229, 230, 232, 233, 234, 235, 236, 237, 238, 239, 240, 241, 242, 243, 244, 247, 248, 250, 251, 252, 253, 255, 256, 257, 258, 260, 262, 263, 264, 270, 271, 272, 274, 276, 279, 281, 282, 283, 284, 286, 287, 288, 289, 291, 292, 293, 294, 295, 296, 298, 299, 300, 302, 303, 305, 306, 307, 308, 309, 311, 314, 315, 317, 318, 319, 321, 322, 323, 324, 325, 327, 329, 330, 331, 333, 334, 335, 336, 337, 340, 341, 342, 343, 344, 345, 346, 348, 349, 350, 351, 352, 353, 354, 355, 356, 357, 358, 359, 362, 363, 364, 365, 367, 368, 370, 373, 374, 375, 376, 377, 378, 379, 380, 381, 382, 383, 384, 385 and 287826-298021. |

The present invention discloses a novel group of bacterial and human oligonucleotides, belonging to the miRNA-like oligonucleotide group, here termed GAM oligonucleotides, for which a specific complementary binding has been determined bioinformatically.

Reference is now made to FIG. 2, which is a simplified block diagram illustrating a bioinformatic oligonucleotide detection system and method constructed and operative in accordance with a preferred embodiment of the present invention.

An important feature of the present invention is a bioinformatic oligonucleotide detection engine 100, which is capable of bioinformatically detecting oligonucleotides of the present invention.

The functionality of the bioinformatic oligonucleotide detection engine 100 includes receiving expressed RNA data 102, sequenced DNA data 104, and protein function data 106; performing a complex process of analysis of this data as elaborated hereinbelow, and based on this analysis provides information, designated by reference numeral 108, identifying and describing features of novel oligonucleotides.

Expressed RNA data 102 comprises published expressed sequence tags (EST) data, published mRNA data, as well as other published RNA data. Sequenced DNA data 104 comprises alphanumeric data representing genomic sequences and preferably including annotations such as information indicating the location of known protein-coding regions relative to the genomic sequences.

Protein function data 106 comprises information from scientific publications e.g. physiological functions of known proteins and their connection, involvement and possible utility in treatment and diagnosis of various diseases.

Expressed RNA data 102 and sequenced DNA data 104 may preferably be obtained from data published by the National Center for Biotechnology Information (NCBI) at the National Institute of Health (NIH) (Jenuth, J. P. (2000). Methods Mol. Biol. 132:301-312(2000), herein incorporated by reference) as well as from various other published data sources. Protein function data 106 may preferably be obtained from any one of numerous relevant published data sources, such as the Online Mendelian Inherited Disease In Man (OMIM™, Hamosh et al., Nucleic Acids Res. 30: 52-55 (2002)) database developed by John Hopkins University, and also published by NCBI (2000).

Prior to or during actual detection of bioinformatically-detected group of novel oligonucleotides 108 by the bioinformatic oligonucleotide detection engine 100, bioinformatic oligonucleotide detection engine training & validation functionality 110 is operative. This functionality uses one or more known miRNA oligonucleotides as a training set to train the bioinformatic oligonucleotide detection engine 100 to bioinformatically recognize miRNA-like oligonucleotides, and their respective potential target binding sites. Bioinformatic oligonucleotide detection engine training & validation functionality 110 is further described hereinbelow with reference to FIG. 3.

The bioinformatic oligonucleotide detection engine 100 preferably comprises several modules which are preferably activated sequentially, and are described as follows:

A non-protein-coding genomic sequence detector 112 operative to bioinformatically detect non-protein-coding genomic sequences. The non-protein-coding genomic sequence detector 112 is further described herein below with reference to FIGS. 4A and 4B.

A hairpin detector 114 operative to bioinformatically detect genomic "hairpin-shaped" sequences, similar to GAM FOLDED PRECURSOR RNA (FIG. 1). The hairpin detector 114 is further described herein below with reference to FIGS. 5A and 5B.

A Dicer-cut location detector 116 operative to bioinformatically detect the location on a GAM FOLDED PRECURSOR RNA which is enzymatically cut by DICER COMPLEX (FIG. 1), yielding "diced" GAM RNA. The Dicer-cut location detector 116 is further described herein below with reference to FIGS. 6A-6C.

A target gene binding site detector 118 operative to bioinformatically detect target genes having binding sites, the nucleotide sequence of which is partially complementary to that of a given genomic sequence, such as a nucleotide sequence cut by DICER COMPLEX. The target gene binding site detector 118 is further described hereinbelow with reference to FIGS. 7A and 7B.

A function & utility analyzer, designated by reference numeral 120, is operative to analyze the function and utility of target genes in order to identify target genes which have a significant clinical function and utility. The function & utility analyzer 120 is further described hereinbelow with reference to FIG. 8

According to an embodiment of the present invention, the bioinformatic oligonucleotide detection engine 100 may employ a cluster of 40 personal computers (PCs; XEON®, 2.8 GHz, with 80 GB storage each) connected by Ethernet to eight servers (2-CPU, XEON™ 1.2-2.2 GHz, with ~200 GB storage each) and combined with an 8-processor server (8-CPU, Xeon 550 Mhz w/8 GB RAM) connected via 2 HBA fiber-channels to an EMC CLARIION™ 100-disks, 3.6 Terabyte storage device. A preferred embodiment of the present invention may also preferably comprise software that utilizes a commercial database software program, such as MICROSOFT ™ SQL Server 2000.

According to a preferred embodiment of the present invention, the bioinformatic oligonucleotide detection engine 100 may employ a cluster of 80 Servers (XEON®, 2.8 GHz, with 80 GB storage each) connected by Ethernet to eight servers (2-CPU, XEON™ 1.2-2.2 GHz, with ~200 GB storage each) and combined with storage device (Promise Technology Inc., RM8000) connected to an 8-disks, 2 Terabytes total. A preferred embodiment of the present invention may also preferably comprise software that utilizes a commercial database software program, such as MICROSOFT ™ SQL Server 2000. It is appreciated that the abovementioned hardware configuration is not meant to be limiting and is given as an illustration only. The present invention may be implemented in a wide variety of hardware and software configurations.

The present invention discloses 21,916 bacterial and 6,100 human novel oligonucleotides of the GAM group of oligonucleotides, which have been detected bioinformatically and 6,056 bacterial and 430 novel polynucleotides of the GR group of polynucleotides, which have been detected bioinformatically. Laboratory confirmation of bioinformatically predicted oligonucleotides of the GAM group of oligonucleotides, and several bioinformatically predicted polynucleotides of the GR group of polynucleotides, is described hereinbelow with reference to FIGS. 13-15D, FIG. 18 and Table 12.

Reference is now made to FIG. 3, which is a simplified flowchart illustrating operation of a preferred embodiment of the bioinformatic oligonucleotide detection engine training & validation functionality 110 described hereinabove with reference to FIG. 2.

Bioinformatic oligonucleotide detection engine training & validation functionality 110 begins by training the bioinformatic oligonucleotide detection engine 100 (FIG. 2) to recognize one or more known miRNA oligonucleotides, as designated by reference numeral 122. This training step comprises hairpin detector training & validation functionality 124, further described hereinbelow with reference to FIG. 5A, Dicer-cut location detector training & validation functionality 126, further described hereinbelow with reference to FIGS. 6A and 6B, and target gene binding site detector training & validation functionality 128, further described hereinbelow with reference to FIG. 7A.

Next, the bioinformatic oligonucleotide detection engine training & validation functionality 110 is operative bioinformatically detect novel oligonucleotides, using bioinformatic oligonucleotide detection engine 100 (FIG. 2), as designated by reference numeral 130. Wet lab experiments are preferably conducted in order to validate expression and preferably function of some samples of the novel oligonucleotides detected by the bioinformatic oligonucleotide detection engine 100, as designated by reference numeral 132. FIGS. 13A-15D, FIG. 18 and Table 12 illustrate examples of wet lab validation of sample novel human oligonucleotides bioinformatically-detected in accordance with a preferred embodiment of the present invention.

Figure 4A:
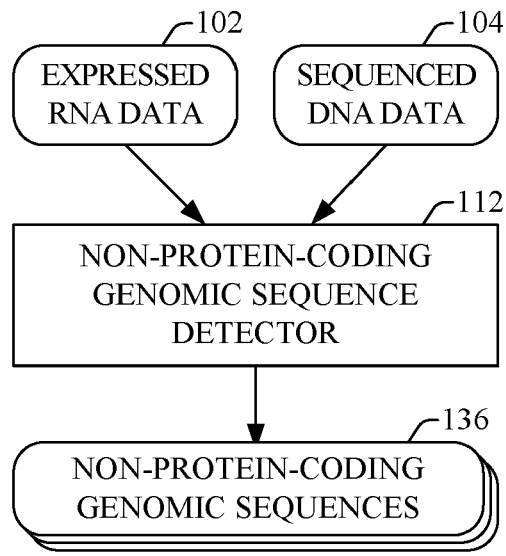
FIG. 4A is a simplified block diagram of a non-coding genomic sequence detector constructed and operative in accordance with a preferred embodiment of the present invention.

Reference is now made to FIG. 4A, which is a simplified block diagram of a preferred implementation of the non-protein-coding genomic sequence detector 112 described hereinabove with reference to FIG. 2. The non-protein-coding genomic sequence detector 112 preferably receives at least two types of published genomic data: Expressed RNA data 102 and sequenced DNA data 104. The expressed RNA data 102 may include, inter alia, EST data, EST clusters data, EST genome alignment data and mRNA data. Sources for expressed RNA data 102 include NCBI dbEST, NCBI Uni-Gene clusters and mapping data, and TIGR gene indices (Kirkness F. and Kerlavage, A. R., Methods Mol. Biol. 69:261-268 (1997)). Sequenced DNA data 104 may include sequence data (FASTA format files), and feature annotations (GenBank file format) mainly from NCBI databases. Based on the abovementioned input data, the non-protein-coding genomic sequence detector 112 produces a plurality of non-protein-coding genomic sequences 136. Preferred operation of the non-protein-coding genomic sequence detector 112 is described hereinbelow with reference to FIG. 4B.

Figure 4B:
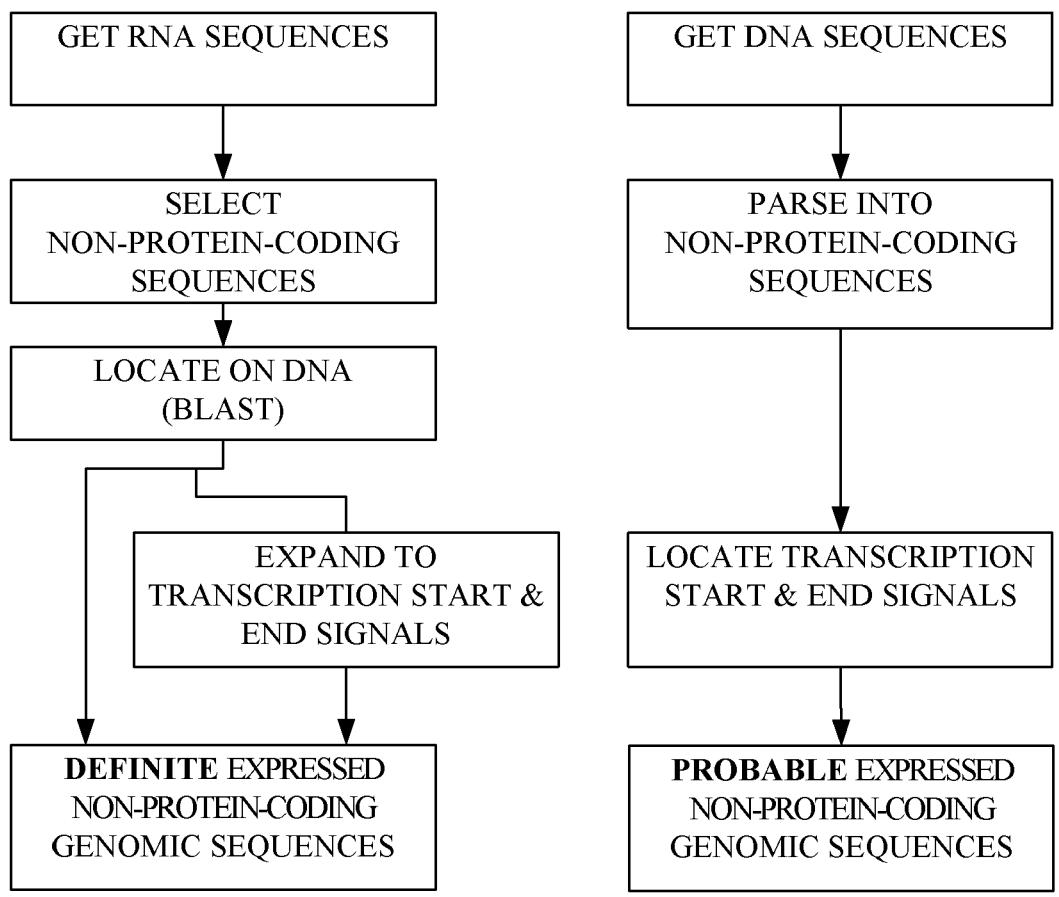
FIG. 4B is a simplified flowchart illustrating operation of a non-coding genomic sequence detector constructed and operative in accordance with a preferred embodiment of the present invention.

Reference is now made to FIG. 4B, which is a simplified flowchart illustrating a preferred operation of the non-protein-coding genomic sequence detector 112 of FIG. 2. Detection of non-protein-coding genomic sequences 136, generally preferably progresses along one of the following two paths:

A first path for detecting non-protein-coding genomic sequences 136 (FIG. 4A) begins with receipt of a plurality of known RNA sequences, such as EST data. Each RNA sequence is first compared with known protein-coding DNA sequences, in order to select only those RNA sequences which are non-protein-coding, i.e. intergenic or intronic sequences. This can preferably be performed by using one of many alignment algorithms known in the art, such as BLAST (Altschul et al., J. Mol. Biol. 215:403-410 (1990)). This sequence comparison preferably also provides localization of the RNA sequence on the DNA sequences.

Alternatively, selection of non-protein-coding RNA sequences and their localization on the DNA sequences can be performed by using publicly available EST cluster data and genomic mapping databases, such as the UNIGENE database published by NCBI or the TIGR database. Such databases, map expressed RNA sequences to DNA sequences encoding them, find the correct orientation of EST sequences, and indicate mapping of ESTs to protein-coding DNA regions, as is well known in the art. Public databases, such as TIGR, may also be used to map an EST to a cluster of ESTs, known in the art as Tentative Human Consensus and assumed to be expressed as one segment. Publicly available genome annotation databases, such as NCBI's GenBank, may also be used to deduce expressed intronic sequences.

Optionally, an attempt may be made to "expand" the non-protein RNA sequences thus found, by searching for transcription start and end signals, respectively upstream and downstream of the location of the RNA on the DNA, as is well known in the art.

A second path for detecting non-protein-coding genomic sequences 136 (FIG. 4A) begins with receipt of DNA sequences. The DNA sequences are parsed into non-protein-coding sequences, using published DNA annotation data, by extracting those DNA sequences which are between known protein-coding sequences. Next, transcription start and end signals are sought. If such signals are found, and depending on their robustness, probable expressed non-protein-coding genomic sequences are obtained. Such approach is especially useful for identifying novel GAM oligonucleotides which are found in proximity to other known miRNA oligonucleotides, or other wet lab validated GAM oligonucleotides. Since, as described hereinbelow with reference to FIG. 9, GAM oligonucleotides are frequently found in clusters; sequences located near known miRNA oligonucleotides are more likely to contain novel GAM oligonucleotides. Optionally, sequence orthology, i.e. sequence conservation in an evolutionary related species, may be used to select genomic sequences having a relatively high probability of containing expressed novel GAM oligonucleotides. It is appreciated that in detecting non-human GAM oligonucleotides of the present invention the bioinformatic oligonucleotide detection engine 100 utilizes the input genomic sequences, without filtering protein-coding regions detected by the non-protein-coding genomic sequence detector 112, hence non-protein-coding genomic sequences 136 refers to GENOMIC SEQUENCES only.

Figure 5A:
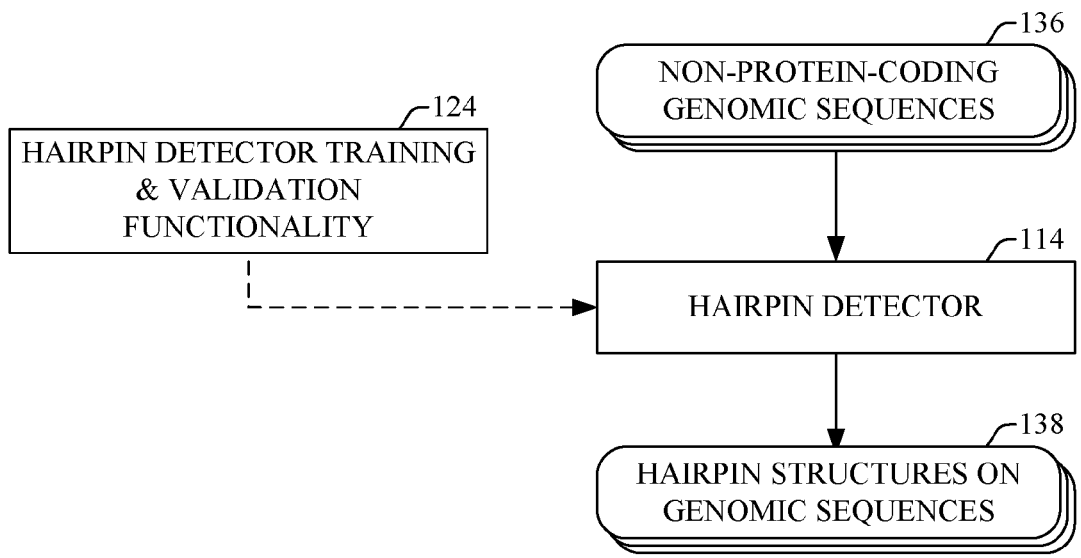
FIG. 5A is a simplified block diagram of a hairpin detector constructed and operative in accordance with a preferred embodiment of the present invention.

Reference is now made to FIG. 5A, which is a simplified block diagram of a preferred implementation of the hairpin detector 114 described hereinabove with reference to FIG. 2.

The goal of the hairpin detector 114 is to detect hairpin-shaped genomic sequences, similar to those of known miRNA oligonucleotides. A hairpin-shaped genomic sequence is a genomic sequence, having a first half which is at least partially complementary to a second half thereof, which causes the halves to folds onto themselves, thereby forming a hairpin structure, as mentioned hereinabove with reference to FIG. 1.

The hairpin detector 114 (FIG. 2) receives a plurality of non-protein-coding genomic sequences 136 (FIG. 4A). Following operation of hairpin detector training & validation functionality 124 (FIG. 3), the hairpin detector 114 is operative to detect and output hairpin-shaped sequences, which are found in the non-protein-coding genomic sequences 136. The hairpin-shaped sequences detected by the hairpin detector 114 are designated hairpin structures on genomic sequences 138. A preferred mode of operation of the hairpin detector 114 is described hereinbelow with reference to FIG. 5B.

Hairpin detector training & validation functionality 124 includes an iterative process of applying the hairpin detector 114 to known hairpin-shaped miRNA precursor sequences, calibrating the hairpin detector 114 such that it identifies a training set of known hairpin-shaped miRNA precursor sequences, as well as other similarly hairpin-shaped sequences. In a preferred embodiment of the present invention, the hairpin detector training & validation functionality 124 trains the hairpin detector 114 and validates each of the steps of operation thereof described hereinbelow with reference to FIG. 5B The hairpin detector training & validation functionality 124 preferably uses two sets of data: the aforesaid training set of known hairpin-shaped miRNA precursor sequences, such as hairpin-shaped miRNA precursor sequences of 440 miRNA oligonucleotides of *H. sapiens, M. musculus, C. elegans, C. Brigssae* and *D. Melanogaster*, annotated in the RFAM database (Griffiths-Jones 2003), and a background set of about 1000 hairpin-shaped sequences found in expressed non-protein-coding human genomic sequences. The background set is expected to comprise some valid, previously undetected hairpin-shaped miRNA-like precursor sequences, and many hairpin-shaped sequences which are not hairpin-shaped miRNA-like precursors.

In a preferred embodiment of the present invention the efficacy of the hairpin detector 114 (FIG. 2) is confirmed. For example, when a similarity threshold is chosen such that 87% of the known hairpin-shaped miRNA precursors are successfully predicted, only 21.8% of the 1000 background set of hairpin-shaped sequences are predicted to be hairpin-shaped miRNA-like precursors.

Figure 5B:
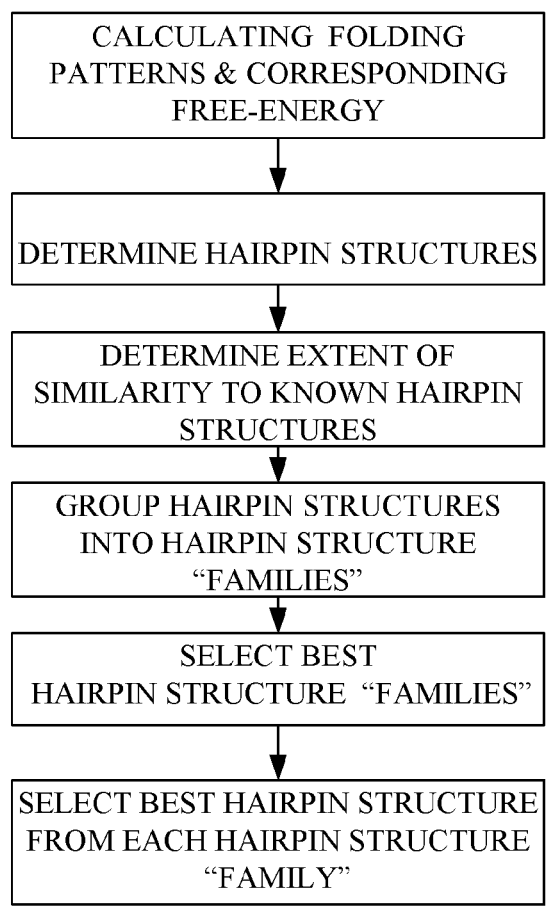
FIG. 5B is a simplified flowchart illustrating operation of a hairpin detector constructed and operative in accordance with a preferred embodiment of the present invention.

Reference is now made to FIG. 5B, which is a simplified flowchart illustrating preferred operation of the hairpin detector 114 of FIG. 2. The hairpin detector 114 preferably initially uses a secondary structure folding algorithm based on free-energy minimization, such as the MFOLD algorithm, described in Mathews et al. J. Mol. Biol. 288:911-940 (1999) and Zuker, M. Nucleic Acids Res. 31: 3406-3415 (2003), the disclosure of which is hereby incorporated by reference. This algorithm is operative to calculate probable secondary structure folding patterns of the non-protein-coding genomic sequences 136 (FIG. 4A) as well as the free-energy of each of these probable secondary folding patterns. The secondary structure folding algorithm, such as the MFOLD algorithm (Mathews, 1997; Zuker 2003), typically provides a listing of the base-pairing of the folded shape, i.e. a listing of each pair of connected nucleotides in the sequence.

Next, the hairpin detector 114 analyzes the results of the secondary structure folding patterns, in order to determine the presence and location of hairpin folding structures. The goal of this second step is to assess the base-pairing listing provided by the secondary structure folding algorithm, in order to determine whether the base-pairing listing describes one or more hairpin type bonding pattern. Preferably, sequence segment corresponding to a hairpin structure is then separately analyzed by the secondary structure folding algorithm in order to determine its exact folding pattern and free-energy.

The hairpin detector 114 then assesses the hairpin structures found by the previous step, comparing them to hairpin structures of known miRNA precursors, using various characteristic hairpin structure features such as its free-energy and its thermodynamic stability, the amount and type of mismatched nucleotides and the existence of sequence repeat-elements, number of mismatched nucleotides in positions 18-22 counting from loop, and Percent of G nucleotide. Only hairpins that bear statistically significant resemblance to the training set of hairpin structures of known miRNA precursors, according to the abovementioned parameters, are accepted.

In a preferred embodiment of the present invention, similarity to the training set of hairpin structures of known miRNA precursors is determined using a "similarity score" which is calculated using a multiplicity of terms, where each term is a function of one of the above-mentioned hairpin structure features. The parameters of each function are found heuristically from the set of hairpin structures of known miRNA precursors, as described hereinabove with reference to hairpin detector training & validation functionality 124 (FIG. 3). The selection of the features and their function parameters is optimized so as to achieve maximized separation between the distribution of similarity scores validated miRNA precursor hairpin structures, and the distribution of similarity scores of hairpin structures detected in the background set mentioned hereinabove with reference to FIG. 5B.

In an alternative preferred embodiment of the present invention, the step described in the preceding paragraph may be split into two stages. A first stage implements a simplified scoring method, typically based on thresholding a subset of the hairpin structure features described hereinabove, and may employ a minimum threshold for hairpin structure length and a maximum threshold for free-energy. A second stage is preferably more stringent, and preferably employs a full calculation of the weighted sum of terms described hereinabove. The second stage preferably is performed only on the subset of hairpin structures that survived the first stage.

The hairpin detector 114 also attempts to select hairpin structures whose thermodynamic stability is similar to that of hairpin structures of known miRNA precursors. This may be achieved in various ways. A preferred embodiment of the present invention utilizes the following methodology, preferably comprising three logical steps:

First, the hairpin detector 114 attempts to group hairpin structures into "families" of closely related hairpin structures. As is known in the art, a secondary structure folding algorithm typically provides multiple alternative folding patterns, for a given genomic sequence and indicates the free-energy of each alternative folding pattern. It is a particular feature of the present invention that the hairpin detector 114 preferably assesses the various hairpin structures appearing in the various alternative folding patterns and groups' hairpin structures which appear at identical or similar sequence locations in various alternative folding patterns into common sequence location based "families" of hairpins. For example, all hairpin structures whose center is within 7 nucleotides of each other may be grouped into a "family". Hairpin structures may also be grouped into a "family" if their nucleotide sequences are identical or overlap to a predetermined degree.

It is also a particular feature of the present invention that the hairpin structure "families" are assessed in order to select only those families which represent hairpin structures that are as thermodynamically stable as those of hairpin structures of known miRNA precursors. Preferably only families which are represented in at least a selected majority of the alternative secondary structure folding patterns, typically 65%, 80% or 100% are considered to be sufficiently stable. Our tests suggest that only about 50% of the hairpin structures, predicted by the MFOLD algorithm with default parameters, are members of sufficiently stable families, comparing to about 90% of the hairpin structures that contain known miRNAs. This percent depends on the size of the fraction that was fold. In an alternative embodiment of the present invention we use fractions of size 1000 nts as preferable size. Different embodiment uses other sizes of genomics sequences, more or less strict demand for representation in the alternative secondary structure folding patterns.

It is an additional particular feature of the present invention that the most suitable hairpin structure is selected from each selected family. For example, a hairpin structure which has the greatest similarity to the hairpin structures appearing in alternative folding patterns of the family may be preferred. Alternatively or additionally, the hairpin structures having relatively low free-energy may be preferred.

Alternatively or additionally considerations of homology to hairpin structures of other organisms and the existence of clusters of thermodynamically stable hairpin structures located adjacent to each other along a sequence may be important in selection of hairpin structures. The tightness of the clusters in terms of their location and the occurrence of both homology and clusters may be of significance.

Figure 6A:
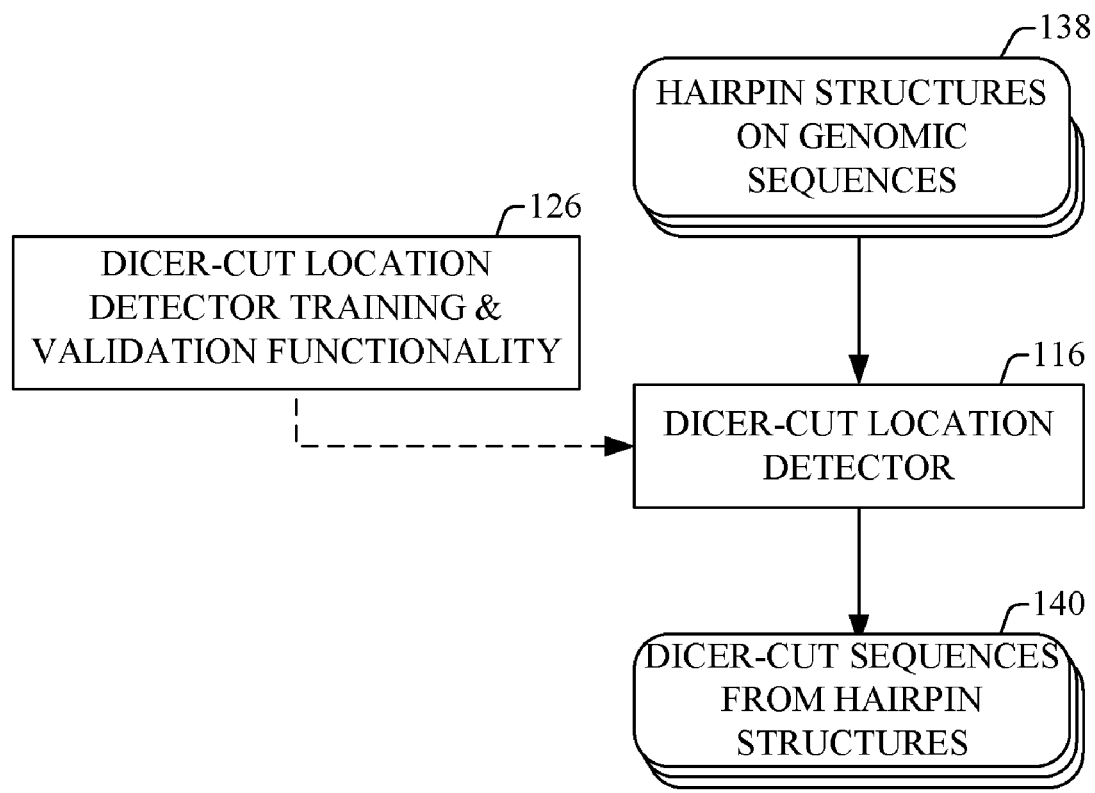
FIG. 6A is a simplified block diagram of a Dicer-cut location detector constructed and operative in accordance with a preferred embodiment of the present invention.
Figure 6B:
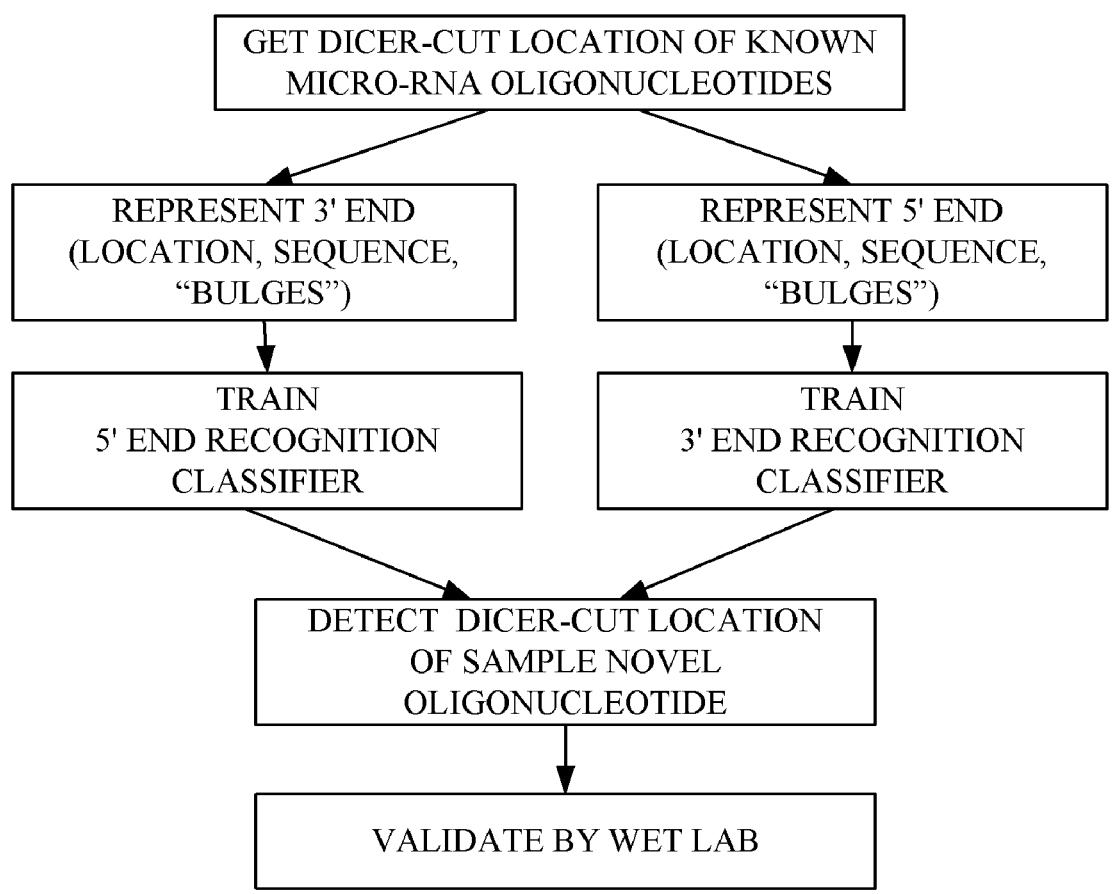
FIG. 6B is a simplified flowchart illustrating training of a Dicer-cut location detector constructed and operative in accordance with a preferred embodiment of the present invention.
Figure 6C:
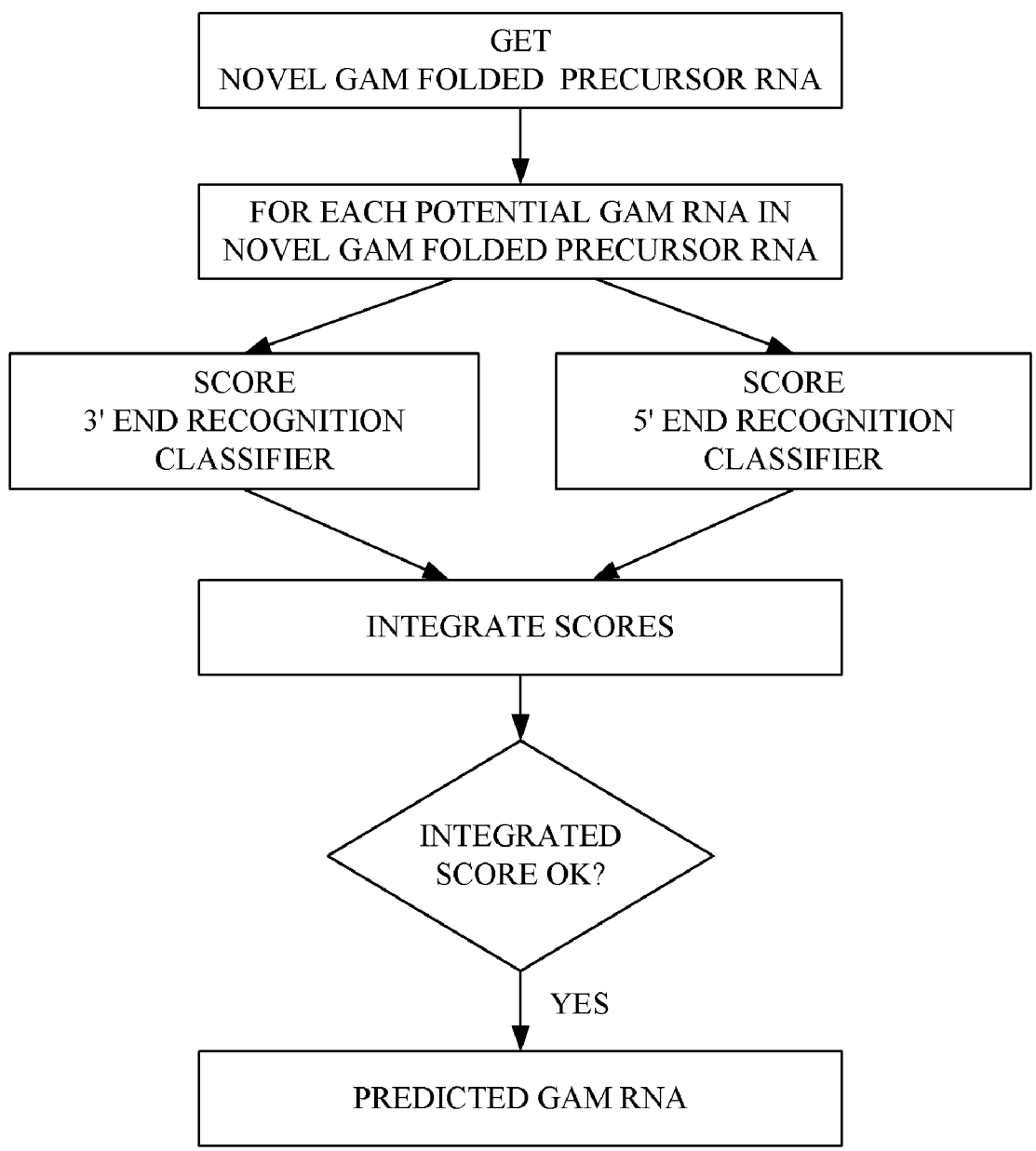
FIG. 6C is a simplified flowchart illustrating operation of a Dicer-cut location detector constructed and operative in accordance with a preferred embodiment of the present invention.

Reference is now made to FIGS. 6A-6C, which together describe the structure and operation of the Dicer-cut location detector 116, described hereinabove with reference to FIG. 2.

Reference is now made to FIG. 6A, which is a simplified block diagram of a preferred implementation of the Dicer-cut location detector 116. The goal of the Dicer-cut location detector 116 is to detect the location in which the DICER COMPLEX, described hereinabove with reference to FIG. 1, dices GAM FOLDED PRECURSOR RNA, yielding GAM RNA.

The Dicer-cut location detector 116 therefore receives a plurality of hairpin structures on genomic sequences, designated by reference numeral 138 (FIG. 5A), and following operation of Dicer-cut location detector training & validation functionality 126 (FIG. 3), is operative to detect a plurality of Dicer-cut sequences from hairpin structures, designated by reference numeral 140.

Reference is now made to FIG. 6B, which is a simplified flowchart illustrating a preferred implementation of Dicer-cut location detector training & validation functionality 126.

A general goal of the Dicer-cut location detector training & validation functionality 126 is to analyze the Dicer-cut locations of known diced miRNA on respective hairpin-shaped miRNA precursors in order to determine a common pattern in these locations, which can be used to predict Dicer-cut locations on GAM folded precursor RNAs.

The Dicer-cut locations of known miRNA precursors are obtained and studied. Locations of the 5' and/or 3' ends of the known diced miRNA oligonucleotides are preferably represented by their respective distances from the 5' end of the corresponding hairpin-shaped miRNA precursor. Additionally or alternatively, the 5' and/or 3' ends of the known diced miRNA oligonucleotides are preferably represented by the relationship between their locations and the locations of one or more nucleotides along the hairpin-shaped miRNA precursor. Additionally or alternatively, the 5' and/or 3' ends of the known diced miRNA oligonucleotides are preferably represented by the relationship between their locations and the locations of one or more bound nucleotide pairs along the hairpin-shaped miRNA precursor. Additionally or alternatively, the 5' and/or 3' ends of the known diced miRNA oligonucleotides are preferably represented by the relationship between their locations and the locations of one or more mismatched nucleotide pairs along the hairpin-shaped miRNA precursor. Additionally or alternatively, the 5' and/or 3' ends of the known diced miRNA oligonucleotides are preferably represented by the relationship between their locations and the locations of one or more unmatched nucleotides along the hairpin-shaped miRNA precursor. Additionally or alternatively, locations of the 5' and/or 3' ends of the known diced miRNA oligonucleotides are preferably represented by their respective distances from the loop located at the center of the corresponding hairpin-shaped miRNA precursor.

One or more of the foregoing location metrics may be employed in the Dicer-cut location detector training & validation functionality 126. Additionally, metrics related to the nucleotide content of the diced miRNA and/or of the hairpin-shaped miRNA precursor may be employed.

In a preferred embodiment of the present invention, Dicer-cut location detector training & validation functionality 126 preferably employs standard machine learning techniques known in the art of machine learning to analyze existing patterns in a given "training set" of examples. Standard machine learning techniques are capable, to a certain degree, of detecting patterns in examples to which they have not been previously exposed that are similar to those in the training set. Such machine learning techniques include, but are not limited to neural networks, Bayesian Modeling, Bayesian Networks, Support Vector Machines (SVM), Genetic Algorithms, Markovian Modeling, Maximum Likelihood Modeling, Nearest Neighbor Algorithms, Decision Trees and other techniques, as is well-known in the art.

In accordance with an embodiment of the present invention, two or more classifiers or predictors based on the abovementioned machine learning techniques are separately trained on the abovementioned training set, and are used jointly in order to predict the Dicer-cut location. As an example, FIG. 6B illustrates operation of two classifiers, a 3' end recognition classifier and a 5' end recognition classifier. Most preferably, the Dicer-cut location detector training & validation functionality 126 implements a "best-of-breed" approach employing a pair of classifiers based on the abovementioned Bayesian Modeling and Nearest Neighbor Algorithms, and accepting only "potential GAM RNAs" that score highly on one of these predictors. In this context, "high scores" means scores that have been demonstrated to have low false positive value when scoring known miRNA oligonucleotides. Alternatively, the Dicer-cut location detector training & validation functionality 126 may implement operation of more or less than two classifiers.

Predictors used in a preferred embodiment of the present invention are further described hereinbelow with reference to FIG. 6C. A computer program listing of a computer program implementation of the Dicer-cut location detector training & validation functionality 126 is enclosed on an electronic medium in computer-readable form, and is hereby incorporated by reference herein.

When evaluated on the abovementioned validation set of 440 published miRNA oligonucleotides using k-fold cross validation (Mitchell, 1997) with k=3, the performance of the resulting predictors is as follows: In 70% of known miRNA oligonucleotides, a 5' end location is correctly determined by a Support Vector Machine predictor within up to two nucleotides; a Nearest Neighbor (EDIT DISTANCE) predictor achieves 56% accuracy (247/440); and a Two-Phased Predictor that uses Bayesian modeling (TWO PHASED) achieves 80% accuracy (352/440) when only the first phase is used. When the second phase (strand choice) is implemented by a naive Bayesian model, the accuracy is 55% (244/440), and when the K-nearest-neighbor modeling is used for the second phase, 374/440 decisions are made and the accuracy is 65% (242/374). A K-nearest-neighbor predictor (FIRST-K) achieves 61% accuracy (268/440). The accuracies of all predictors are considerably higher on top-scoring subsets of published miRNA oligonucleotides.

Finally, in order to validate the efficacy and accuracy of the Dicer-cut location detector 116, a sample of novel oligonucleotides detected thereby is preferably selected, and validated by wet lab experiments. Laboratory results validating the efficacy of the Dicer-cut location detector 116 are described hereinbelow with reference to FIGS. 13-15D, FIG. 18 and also in the enclosed file Table 12.

Reference is now made to FIG. 6C, which is a simplified flowchart illustrating an operation of a Dicer-cut location detector 116 (FIG. 2), constructed and operative in accordance with a preferred embodiment of the present invention. The Dicer-cut location detector 116 preferably comprises a machine learning computer program module, which is trained to recognize Dicer-cut locations on known hairpin-shaped miRNA precursors, and based on this training, is operable to detect Dicer-cut locations of novel GAM RNA (FIG. 1) on GAM FOLDED PRECURSOR RNA (FIG. 1). In a preferred embodiment of the present invention, the Dicer-cut location module preferably utilizes machine learning algorithms, including but not limited to Support Vector Machine, Bayesian modeling, Nearest Neighbors, and K-nearest-neighbor algorithms that are known in the art.

When initially assessing a novel GAM FOLDED PRECURSOR RNA, each 19-24 nt-long segment thereof is considered to be a potential GAM RNA, because the Dicer-cut location is initially unknown.

For each such potential GAM RNA, the location of its 5' end or the locations of its 5' and 3' ends are scored by at least one recognition classifier or predictor, operating on features such as the following: Locations of the 5' and/or 3' ends of the known diced miRNA oligonucleotides, which are preferably represented by their respective distances from the 5' end of the corresponding hairpin-shaped miRNA precursor. Additionally or alternatively, the 5' and/or 3' ends of the known diced miRNA oligonucleotides, which are preferably represented by the relationship between their locations and the locations of one or more nucleotides along the hairpin-shaped miRNA precursor. Additionally or alternatively, the 5' and/or 3' ends of the known diced miRNA oligonucleotides, which are preferably represented by the relationship between their locations and the locations of one or more bound nucleotide pairs along the hairpin-shaped miRNA precursor. Additionally or alternatively, the 5' and/or 3' ends of the known diced miRNA oligonucleotides, which are preferably represented by the relationship between their locations and the locations of one or more mismatched nucleotide pairs along the hairpin-shaped miRNA precursor. Additionally or alternatively, the 5' and/or 3' ends of the known diced miRNA oligonucleotides, which are preferably represented by the relationship between their locations and the locations of one or more unmatched nucleotides along the hairpin-shaped miRNA precursor. Additionally or alternatively, locations of the 5' and/or 3' ends of the known diced miRNA oligonucleotides, which are preferably represented by their respective distances from the loop located at the center of the corresponding hairpin-shaped miRNA precursor. Additionally or alternatively, metrics related to the nucleotide content of the diced miRNA and/or of the hairpin-shaped miRNA precursor.

In a preferred embodiment of the present invention, the Dicer-cut location detector 116 (FIG. 2) may use a Support Vector Machine predictor.

In another preferred embodiment of the present invention, the Dicer-cut location detector 116 (FIG. 2) preferably employs an "EDIT DISTANCE" predictor, which seeks sequences that are similar to those of known miRNA oligonucleotides, utilizing a Nearest Neighbor algorithm, where a similarity metric between two sequences is a variant of the Edit Distance algorithm (Gusfield, 1997). The EDIT DISTANCE predictor is based on an observation that miRNA oligonucleotides tend to form clusters, the members of which show marked sequence similarity.

In yet another preferred embodiment of the present invention, the Dicer-cut location detector 116 (FIG. 2) preferably uses a "TWO PHASE" predictor, which predicts the Dicer-cut location in two distinct phases: (a) selecting a double-stranded segment of the GAM FOLDED PRECURSOR RNA (FIG. 1) comprising the GAM RNA by naive Bayesian modeling and (b) detecting which strand of the double-stranded segment contains GAM RNA (FIG. 1) by employing either naive or K-nearest-neighbor modeling. K-nearest-neighbor modeling is a variant of the "FIRST-K" predictor described hereinbelow, with parameters optimized for this specific task. The "TWO PHASE" predictor may be operated in two modes: either utilizing only the first phase and thereby producing two alternative Dicer-cut location predictions, or utilizing both phases and thereby producing only one final Dicer-cut location.

In still another preferred embodiment of the present invention, the Dicer-cut location detector 116 preferably uses a "FIRST-K" predictor, which utilizes a K-nearest-neighbor algorithm. The similarity metric between any two sequences is 1-E/L, where L is a parameter, preferably 8-10 and E is the edit distance between the two sequences, taking into account only the first L nucleotides of each sequence. If the K-nearest-neighbor scores of two or more locations on the GAM FOLDED PRECURSOR RNA (FIG. 1) are not significantly different, these locations are further ranked by a Bayesian model, similar to the one described hereinabove.

In accordance with an embodiment of the present invention, scores of two or more of the abovementioned classifiers or predictors are integrated, yielding an integrated score for each potential GAM RNA. As an example, FIG. 6C illustrates an integration of scores from two classifiers, a 3' end recognition classifier and a 5' end recognition classifier, the scores of which are integrated to yield an integrated score. Most preferably, the INTEGRATED SCORE of FIG. 6C preferably implements a "best-of-breed" approach employing a pair of classifiers and accepting only "potential GAM RNAs" that score highly on one of the abovementioned "EDIT DISTANCE" or "TWO PHASE" predictors. In this context, "high scores" means scores that have been demonstrated to have low false positive value when scoring known miRNA oligonucleotides. Alternatively, the INTEGRATED SCORE may be derived from operation of more or less than two classifiers.

The INTEGRATED SCORE is evaluated as follows: (a) the "potential GAM RNA" having the highest score is preferably taken to be the most probable GAM RNA, and (b) if the integrated score of this most probable GAM RNA is higher than a pre-defined threshold, then the most probable GAM RNA is accepted as a PREDICTED GAM RNA. Preferably, this evaluation technique is not limited to the highest scoring potential GAM RNA.

In a preferred embodiment of the present invention, PREDICTED GAM RNAs comprising a low complexity nucleotide sequence (e.g., ATATATA) may optionally be filtered out, because there is a high probability that they are part of a repeated element in the DNA, and are therefore not functional, as is known in the art. For each PREDICTED GAM RNA sequence, the number of occurrences of each two nt combination (AA, AT, AC) comprised in that sequence is counted. PREDICTED GAM RNA sequences where the sum of the two most probable combinations is higher than a threshold, preferably 8-10, are filtered out. As an example, when the threshold is set such that 2% of the known miRNA oligonucleotides are filtered out, 30% of the predicted GAM RNAs are filtered out.

Figure 7A:
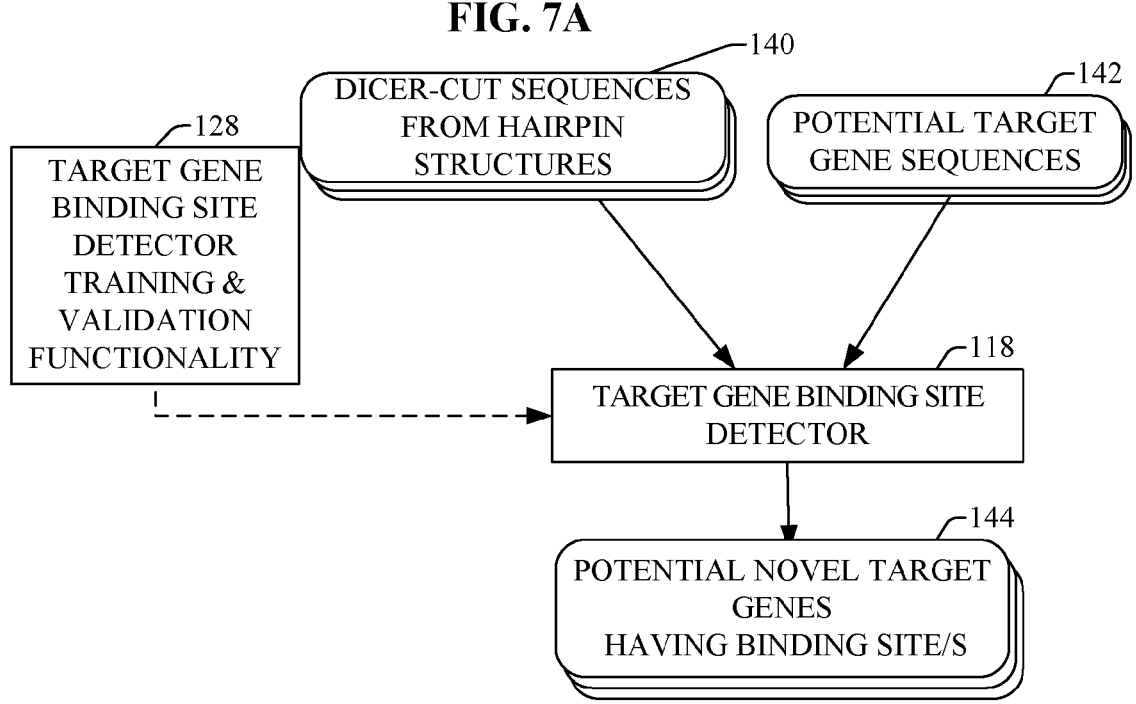
FIG. 7A is a simplified block diagram of a target gene binding site detector constructed and operative in accordance with a preferred embodiment of the present invention.

Reference is now made to FIG. 7A, which is a simplified block diagram of a preferred implementation of the target gene binding site detector 118 described hereinabove with reference to FIG. 2. The goal of the target gene binding site detector 118 is to detect one or more binding sites located in 3'UTRs of the mRNA of a known gene, such as BINDING SITE I, BINDING SITE II and BINDING SITE III (FIG. 1), the nucleotide sequence of which binding sites is partially or fully complementary to a GAM RNA, thereby determining that the abovementioned known gene is a target gene of the GAM RNA.

The target gene binding site detector 118 (FIG. 2) receives a plurality of Dicer-cut sequences from hairpin structures 140 (FIG. 6A) and a plurality of potential target gene sequences 142, which are derived from sequenced DNA data 104 (FIG. 2).

The target gene binding site detector training & validation functionality 128 (FIG. 3) is operative to train the target gene binding site detector 118 on known miRNA oligonucleotides and their respective target genes and to build a background model for an evaluation of the probability of achieving similar results randomly (P value) for the target gene binding site detector 118 results. The target gene binding site detector training & validation functionality 128 constructs the model by analyzing both heuristically and computationally the results of the target gene binding site detector 118.

Following operation of target gene binding site detector training & validation functionality 128 (FIG. 3), the target gene binding site detector 118 is operative to detect a plurality of potential novel target genes having binding site/s 144, the nucleotide sequence of which is partially or fully complementary to that of each of the plurality of Dicer-cut sequences from hairpin structures 140. Preferred operation of the target gene binding site detector 118 is further described hereinbelow with reference to FIG. 7B.

Figure 7B:
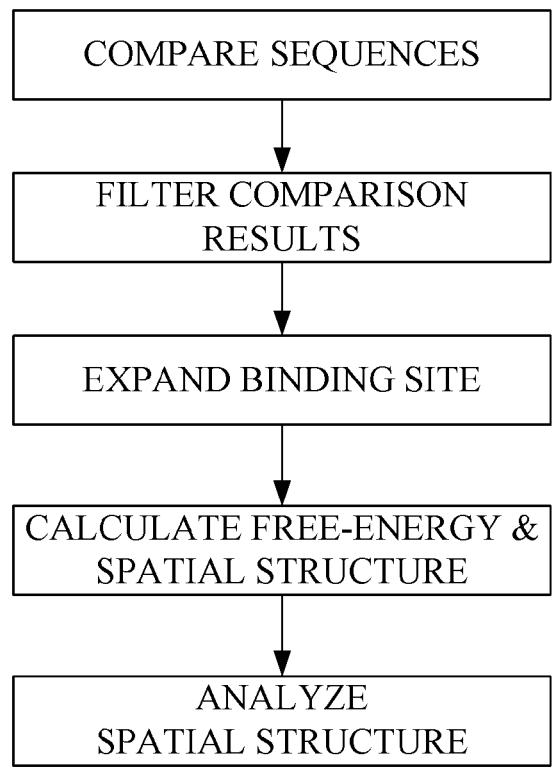
FIG. 7B is a simplified flowchart illustrating operation of a target gene binding site detector constructed and operative in accordance with a preferred embodiment of the present invention.

Reference is now made to FIG. 7B, which is a simplified flowchart illustrating a preferred operation of the target gene binding site detector 118 of FIG. 2.

In an embodiment of the present invention, the target gene binding site detector 118 first compares nucleotide sequences of each of the plurality of Dicer-cut sequences from hairpin structures 140 (FIG. 6A) to the potential target gene sequences 142 (FIG. 7A), such as 3' side UTRs of known mRNAs, in order to find crude potential matches. This step may be performed using a simple alignment algorithm such as BLAST.

Then, the target gene binding site detector 118 filters these crude potential matches, to find closer matches, which more closely resemble published miRNA oligonucleotide binding sites.

Next, the target gene binding site detector 118 expands the nucleotide sequences of the 3'UTR binding site found by the sequence comparison algorithm (e.g. BLAST or EDIT DISTANCE). A determination is made whether any sub-sequence of the expanded sequence may improve the match. The best match is considered the alignment.

Free-energy and spatial structure are computed for the resulting binding sites. Calculation of spatial structure may be performed by a secondary structure folding algorithm based on free-energy minimization, such as the MFOLD algorithm described in Mathews et al. (J. Mol. Biol. 288: 911-940 (1999)) and Zuker (Nucleic Acids Res. 31: 3406-3415 (2003)), the disclosure of which is hereby incorporated by reference. Free-energy, spatial structure and the above preferences are reflected in scoring. The resulting scores are compared with scores characteristic of known binding sites of published miRNA oligonucleotides, and each binding site is given a score that reflects its resemblance to these known binding sites.

Finally, the target gene binding site detector 118 analyzes the spatial structure of the binding site. Each 3'UTR-GAM oligonucleotide pair is given a score. Multiple binding sites of the same GAM oligonucleotides to a 3'UTR are given higher scores than those that bind only once to a 3'UTR.

In a preferred embodiment of the present invention, performance of the target gene binding site detector 118 may be improved by integrating several of the abovementioned logical steps, using the methodology described hereinbelow.

For each of the Dicer-cut sequence from hairpin structures 140, its starting segment, e.g. a segment comprising the first 8 nts from its 5' end, is obtained. For each starting segment, all of the 9 nt segments that are highly complementary to the starting segment are calculated. These calculated segments are referred to here as "potential binding site end segments". In a preferred embodiment of the present invention, for each 8 nt starting segment, the potential binding site end segments are all 9 nt segments whose complementary sequence contains a 7-9 nt sub-sequence that is not different from the starting segment by more than an insertion, deletion or replacement of one nt. Calculation of potential binding site end segments is preferably performed by a pre-processing tool that maps all possible 8 nt segments to their respective 9 nt segments.

Next, the mRNAs 3'UTRs is parsed into all the segments, with the same length as the potential binding site end segments, preferably 9 nt segments, comprised in the 3'UTR. Location of each such segment is noted, stored in a performance-efficient data structure and compared to the potential binding site end segments calculated in the previous step.

The target gene binding site detector 118 then expands the binding site sequence, preferably in the binding site 5' direction (i.e. immediately upstream), assessing the degree of its alignment to the Dicer-cut sequence from hairpin structures 140. Preferably, an alignment algorithm is implemented which uses specific weighting parameters based on an analysis of known miRNA oligonucleotide binding sites. As an example, it is apparent that a good match of the 3' end of the binding site is critically important, a match of the 5' end is less important but can compensate for a small number of mismatches at the 3' end of the binding site, and a match of the middle portion of the binding site is much less important.

Next, the number of binding sites found in a specific 3'UTR, the degree of alignment of each of these binding sites, and their proximity to each other are assessed and compared to these properties found in known binding sites of published miRNA oligonucleotides. In a preferred embodiment, the fact that many of the known binding sites are clustered is used to evaluate the P value of obtaining a cluster of a few binding sites on the same target gene 3'UTR in the following way. It scans different score thresholds and calculates for each threshold the number and positions of possible binding sites with a score above the threshold. It then gets a P value for each threshold from a preprocessed calculated background matrix, described hereinbelow, and a number and positions of binding sites combination. The output score for each Dicer-cut sequences from hairpin structures 140 and potential target gene sequences 142 is the minimal P value, normalized with the number of threshold trails using a Bernoulli distribution. A preference of low P value pairs is made.

As mentioned hereinabove, for each target gene, a preprocessed calculated background matrix is built. The matrix includes rows for each number of miRNA oligonucleotide binding sites (in the preferred embodiment, the matrix includes 7 rows to accommodate 0 to 6 binding sites), and columns for each different score threshold (in the preferred embodiment, the matrix includes 5 columns for 5 different thresholds). Each matrix cell, corresponding to a specific number of binding sites and thresholds, is set to be the probability of getting equal or higher number binding sites and an equal or higher score using random 22 nt-long sequences with the same nucleotide distribution as known miRNA oligonucleotides (29.5% T, 24.5% A, 25% G and 21% C). Those probabilities are calculated by running the above procedure for 10000 random sequences that preserved the known miRNA nucleotide distribution (these sequence will be also referred to as miRNA oligonucleotide random sequences). The P value can be estimated as the number of random sequences that obeys the matrix cell requirement divided by the total number of random sequences (10000). In the preferred embodiment, 2 matrices are calculated. The P values of the second matrix are calculated under a constraint that at least two of the binding site positions are under a heuristically-determined constant value. The values of the second matrix are calculated without this constraint. The target gene binding site detector 118 uses the second matrix if the binding site positions agree with the constraint. Otherwise, it uses the first. In an alternative embodiment, only one matrix is calculated without any constraint on the binding sites positions.

A test performed using the target gene binding site detector 118 shows that all of the known miRNA oligonucleotide target genes are found using this algorithm with a P value of less than 0.5%. Running known miRNA oligonucleotides against 3400 potential 3'UTR of target gene sequences yields on average 32 target genes for each miRNA oligonucleotide with a P value less than 0.5%, while background sequences, as well as inverse or complement sequence of known miRNA oligonucleotide (which preserve their high order sequence statistics) found, as expected, 17 target genes on average. This result reflects that the algorithm has the ability to detect real target genes with 47% accuracy.

Finally, orthology data may optionally be used to further prefer binding sites based on their conservation. Preferably, this may be used in cases such as (a) where both the target mRNA and miRNA oligonucleotide have orthologues in another organism, e.g. Human-Mouse orthology, or (b) where a miRNA oligonucleotide (e.g. viral miRNA oligonucleotide) targets two mRNAs in orthologous organisms. In such cases, binding sites that are conserved are preferred.

In accordance with another preferred embodiment of the present invention, binding sites may be searched by a reverse process. Sequences of K (preferably 22) nucleotides in a UTR of a target gene are assessed as potential binding sites. A sequence comparison algorithm, such as BLAST or EDIT DISTANCE variant, is then used to search elsewhere in the genome for partially or fully complementary sequences that are found in known miRNA oligonucleotides or computationally-predicted GAM oligonucleotides. Only complementary sequences that meet predetermined spatial structure and free-energy criteria as described hereinabove, are accepted. Clustered binding sites are strongly preferred and potential binding sites and potential GAM oligonucleotides that occur in evolutionarily-conserved genomic sequences are also preferred. Scoring of candidate binding sites takes into account free-energy and spatial structure of the binding site complexes, as well as the aforesaid preferences.

The 3'UTR of each bacterial gene is extracted from the 500 nts that lay downstream to the gene-coding region. Care is taken that the extracted 3'UTR is not partly covered by the predicted 5'UTR of the next gene-coding region, considered 300 nts upstream. This method is applied on known (not hypothetical) bacterial genes of completed pathogenic eubacterial genomes taken from the updated NCBI Ref_seq database on 17 Mar. 2004.

Figure 8:
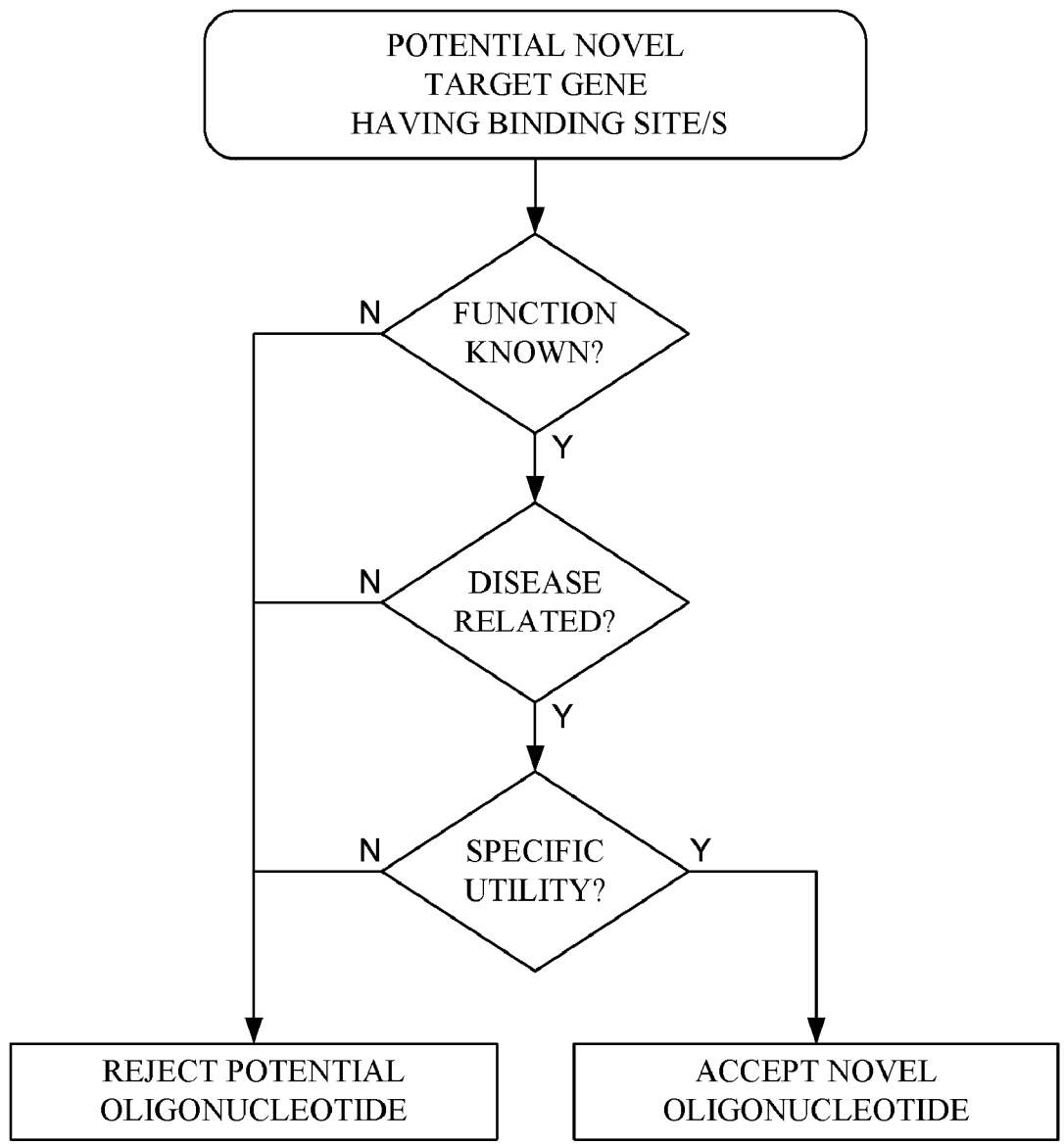
FIG. 8 is a simplified flowchart illustrating operation of a function and utility analyzer constructed and operative in accordance with a preferred embodiment of the present invention.

Reference is now made to FIG. 8, which is a simplified flowchart illustrating a preferred operation of the function & utility analyzer 120 described hereinabove with reference to FIG. 2. The goal of the function & utility analyzer 120 is to determine if a potential target gene is in fact a valid clinically useful target gene. Since a potential novel GAM oligonucleotide binding a binding site in the UTR of a target gene is understood to inhibit expression of that target gene, and if that target gene is shown to have a valid clinical utility, then in such a case it follows that the potential novel oligonucleotide itself also has a valid useful function which is the opposite of that of the target gene.

The function & utility analyzer 120 preferably receives as input a plurality of potential novel target genes having binding site/s 144 (FIG. 7A), generated by the target gene binding site detector 118 (FIG. 2). Each potential oligonucleotide is evaluated as follows: First, the system checks to see if the function of the potential target gene is scientifically well established. Preferably, this can be achieved bioinformatically by searching various published data sources presenting information on known function of proteins. Many such data sources exist and are published, as is well known in the art. Next, for those target genes the function of which is scientifically known and is well documented, the system then checks if scientific research data exists which links them to known diseases. For example, a preferred embodiment of the present invention utilizes the OMIM™ (Hamosh et al, 2002) database published by NCBI, which summarizes research publications relating to genes which have been shown to be associated with diseases. Finally, the specific possible utility of the target gene is evaluated. While this process too may be facilitated by bioinformatic means, it might require manual evaluation of published scientific research regarding the target gene, in order to determine the utility of the target gene to the diagnosis and or treatment of specific disease. Only potential novel oligonucleotides, the target genes of which have passed all three examinations, are accepted as novel oligonucleotide.

Figure 9:
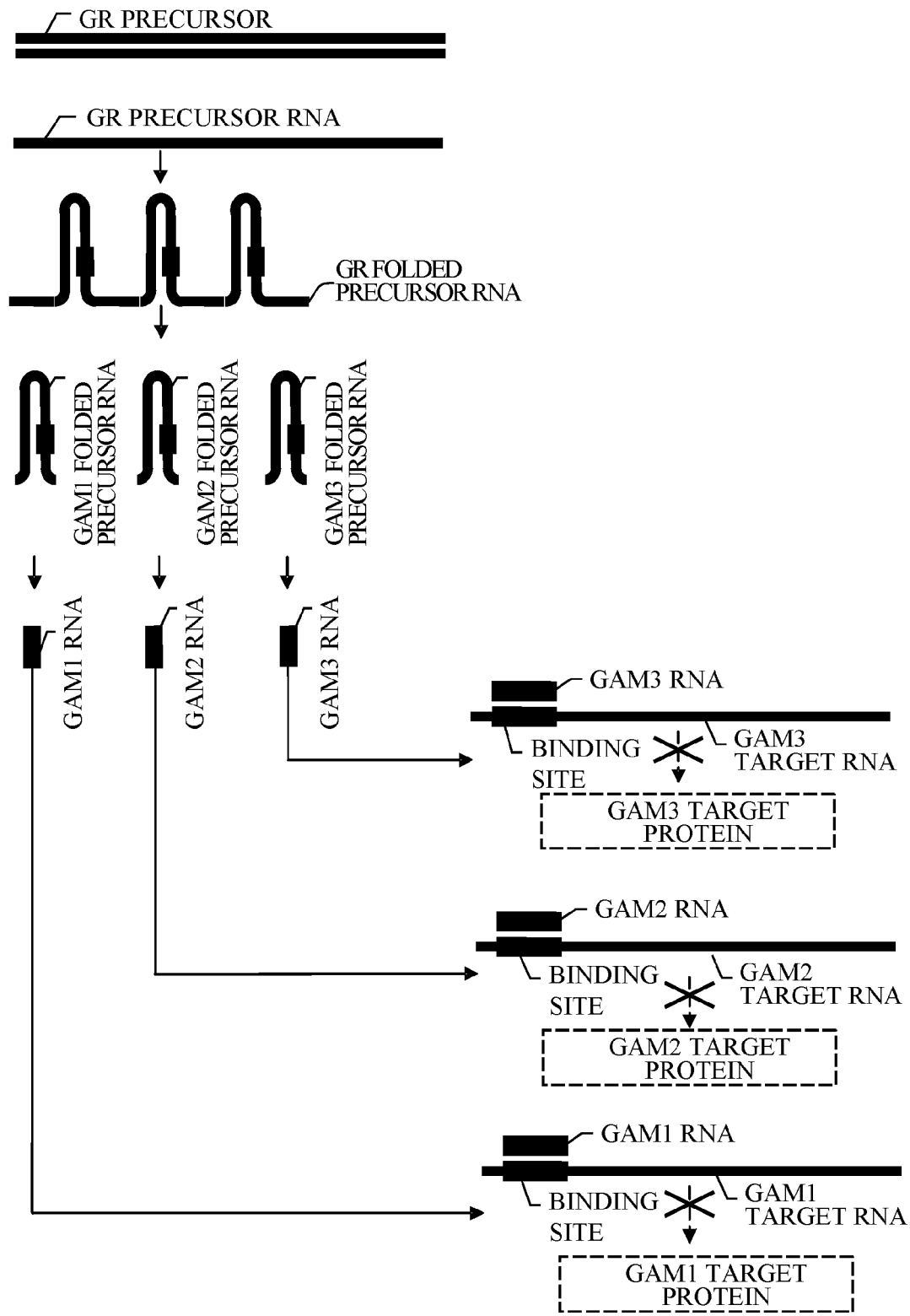
FIG. 9 is a simplified diagram describing a novel bioinformatically-detected group of regulatory polynucleotides, referred to here as Genomic Record (GR) polynucleotides, each of which encodes an "operon-like" cluster of novel microRNA-like oligonucleotides, which in turn modulate expression of one or more target genes.

Reference is now made to FIG. 9, which is a simplified diagram describing each of a plurality of novel bioinformatically-detected regulatory polynucleotide referred to in this Table as the Genomic Record (GR) polynucleotide. GR encodes an operon-like cluster of novel miRNA-like oligonucleotides, each of which in turn modulates expression of at least one target gene. The function and utility of at least one target gene is known in the art.

The GR PRECURSOR is a novel, bioinformatically-detected, regulatory, non-protein-coding polynucleotide. The method by which the GR PRECURSOR is detected is described hereinabove with additional reference to FIGS. 1-9.

GR PRECURSOR is preferably encoded by the bacterial genome and contains a cluster of novel bacterial oligonucleotides, which preferably bind to human target genes or to bacterium genes. Alternatively or additionally, GR PRECURSOR is encoded by the human genome and contains a cluster of novel human oligonucleotides, which preferably bind to bacterial target genes or to human genes.

The GR PRECURSOR encodes GR PRECURSOR RNA that is typically several hundred to several thousand nts long. The GR PRECURSOR RNA folds spatially, forming the GR FOLDED PRECURSOR RNA. It is appreciated that the GR FOLDED PRECURSOR RNA comprises a plurality of what is known in the art as hairpin structures. Hairpin structures result from the presence of segments of the nucleotide sequence of GR PRECURSOR RNA in which the first half of each such segment has a nucleotide sequence which is at least a partial, and sometimes an accurate, reverse-complement sequence of the second half thereof, as is well known in the art.

The GR FOLDED PRECURSOR RNA is naturally processed by cellular enzymatic activity into a plurality of separate GAM precursor RNAs herein schematically represented by GAM1 FOLDED PRECURSOR RNA through GAM3 FOLDED PRECURSOR RNA. Each GAM folded precursor RNA is a hairpin-shaped RNA segment, corresponding to GAM FOLDED PRECURSOR RNA of FIG. 1.

The abovementioned GAM folded precursor RNAs are diced by DICER COMPLEX of FIG. 1, yielding short RNA segments of about 22 nts in length schematically represented by GAM1 RNA through GAM3 RNA. Each GAM RNA corresponds to GAM RNA of FIG. 1. GAM1 RNA, GAM2 RNA and GAM3 RNA each bind complementarily to binding sites located in the untranslated regions of their respective target genes, designated GAM1 TARGET RNA, GAM2 TARGET RNA and GAM3 TARGET RNA, respectively. These target binding sites correspond to BINDING SITE I, BINDING SITE II and BINDING SITE III of FIG. 1. The binding of each GAM RNA to its target RNA inhibits the translation of its respective target proteins, designated GAM1 TARGET PROTEIN, GAM2 TARGET PROTEIN and GAM3 TARGET PROTEIN, respectively.

It is appreciated that the specific functions, and accordingly the utilities, of the GR polynucleotide are correlated with and may be deduced from the identity of the target genes that are inhibited by GAM RNAs that are present in the operon-like cluster of the polynucleotide. Thus, for the GR polynucleotide, schematically represented by GAM1 TARGET PROTEIN through GAM3 TARGET PROTEIN that are inhibited by the GAM RNA. The function of these target genes is elaborated in Table 8, hereby incorporated herein.

Figure 10:
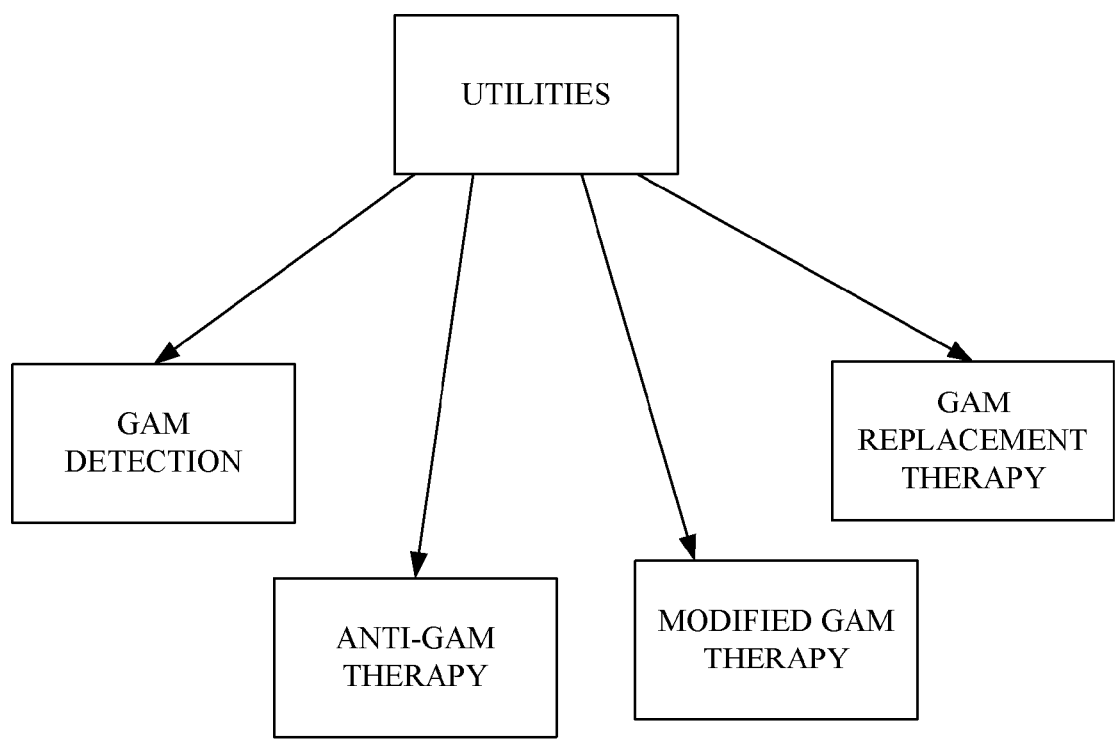
FIG. 10 is a block diagram illustrating different utilities of novel oligonucleotides and novel operon-like polynucleotides, both of the present invention.

Reference is now made to FIG. 10, which is a block diagram illustrating different utilities of oligonucleotide of the novel group of oligonucleotides of the present invention referred to here as GAM oligonucleotides and GR polynucleotides. The present invention discloses a first plurality of novel oligonucleotides referred to here as GAM oligonucleotides and a second plurality of operon-like polynucleotides referred to here as GR polynucleotides, each of the GR polynucleotide encoding a plurality of GAM oligonucleotides. The present invention further discloses a very large number of known target genes, which are bound by, and the expression of which is modulated by each of the novel oligonucleotides of the present invention. Published scientific data referenced by the present invention provides specific, substantial, and credible evidence that the abovementioned target genes modulated by novel oligonucleotides of the present invention, are associated with various diseases. Specific novel oligonucleotides of the present invention, target genes thereof and diseases associated therewith, are described hereinbelow with reference to Tables 1 through 12. It is therefore appreciated that a function of GAM oligonucleotides and GR polynucleotides of the present invention is modulation of expression of target genes related to known bacterial diseases, and that therefore utilities of novel oligonucleotides of the present invention include diagnosis and treatment of the abovementioned diseases.

FIG. 10 describes various types of diagnostic and therapeutic utilities of novel oligonucleotides of the present invention. A utility of novel oligonucleotide of the present invention is detection of GAM oligonucleotides and of GR polynucleotides. It is appreciated that since GAM oligonucleotides and GR polynucleotides modulate expression of disease related target genes, that detection of expression of GAM oligonucleotides in clinical scenarios associated with said bacterial diseases is a specific, substantial and credible utility. Diagnosis of novel oligonucleotides of the present invention may preferably be implemented by RNA expression detection techniques, including but not limited to biochips, as is well known in the art. Diagnosis of expression of oligonucleotides of the present invention may be useful for research purposes, in order to further understand the connection between the novel oligonucleotides of the present invention and the abovementioned related bacterial diseases, for disease diagnosis and prevention purposes, and for monitoring disease progress.

Another utility of novel oligonucleotides of the present invention is anti-GAM therapy, a mode of therapy which allows up regulation of a bacterial disease-related target gene of a novel GAM oligonucleotide of the present invention, by lowering levels of the novel GAM oligonucleotide which naturally inhibits expression of that target gene. This mode of therapy is particularly useful with respect to target genes which have been shown to be under-expressed in association with a specific bacterial disease. Anti-GAM therapy is further discussed hereinbelow with reference to FIGS. 11A and 11B.

A further utility of novel oligonucleotides of the present invention is GAM replacement therapy, a mode of therapy which achieves down regulation of a bacterial disease related target gene of a novel GAM oligonucleotide of the present invention, by raising levels of the GAM which naturally inhibits expression of that target gene. This mode of therapy is particularly useful with respect to target genes which have been shown to be over-expressed in association with a specific bacterial disease. GAM replacement therapy involves introduction of supplementary GAM products into a cell, or stimulation of a cell to produce excess GAM products. GAM replacement therapy may preferably be achieved by transfecting cells with an artificial DNA molecule encoding a GAM which causes the cells to produce the GAM product, as is well known in the art.

Yet a further utility of novel oligonucleotides of the present invention is modified GAM therapy. Disease conditions are likely to exist, in which a mutation in a binding site of a GAM RNA prevents natural GAM RNA to effectively bind inhibit a bacterial disease related target gene, causing up regulation of that target gene, and thereby contributing to the disease pathology. In such conditions, a modified GAM oligonucleotides is designed which effectively binds the mutated GAM binding site, i.e. is an effective anti-sense of the mutated GAM binding site, and is introduced in disease effected cells. Modified GAM therapy is preferably achieved by transfecting cells with an artificial DNA molecule encoding the modified GAM which causes the cells to produce the modified GAM product, as is well known in the art.

Reference is now made to FIGS. 11A and 11B, which are simplified diagrams which when taken together illustrate anti-GAM therapy mentioned hereinabove with reference to FIG. 10. A utility of novel GAMs of the present invention is anti-GAM therapy, a mode of therapy which allows up regulation of a bacterial disease-related target gene of a novel GAM of the present invention, by lowering levels of the novel GAM which naturally inhibits expression of that target gene. FIG. 11A shows a normal GAM inhibiting translation of a target gene by binding of GAM RNA to a BINDING SITE found in an untranslated region of GAM TARGET RNA, as described hereinabove with reference to FIG. 1.

FIG. 11B shows an example of anti-GAM therapy. ANTI-GAM RNA is short artificial RNA molecule the sequence of which is an anti-sense of GAM RNA. Anti-GAM treatment comprises transfecting diseased cells with ANTI-GAM RNA, or with a DNA encoding thereof. The ANTI-GAM RNA binds the natural GAM RNA, thereby preventing binding of natural GAM RNA to its BINDING SITE. This prevents natural translation inhibition of GAM TARGET RNA by GAM RNA, thereby up regulating expression of GAM TARGET PROTEIN.

It is appreciated that anti-GAM therapy is particularly useful with respect to target genes which have been shown to be under-expressed in association with a specific bacterial disease.

Furthermore, anti-GAM therapy is particularly useful, since it may be used in situations in which technologies known in the art as RNAi and siRNA can not be utilized. As in known in the art, RNAi and siRNA are technologies which offer means for artificially inhibiting expression of a target protein, by artificially designed short RNA segments which bind complementarily to mRNA of said target protein. However, RNAi and siRNA can not be used to directly up regulate translation of target proteins.

Figure 12A:
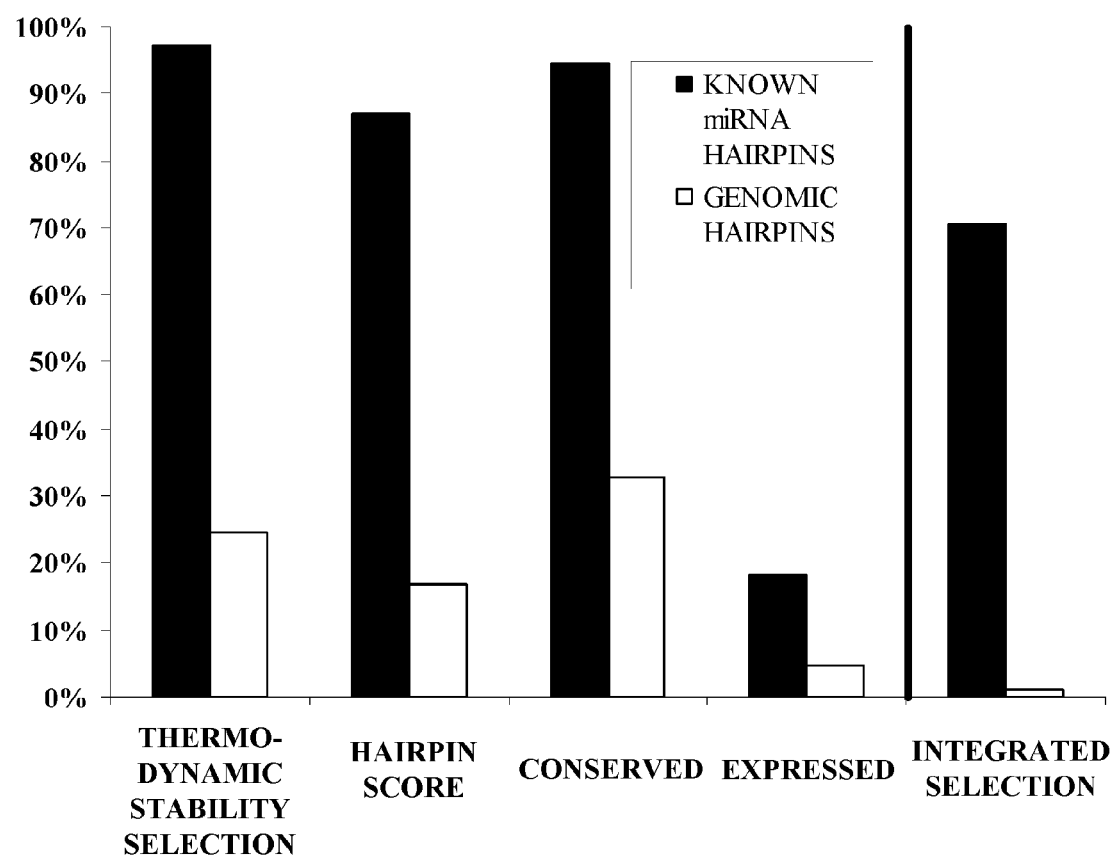
FIG. 12A is a bar graph illustrating performance results of a hairpin detector constructed and operative in accordance with a preferred embodiment of the present invention.

Reference is now made to FIG. 12A, which is a bar graph illustrating performance results of the hairpin detector 114 (FIG. 2) constructed and operative in accordance with a preferred embodiment of the present invention.

FIG. 12A illustrates efficacy of several features used by the hairpin detector 114 to detect GAM FOLDED PRECURSOR RNAs (FIG. 1). The values of each of these features is compared between a set of published miRNA precursor oligonucleotides, represented by shaded bars, and a set of random hairpins folded from the human genome denoted hereinbelow as a hairpin background set, represented by white bars. The published miRNA precursor oligonucleotides set is taken from RFAM database, Release 2.1 and includes 148 miRNA oligonucleotides from *H. Sapiens*. The background set comprises a set of 10,000 hairpins folded from the human genome.

It is appreciated that the hairpin background set is expected to comprise some valid, previously undetected hairpin-shaped miRNA precursor-like GAM FOLDED PRECURSOR RNAs of the present invention, and many hairpin-shaped sequences that are not hairpin-shaped miRNA-like precursors.

For each feature, the bars depict the percent of known miRNA hairpin precursors (shaded bars) and the percent of background hairpins (white bars) that pass the threshold for that feature. The percent of known miRNA oligonucleotides that pass the threshold indicates the sensitivity of the feature, while the corresponding background percent implies the specificity of the feature, although not precisely, because the background set comprises both true and false examples.

The first bar pair, labeled Thermodynamic Stability Selection, depicts hairpins that have passed the selection of "families" of closely related hairpin structures, as described hereinabove with reference to FIG. 5B.

The second bar pair, labeled Hairpin Score, depicts hairpins that have been selected by hairpin detector 114 (FIG. 5B), regardless of the "families" selection.

The third bar pair, labeled Conserved, depicts hairpins that are conserved in human, mouse and rat, (UCSC Goldenpath™ HG16 database).

The fourth bar pair, labeled Expressed, depicts hairpins that are found in EST blocks.

The fifth bar pair, labeled Integrated Selection, depicts hairpin structures predicted by a preferred embodiment of the present invention to be valid GAM PRECURSORs. In a preferred embodiment of the present invention, a hairpin may be considered to be a GAM PRECURSOR if its hairpin detector score is above 0, and it is in one of the following groups: a) in an intron and conserved or b) in an intergenic region and conserved or c) in an intergenic region and expressed, as described below. Further filtering of GAM precursor may be obtained by selecting hairpins with a high score of Dicer-cut location detector 116 as described hereinabove with reference to FIGS. 6A-6C, and with predicted miRNA oligonucleotides, which pass the low complexity filter as described hereinabove, and whose targets are selected by the target gene binding site detector 118 as described hereinabove with reference to FIGS. 7A-7B.

It is appreciated that these results validate the sensitivity and specificity of the hairpin detector 114 (FIG. 2) in identifying novel GAM FOLDED PRECURSOR RNAs, and in effectively distinguishing them from the abundant hairpins found in the genome.

Figure 12B:
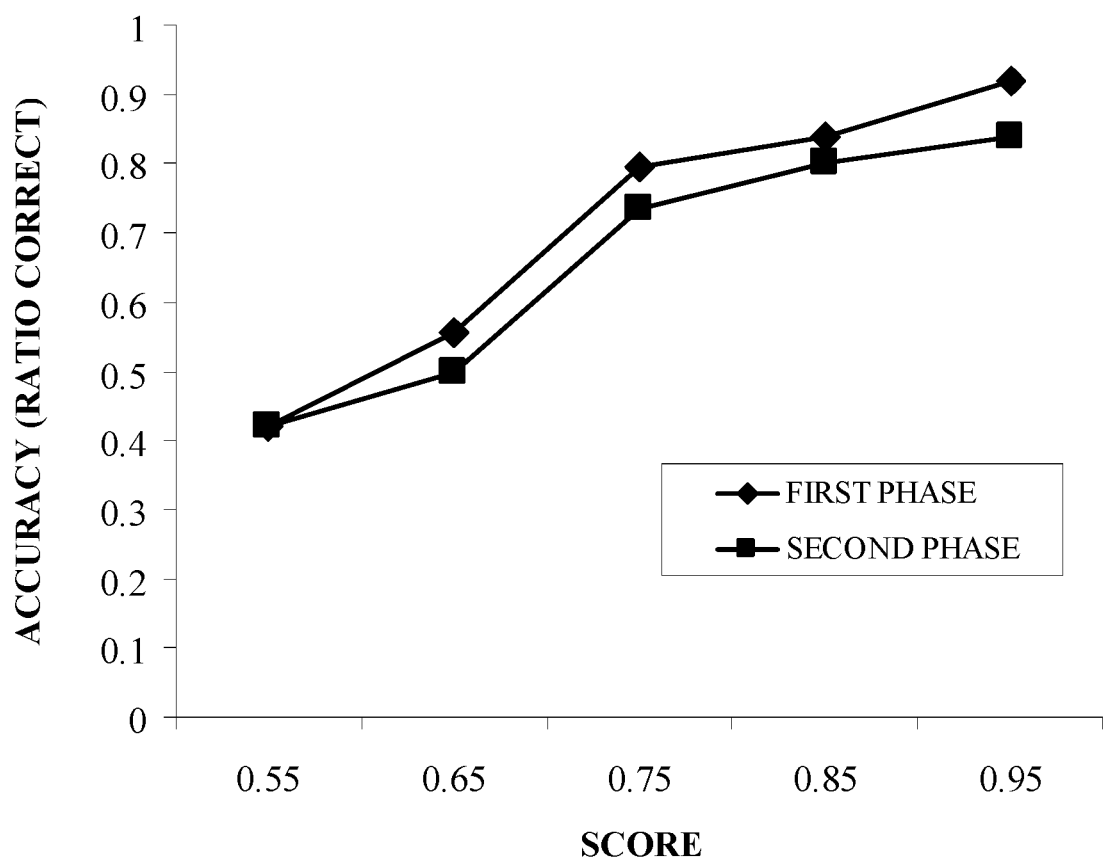
FIG. 12B is a line graph illustrating accuracy of a Dicer-cut location detector constructed and operative in accordance with a preferred embodiment of the present invention.

Reference is now made to FIG. 12B, which is a line graph illustrating accuracy of a Dicer-cut location detector 116 (FIG. 2) constructed and operative in accordance with a preferred embodiment of the present invention.

To determine the accuracy of the Dicer-cut location detector 116, a stringent training and test set was chosen from the abovementioned set of 440 known miRNA oligonucleotides, such that no two miRNA oligonucleotides in the set are homologous. This was performed to get a lower bound on the accuracy and avoid effects of similar known miRNA oligonucleotides appearing in both the training and test sets. On this stringent set of size 204, mfold cross validation with k=3 was performed to determine the percent of known miRNA oligonucleotides in which the Dicer-cut location detector 116 described hereinabove predicted the correct miRNA oligonucleotide up to two nucleotides from the correct location. The accuracy of the TWO PHASED predictor is depicted in the graph. The accuracy of the first phase of the TWO PHASED predictor is depicted by the upper line, and that of both phases of the TWO PHASED predictor is depicted by the lower line. Both are binned by the predictor score, where the score is the score of the first stage.

It is appreciated that these results validate the accuracy of the Dicer-cut location detector 116.

Figure 12C:
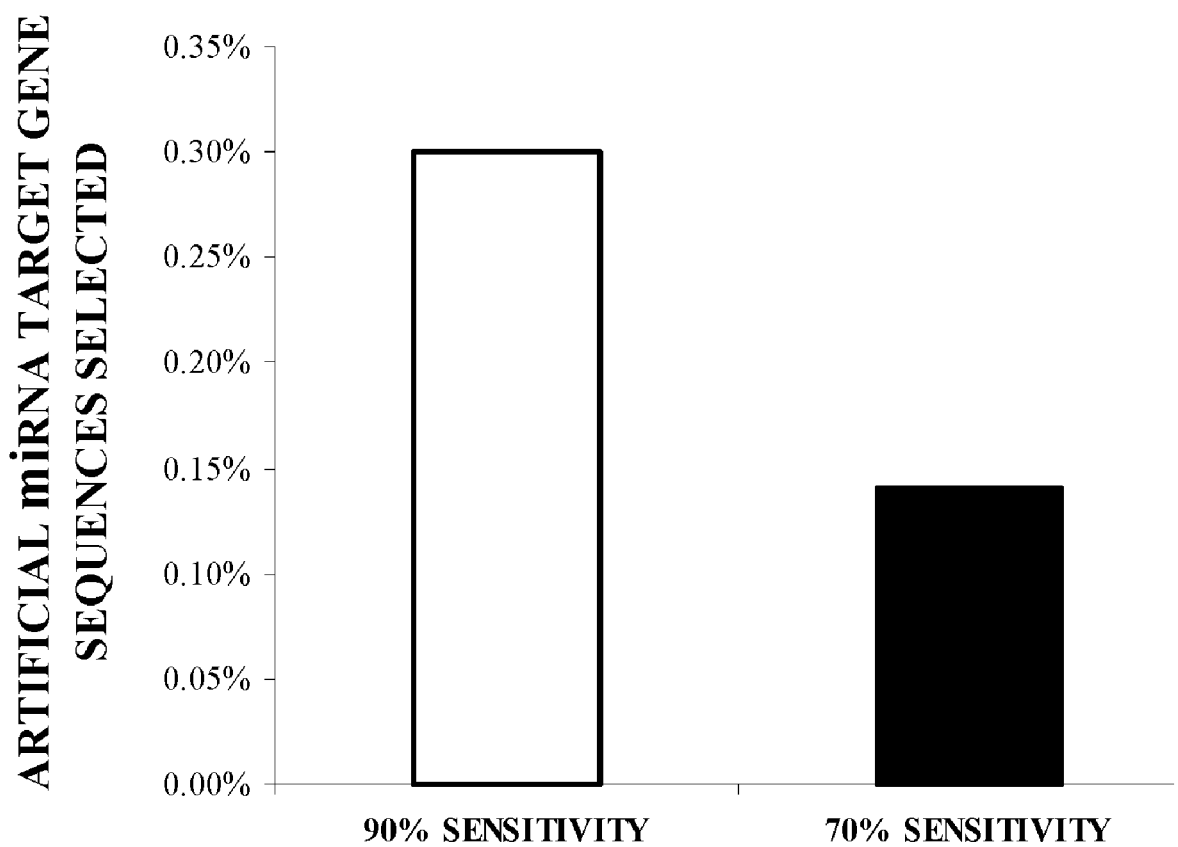
FIG. 12C is a bar graph illustrating performance results of the target gene binding site detector 118, constructed and operative in accordance with a preferred embodiment of the present invention.

Reference is now made to FIG. 12C, which is a bar graph illustrating the performance results of the target gene binding site detector 118 (FIG. 7A) constructed and operative in accordance with a preferred embodiment of the present invention.

FIG. 12C illustrates specificity and sensitivity of the target gene binding site detector 118. The values presented are the result of testing 10000 artificial miRNA oligonucleotide sequences (random 22 nt sequences with the same base composition as published miRNA oligonucleotide sequence). Adjusting the threshold parameters to fulfill 90% sensitivity of validated, published miRNA-3'UTR pairs, requires the P VAL of potential target gene sequences-Dicer-cut sequences to be less than 0.01 and also the P VAL of potential target ortholog gene sequences-Dicer-cut sequences to be less than 0.05. The target gene binding site detector 118 can filter out 99.7% of potential miRNA/gene pairs, leaving only the 0.3% that contain the most promising potential miRNA/gene pairs. Limiting the condition for the P VAL of potential target ortholog gene sequences-Dicer-cut sequences to be less than 0.01 reduces the sensitivity ratio to 70% but filters out more then 50% of the remaining 0.3%, to a final ratio of less than 0.15%.

It is appreciated that these results validate the sensitivity and specificity of the target gene binding site detector 118.

Reference is now made to FIG. 13, which is a summary table of laboratory results validating the expression of 29 novel human GAM RNA oligonucleotides in HeLa cells or, alternatively, in liver or thymus tissues detected by the bioinformatic oligonucleotide detection engine 100 (FIG. 2).

As a positive control, we used a reference set of eight known human miRNA oligonucleotides: hsa-MIR-21; hsa-MIR-27b; hsa-MIR-186; hsa-MIR-93; hsa-MIR-26a; hsa-MIR-191; hsa-MIR-31; and hsa-MIR-92. All positive controls were successfully validated by sequencing.

The table of FIG. 13 lists all GAM RNA predictions whose expression was validated. The field "Primer Sequence" contains the "specific" part of the primer; the field "Sequenced sequence" represents the nucleotide sequence detected by cloning (excluding the hemispecific primer sequence); the field "Predicted GAM RNA" contains the GAM RNA predicted sequence; the field "Distance indicate the distance from Primer; the number of mismatches between the "specific" region of the primer and the corresponding part of the GAM RNA sequence; the field "GAM Name" contains GAM RNA PRECURSOR ID followed by "A" or "B", which represents the GAM RNA position on the precursor as elaborated in the attached Tables.

A primer was designed such that its first half, the 5' region, is complementary to the adaptor sequence and its second half, the 3' region, anneals to the 5' terminus of GAM RNA sequence, yielding a hemispecific primer (as elaborated hereinbelow in the Methods section). A sample of 13 predicted GAM RNA sequences was examined by PCR using hemispecific primers and a primer specific to the 3' adaptor. PCR products were cloned into plasmid vectors and then sequenced. For all 13 predicted GAM RNA sequences, the GAM RNA sequence found in the hemispecific primer plus the sequence observed between the hemispecific primer and the 3' adaptor was completely included in the expected GAM RNA sequence (rows 1-7, and 29). The rest are GAM RNA predictions that were verified by cloning and sequencing, yet, by using a primer that was originally designed for a slightly different prediction.

It is appreciated that failure to detect a predicted oligonucleotide in the lab does not necessarily indicate a mistaken bioinformatic prediction. Rather, it may be due to technical sensitivity limitation of the lab test, or because the predicted oligonucleotides are not expressed in the tissue examined, or at the development phase tested. The observed GAM RNAs may be strongly expressed in HeLa cells while the original GAM RNAs are expressed at low levels in HeLa cells or not expressed at all. Under such circumstances, primer sequences containing up to three mismatches from a specific GAM RNA sequence may amplify it. Thus, we also considered cases in which differences of up to 3 mismatches in the hemispecific primer occur.

The 3' terminus of observed GAM RNA sequences is often truncated or extended by one or two nucleotides. Cloned sequences that were sequenced from both 5' and 3' termini have an asterisk appended to the row number.

Interestingly, the primer sequence followed by the observed cloned sequence is contained within five GAM RNA sequences of different lengths, and belong to 24 precursors derived from distinct loci (Row 29). Out of these, one precursor appears four times in the genome and its corresponding GAM Names are 351973-A, 352169-A, 352445-A and 358164-A.

The sequence presented in Row 29 is a representative of the group of five GAM RNAs. The full list of GAM RNA sequences and their corresponding precursors is as follows (each GAM RNA sequence is followed by the GAM Name): TCACTGCAACCTCCACCTCCCA (SEQ ID NO: 4254782) (352092, 352651, 355761), TCACTGCAACCTC-CACCTCCCG (SEQ ID NO: 4254783) (351868, 352440, 351973, 352169, 352445, 358164, 353737, 352382, 352235, 352232, 352268, 351919, 352473, 352444, 353638, 353004, 352925, 352943), TCACTGCAACCTCCACCTCCTG (SEQ ID NO: 4254784) (358311), TCACTGCAACCTC-CACCTTCAG (SEQ ID NO: 4254785) (353323), and TCACTGCAACCTCCACCTTCCG (SEQ ID NO: 4254786) (353856).

Method Section
Cell Lines

Three common human cell lines, obtained from Dr. Yonat Shemer at Soroka Medical Center, Be'er Sheva, Israel, were used for RNA extraction; Human Embryonic Kidney HEK-293 cells, Human Cervix Adenocarcinoma HeLa cells and Human Prostate Carcinoma PC3 cells.

RNA Purification

Several sources of RNA were used to prepare libraries:

Total HeLa S100 RNA was prepared from HeLa S100 cellular fraction (4 C Biotech, Belgium) through an SDS (1%)-Proteinase K (200 g/ml) 30 minute incubation at 37 C followed by an acid Phenol-Chloroform purification and iso-propanol precipitation (Sambrook et al; Molecular Cloning-A Laboratory Manual).

Total HeLa, HEK-293 and PC3 cell RNA was prepared using the standard Tri-Reagent protocol (Sigma) according to the manufacturer's instructions, except that 1 volume of isopropanol was substituted with 3 volumes of ethanol.

Nuclear and Cytoplasmic RNA was prepared from HeLa or HEK-293 cells in the following manner:

Cell were washed and harvested in ice-cold PBS and precipitated in a swing-out rotor at 1200 rpm at 4 C for 5 minutes. Pellets were loosened by gentle vortexing. 4 ml of "NP40 lysis buffer" (10 mM Tris HCl, 5 mM MgCl2, 10 mM NaCl, 0.5% Nonidet P40, 1 mM Spermidine, 1 mM DTT, 140 U/ml rRnasine) was then added per 5*10^7 cells. Cells and lysis buffer were incubated for 5 minutes on ice and centrifuged in a swing-out rotor at 500×g at 4 C for 5 minutes. Supernatant, termed cytoplasm, is carefully removed to a tube containing SDS (1% final) and proteinase-K (200 g/ml final). Pellet, termed nuclear fraction, is re-washed and incubated with a similar amount of fresh lysis buffer. Lysis is monitored visually under a microscope at this stage, typically for 5 minutes. Nuclei are pelleted in a swing-out rotor at 500×g at 4 C for 5 minutes. Supernatant is pooled, incubated at 37 C for 30 minutes, Phenol/Chloroform-extracted, and RNA is alcohol-precipitated (Sambrook et al). Nuclei are loosened and then homogenized immediately in >10 volumes of Tri-Reagent (Sigma). Nuclear RNA is then prepared according to the manufacturer's instructions.

Total Tissue RNA

Total tissue RNA was obtained from Ambion USA, and included Human Liver, Thymus, Placenta, Testes and Brain.

RNA Size Fractionation

RNA used for libraries was always size-fractionated. Fractionation was done by loading up to 500 microgram RNA per YM100 Amicon Microcon column (Millipore) followed by a 500×g centrifugation for 40 minutes at 4 C. Flow-through "YM100" RNA is about one quarter of the total RNA and was used for library preparation or fractionated further by loading onto a YM30 Amicon Microcon column (Millipore) followed by a 13,500×g centrifugation for 25 minutes at 4 C. Flow-through "YM30" was used for library preparation "as is" and consists of less than 0.5% of total RNA. Additional size fractionation was achieved during library preparation.

Library Preparation

Two types of cDNA libraries, designated "One-tailed" and "Ligation", were prepared from the one of the abovementioned fractionated RNA samples. RNA was dephosphorylated and ligated to an RNA (designated with lowercase letters)-DNA (designated with UPPERCASE letters)hybrid 5'-phosphorylated, 3'idT blocked 3'-adapter (5'-P-uuuAAC-CGCATCCTTCTC-idT-3' (SEQ ID NO: 4254787) Dharma-con #P-002045-01-05)(as elaborated in Elbashir et al., Genes Dev. 15:188-200 (2001)) resulting in ligation only of RNase III type cleavage products. 3'-Ligated RNA was excised and purified from a half 6%,half 13% polyacrylamide gel to remove excess adapter with a Nanosep 0.2 microM centrifugal device (Pall) according to instructions, and precipitated with glycogen and 3 volumes of ethanol. Pellet was resuspended in a minimal volume of water.

For the "Ligation" library, a DNA (UPPERCASE)-RNA (lowercase) hybrid 5'-adapter (5'-TACTAATACGACTCAC-Taaa-3' (SEQ ID NO: 4254788) Dharmacon #P-002046-01-05)was ligated to the 3'-adapted RNA, reverse transcribed with "EcoRI-RT":(5'-GACTA GCTGGAATTCAAGGAT-GCGGTTAAA-3') (SEQ ID NO: 4254789), PCR-amplified with two external primers essentially as in Elbashir et al. (2001),except that primers were "EcoRI-RT" and "PstI Fwd" (5'-CAGCCAACGCTGCAGATACGACTCACTAAA-3').

(SEQ ID NO: 4254790) This PCR product was used as a template for a second round of PCR with one hemispecific and one external primer or with two hemispecific primers.

For the "One-tailed" library, the 3'-adapted RNA was annealed to 20 pmol primer "EcoRI RT"by heating to 70 C and cooling 0.1 C/sec to 30 C and then reverse-transcribed with Superscript II RT (according to manufacturer's instructions, Invitrogen) in a 20 microliters volume for 10 alternating 5 minute cycles of 37 C and 45 C. Subsequently, RNA was digested with 1 microliter 2M NaOH and 2mM EDTA at 65 C for 10 minutes. cDNA was loaded on a polyacrylamide gel, excised and gel-purified from excess primer as above (invisible, judged by primer run alongside) and resuspended in 13 microliters of water. Purified cDNA was then oligo-dC tailed with 400U of recombinant terminal transferase (Roche Molecular Biochemicals), 1 microliter 100 microM dCTP, 1 microliter 15mM CoCl2,and 4 microliters reaction buffer, to a final volume of 20 microliters for 15 minutes at 37 C. Reaction was stopped with 2 microliters 0.2M EDTA and 15 microliters 3M NaOAc pH 5.2.Volume was adjusted to 150 microliters with water, Phenol: Bromochloropropane 10:1 extracted and subsequently precipitated with glycogen and 3 volumes of ethanol. C-tailed cDNA was used as a template for PCR with the external primers "T3-PstBsg(G/I)18"(5'-AAT-TAACCCTCACTAAAGGCTGCAGGTGCAG-GIGGGIIGGGIIGG GIIGN-3' (SEQ ID NO: 4254791) where I stands for Inosine and N for any of the 4 possible deoxynucleotides), and with "EcoRI Nested"(5'-GGAAT-TCAAGGATGCGGTTA-3') (SEQ ID NO: 4254792). This PCR product was used as a template for a second round of PCR with one hemispecific and one external primer or with two hemispecific primers.

Primer Design and PCR

Hemispecific primers were constructed for each predicted GAM RNA oligonucleotide by an in-house program designed to choose about half of the 5' or 3' sequence of the GAM RNA corresponding to a TM of about 30 -34 C constrained by an optimized 3' clamp, appended to the cloning adapter sequence (for "One-tailed" libraries, 5'-GGN-NGGGNNG (SEQ ID NO: 4254793) on the 5' end or TTTAACCGCATC-3' (SEQ ID NO: 4254794) on the 3' end of the GAM RNA; for "Ligation" libraries, the same 3' adapter and 5'-CGACTCACTAAA (SEQ ID NO: 4254795) on the 5' end of the GAM RNA). Consequently, a fully complementary primer of a TM higher than 60 C was created covering only one half of the GAM RNA sequence permitting the unbiased elucidation by sequencing of the other half.

For each primer, the following criteria were used: Primers were graded according to the TM of the primer half and the nucleotide content of 3 nucleotides of the 3' clamp from worst to best, roughly: GGG-3'<CCC-3'<TTT-3'/AAA-3'<GG-3'<CC-3'<a TM lower than 30<a TM higher than 34<TT-3'/AA-3'<3G/C nucleotide combination <3 A/T nucleotide combination <any combination of two/three different nucleotides <any combination of three/three different nucleotides.

Validation PCR Product by Southern Blot

GAM RNA oligonucleotides were validated by hybridization of Polymerase Chain Reaction (PCR)-product Southern blots with a probe to the predicted GAM RNA.

PCR product sequences were confirmed by Southern blot (Southern E. M., Biotechnology 1992, 24:122-139 (1975)) and hybridization with DNA oligonucleotide probes synthesized as complementary (antisense) to predicted GAM RNA oligonucleotides. Gels were transferred onto a Biodyne PLUS 0.45 m (Pall) positively charged nylon membrane and UV cross-linked. Hybridization was performed overnight with DIG-labeled probes at 42 C in DIG Easy-Hyb buffer (Roche). Membranes were washed twice with 2×SSC and 0.1% SDS for 10 minutes at 42 C and then washed twice with 0.5×SSC and 0.1% SDS for 5 min at 42 C. The membrane was then developed by using a DIG luminescent detection kit (Roche) using anti-DIG and CSPD reaction, according to the manufacturer's protocol. All probes were prepared according to the manufacturer's (Roche Molecular Biochemicals) protocols: Digoxigenin (DIG) labeled antisense transcripts were prepared from purified PCR products using a DIG RNA labeling kit with T3 RNA polymerase. DIG-labeled PCR was prepared by using a DIG PCR labeling kit. 3'-DIG-tailed oligo ssDNA anti-sense probes, containing DIG-dUTP and dATP at an average tail length of 50 nts were prepared from 100 pmole oligonucleotides with the DIG Oligonucleotide Labeling Kit. Control reactions contained all of the components of the test reaction except library template.

Validation of PCR Product by Nested PCR on the Ligation

To further validate predicted GAM PCR product sequence derived from hemi-primers, a PCR-based diagnostic technique was devised to amplify only those products containing at least two additional nucleotides of the non hemi-primer defined part of the predicted GAM RNA oligonucleotide. In essence, a diagnostic primer was designed so that its 3' end, which is the specificity determining side, was identical to the desired GAM RNA oligonucleotide, 2-10 nts (typically 4-7, chosen for maximum specificity) further into its 3' end than the nucleotide stretch primed by the hemi-primer. The hemi-primer PCR product was first ligated into a T-cloning vector (pTZ57/T or pGEM-T) as described hereinabove. The ligation reaction mixture was used as template for the diagnostic PCR under strict annealing conditions with the new diagnostic primer in conjunction with a general plasmid-homologous primer, resulting in a distinct ~200 base-pair product. This PCR product can be directly sequenced, permitting the elucidation of the remaining nucleotides up to the 3' of the mature GAM RNA oligonucleotide adjacent to the 3' adapter. Alternatively, following analysis of the diagnostic PCR reaction on an agarose gel, positive ligation reactions (containing a band of the expected size) were transformed into E. coli. Using this same diagnostic technique and as an alternative to screening by Southern blot colony hybridization, transformed bacterial colonies were screened by colony-PCR (Gussow, D. and Clackson, T, Nucleic Acids Res. 17:4000 (1989)) with the nested primer and the vector primer, prior to plasmid purification and sequencing.

Validation of PCR Product by Cloning and Sequencing

PCR products were inserted into pGEM-T (Promega) or pTZ57/T (MBI Fermentas), heat-shock transformed into competent JM109 E. coli (Promega) and seeded on LB-Ampicilin plates with IPTG and Xgal. White and light blue colonies were transferred to duplicate gridded plates, one of which was blotted onto a membrane (Biodyne Plus, Pall) for hybridization with DIG tailed oligo probes (according to instructions, Roche) complementary to the expected GAM. Plasmid DNA from positive colonies was sequenced.

It is appreciated that the results summarize in FIG. 13 validate the efficacy of the bioinformatic oligonucleotide detection engine 100 of the present invention.

Figures 14A, 14B, 14C:
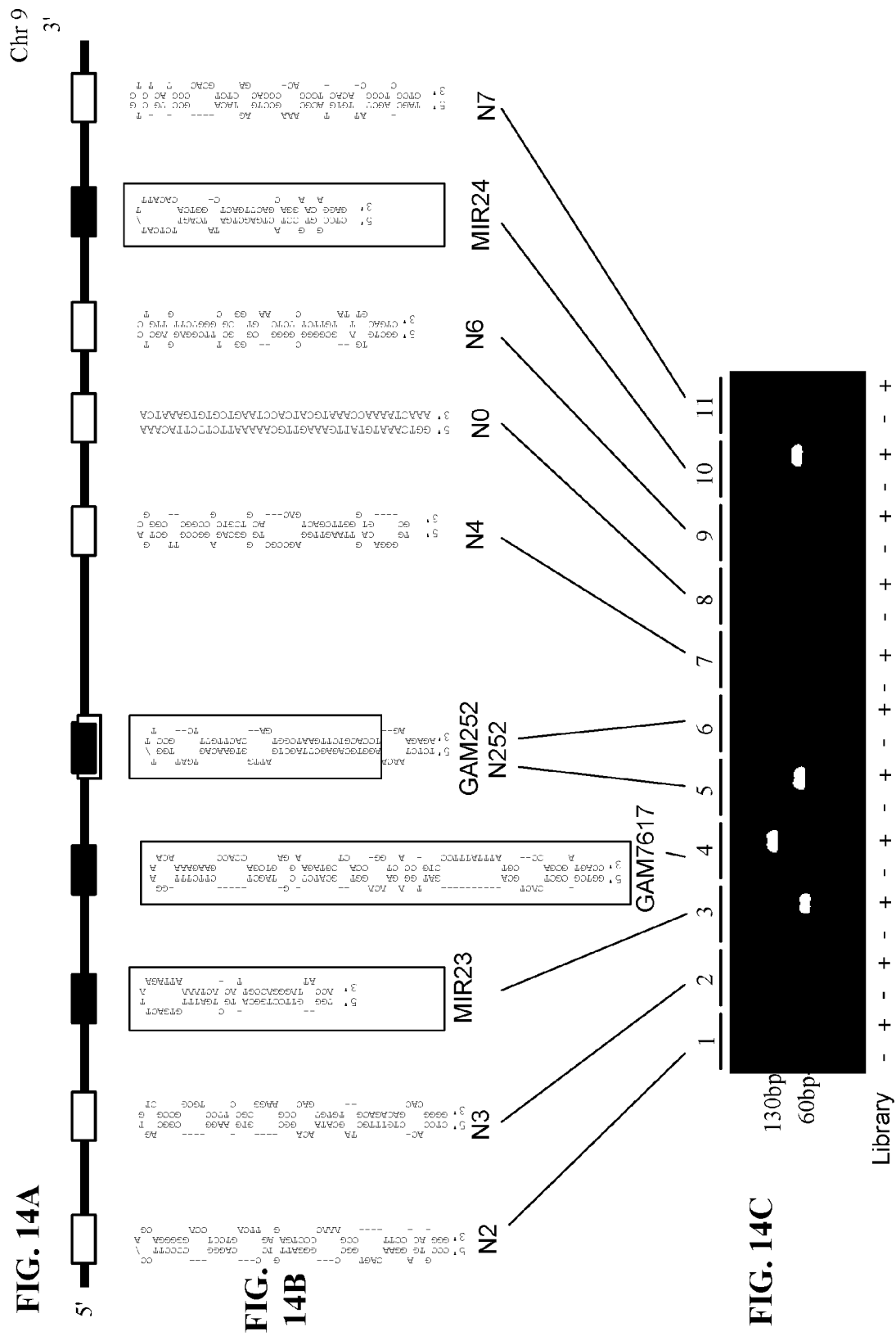
FIG. 14A is a schematic representation of an "operon-like" cluster of novel human hairpin sequences detected by a bioinformatic oligonucleotide detection engine constructed and operative in accordance with a preferred embodiment of the present invention, and non-GAM hairpin sequences used as negative controls thereto.
FIG. 14B is a schematic representation of secondary folding of hairpins of the operon-like cluster of FIG. 14A. The hairpins shown are as follows N2 (SEQ ID NO: 4254760), N3 (SEQ ID NO: 4254761), MIR23 (SEQ ID NO: 4254762), GAM22 (SEQ ID NO: 4254763), GAM7617 (SEQ ID NO: 4254764), N252 (SEQ ID NO: 4254765), N4 (SEQ ID NO: 4254766), N0 (SEQ ID NO: 4254767), N6 (SEQ ID NO: 4254768), MIR24 (SEQ ID NO: 4254769), and N7 (SEQ ID NO: 4254770)
FIG. 14C is a picture of laboratory results demonstrating expression of novel oligonucleotides of FIGS. 14A and 14B and lack of expression of the negative controls, thereby validating efficacy of bioinformatic detection of GAM oligonucleotides and GR polynucleotides detected by a bioinformatic oligonucleotide detection engine, constructed and operative in accordance with a preferred embodiment of the present invention.

Reference is now made to FIG. 14A, which is a schematic representation of a novel human GR polynucleotide, located on chromosome 9, comprising 2 known human miRNA oligonucleotides—MIR24 and MIR23, and 2 novel GAM oligonucleotides, herein designated GAM7617 and GAM252 (later discovered by other researchers as hsa-mir-27b), all marked by solid black boxes. FIG. 14A also schematically illustrates 6 non-GAM hairpin sequences, and one non-hairpin sequence, all marked by white boxes, and serving as negative controls. By "non-GAM hairpin sequences" is meant sequences of a similar length to known miRNA precursor sequences, which form hairpin secondary folding pattern similar to miRNA precursor hairpins, and yet which are assessed by the bioinformatic oligonucleotide detection engine 100 not to be valid GAM PRECURSOR hairpins. It is appreciated that FIG. 14A is a simplified schematic representation, reflecting only the order in which the segments of interest appear relative to one another, and not a proportional distance between the segments.

Reference is now made to FIG. 14B, which is a schematic representation of secondary folding of each of the MIRs and GAMs of the GR MIR24, MIR23, GAM7617 and GAM252, and of the negative control non-GAM hairpins, herein designated N2, N3, N252, N4, N6 and N7. N0 is a non-hairpin control, of a similar length to that of known miRNA precursor hairpins. It is appreciated that the negative controls are situated adjacent to and in between real miRNA oligonucleotides and GAM predicted oligonucleotides and demonstrates similar secondary folding patterns to that of known MIRs and GAMs.

Reference is now made to FIG. 14C, which is a picture of laboratory results of a PCR test upon a YM100 size-fractionated "ligation" library, utilizing a set of specific primer pairs located directly inside the boundaries of the hairpins. Due to the nature of the library the only PCR amplifiable products can result from RNaseIII type enzyme cleaved RNA, as expected for legitimate hairpin precursors presumed to be produced by DROSHA (Lee et al, Nature 425 415-419, 2003). FIG. 14C demonstrates expression of hairpin precursors of known miRNA oligonucleotides hsa-mir23 and hsa-mir24, and of novel bioinformatically-detected GAM7617 and GAM252 hairpins predicted bioinformatically by a system constructed and operative in accordance with a preferred embodiment of the present invention. FIG. 14C also shows that none of the 7 controls (6 hairpins designated N2, N3, N23, N4, N6 and N7 and 1 non-hairpin sequence designated N0) were expressed. N252 is a negative control sequence partially overlapping GAM252.

In the picture, test lanes including template are designated "+" and the control lane is designated "−". The control reaction contained all the components of the test reaction except library template. It is appreciated that for each of the tested hairpins, a clear PCR band appears in the test ("+") lane, but not in the control ("−") lane.

FIGS. 14A through 14C, when taken together validate the efficacy of the bioinformatic oligonucleotide detection engine in: (a) detecting known miRNA oligonucleotides; (b) detecting novel GAM PRECURSOR hairpins which are found adjacent to these miRNA oligonucleotides, and which despite exhaustive prior biological efforts and bioinformatic detection efforts, went undetected; (c) discerning between GAM (or MIR) PRECURSOR hairpins, and non-GAM hairpins.

It is appreciated that the ability to discern GAM-hairpins from non-GAM-hairpins is very significant in detecting GAM oligonucleotides since hairpins are highly abundant in the genome. Other miRNA prediction programs have not been able to address this challenge successfully.

Reference is now made to FIG. 15A, which is an annotated sequence of an EST comprising a novel GAM oligonucleotides detected by the oligonucleotide detection system of the present invention. FIG. 15A shows the nucleotide sequence of a known human non-protein-coding EST (Expressed Sequence Tag), identified as EST72223. The EST72223 clone obtained from TIGR database (Kirkness and Kerlavage, 1997) was sequenced to yield the above 705 bp transcript with a polyadenyl tail. It is appreciated that the sequence of this EST comprises sequences of one known miRNA oligonucleotide, identified as hsa-MIR98, and of one novel GAM oligonucleotide referred to here as GAM25, detected by the bioinformatic oligonucleotide detection engine 100 (FIG. 2) of the present invention.

The sequences of the precursors of the known MIR98 and of the predicted GAM25 precursors are marked in bold, the sequences of the established miRNA 98 and of the predicted miRNA-like oligonucleotide GAM25 are underlined.

Figure 15D:
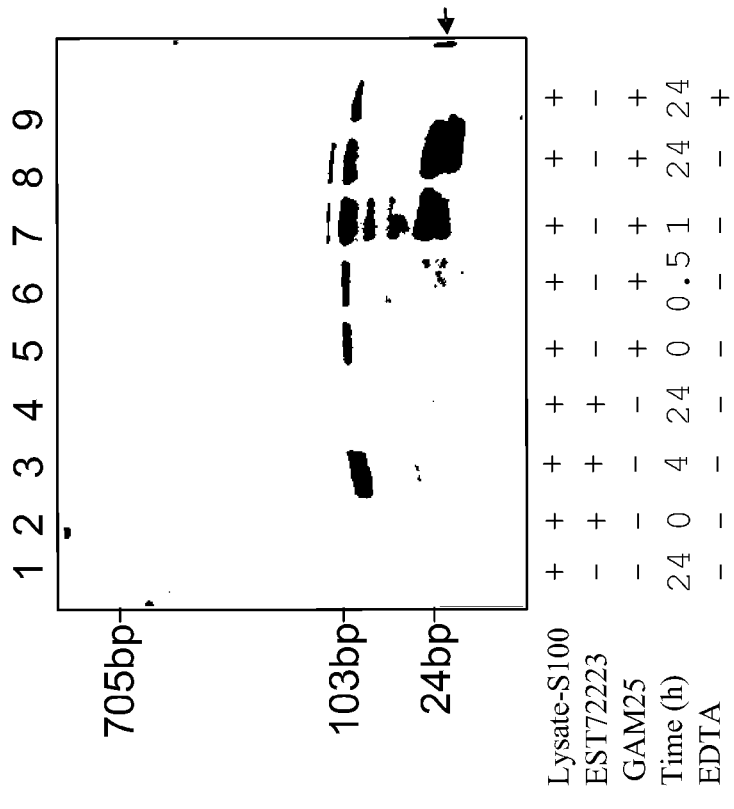
Figure 15C:
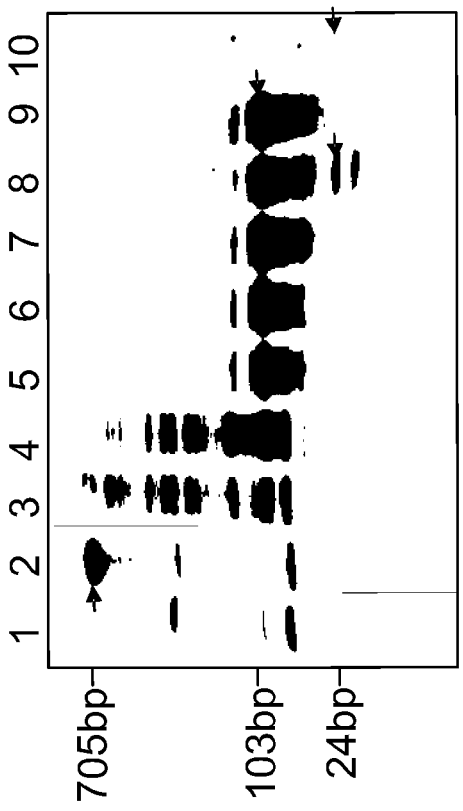

Reference is now made to FIGS. 15B, 15C and 15D, which are pictures of laboratory results, which when taken together demonstrate laboratory confirmation of expression of the bioinformatically-detected novel oligonucleotide of FIG. 15A.

In two parallel experiments, an enzymatically synthesized capped, EST72223 RNA transcript, was incubated with Hela S100 lysate for 0 minutes, 4 hours and 24 hours. RNA was subsequently harvested, run on a denaturing polyacrylamide gel, and reacted with either a 102 nt antisense MIR98 probe or a 145 nt antisenseGAM25 precursor transcript probe respectively. The Northern blot results of these experiments demonstrated processing of EST72223 RNA by Hela lysate (lanes 2-4, in FIGS. 15B and 15C), into ~80 bp and ~22 bp segments, which reacted with the MIR98 precursor probe (FIG. 15B), and into ~100 bp and ~24 bp segments, which reacted with the GAM25 precursor probe (FIG. 15C). These results demonstrate the processing of EST72223 by Hela lysate into MIR98 precursor and GAM25 precursor. It is also appreciated from FIG. 15C (lane 1) that Hela lysate itself reacted with the GAM25 precursor probe, in a number of bands, including a ~100 bp band, indicating that GAM25-precursor is endogenously expressed in Hela cells. The presence of additional bands, higher than 100 bp in lanes 5-9 probably corresponds to the presence of nucleotide sequences in Hela lysate, which contain the GAM25 sequence.

In addition, in order to demonstrate the kinetics and specificity of the processing of MIR98 and GAM25 precursors into their respective mature, "diced" segments, transcripts of MIR98 and of the bioinformatically predicted GAM25 precursors were similarly incubated with Hela S100 lysate, for 0 minutes, 30 minutes, 1 hour and 24 hours, and for 24 hours with the addition of EDTA, added to inhibit Dicer activity, following which RNA was harvested, run on a polyacrylamide gel and reacted with MIR98 and GAM25 precursor probes. Capped transcripts were prepared for in vitro RNA cleavage assays with T7 RNA polymerase, including a m7G (5') ppp (5') G-capping reaction using the T7-mMessage mMachine kit (Ambion). Purified PCR products were used as template for the reaction. These were amplified for each assay with specific primers containing a T7 promoter at the 5' end and a T3 RNA polymerase promoter at the 3' end. Capped RNA transcripts were incubated at 30 C in supplemented, dialysis concentrated, Hela S100 cytoplasmic extract (4C Biotech, Seneffe, Belgium). The Hela S100 was supplemented by dialysis to a final concentration of 20 mM Hepes, 100 mM KCl, 2.5 mM MgCl2, 0.5 mM DTT, 20% glycerol and protease inhibitor cocktail tablets (Complete mini Roche Molecular Biochemicals). After addition of all components, final concentrations were 100 mM capped target RNA, 2 mM ATP, 0.2 mM GTP, 500 U/ml RNasin, 25 microgram/ml creatine kinase, 25 mM creatine phosphate, 2.5 mM DTT and 50% S100 extract. Proteinase K, used to enhance Dicer activity (Zhang et al., EMBO J. 21, 5875-5885 (2002)) was dissolved in 50 mM Tris-HCl pH 8, 5 mM CaCl2, and 50% glycerol, was added to a final concentration of 0.6 mg/ml. Cleavage reactions were stopped by the addition of 8 volumes of proteinase K buffer 200 Mm Tris-Hcl, pH 7.5, 25 m M EDTA, 300 mM NaCl, and 2% SDS) and incubated at 65 C for 15 min at different time points (0, 0.5, 1, 4, 24 h) and subjected to phenol/chloroform extraction. Pellets were dissolved in water and kept frozen. Samples were analyzed on a segmented half 6%, half 13% polyacrylamide 1XTBE-7M Urea gel.

The Northern blot results of these experiments demonstrated an accumulation of a ~22 bp segment which reacted with the MIR98 precursor probe, and of a ~24 bp segment which reacted with the GAM25 precursor probe, over time (lanes 5-8). Absence of these segments when incubated with EDTA (lane 9), which is known to inhibit Dicer enzyme (Zhang et al., 2002), supports the notion that the processing of MIR98 and GAM25 precursors into their "diced" segments is mediated by Dicer enzyme, found in Hela lysate. Other RNases do not utilize divalent cations and are thus not inhibited by EDTA. The molecular sizes of EST72223, MIR-98 and GAM25 and their corresponding precursors are indicated by arrows.

FIG. 15D present Northern blot results of same above experiments with GAM25 probe (24 nt). The results clearly demonstrated the accumulation of mature GAM25 oligonucleotide after 24 h.

To validate the identity of the band shown by the lower arrow in FIGS. 15C and 15D, a RNA band parallel to a marker of 24 base was excised from the gel and cloned as in Elbashir et al (2001) and sequenced. Ninety clones corresponded to the sequence of mature GAM25 oligonucleotide, three corresponded to GAM25* (the opposite arm of the hairpin with a 1-3 nt 3' overhang) and two to the hairpin-loop.

GAM25 was also validated endogenously by sequencing from both sides from a HeLa YM100 total-RNA "ligation" libraries, utilizing hemispecific primers as described in FIG. 13.

Taken together, these results validate the presence and processing of a novel miRNA-like oligonucleotide, GAM25, which was predicted bioinformatically. The processing of this novel GAM oligonucleotide product, by Hela lysate from EST72223, through its precursor, to its final form was similar to that observed for known miRNA oligonucleotide, MIR98.

Transcript products were 705 nt (EST72223),102 nt (MIR98 precursor), 125 nt (GAM25 precursor)long. EST72223 was PCR-amplified with T7-EST 72223 forward primer: 5'-TAATACGACTC ACTATAGGCCCTTATTA-GAGGATTCTGCT-3' (SEQ ID NO: 4254796) and T3-EST72223 reverse primer: "-AATTAACCCTCAC-TAAAGGTTTTTTTTTCCTGAGACAGAGT-3' (SEQ ID NO: 4254797). MIR98 was PCR-amplified using EST72223 as a template with T7MIR98 forward primer: 5'-TAATAC-GACTCACTATAGGGTGAGGTAGTAAGTTGTATTGTT -3' (SEQ ID NO: 4254798) and T3MIR98 reverse primer: 5'-AATTAACCCTCACTAAAGGGAAAGTAG-TAAGTTGTATA GTT-3' (SEQ ID NO: 4254799). GAM25 was PCR-amplified using EST72223 as a template with GAM25 forward primer:

5'-AGGCAGGAGAATTGCTTGA-3' (SEQ ID NO: 4254800) and T3-EST72223 reverse primer: 5'-AATTAAC-CCTCACTAAAGGCC TGAGACAGAGTCTTGCTC- 3' (SEQ ID NO: 4254801).

It is appreciated that the data presented in FIGS. 15A, 15B, 15C and 15D when taken together validate the function of the bioinformatic oligonucleotide detection engine 100 of FIG. 2. FIG. 15A shows a novel GAM oligonucleotide bioinformatically-detected by the bioinformatic oligonucleotide detection engine 100, and FIGS. 15C and 15D show laboratory confirmation of the expression of this novel oligonucleotide. This is in accord with the engine training and validation methodology described hereinabove with reference to FIG. 2.

Figure 16A:
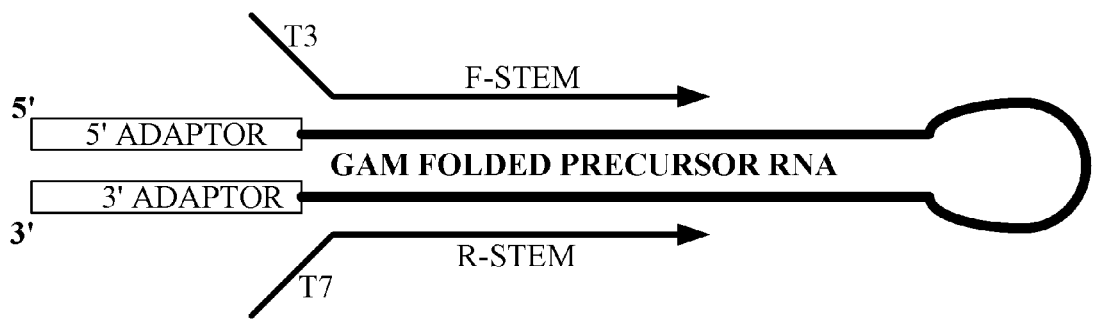
FIGS. 16A, 16B and 16C are schematic diagrams which, when taken together, represent methods of designing primers to identify specific hairpin oligonucleotides in accordance with a preferred embodiment of the present invention.
Figure 16B:
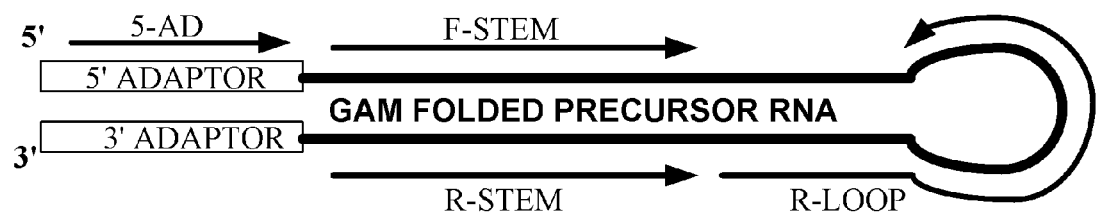
Figure 16C:
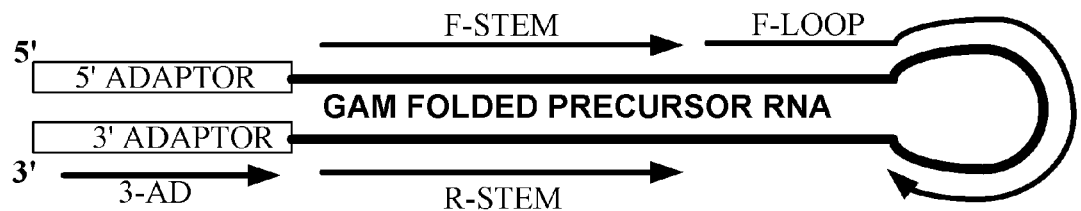

Reference is now made to FIGS. 16A-C, which schematically represent three methods that are employed to identify GAM FOLDED PRECURSOR RNA from libraries. Each method involves the design of specific primers for PCR amplification followed by sequencing. The libraries include hairpins as double-stranded DNA with two different adaptors ligated to their 5' and 3' ends.

Reference is now made to FIG. 16A, which depicts a first method that uses primers designed to the stems of the hairpins. Since the stem of the hairpins often has bulges, mismatches, as well as G-T pairing, which is less significant in DNA than is G-U pairing in the original RNA hairpin, the primer pairs were engineered to have the lowest possible match to the other strand of the stem. Thus, the F-Stem primer, derived from the 5' stem region of the hairpin, was chosen to have minimal match to the 3' stem region of the same hairpin. Similarly, the R-stem primer, derived from the 3' region of the hairpin (reverse complementary to its sequence), was chosen to have minimal match to the 5' stem region of the same hairpin. The F-Stem primer was extended in its 5' sequence with the T3 primer (5'-ATTAACCCTCAC-TAAAGGGA-3') (SEQ ID NO: 4254802) and the R-Stem primer was extended in its 5' sequence with the T7 primer (5'-TAATACGACTCACTATAGGG) (SEQ ID NO: 4254803).The extension is needed to obtain a large enough fragment for direct sequencing of the PCR product. Sequence data from the amplified hairpins is obtained in two ways. One way is the direct sequencing of the PCR products using the T3 primer that matches the extension of the F-Stem primer. Another way is the cloning of the PCR products into a plasmid, followed by PCR screening of individual bacterial colonies using a primer specific to the plasmid vector and either the R-Loop (FIG. 16B) or the F-Loop (FIG. 16C) primer. Positive PCR products are then sent for direct sequencing using the vector-specific primer.

Reference is now made to FIG. 16B, which depicts a second method in which R-Stem primer and R-Loop primers are used in a nested-PCR approach. First, PCR is performed with the R-Stem primer and the primer that matches the 5' adaptor sequence (5-ad primer). PCR products are then amplified in a second PCR using the R-Loop and 5-ad primers. As mentioned hereinabove, sequence data from the amplified hairpins is obtained in two ways. One way is the direct sequencing of the PCR products using the 5-ad primer. Another way is the cloning of the PCR products into a plasmid, followed by PCR screening of individual bacterial colonies using a primer specific to the plasmid vector and F-Stem primer. Positive PCR products are then sent for direct sequencing using the vector-specific primer. It should be noted that optionally an extended R-Loop primer is designed that includes a T7 sequence extension, as described hereinabove (FIG. 16A) for the R-Stem primer. This is important in the first sequencing option in cases where the PCR product is too short for sequencing.

Reference is now made to FIG. 16C, which depicts a third method, which is the exact reverse of the second method described hereinabove (FIG. 16B). F-Stem and F-Loop primers are used in a nested-PCR approach. First, PCR is performed with the F-Stem primer and the primer that matches the 3' adaptor sequence (3-ad primer). PCR products are then amplified in a second PCR using the F-Loop and 3-ad primers. As in the other two methods, sequence data from the amplified hairpins is obtained in two ways. One way is the direct sequencing of the PCR products using the F-Loop primer. Another way is the cloning of the PCR products into a plasmid, followed by PCR screening of individual bacterial colonies using a primer specific to the plasmid vector and R-Stem primer. Positive PCR products are then sent for direct sequencing using the vector-specific primer. It should be noted that optionally an extended F-Loop primer is designed that includes a T3 sequence extension, as described hereinabove (FIG. 16A) for the F-Stem primer. This is important in the first sequencing option in cases where the PCR product is too short for sequencing and also in order to enable the use of T3 primer.

In an embodiment of the present invention, the three methods mentioned hereinabove may be employed to validate the expression of GAM FOLDED PRECURSOR RNA.

Figure 17A:
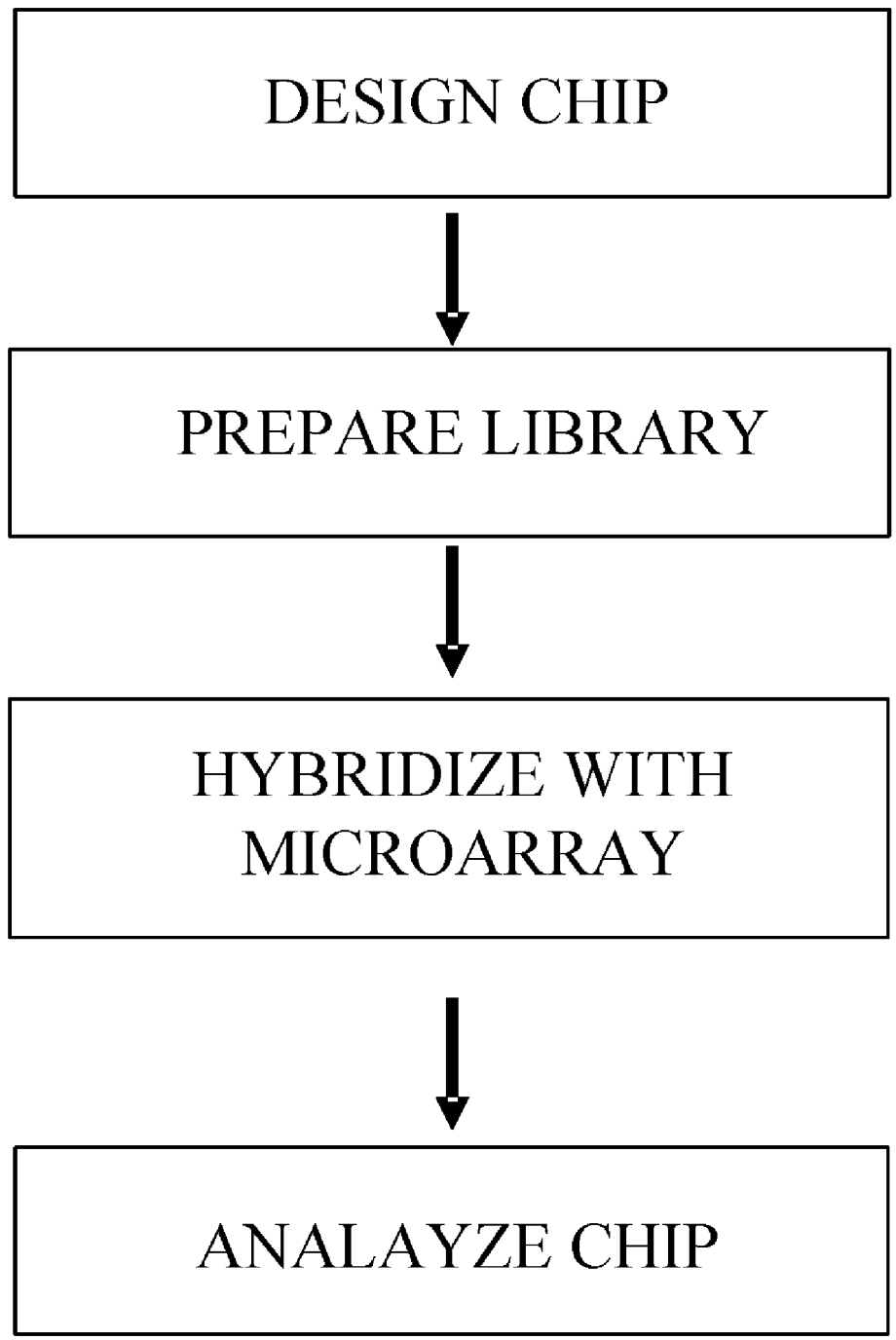
FIG. 17A is a simplified flowchart illustrating construction of a microarray constructed and operative to identify novel oligonucleotides of the present invention, in accordance with a preferred embodiment of the present invention.

Reference is now made to FIG. 17A, which is a flow chart with a general description of the design of the microarray to identify expression of published miRNA oligonucleotides, and of novel GAM oligonucleotides of the present invention.

Figure 17B:
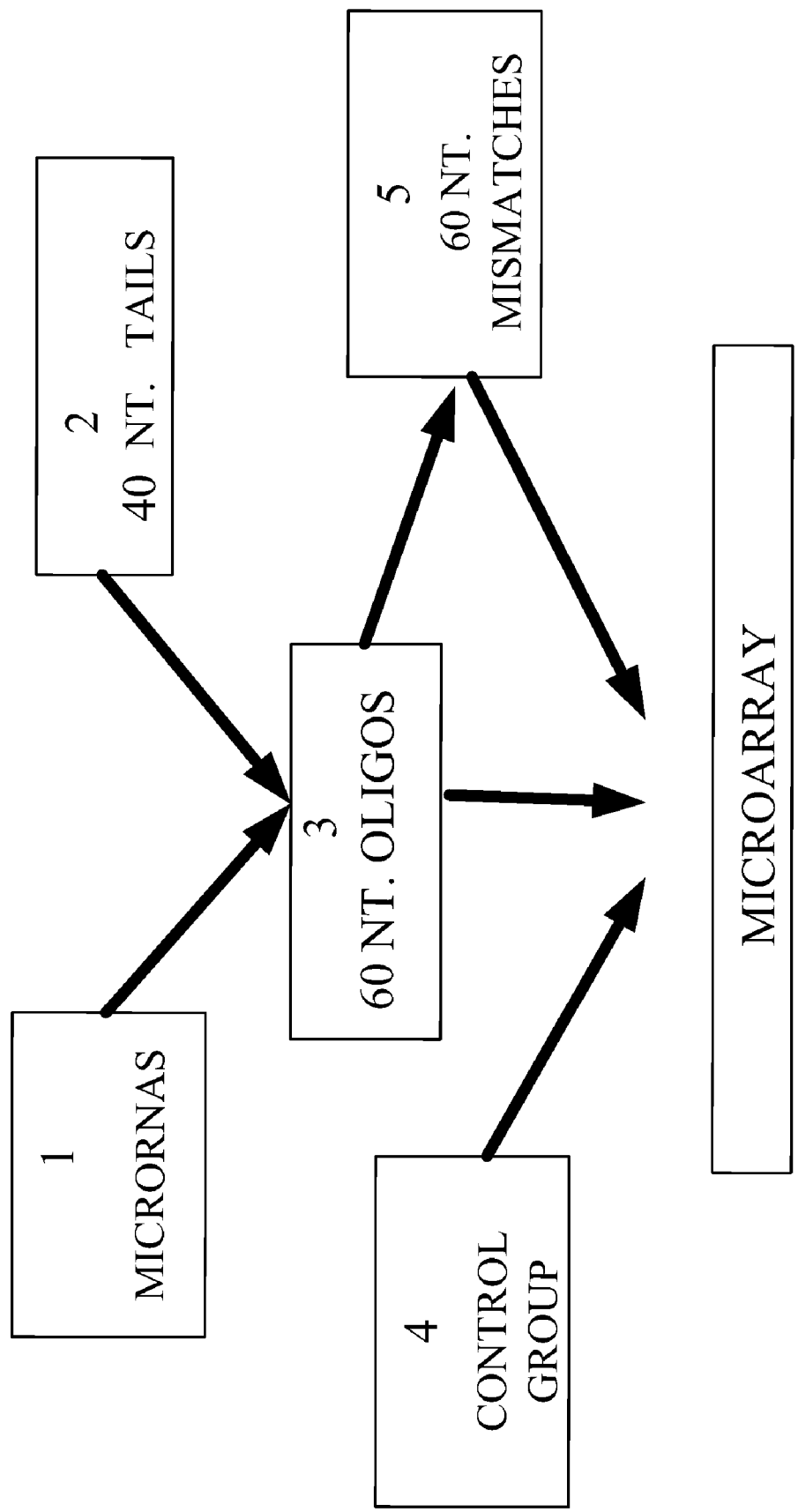
FIG. 17B is a simplified block diagram illustrating design of a microarray constructed and operative to identify novel oligonucleotides of the present invention, in accordance with a preferred embodiment of the present invention.
Figure 17C:
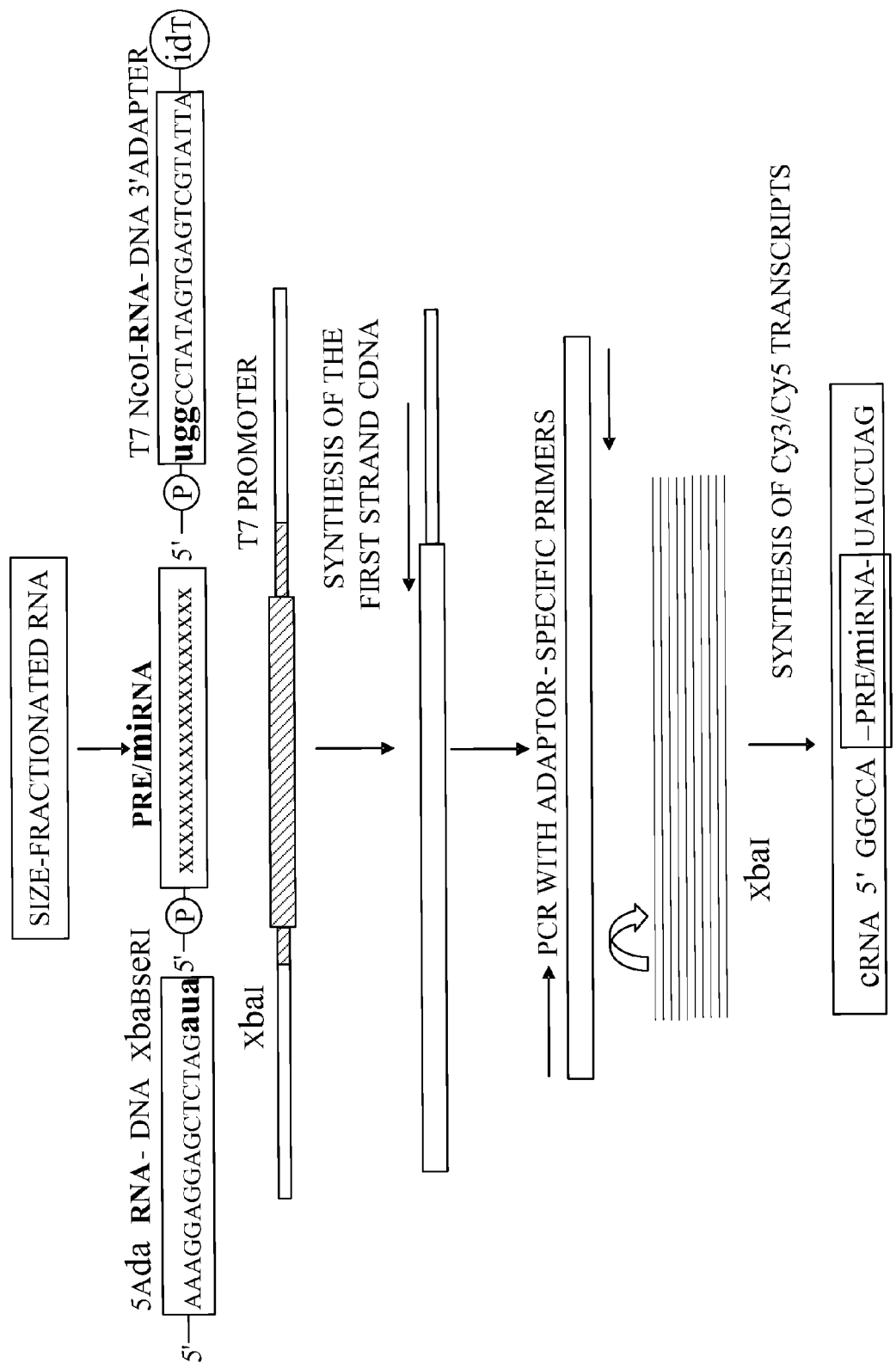
FIG. 17C is a flowchart illustrating a mode of preparation and amplification of a cDNA library in accordance with a preferred embodiment of the present invention. Shown in FIG. 17C are the following adapters: 5Ada RNA-DNA XbaBSerI (SEQ ID NO: 4254776) and T7 NcoI RNA-DNA 3' Adapator (SEQ ID NO: 4254777).

A microarray that identifies miRNA oligonucleotides is designed (FIG. 17B). The DNA microarray is prepared by Agilent according to their SurePrint Procedure (reference describing their technology can be obtained from the Agilent website, http://www.agilent.com). In this procedure, the oligonucleotide probes are synthesized on the glass surface. Other methods can also be used to prepare such microarray including the printing of pre-synthesized oligonucleotides on glass surface or using the photolithography method developed by Affymetrix (Lockhart D J et al., Nat Biotechnol. 14:1675-1680 (1996)). The 60-mer sequences from the design are synthesized on the DNA microarray. The oligonucleotides on the microarray, termed "probes" are of the exact sequence as the designed 60-mer sequences. Importantly, the 60-mer sequences and the probes are in the sense orientation with regards to the miRNA oligonucleotides. Next, a cDNA library is created from size-fractionated RNA, amplified, and converted back to RNA (FIG. 17C). The resulting RNA is termed "cRNA". The conversion to RNA is done using a T7 RNA polymerase promoter found on the 3' adaptor (FIG. 17C; T7 Ncol-RNA-DNA 3'Adaptor). Since the conversion to cRNA is done in the reverse direction compared to the orientation of the miRNA oligonucleotides, the cRNA is reverse complementary to the probes and is able to hybridize to it. This amplified RNA is hybridized with the microarray that identifies miRNA oligonucleotides, and the results are analyzed to indicate the relative level of miRNA oligonucleotides (and hairpins) that are present in the total RNA of the tissue (FIG. 18).

Reference is now made to FIG. 17B, which describes how the microarray to identify miRNA oligonucleotides is designed. miRNA oligonucleotide sequences or potential predicted miRNA oligonucleotides are generated by using known or predicted hairpins as input. Overlapping potential miRNA oligonucleotides are combined to form one larger sub-sequence within a hairpin.

To generate non-expressed sequences (tails), artificial sequences are generated that are 40 nts in length, which do not appear in the respective organism genome, do not have greater than 40% homology to sequences that appear in the genome, and with no 15-nucleotide window that has greater than 80% homology to sequences that appear in the genome.

To generate probe sequences, the most probable miRNA oligonucleotide sequences are placed at position 3 (from the 5' end) of the probe. Then, a tail sub-sequence to the miRNA oligonucleotide sequence was attached such that the combined sequence length will meet the required probe length (60 nts for Agilent microarrays).

The tails method provides better specificity compared to the triplet method. In the triplet method, it cannot be ascertained that the design sequence, and not an uncontrolled window from the triplet probe sequence, was responsible for hybridizing to the probe. Further, the tails method allows the use of different lengths for the potential predicted miRNA oligonucleotide (of combined, overlapping miRNA oligonucleotides).

Hundreds of control probes were examined in order to ensure the specificity of the microarray. Negative controls contain probes which should have low intensity signal. For other control groups, the concentration of certain specific groups of interest in the library are monitored. Negative controls include tail sequences and non-hairpin sequences. Other controls include mRNA for coding genes, tRNA, and snoRNA.

For each probe that represents known or predicted miRNA oligonucleotides, additional mismatch probes were assigned in order to verify that the probe intensity is due to perfect match (or as close as possible to a perfect match) binding between the target miRNA oligonucleotide cRNA and its respective complementary sequence on the probe. Mismatches are generated by changing nucleotides in different positions on the probe with their respective complementary nucleotides (A<->T, G<->C, and vice versa). Mismatches in the tail region should not generate a significant change in the intensity of the probe signal, while mismatches in the miRNA oligonucleotide sequences should induce a drastic decrease in the probe intensity signal. Mismatches at various positions within the miRNA oligonucleotide sequence enable us to detect whether the binding of the probe is a result of perfect match or, alternatively, nearly perfect match binding.

Based on the above scheme, we designed a DNA microarray prepared by Agilent using their SurePrint technology. Table 11 is a detailed list of microarray chip probes Known miRNA Oligonucleotides:

The miRNA oligonucleotides and their respective precursor sequences are taken from Sanger Database to yield a total of 186 distinct miRNA oligonucleotide and precursor pairs. The following different probes are constructed:

1. Single miRNA Oligonucleotide Probes:

From each precursor, 26-mer containing the miRNA oligonucleotide were taken, then assigned 3 probes for each extended miRNA oligonucleotide sequence: 1. the 26-mer are at the 5' of the 60-mer probe, 2. the 26-mer are at the 3' of the 60-mer probe, 3. the 26-mer are in the middle of the 60-mer probe. Two different 34-mer subsequences from the design tails are attached to the 26-mer to accomplish 60-mer probe. For a subset of 32 of Single miRNA oligonucleotide probes, six additional mismatches mutations probes were designed:

4 block mismatches at 5' end of the miRNA oligonucleotide;

6 block mismatches at 3' end of the miRNA oligonucleotide;

1 mismatch at position 10 of the miRNA oligonucleotide;

2 mismatches at positions 8 and 17 of the miRNA oligonucleotide;

3 mismatches at positions 6, 12 and 18 of the miRNA oligonucleotide; and 6 mismatches at different positions out of the miRNA oligonucleotide.

2. Duplex miRNA Oligonucleotide Probes:

From each precursor, a 30-mer containing the miRNA oligonucleotide was taken, then duplicated to obtain 60-mer probe. For a subset of 32 of probes, three additional mismatch mutation probes were designed:

2 mismatches on the first miRNA oligonucleotide;

2 mismatches on the second miRNA oligonucleotide; and 2 mismatches on each of the miRNA oligonucleotides.

3. Triplet miRNA Oligonucleotide Probes:

Following Krichevsky's work (Krichevsky et al., RNA 9:1274-1281 (2003)), head to tail ~22-mer length miRNA oligonucleotide sequences were attached to obtain 60-mer probes containing up to three repeats of the same miRNA oligonucleotide sequence. For a subset of 32 probes, three additional mismatch mutation probes were designed:

2 mismatches on the first miRNA oligonucleotide;

2 mismatches on the second miRNA oligonucleotide; and 2 mismatches on each of the miRNA oligonucleotides.

4. Precursor with miRNA Oligonucleotide Probes:

For each precursor, 60-mer containing the miRNA oligonucleotide were taken.

5. Precursor without miRNA Oligonucleotide Probes:

For each precursor, a 60-mer containing no more then 16-mer of the miRNA oligonucleotide was taken. For a subset of 32 probes, additional mismatch probes containing four mismatches were designed.

Control Groups:

1. 100 60-mer sequences from representative ribosomal RNAs.
2. 85 60-mer sequences from representatives tRNAs.
3. 19 60-mer sequences from representative snoRNA.
4. 294 random 26-mer sequences from human genome not contained in published or predicted precursor sequences, placing them at the probe's 5' and attached 34-mer tail described above.
5. Negative Control: 182 different 60-mer probes contained different combinations of 10 nt-long sequences, in which each 10 nt-long sequence is very rare in the human genome, and the 60-mer combination is extremely rare.

Predicted GAM RNAs:

There are 8642 pairs of predicted GAM RNA and their respective precursors. From each precursor, a 26-mer containing the GAM RNA was placed at the 5' of the 60-mer probe and a 34-mer tail was attached to it. For each predicted probe, a mutation probes with 2 mismatches at positions 10 and 15 of the GAM RNA were added.

For a subset of 661 predicted precursors, up to 2 probes each containing one side of the precursor including any possible GAM RNA in it were added.

Microarray Analysis:

Based on known miRNA oligonucleotide probes, a preferred position of the miRNA oligonucleotide on the probe was evaluated, and hybridization conditions adjusted and the amount of cRNA to optimize microarray sensitivity and specificity ascertained. Negative controls are used to calculate background signal mean and standard deviation. Different probes of the same miRNA oligonucleotide are used to calculate signal standard deviation as a function of the signal.

For each probe, BG_Z_Score=(log(probe signal)−mean of log(negative control signal))/(log(negative control signal) standard deviation) were calculated.

For a probe with a reference probe with 2 mismatches on the miRNA oligonucleotide, MM_Z_Score MM_Z_Score= (log(perfect match signal)−log(reference mismatch signal))/ (standard deviation of log(signals) as the reference mismatch log(signal)) were calculated.

BG_Z_Score and MM_Z_Score are used to decide whether the probe is on and its reliability.

Reference is now made to FIG. 17C, which is a flowchart describing how the cDNA library was prepared from RNA and amplified. The general procedure was performed as described previously (Elbashir S M, Lendeckel W, Tuschl T. RNA interference is mediated by 21- and 22-nucleotide RNAs. Genes Dev. 2001 15:188-200) with several modifications, which will be described hereinbelow.

First, the starting material is prepared. Instead of starting with standard total RNA, the total RNA was size-fractionated using an YM-100 Microcon column (Millipore Corporation, Billerica, Mass., USA) in the present protocol. Further, the present protocol uses human tissue or cell lines instead of a *Drosophila* in vitro system as starting materials. Finally, 3 micrograms of size-fractionated total RNA was used for the ligation of adaptor sequences.

Libraries used for microarray hybridization are listed hereinbelow: "A" library is composed of a mix of libraries from Total HeLa YM100 RNA and Nuclear HeLa YM100 RNA; "B" library is composed of a mix of libraries from Total HEK293 YM100 RNA and Nuclear HEK293 YM100 RNA; "C" library is composed of a mix of YM100 RNA libraries from Total PC3, Nuclear PC3 and from PC3 cells in which Dicer expression was transiently silenced by Dicer specific siRNA; "D" library is prepared from YM100 RNA from Total Human Brain (Ambion Cat#7962); "E" library is prepared from YM100 RNA from Total Human Liver (Ambion Cat#7960); "F" library is prepared from YM100 RNA from Total Human Thymus (Ambion Cat#7964); "G" library is prepared from YM100 RNA from Total Human Testis (Ambion Cat#7972); and "H" library is prepared from YM100 RNA from Total Human Placenta (Ambion Cat#7950).

Library letters appended by a numeral "1" or "2" are digested by XbaI (NEB); Library letters affixed by a numeral "3" are digested by Xba1 and Spel (NEB); Library letters appended by a numeral "4" are digested by Xba1 and the transcribed cRNA is then size-fractionated by YM30, retaining the upper fraction consisting of 60 nts and longer; Library letters affixed by a numeral "5" are digested by Xba1 and the transcribed cRNA is then size-fractionated by YM30 retaining the flow-through fraction consequently concentrated with YM10 consisting of 30 nts-60 nts; Library letters affixed by a numeral "6" are digested by Xba1 and the DNA is fractionated on a 13% native acrylamide gel from 40-60 nt, electroeluted on a GeBaFlex Maxi column (GeBa Israel), and lyophilized; Library letters affixed by a numeral "7" are digested by Xba1 and the DNA is fractionated on a 13% native acrylamide gel from 80-160 nt, electroeluted and lyophilized.

Next, unique RNA-DNA hybrid adaptor sequences with a T7 promoter were designed. This step is also different than other protocols that create libraries for microarrays. Most protocols use complements to the polyA tails of mRNA with a T7 promoter to amplify only mRNA. However, in the present invention, adaptors are used to amplify all of the RNA within the size-fractionated starting material. The adaptor sequences are ligated to the size-fractionated RNA as described in FIG. 13, with subsequent gel-fractionation steps. The RNA is then converted to first strand cDNA using reverse transcription.

Next, the cDNA is amplified using PCR with adaptor-specific primers. At this point, there is the optional step of removing the tRNA, which is likely to be present because of its low molecular weight, but may add background noise in the present experiments. All tRNA contain the sequence ACC at their 3' end, and the adaptor contains GGT at its 5' end. This sequence together (GGTACC) is the target site for NcoI restriction digestion. Thus, adding the restriction enzyme NcoI either before or during PCR amplification will effectively prevent the exponential amplification of the cDNA sequences that are complements of the tRNAs.

The amplified DNA is restriction enzyme-digested with Xba1 (and, optionally, with Pst or Spel) to remove the majority of the adaptor sequences that were initially added to the RNA. Using the first set of RNA-DNA hybrid adaptors listed below, the first two sets of primers listed below, and Xba1 restriction digest yields the following cRNA products: 5'GGCCA-PRE/miRNA-UAUCUAG, where PRE is defined as GAM PRECURSOR (palindrome). Using the second set of RNA-DNA hybrid adaptors listed below, the second set of primers listed below, and Xba1 and Pst restriction digest yields the following, smaller cRNA products: 5'GG-PRE/ miRNA-C*.

Then, cDNA is transcribed to cRNA utilizing an RNA polymerase e.g. T7 dictated by the promoter incorporated in the adaptor. cRNA may be labeled in the course of transcription with aminoallyl or fluorescent nucleotides such as Cy3- or Cy5-UTP and CTP among other labels, and cRNA sequences thus transcribed and labeled are hybridized with the microarray.

The following RNA-DNA hybrid adaptors are included in the present invention:

Name: T7 Ncol-RNA-DNA 3'Adapter
   Sequence: 5'(5phos)rUrGrGCCTATAGTGAGTCG-TATTA (SEQ ID NO: 4254806) (3InvdT)3'
2. Name: 5Ada RNA-DNA XbaBseRI
   Sequence: 5'AAAGGAGGAGCTCTAGrArUrA 3' (SEQ ID NO: 4254807) or optionally:
3. Name: 5Ada MC RNA-DNA PstAtaBser
   Sequence: 5'CCTAGGAGGAGGACGTCTGrCrArG 3' (SEQ ID NO: 4254808)
4. Name: 3'Ada nT7 MC RNA-DNA
   Sequence: 5'(5phos)rCrCrUATAGTGAGTCGTAT-TATCT (3InvdT) 3' (SEQ ID NO: 4254809)

The following DNA primers are included in the present invention:

1. Name: T7 Ncol-RT-PCR primer
   Sequence: 5'TAATACGACTCACTATAGGCCA 3' (SEQ ID NO: 4254810)
2. Name: T7Nhel Spel-RT-PCR primer
   Sequence: 5'GCTAGCACTAGTTAATACGACTCAC-TATAGGCCA 3' (SEQ ID NO: 4254811)
3. Name: 5Ada XbaBseRI Fwd
   Sequence: 5'AAAGGAGGAGCTCTAGATA 3' (SEQ ID NO: 4254812)
4. Name: Pst-5Ada XbaBseRI Fwd
   Sequence: 5'TGACCTGCAGAAAGGAGGAGCTCTA-GATA 3' (SEQ ID NO: 4254813)
   or optionally:
5. Name: 5Ada MC PstAtaBser fwd
   Sequence: 5'ATCCTAGGAGGAGGACGTCTGCAG 3' (SEQ ID NO: 4254814)
6. Name: RT nT7 MC Xbal
   Sequence: 5'GCTCTAGGATAATACGACTCACTAT-AGG 3' (SEQ ID NO: 4254815)

Figure 18A:
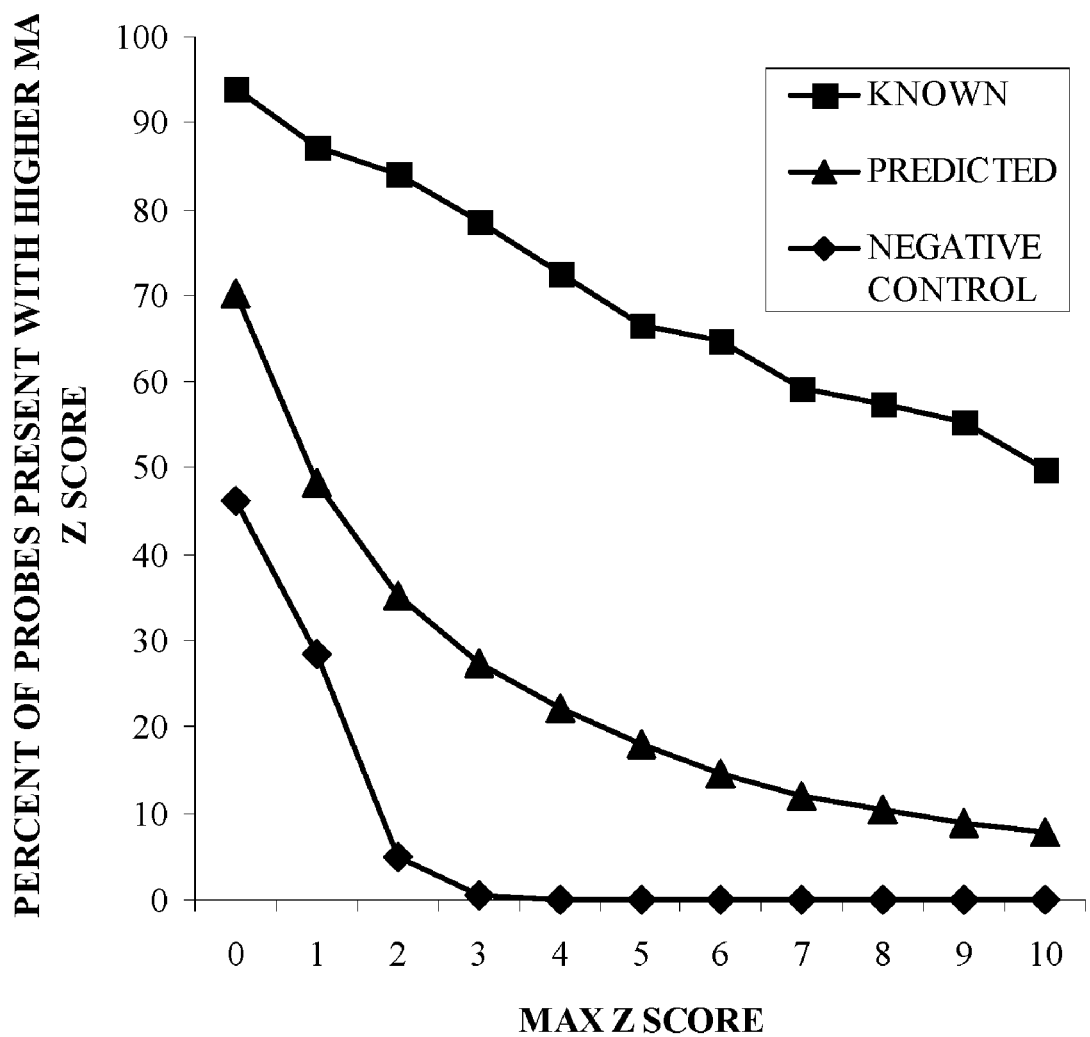
FIG. 18A is a line graph showing results of detection of known microRNA oligonucleotides and of novel GAM oligonucleotides, using a microarray constructed and operative in accordance with a preferred embodiment of the present invention.

Reference is now made to FIG. 18A, which demonstrates the detection of known miRNA oligonucleotides and of novel GAM oligonucleotides, using a microarray constructed and operative in accordance with a preferred embodiment of the present invention. Based on negative control probe intensity signals, we evaluated the background, non-specific, logarithmic intensity distribution, and extracted its mean, designated BG_mean, and standard deviation, designated BG_std. In order to normalize intensity signals between different microarray experiments, a Z score, which is a statistical measure that quantifies the distance (measured in standard deviations) that a data point is from the mean of a data set, was calculated for each probe with respect to the negative control using the following Z score formula: Z=(logarithm of probe signal BG_mean)/BG_std. We performed microarray experiments using RNA extracted from several different tissues and we calculated each probes maximum Z score. FIG. 18A shows the percentages of known, predicted and negative control groups that have a higher max Z score than a specified threshold as a function of max Z score threshold. The negative control group plot, included as a reference, considers probe with a max Z score greater then 4 as a reliable probe with meaningful signals. The sensitivity of our method was demonstrated by the detection of almost 80% of the known published miRNA oligonucleotides in at least one of the examined tissues. At a threshold of 4 for the max Z score, 28% of the predicted GAMs are present in at least one of the examined tissues.

Figure 18B:
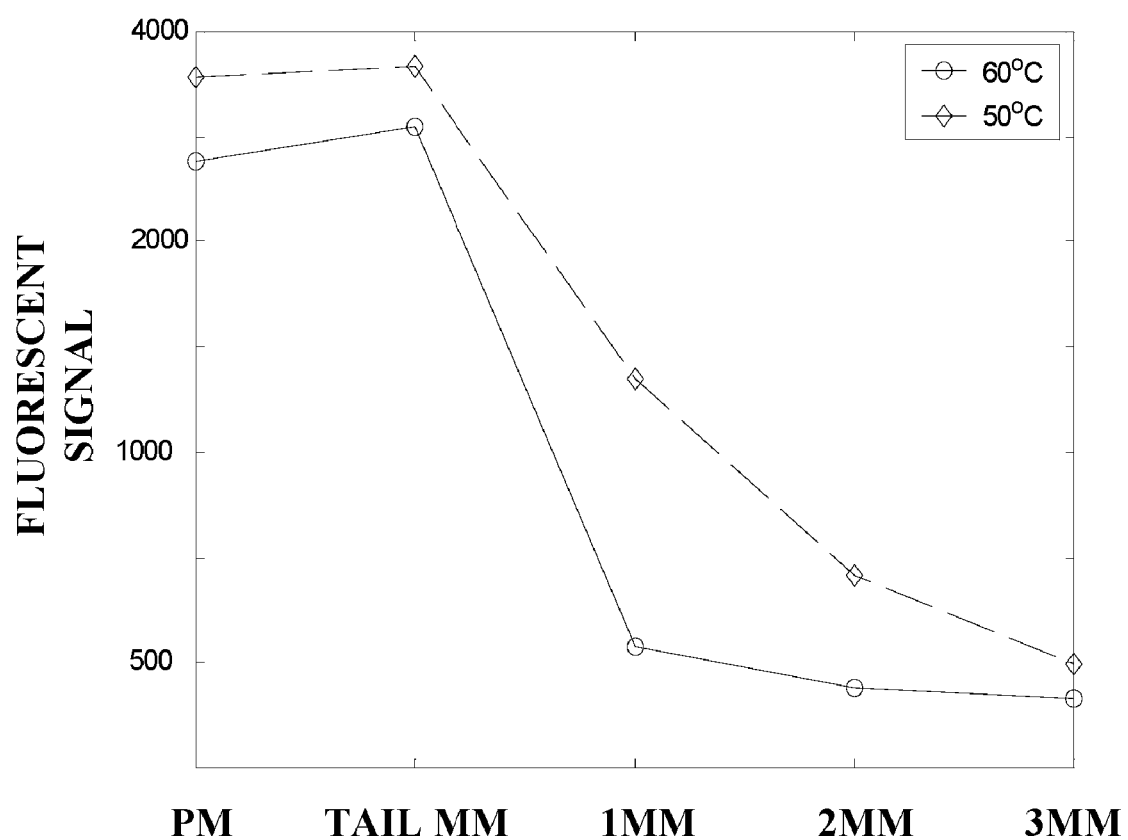
FIG. 18B is a line graph showing specificity of hybridization of a microarray constructed and operative in accordance with a preferred embodiment of the present invention.

Reference is now made to FIG. 18B, which is a line graph showing specificity of hybridization of a microarray constructed and operative in accordance with a preferred embodiment of the present invention and described hereinabove with reference to FIGS. 17A-17C.

The average signal of known miRNA oligonucleotides in Library A2 is presented on a logarithmic scale as a function of the following probe types under two different hybridization conditions: 50 C and 60 C: perfect match (PM), six mismatches on the tail (TAIL MM), one mismatch on the miRNA oligonucleotide (1 MM), two separate mismatches on the miRNA oligonucleotide (2 MM), three separate mismatches on the miRNA oligonucleotide (3 MM). The relative equality of perfect match probes and probes with the same miRNA oligonucleotide but many mismatches over the tail attest to the independence between the tail and the probe signal. At a hybridization temperature of 60 C, one mismatch in the middle of the miRNA oligonucleotide is enough to dramatically reduce the probe signal. Conducting chip hybridization at 60 C ensures that a probe has a very high specificity.

It is appreciated that these results demonstrate the specificity of the microarray of the present invention in detecting expression of miRNA oligonucleotides.

Reference is now made to FIG. 18C, which is a summary table demonstrating detection of known miRNA oligonucleotides using a microarray constructed and operative in accordance with a preferred embodiment of the present invention and described hereinabove with reference to FIGS. 17A-17C.

Labeled cRNA from HeLa cells and Human Liver, Brain, Thymus, Placenta, and Testes was used for 6 different hybridizations. The table contains the quantitative values obtained for each miRNA oligonucleotide probe. For each miRNA oligonucleotide, the highest value (or values) is given in bolded font while lower values are given in regular font size. Results for MIR-124A, MIR-9 and MIR-122A are exactly as expected from previous studies. The References column contains the relevant references in the published literature for each case. In addition to these miRNA oligonucleotides, the table shows other known miRNA oligonucleotides that are expressed in a tissue-specific manner. The results indicate that MIR-128A, MIR-129 and MIR-128B are highly enriched in Brain; MIR-194, MIR-148 and MIR-192 are highly enriched in Liver; mIR-96, MIR-150, MIR-205, MIR-182 and MIR-183 are highly enriched in Thymus; MIR-204, MIR-10B, MIR-154 and MIR134 are highly enriched in Testes; and MIR-122, MIR-210, MIR-221, MIR-141, MIR-23A, MIR-200C and MIR-136 are highly enriched in Placenta. In most cases, low but significant levels are observed in the other tissues. However, in some cases, miRNA oligonucleotides are also expressed at relative high levels in an additional tissue.

It is appreciated that these results reproduce previously published studies of expression of known miRNA oligonucleotides. These results demonstrate the reliability of the microarray of the present invention in detecting expression of published miRNA oligonucleotides, and of novel GAM oligonucleotides of the present invention.

DETAILED DESCRIPTION OF TABLES

Table 1 comprises data relating the SEQ ID NO of oligonucleotides of the present invention to their corresponding GAM NAME, and contains the following fields: GAM SEQ-ID: GAM SEQ ID NO, as in the Sequence Listing; GAM NAME: Rosetta Genomics Ltd. nomenclature (see below); GAM RNA SEQUENCE: Sequence (5' to 3') of the mature, "diced" GAM RNA; GAM ORGANISM: identity of the organism encoding the GAM oligonucleotide; GAM POS: Dicer-cut location (see below); and Table 2 comprises detailed textual description according to the description of FIG. 1 of each of a plurality of novel GAM oligonucleotides of the present invention, and contains the following fields: GAM NAME: Rosetta Genomics Ltd. nomenclature (see below); GAM ORGANISM: identity of the organism encoding the GAM oligonucleotide; PRECUR SEQ-ID:GAM precursor Seq-ID, as in the Sequence Listing; PRECURSOR SEQUENCE: Sequence (5' to 3') of the GAM precursor; GAM DESCRIPTION: Detailed description of GAM oligonucleotide with reference to FIG. 1; and Table 3 comprises data relating to the source and location of novel GAM oligonucleotides of the present invention, and contains the following fields: GAM NAME: Rosetta Genomics Ltd. nomenclature (see below); PRECUR SEQ-ID: GAM precursor SEQ ID NO, as in the Sequence Listing; GAM ORGANISM: identity of the organism encodes the GAM oligonucleotide; SOURCE: For human GAM—chromosome encoding the human GAM oligonucleotide, otherwise—accession ID (GenBank, NCBI); STRAND: Orientation of the strand, "+" for the plus strand, "−" for the minus strand; SRC-START OFFSET: Start offset of GAM precursor sequence relative to the SOURCE; SRC-END OFFSET: End offset of GAM precursor sequence relative to the SOURCE; and Table 4 comprises data relating to GAM precursors of novel GAM oligonucleotides of the present invention, and contains the following fields: GAM NAME: Rosetta Genomics Ltd. nomenclature (see below); PRECUR SEQ-ID: GAM precursor Seq-ID, as in the Sequence Listing; GAM ORGANISM: identity of the organism encoding the GAM oligonucleotide; PRECURSOR-SEQUENCE: GAM precursor nucleotide sequence (5' to 3'); GAM FOLDED PRECURSOR RNA: Schematic representation of the GAM folded precursor, beginning 5' end (beginning of upper row) to 3' end (beginning of lower row), where the hairpin loop is positioned at the right part of the draw; and Table 5 comprises data relating to GAM oligonucleotides of the present invention, and contains the following fields: GAM NAME: Rosetta Genomics Ltd. nomenclature (see below); GAM ORGANISM: identity of the organism encoding the GAM oligonucleotide; GAM RNA SEQUENCE: Sequence (5' to 3') of the mature, "diced" GAM RNA; PRECUR SEQ-ID: GAM precursor Seq-ID, as in the Sequence Listing; GAM POS: Dicer-cut location (see below); and Table 6 comprises data relating SEQ ID NO of the GAM target gene binding site sequence to TARGET gene name and target binding site sequence, and contains the following fields: TARGET BINDING SITE SEQ-ID: Target binding site SEQ ID NO, as in the Sequence Listing; TARGET ORGANISM: identity of organism encode the TARGET gene; TARGET: GAM target gene name; TARGET BINDING SITE SEQUENCE: Nucleotide sequence (5' to 3') of the target binding site; and Table 7 comprises data relating to target-genes and binding sites of GAM oligonucleotides of the present invention, and contains the following fields: GAM NAME: Rosetta Genomics Ltd. nomenclature (see below); GAM ORGANISM: identity of the organism encoding the GAM oligonucleotide; GAM RNA SEQUENCE: Sequence (5' to 3') of the mature, "diced" GAM RNA; TARGET: GAM target gene name; TARGET REF-ID: For human target genes—Target accession number (RefSeq, GenBank); Otherwise—the location of the target gene on the genome annotation. TARGET ORGANISM: identity of organism encode the TARGET gene; UTR: Untranslated region of binding site/s (3' or 5');

TARGET BS-SEQ: Nucleotide sequence (5' to 3') of the target binding site; BINDING SITE-DRAW: Schematic representation of the binding site, upper row represent 5' to 3' sequence of the TARGET, Lower row represent 3' to 5' Sequence of the GAM RNA; GAM POS: Dicer-cut location (see below); and Table 8 comprises data relating to functions and utilities of novel GAM oligonucleotides of the present invention, and contains the following fields: GAM NAME: Rosetta Genomics Ltd. nomenclature (see below); GAM RNA SEQUENCE: Sequence (5' to 3') of the mature, "diced" GAM RNA; GAM ORGANISM: identity of the organism encoding the GAM oligonucleotide; TARGET: GAM target gene name; TARGET ORGANISM: identity of organism encode the TARGET gene; GAM FUNCTION: Description of the GAM functions and utilities; GAM POS: Dicer-cut location (see below); and Table 9 comprises references of GAMs target genes and contains the following fields: TARGET: Target gene name; TARGET ORGANISM: identity of organism encode the TARGET gene; REFERENCES: reference relating to the target gene; and Table 10 comprises data relating to novel GR (Genomic Record) polynucleotides of the present invention, and contains the following fields: GR NAME: Rosetta Genomics Ltd. nomenclature (see below); GR ORGANISM: identity of the organism encoding the GR polynucleotide; GR DESCRIPTION: Detailed description of a GR polynucleotide, with reference to FIG. 9; and Table 11 comprises data of all sequences printed on the microarray of the microarray experiment, as described herein above with reference to FIG. 17 and include the following fields: PROBE SEQUENCE: the sequence that was printed on the chip PROBE TYPE: as described in detail in FIG. 17 in chip design section and summarized as follows: Known: published miRNA sequence; Known_mis1: similar to published miRNA sequence, but with 1 mismatch mutation on the miRNA sequence; Known_mis2: similar to published miRNA sequence, but with 2 mismatch mutations on the miRNA sequence; Known_mis3: similar to published miRNA sequence, but with 3 mismatch mutations on the miRNA sequence; Known_mis4: similar to published miRNA sequence, but with 6 mismatch mutations on regions other than the miRNA sequence; Predicted: predicted GAM RNA sequences; Mismatch: sequences that are similar to predicted GAM RNA sequences but with 2 mismatches; Edges 1: left half of GAM RNA sequences; Edges2: right half of GAM RNA sequences extended with its hairpin precursor (palindrome); Control1: negative control; Control2: random sequences; Control3: tRNA; Control4: snoRNA; Control5: mRNA; Control6: other; GAM RNA SEQ ID/MIR NAME: GAM oligonucleotide using Rosetta Genomics Ltd. Nomenclature (see below) or published miRNA oligonucleotide terminology; GAM RNA SEQUENCE: Sequence (5' to 3') of the mature, "diced" GAM RNA; LIBRARY: the library name as defined in FIG. 17C; SIGNAL: Raw signal data for library; BACKGROUND Z-SCORE: Z-score of probe signal with respect to background, negative control signals; MISMATCH Z-SCORE: Z-score of probe signal with respect to its mismatch probe signal; and Table 12 comprises data related to the GAM RNA SEQUENCEs included in the present invention that were validated by laboratory means. If the validated sequence appeared in more than one GAM precursor, the GAM RNA SEQ-ID indicated may be arbitrarily chosen. The table includes the following fields: VALIDATION METHOD: the type of validation performed on the sequence. The microarray validations are divided into four groups: a) "Chip strong" refers to GAM oligonucleotide sequences whose intensity (SIGNAL) on the microarray "chip" was more than 6 standard deviations above the background intensity, and the differential to the corresponding mismatch intensity was more than 2 standard deviations, where in this case the standard deviation is of the intensity of identical probes; b) "Chip" refers to GAM oligonucleotide sequences, whose intensity was more than 4 standard deviations above the background intensity; c) "Sequenced" refers to GAM oligonucleotide sequences that were sequenced; and d) "Chip strong, Sequenced" refers to miRNA oligonucleotide sequences that were both detected in the microarray as "Chip strong" and sequenced. "Sequenced" is described hereinabove with reference to FIG. 13. Other validations are from microarray experiments as described hereinabove with reference to FIGS. 17A-C and 18A-C; SIGNAL: a raw signal data; BACKGROUND Z-SCORE: a Z-score of probe signal with respect to background, negative control signals; MISMATCH Z-SCORE: a Z-score of probe signal with respect to its mismatch probe signal; and Table 13 comprises sequence data of GAMs associated with different bacterial infections. Each row refers to a specific bacterial infection, and lists the SEQ ID NOs of GAMs that target genes associated with that bacterial infection. The table contains the following fields: ROW#: index of the row number; INFECTION NAME: name of the infecting organism; and SEQ ID NOs OF GAMS ASSOCIATED WITH INFECTION: list of sequence listing IDs of GAMs targeting genes that are associated with the specified infection.

The following conventions and abbreviations are used in the tables: The nucleotide "U" is represented as "T" in the tables, and;

GAM NAME or GR NAME are names for nucleotide sequences of the present invention given by Rosetta Genomics Ltd. nomenclature method. All GAMs/GRs are designated by GAMx/GRx where x is a unique ID.

GAM POS is a position of the GAM RNA on the GAM PRECURSOR RNA sequence. This position is the Dicer-cut location: A indicates a probable Dicer-cut location; B indicates an alternative Dicer-cut location.

All human nucleotide sequences of the present invention as well as their chromosomal location and strand orientation are derived from sequence records of UCSC-hg16 version, which is based on NCBI, Build34 database (April, 2003).

All bacterial sequences of the present invention as well as their genomic location are derived from NCBI, RefSeq database.

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| ACTCACTGCAACCTCCACCTCC | Sequenced | | | | 323 |
| ACTGCACTCCAGCCTGGGCTAC | Sequenced | | | | 13 |
| AATCACTTGAACCCAAGAAGTG | Sequenced | | | | 5 |
| AATCGCTTGAACCCAGGAAGTG | Sequenced | | | | 6 |
| TTCAAGTGTTTAAGTTCTGCTT | Sequenced | | | | 305 |
| AGGCAGAGAGGACCAGAGACT | Sequenced | | | | 331 |
| CACTGCACTCCAGCCCGAGCAA | Sequenced | | | | 46 |
| CCCGGGTGGAGCCTGGGCTGTG | Sequenced | | | | 361 |
| GGGCGTGGAGCTGGAATGATGT | Sequenced | | | | 125 |
| TGATAGATCCATATTTTGGTAA | Sequenced | | | | 279 |
| AGCAAGACCAGGGTTTTGTGTT | Sequenced | | | | 326 |
| TCACTGCAACCTCCACCTCCCA | Sequenced | | | | 198 |
| ATTGTTGCCCATGTTTTTATTT | Sequenced | | | | 40 |
| CTGGACTGAGCTCCTTGAGGCC | Sequenced | | | | 383 |
| AGGCCAAGAAGGAAGCAGAGG | Sequenced | | | | 25 |
| ATTAGGAGAGTGGGTGCTAAGT | Sequenced | | | | 38 |
| AGTTTGTGTAAGAAAAGC | Sequenced | | | | 338 |
| AGGAAAAAAATTAATGTGAGTC | Sequenced | | | | 22 |
| TCACTGCAACCTCCACCAGCCT | Sequenced | | | | 197 |
| GTGACAGTGAATCTAGACAGAC | Sequenced | | | | 134 |
| TATTCATTGCCCATGTTTGTGA | Sequenced | | | | 262 |
| TGGGTTTTGTTTGTACAGTGTA | Sequenced | | | | 229 |
| CTCAGCTCATCCACTAAATCCC | Sequenced | | | | 377 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| TCACTGCAACCTCCACCTTCAG | Sequenced | | | | 263 |
| GGGAAATAATTAATGTGAAGTC | Sequenced | | | | 124 |
| TGGAGGAGAGTTTGTCAGTATAG | Sequenced | | | | 298 |
| GGAATGGTGGTTGTATGGTTG | Sequenced | | | | 116 |
| TCACTGCAACCTCCACCTTCCG | Sequenced | | | | 201 |
| TTCTGATGGTTAAGTTCTGTCA | Sequenced | | | | 306 |
| AGGGCAGGAGGTCCGTCCCTTC | Sequenced | | | | 27 |
| TCACTGCAACCTCCACCACGTG | Sequenced | | | | 196 |
| TCTAAGAGAAAGGAAGTTCAGA | Sequenced | | | | 272 |
| GAAGTTTGAAGCCTGTTGTTCA | Sequenced | | | | 95 |
| CTAGACTGAAGCTCCTTGAGGA | Sequenced | | | | 74 |
| AATTGCTTGAACCCAGGAAGTGGA | Sequenced | | | | 8 |
| CACTGCAACCTCCACCTCCTGG | Chip strong, Sequenced | 31393 | 19.150194 | 22.611071 | 45 |
| TCACTGCAACCTCCACCTCCCG | Chip strong, Sequenced | 31810 | 20.186802 | 16.772465 | 199 |
| TCACTGCAACCTCCACCTCCTG | Chip strong, Sequenced | 45662 | 20.504339 | 18.911047 | 200 |
| ATGGTAGCTGTCCACATCAGGA | Chip strong | 8208 | 25.85717 | 21.352978 | 36 |
| TCAGCTCCTACCCCGGCCCCAG | Chip strong | 8279.5 | 11.228731 | 17.399603 | 204 |
| GTTTCTCTGGGCTTGGCAT | Chip strong | 8298 | 10.689093 | 5.6611276 | 257 |
| TGGTCTGGCCCACATGGTC | Chip strong | 8349 | 13.022524 | 4.8629713 | 231 |
| GTGCTGGTGCTCGCTCCTCTGG | Chip strong | 8165 | 11.725875 | 9.7062302 | 251 |
| CTCAGGTGATCCACCCCTCTTG | Chip strong | 8190 | 8.7424583 | 3.9819176 | 75 |
| TGCAGGTTGCTGGTCTGATCTC | Chip strong | 8079 | 24.743416 | 17.869699 | 283 |
| AGTCATTATCTCCTGGACC | Chip strong | 7790 | 10.371323 | 17.396904 | 30 |
| GCTGCACCCCAGCCTGGGTAAC | Chip strong | 7858 | 6.2366548 | 20.271864 | 162 |
| CACTTCCCTTCTCTGCTCATGG | Chip strong | 7886.5 | 8.1030474 | 7.7415953 | 347 |
| TGCTGGCTATCCTGCGCCTTTC | Chip strong | 7903 | 10.469044 | 13.746831 | 225 |
| GGCTGCTGGTTTCTTGTTTTAG | Chip strong | 7926 | 12.94939 | 11.212504 | 176 |
| CTTCCTGCCTCTCGCCGCCCGC | Chip strong | 7982 | 10.846725 | 2.7860351 | 89 |
| CTGCTCTGGTTTCCTCTGTC | Chip strong | 7506.5 | 7.7015729 | 15.622507 | 86 |
| GCCTCCAGGTCGGTCTTTCTCT | Chip strong | 7529 | 13.077046 | 6.7496343 | 104 |
| CCCTCTTGGCTTCTATCCCACC | Chip strong | 7596 | 7.1978688 | 6.3785648 | 363 |
| CAGCTGGTGCTTGCCTGGCTAA | Chip strong | 7373 | 13.676201 | 7.9258513 | 351 |
| TCTCCCAGATCCTTTAGCCTCC | Chip strong | 7384.5 | 14.663905 | 2.166656 | 274 |
| TTTCTTGGGCCGTGTGCTGGT | Chip strong | 7386 | 8.0159159 | 10.662634 | 248 |
| ATCACTTTGAGTCCAGGAGTTT | Chip strong | 7335 | 6.5335536 | 19.718058 | 32 |
| GAGCCGCCCTCCACGATGTCCC | Chip strong | 7252 | 8.6663809 | 14.735928 | 142 |
| CCTCACTCAGGTTTGGACCCTG | Chip strong | 7301 | 15.895414 | 5.3846102 | 61 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| GGGTTACTCTGTGTTGGTCAGG | Chip strong | 7310 | 8.6937799 | 12.815997 | 129 |
| TGCTCTGATTTTTGCCCCAGC | Chip strong | 7060.5 | 10.413313 | 7.7476549 | 291 |
| GCTGTTTTCCCATAGCTGGTCA | Chip strong | 7061 | 19.803032 | 6.222959 | 164 |
| GCTAGGCTGCTGGCCACTGAGG | Chip strong | 6972.5 | 13.127683 | 19.686853 | 159 |
| TGCTTGCTGTGGTTGGCTGGTA | Chip strong | 6974 | 21.75724 | 11.332961 | 296 |
| TCAGCCTCCTCCACCCCAGAGT | Chip strong | 6996.5 | 14.03341 | 7.0927162 | 264 |
| GGGGAACGCGCTGGCCCGCGCC | Chip strong | 7005 | 6.2445078 | 11.806351 | 127 |
| CTCTGTGATATGGTTTGTAATA | Chip strong | 6862 | 19.265455 | 13.692534 | 84 |
| CATTCTGTGAGCTGCTGGCTTT | Chip strong | 6884 | 11.220102 | 9.6062307 | 52 |
| CTCGACTTCCCTGGCTTGCGTGA | Chip strong | 6890 | 6.5380254 | 11.584653 | 78 |
| GGCGGCCCAGGCGCTTGGAGAT | Chip strong | 6899.5 | 8.1672001 | 10.434432 | 172 |
| TGCCGCCCGGCCATCTCGGCTC | Chip strong | 6915.5 | 13.391404 | 5.9536037 | 220 |
| TCTCTATGCCATGCTGGCCT | Chip strong | 6926 | 17.665062 | 2.5852687 | 217 |
| ACATTCTCTGATTGGTGCCTCC | Chip strong | 6695 | 12.723179 | 6.4453721 | 319 |
| CTGTGCTCTTTCCACGGCCCCA | Chip strong | 6477.5 | 13.662484 | 9.3280506 | 139 |
| AAGGCCGCCCCTTCATGCTCCT | Chip strong | 6358.5 | 9.1175785 | 8.5895061 | 1 |
| CAGCAGCTCAGCCTCCTTCCCA | Chip strong | 6588 | 11.002058 | 9.0820408 | 349 |
| CAGTTTGTCCCCATGGCCATGT | Chip strong | 6591.5 | 13.401958 | 5.2375259 | 354 |
| TGGAGCTGGGTCTGGGCA | Chip strong | 6426 | 15.46969 | 17.843594 | 297 |
| CCTGGTCGGCGTGGTGACGGCG | Chip strong | 6434.5 | 6.2044091 | 6.2762375 | 369 |
| TCCTACGGTGGCCACAGTCTGG | Chip strong | 6256 | 7.9984035 | 3.2358623 | 210 |
| CGTTCACTCCCTTGCCCCTCGG | Chip strong | 6280.5 | 7.0008011 | 9.7373304 | 73 |
| TGTCTGGCTTTCTTCAGTTAGC | Chip strong | 6191 | 9.9906111 | 15.989508 | 236 |
| TGCTGCACCCTCTGCCTCCGGG | Chip strong | 6094.5 | 6.9428978 | 10.588869 | 293 |
| GCAGCATCCCGGCCTCCACTGT | Chip strong | 5995 | 7.2606683 | 11.881517 | 147 |
| TGTGGTAGTCACGGCCCGCCAC | Chip strong | 5909.5 | 23.027369 | 15.816967 | 304 |
| CTTGCCTGCCCTGTGTCATAAA | Chip strong | 5903.5 | 13.361271 | 3.0393276 | 91 |
| TTCACTGCTCTAGCCCTAATTT | Chip strong | 5739 | 15.599205 | 7.8376389 | 240 |
| TCCATTGGCCTTTTATCCTAGA | Chip strong | 5760 | 15.329782 | 8.1126537 | 209 |
| TGCCTAGCCAAGTCCAGTATTT | Chip strong | 5823 | 17.976177 | 16.478537 | 221 |
| TTCTGGCTTCTCCCAGGCGGCC | Chip strong | 5582 | 8.2352791 | 10.879703 | 243 |
| ATGGCCCTCTTATCACAGCTCC | Chip strong | 5586.5 | 21.480997 | 6.3762493 | 342 |
| ACTGCACTCCATCCAGCCTGGC | Chip strong | 5668 | 7.6480083 | 10.938603 | 324 |
| TGCCTGCCCCAGCTGAGATATC | Chip strong | 5686 | 10.380668 | 15.221783 | 287 |
| GCTCGCTGGGGTCTGCAGGCGG | Chip strong | 5502 | 7.7859778 | 10.874097 | 111 |
| GCAGCTCCTGGAGGTGAGAGGCG | Chip strong | 5368 | 7.8018293 | 15.956004 | 100 |
| CTCATTGTAGCCTCCAGTTCTTG | Chip strong | 5375 | 10.634505 | 9.6296253 | 379 |
| AGGCTGGTTAGATTTGTGGTCT | Chip strong | 5392 | 20.112637 | 16.324888 | 26 |
| GCTGCACTTCAGCCTGGGTGTC | Chip strong | 5310 | 7.5533419 | 15.940791 | 113 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| GCCCTTTGTGTCTGGCTGGGGT | Chip strong | 5320 | 11.978069 | 10.261797 | 152 |
| TTCTCTGTGCTGGGTCCTGAGG | Chip strong | 5272.5 | 8.1261625 | 9.2259359 | 242 |
| AGATTTCCCTTCCTGCTTGCCT | Chip strong | 5251 | 6.0291886 | 13.065763 | 17 |
| TGCGTTCCAGTTGCTGCCAGGC | Chip strong | 5079 | 11.194171 | 5.7294831 | 290 |
| CTGGCTAAGATCCAAGAAAGGC | Chip strong | 5036 | 14.178236 | 6.6532001 | 385 |
| TCATTGCAACCTCCTCCTGGGT | Chip strong | 5039.5 | 18.95397 | 9.7537737 | 207 |
| TTGACATGCCTCCTACATGATC | Chip strong | 5065 | 12.953059 | 10.809283 | 307 |
| CCTGCTCTCTGTTCTTAAGCTT | Chip strong | 5021 | 9.0648565 | 7.4354005 | 64 |
| TGCACCACTGCACCCCAGTCTG | Chip strong | 5009 | 7.3463378 | 16.848854 | 281 |
| TGCTGCCCTAAGACCACCTT | Chip strong | 4950 | 11.124713 | 13.249466 | 294 |
| GGGAGTTGTGGTTGGCTTCTGG | Chip strong | 4978 | 8.3206406 | 9.2158394 | 179 |
| GGCCGTGGTCGCTGACTCTCGT | Chip strong | 4980 | 6.9448657 | 12.094063 | 120 |
| TAGGTATGGCTTGTGGCACAGC | Chip strong | 4840 | 23.281979 | 15.36544 | 261 |
| GCGCCGCCATCCGCATCCTCGT | Chip strong | 4801 | 16.34218 | 9.281786 | 107 |
| CTGGTGTTGGGTCTTGCTTTTA | Chip strong | 4756 | 6.5764294 | 8.8639517 | 138 |
| ATGGGCCTCCTATTATCCCCAT | Chip strong | 4745.5 | 13.363207 | 5.1394033 | 34 |
| CGCCCAGGCTGGAGTGCCAGTG | Chip strong | 4722 | 9.6376123 | 13.758563 | 69 |
| CGACCTTGTGATCCTCCCGCCT | Chip strong | 4594 | 7.4134154 | 4.4487605 | 370 |
| CTCAGTGCAACCTCCGCCTACT | Chip strong | 4516 | 8.8905106 | 13.512998 | 76 |
| GGCTCTGGCTTTGGAGGAGCAG | Chip strong | 4483.5 | 6.8781896 | 14.473881 | 174 |
| GGGCTTTTGGAATGGTCTGT | Chip strong | 4463 | 9.6709318 | 2.0551727 | 126 |
| AGTCGCTGGACCATCAGAGCCT | Chip strong | 4419 | 12.240126 | 13.100382 | 335 |
| GGTGGTGGAGCGGGCCCAGGCC | Chip strong | 4320.5 | 7.4591732 | 12.328825 | 185 |
| TCCAGCTGTCCACGTCTTCCTG | Chip strong | 4070 | 6.5770264 | 7.9605851 | 265 |
| ATGGTACTCCAGCCTGGGTGAC | Chip strong | 4173 | 7.3957338 | 16.409479 | 35 |
| ATTCTGTGCTAACTGCAGGCCA | Chip strong | 4140 | 19.305922 | 11.530575 | 343 |
| GACCTCGTGATCCGCCTGCTTT | Chip strong | 4080.5 | 7.6009617 | 13.947659 | 97 |
| TGGTGCAGCGTGTGGTGGCTCT | Chip strong | 4082.5 | 9.6208868 | 12.887189 | 302 |
| TGGTCGGGCTGCATCTTCCGGC | Chip strong | 4093 | 8.0100813 | 2.1106353 | 230 |
| CACTGCAGCCTCCATCTCTGGG | Chip strong | 4050 | 6.9180322 | 10.574921 | 47 |
| ATGGTGCTGGTGGGAGTGTATT | Chip strong | 4053 | 18.971554 | 14.625937 | 37 |
| TGCCTGCCGTTAAATGTTACTT | Chip strong | 3936 | 12.749383 | 11.509386 | 222 |
| GACCTTGTGATCCGCCCACTTT | Chip strong | 3834 | 7.5950313 | 9.0545225 | 141 |
| CAACTCACTGCGGCCTCAACCT | Chip strong | 3783 | 9.680912 | 5.8278494 | 41 |
| CTGGAGGAGCTGCCATG | Chip strong | 3669 | 12.842446 | 14.933422 | 384 |
| TAGCTCCTCCCAGATCTCATCT | Chip strong | 3659 | 10.385338 | 3.9473054 | 192 |
| TTGGGGGAGGCCTGCTGCCCAT | Chip strong | 3549 | 9.3567915 | 8.3044834 | 310 |
| GTTGGTCTTCATTAAATGCTTT | Chip strong | 3499.5 | 17.153486 | 5.8892236 | 255 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| GGTGGCTATGGCTGTGCTCGC | Chip strong | 3426.5 | 15.917648 | 2.9563422 | 132 |
| GATGTCGTGATCCACCCGCCTT | Chip strong | 3425 | 7.313684 | 10.200798 | 145 |
| AGTGGCGTGATCTCGGCTCGGT | Chip strong | 3395 | 8.8775339 | 14.742507 | 336 |
| GTGCTTAAAGAATGGCTGTCCG | Chip strong | 3362 | 26.398634 | 13.195816 | 252 |
| TCACTGCAAGCTCCACCCTCCG | Chip strong | 3370 | 12.960393 | 9.7885542 | 202 |
| CGGCACTGTAGTCTGGCTGGGA | Chip strong | 3297 | 6.7212648 | 9.1534166 | 374 |
| CTGGCTAGATGTGTGGCCATGA | Chip strong | 3221 | 21.032122 | 14.058989 | 137 |
| AACCTTGTGATCCACCCACCTT | Chip strong | 3034 | 7.7903786 | 12.639959 | 313 |
| AGCTGGCTTACTTGAGATGCAT | Chip strong | 3049 | 8.8567095 | 7.4132333 | 329 |
| GGGGCTTCTAGGGTGCCAGATC | Chip strong | 3012.5 | 13.356146 | 7.901947 | 181 |
| GGCCCAGGTTGGAGTGCAGTGA | Chip strong | 2994 | 8.0930119 | 10.374014 | 168 |
| GGCCCAGTGCAAGCTCTTTCTG | Chip strong | 2960 | 7.6298795 | 6.4523926 | 118 |
| GCCCTTGAAGCTCTGACCCGCT | Chip strong | 2947 | 7.6962008 | 2.815666 | 151 |
| GCTGGCTCCACCTGCTGCCAGG | Chip strong | 2916 | 6.3332305 | 13.052609 | 115 |
| CCACTGAGGTAGCTGGTGACTG | Chip strong | 2861 | 16.719574 | 7.8953633 | 54 |
| CCTCCGGTCATTGTGCGGGCCT | Chip strong | 2835 | 12.644177 | 5.132216 | 366 |
| AGGATCTTGCTATGTTGGCCAG | Chip strong | 2784 | 10.949057 | 7.9714575 | 330 |
| TGGTGCTAGTTAAATCTTCAGG | Chip strong | 2715 | 17.999035 | 10.341267 | 232 |
| GCACTGCTGCCTCCTGG | Chip strong | 2627 | 6.3458524 | 7.414557 | 99 |
| TTATAATGTATAGCTGTGCCTG | Chip strong | 2566.5 | 15.056374 | 8.2182913 | 238 |
| TGCTTCTAGGGAGGCCGCAGGA | Chip strong | 2554 | 12.58359 | 11.930317 | 295 |
| TAGAACTATGGCTATGTGCCA | Chip strong | 2523.5 | 18.843672 | 7.4688845 | 259 |
| GACCCATCCTCCACTTGGCAGC | Chip strong | 2498 | 6.505065 | 6.8388047 | 96 |
| GCCTAGTGGATTTGAAGGGCC | Chip strong | 2352 | 20.613605 | 8.8114462 | 153 |
| TGCCCACTGCTGGCCACCACCC | Chip strong | 32112 | 15.630626 | 16.785101 | 219 |
| GGCTGGCCCCATCCAGGCTGGCA | Chip strong | 65518 | 10.117671 | 10.864906 | 121 |
| ACAAAGCGCTTCTCTTTAGAGT | Chip strong | 65518 | 11.238881 | 26.766436 | 9 |
| GGGGCTGGTCTTTCCACTTACT | Chip strong | 65518 | 11.24554 | 19.391401 | 180 |
| GGAGGCTGGCCTTCAGACGGGT | Chip strong | 65518 | 12.034198 | 25.266558 | 166 |
| ACGCGCTGGGCGCTGGCCAAT | Chip strong | 65518 | 13.337035 | 9.5484018 | 12 |
| ACAAAGTGCCTCCTTTTAGAGT | Chip strong | 65518 | 13.412503 | 32.421429 | 10 |
| CGCCTGGCCCCCAGTACTTTGT | Chip strong | 65518 | 14.386203 | 22.674049 | 373 |
| GCCTGGCCTAAATTAGTAATTT | Chip strong | 65518 | 14.47023 | 33.939186 | 155 |
| CCCTCTGGCCCCTGTGGTGGAT | Chip strong | 65518 | 14.648276 | 19.804953 | 362 |
| CTGCCTGCCTGGCCCAGGAACC | Chip strong | 65518 | 14.752467 | 36.164337 | 381 |
| CGCCCGCTGGCCCTGCGATCTC | Chip strong | 65518 | 15.196337 | 33.776985 | 70 |
| AGGACCTGTCCCCTGGCCCACT | Chip strong | 65518 | 15.796532 | 15.770715 | 24 |
| CAGCAGCACACTGTGGTTTGTA | Chip strong | 65518 | 16.623587 | 30.172779 | 348 |
| CCGCCTGGCCCATTGCAGGGCA | Chip strong | 65518 | 19.692606 | 29.045151 | 365 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| CACTGCACTCCAGCTCTGGGT | Chip strong | 65518 | 20.15584 | 31.571056 | 345 |
| ACAAAGTGCCTCCCTTTAGAGT | Chip strong | 65518 | 22.461653 | 34.028076 | 316 |
| CCCCACTGTCCCCGGAGCTGGC | Chip strong | 65518 | 22.799175 | 24.102064 | 358 |
| GGCGCTGGCCTGTGGGATCCCG | Chip strong | 65518 | 24.841112 | 31.449797 | 171 |
| GCGGCGGCGGTAGCAAAAATGA | Chip strong | 65518 | 27.5298 | 22.089998 | 109 |
| AGGGTTGTGTGCTGGCCGCTGG | Chip strong | 65518 | 29.01285 | 32.102142 | 28 |
| GGTGGCCCCTGGGAGATGCTGG | Chip strong | 65518 | 31.295538 | 14.111359 | 131 |
| CACTGCACTCCAGCCTGGGCAA | Chip strong | 65518 | 36.446095 | 33.140068 | 12852 |
| TGTGCTGGCCTTTGGTGACTTC | Chip strong | 65518 | 44.612064 | 26.016636 | 237 |
| CATGCTGGCCCACACCCGCTGC | Chip strong | 57891 | 37.069935 | 17.358248 | 50 |
| GGCTTCCTGCCTCGGGCTGGCC | Chip strong | 58372 | 13.006404 | 4.4936109 | 177 |
| GCCTGGCCTAATTCCAGCATTT | Chip strong | 62842.5 | 16.076189 | 31.293688 | 156 |
| GAAGGGGAAGAGAGCTGGCCG | Chip strong | 63993 | 20.677708 | 18.040138 | 94 |
| CCCGGCACCTCCGCTGCACAC | Chip strong | 50589.5 | 17.716768 | 10.848449 | 360 |
| ATGCCACTGCGCTCCAGCCTGA | Chip strong | 50941.5 | 15.106459 | 30.447573 | 341 |
| CCCCACTGTTTTCTTCATCCTA | Chip strong | 50957 | 32.576454 | 4.8442335 | 359 |
| CTTGGAGTAGGTCATTGGGTGG | Chip strong | 51071 | 16.39068 | 33.942337 | 92 |
| AGGTGCTGGGGCTTGGCCTGCT | Chip strong | 54992 | 14.781937 | 19.839622 | 333 |
| TGCCCGGATACCCCTGGCCTC | Chip strong | 46111 | 13.316625 | 10.030684 | 285 |
| ATTGCACTCCAGCCTGAGCAAA | Chip strong | 46579 | 22.505102 | 33.557095 | 39 |
| TCTCTTCGCTGGCCCTCGGGGA | Chip strong | 47791.5 | 15.379544 | 20.008915 | 276 |
| CCGTCCCCGGTGCTGCCTGCGC | Chip strong | 48514 | 9.4747534 | 7.9190497 | 60 |
| TGCTAGCTGCCCGAAGGTCTCA | Chip strong | 39989 | 47.058292 | 15.67876 | 223 |
| CCTGGCCGCTGTGCCCCCT | Chip strong | 40002 | 11.873036 | 10.703612 | 65 |
| ACACTTTGCCCCTGGCCGCCTT | Chip strong | 42189 | 12.009233 | 22.436626 | 317 |
| TGACCTCCTTTCTCGACTAATT | Chip strong | 43651 | 10.281033 | 24.914602 | 278 |
| CTGCTGCGCTGGCCGTCACGGT | Chip strong | 45168 | 18.758972 | 18.507338 | 382 |
| TTATTGCACTCCAGCCTGGGTA | Chip strong | 45303 | 21.338472 | 22.149384 | 239 |
| CTCAGTGCTGCTGGCTCCTGTC | Chip strong | 30057 | 40.88406 | 25.543219 | 378 |
| GACCCCTAAACCCGCTGGGCTG | Chip strong | 30088.5 | 13.552105 | 6.4749699 | 140 |
| CCTGGCTCTGGCTTCCTGTTGT | Chip strong | 34525 | 11.373339 | 6.4300051 | 368 |
| ACCCTGGCCGACTGCCCCTT | Chip strong | 35652 | 12.982363 | 11.41268 | 11 |
| GCCTGGCCTCCTACAGTACTTT | Chip strong | 35866 | 15.014146 | 23.263319 | 157 |
| GCCCTTCGGAAAGCGTCGCCTG | Chip strong | 37481 | 13.375318 | 6.6135831 | 150 |
| TGCCTGGCCTCCTGATTCCCTC | Chip strong | 37634.5 | 13.004288 | 2.9085336 | 288 |
| CCAGACCATTTTGCCTTACC | Chip strong | 38076 | 30.955603 | 11.095823 | 55 |
| CGTAAGTCACAGCGCCTGGCCC | Chip strong | 38826 | 11.506068 | 25.787857 | 72 |
| CAGGCTCTTCCCTCTGGCCAAG | Chip strong | 25089 | 10.865691 | 11.601097 | 352 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| GATGAGTTTGCCTGGCCTGCAG | Chip strong | 25445.5 | 12.297516 | 17.035336 | 143 |
| GCTGTAAGTCACCTGGCCCGAT | Chip strong | 26191 | 8.8471966 | 25.053482 | 163 |
| AGAAGGGCTGGCAGGAGTT | Chip strong | 26652 | 14.563484 | 25.132761 | 16 |
| TGCCTGGCCTCTTCAGCACTTC | Chip strong | 27021 | 10.873885 | 26.68429 | 289 |
| GGTGCCCCATCGCGGGTGGCTG | Chip strong | 27077 | 14.316696 | 22.61035 | 130 |
| GCTCCTGGCCGGGCTGCTCCTG | Chip strong | 27106 | 14.495318 | 9.280777 | 161 |
| AAGTGCTCATAGTGCAGGTAGT | Chip strong | 27166.5 | 9.1624584 | 28.31859 | 4 |
| CAGGAAAAGGCGGCTCGGGGCT | Chip strong | 27684.5 | 9.7338009 | 6.1309323 | 49 |
| TCACGCGCCCTCCTGGGCCCTG | Chip strong | 28630 | 10.411592 | 10.865385 | 195 |
| GGCGTGCCCTGGCCCCGAGGCT | Chip strong | 28813 | 10.987214 | 21.873014 | 173 |
| TCCTGGGGCTTGTCGCTGGCCA | Chip strong | 28926 | 12.960393 | 7.4913173 | 216 |
| GCTTCAGAGAGGGGTGAAGCTG | Chip strong | 21900 | 17.158428 | 13.963737 | 165 |
| CTCTCCTTGGCCACCTCCATGA | Chip strong | 23276 | 12.960393 | 7.0737572 | 81 |
| GGCTGGTGGCTGGTTCTGGACC | Chip strong | 20736.5 | 31.680035 | 17.914019 | 122 |
| CACCCGCTGGTCCCTGCAGTTC | Chip strong | 20816 | 8.5344362 | 27.261486 | 42 |
| CCCTGGCTCACTTTCTGTTGTG | Chip strong | 20839 | 26.185976 | 5.4283981 | 364 |
| GGTAGTCTTTGTCCCCTGGC | Chip strong | 20872 | 12.44091 | 3.1238594 | 182 |
| CATCACCCCAGACCTCAGTGC | Chip strong | 20958.5 | 35.708847 | 4.6072259 | 355 |
| GGCTGGTTAGATTTGTGGTCTT | Chip strong | 21258 | 33.569485 | 15.757149 | 123 |
| TTGGTCCCCTTCAACCAGCTAC | Chip strong | 20228 | 9.5504265 | 23.87529 | 246 |
| TCAGGGGTTGGCTTGTTGTGTT | Chip strong | 20519.5 | 8.8405285 | 21.048086 | 206 |
| TACTGCACTCCAGCCTTGCCAA | Chip strong | 18364 | 10.029301 | 16.731598 | 258 |
| AATTGCACGGTATCCATCTGTA | Chip strong | 18407 | 8.3120737 | 26.950815 | 7 |
| TGGTTCTTCGCTGGGCGGCTGC | Chip strong | 18451 | 17.683105 | 11.562138 | 234 |
| CCCTGCCTGTCCTGGTCCCGTT | Chip strong | 18466 | 9.747386 | 21.814604 | 59 |
| TCTCCACAGCTGGCCCCCAAGA | Chip strong | 19483.5 | 23.591568 | 26.742323 | 273 |
| CCTCGCTCTCCATTCGGCCCTC | Chip strong | 9378.5 | 6.9943829 | 8.7534571 | 367 |
| GGCCGGGTGCTCTGGAGGTGCT | Chip strong | 14393 | 11.734104 | 12.172738 | 119 |
| AGCTCCTGGCTTCAAGCAATCC | Chip strong | 14107 | 10.339123 | 18.669428 | 20 |
| TTTAAATCACAACTCTGCCCCT | Chip strong | 15129 | 15.825633 | 8.2785378 | 247 |
| GTAGCTGTGTTCATTCTGGATG | Chip strong | 15186.5 | 37.683685 | 11.412519 | 187 |
| AAGTGCTAGTGAGTCTATTGTA | Chip strong | 15263 | 30.581371 | 17.914198 | 3 |
| GCCCCAGCTCACCGGCTCACTG | Chip strong | 15345 | 20.667051 | 7.4258513 | 103 |
| GTGCGGCCTGGCCTTCAAGTGG | Chip strong | 15350 | 9.6908836 | 19.487803 | 250 |
| GTTGGTTTTAGCTTGGCCCATT | Chip strong | 15833 | 22.509586 | 7.6416044 | 256 |
| TTGATGCCCCGTCCTGTACACT | Chip strong | 16077 | 20.144415 | 22.335653 | 308 |
| GCAGGGAACTGGCTGGGCTTT | Chip strong | 16084 | 7.1124773 | 22.951672 | 102 |
| ACCATCTCCTGTGCCTCCAGCT | Chip strong | 16520 | 12.522655 | 19.197701 | 320 |
| AAGTGATACGCCTGCCTCGGCC | Chip strong | 16691 | 9.2873106 | 2.0918362 | 2 |

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| GCCTGGCCAACATAGTGGGACC | Chip strong | 16749 | 8.6138811 | 20.486101 | 154 |
| TCCTGGCCATCCAGCCTGGGA | Chip strong | 16778 | 7.2028656 | 18.973217 | 214 |
| TCCTCCAGAGCTTCATCCTGCC | Chip strong | 16927 | 20.0035 | 5.2284846 | 212 |
| GCGCCTGTGCCTCCTAA | Chip strong | 17094 | 12.760594 | 23.842529 | 108 |
| CTTGATTTTGTCTCTGGCCCTG | Chip strong | 17456.5 | 9.4672995 | 8.272316 | 90 |
| CCTGTGGTCCCTGTCTGTGCCT | Chip strong | 17748 | 13.149311 | 10.342139 | 66 |
| ACTTGGAACTGGCCCCTTTCAT | Chip strong | 17782 | 14.512917 | 23.881441 | 15 |
| TTCCCTGGGACTGGCCTGCACC | Chip strong | 17948.5 | 9.3010607 | 15.061718 | 241 |
| GATTACTGGTATTTGCTGGCTCC | Chip strong | 13394 | 25.892035 | 5.407784 | 146 |
| AGGTGGCCACAAGGTGGCTGGC | Chip strong | 13621 | 20.378857 | 17.680929 | 334 |
| GGCTGCTGGTCTTTCATAGTGGG | Chip strong | 12604.5 | 21.291653 | 18.561375 | 175 |
| CCCCTGCTGTGCTTGCATGGCT | Chip strong | 12605 | 18.076384 | 11.74684 | 57 |
| TGGCTTTAGTAATAAGTTTCTC | Chip strong | 12660 | 16.773508 | 11.141039 | 226 |
| TCTCTAGTCCTGCCTCCCC | Chip strong | 12753 | 19.169752 | 7.0407801 | 275 |
| TTGTCACTGCACTCCAGTCTGG | Chip strong | 12372.5 | 9.9857264 | 24.029345 | 311 |
| GGGAAGCTGGTCACCCACAGGC | Chip strong | 12450 | 11.913556 | 20.388573 | 178 |
| CTCCTTGCTGGTCTGGTGTAAT | Chip strong | 12887 | 13.768332 | 6.9087734 | 77 |
| TGGGTCTCTGGCCACCCCAGCC | Chip strong | 12948.5 | 8.0436459 | 19.699574 | 228 |
| CGGCGAGCGGGACCTGCGCCTG | Chip strong | 13179 | 8.3394403 | 5.5586901 | 375 |
| GCTCACAGCCTCCCCCGGCCTG | Chip strong | 13198 | 7.8765292 | 3.4258959 | 160 |
| TTTGGTCCCCTTCAACCAGCTA | Chip strong | 13310 | 7.6353297 | 18.880299 | 249 |
| TTGCTAGTGTTTGGTTGATGGT | Chip strong | 13321 | 29.278065 | 21.353354 | 309 |
| TGGGTCCTGGCTGAAGATCTCT | Chip strong | 13345 | 7.4858232 | 22.909485 | 227 |
| AGCAGAGCAGTCTCCGCTCA | Chip strong | 11919 | 6.4712315 | 22.303505 | 327 |
| TCTGCCTCCAGGAGCTGGCA | Chip strong | 12022.5 | 6.4897313 | 19.629604 | 218 |
| CTCTGATGTCTGCCCCTCACCT | Chip strong | 12084 | 23.231821 | 2.7038672 | 83 |
| TGGTGGAGGCGCTGCTGGCCAG | Chip strong | 11424 | 10.211181 | 12.62489 | 233 |
| CGCCTCCTCTCTGTCCTGATTT | Chip strong | 11564 | 15.306285 | 4.1242805 | 372 |
| AGGTGCTCTGTGTATGCATAGA | Chip strong | 11593 | 19.340197 | 19.182079 | 29 |
| GGCCGTCCCTAGAGATGGGGTT | Chip strong | 11689.5 | 8.4446125 | 7.2657032 | 170 |
| CATTATTCTCAGTTCTGTGCAG | Chip strong | 11732.5 | 27.869678 | 16.957344 | 51 |
| TGGTTTCCCTTTTGGCCTCTCC | Chip strong | 10935 | 11.08107 | 6.0971227 | 303 |
| CTGGCCCCTTTCATTCTGGAAG | Chip strong | 11008.5 | 19.356289 | 14.29258 | 87 |
| ATAGCAGCGCTGGCCCTCTGCC | Chip strong | 11135.5 | 8.3489428 | 16.26886 | 339 |
| TGCAGCCTCTTGTTTCAGCCCC | Chip strong | 11243 | 17.256807 | 2.5227482 | 282 |
| GGGTCTCTGTTGGCTTCTT | Chip strong | 11264.5 | 7.8554482 | 5.5741806 | 128 |
| AGCCTCTGGTCCTTTTTTCCCT | Chip strong | 11308.5 | 17.074085 | 5.3993454 | 328 |
| AGCTGGTTTAATATGCTGTCTG | Chip strong | 11390 | 14.25641 | 8.7015753 | 21 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| CACTGCCTTGGCCACCTATCCT | Chip strong | 10671 | 9.1234684 | 14.108407 | 346 |
| GCCTTGGTGGTTTTGGTAGT | Chip strong | 10696 | 15.110422 | 8.3110876 | 106 |
| GTGGTAGCTCCAGGCTGTCTGA | Chip strong | 10711 | 30.533655 | 22.150589 | 253 |
| TGCTCTGATTTTTGCCCCAGCT | Chip strong | 10768.5 | 14.230415 | 7.0602937 | 292 |
| TCCTGGGCTTTGGCTTGTTGGG | Chip strong | 10813.5 | 7.7058806 | 7.1675959 | 215 |
| TCCACTGTCCCTGGCACTTTT | Chip strong | 9134 | 6.4327211 | 12.8872 | 208 |
| CGCCATGTCCAGCGTCTTCGGG | Chip strong | 8765 | 20.334946 | 20.485155 | 68 |
| CATTGCACTCCAGCCTCCCATA | Chip strong | 10435 | 16.077471 | 9.6274853 | 53 |
| AGAGTCTCCCTGTGTTGCCCTG | Chip strong | 10467 | 7.4270558 | 12.602409 | 325 |
| TCCTTCCTCTGTCAGGCAGGCC | Chip strong | 10471 | 20.063852 | 2.295146 | 270 |
| ACTGCACTGCAGCCTGGCCAAC | Chip strong | 10584 | 7.3915148 | 12.856659 | 14 |
| TTCTTCTGCCCCTTGCCTGACA | Chip strong | 10593.5 | 16.647232 | 9.2061243 | 244 |
| CCAGTACGTTGCTCAGCTCCTC | Chip strong | 10610.5 | 11.484417 | 2.7025924 | 357 |
| CGCCGCCCTCCGAGGACTCCTT | Chip strong | 10614 | 8.6334085 | 6.5864415 | 371 |
| TTGCTCAGGCTGGCGTGCAATG | Chip strong | 9724 | 11.115126 | 19.742767 | 245 |
| CCCGCGATCTCCTTGTGGCCGT | Chip strong | 9728 | 11.945862 | 6.9863696 | 58 |
| CACCTGGCTGGCAATTTATAAT | Chip strong | 9852 | 8.0965796 | 17.484594 | 43 |
| TCAGGGCTGCACTGGCTGGTCT | Chip strong | 9852 | 10.620815 | 11.96568 | 205 |
| TGGAGTTGGCTGCAGATGAGTC | Chip strong | 9954 | 13.087917 | 15.585505 | 299 |
| TGCCTAGGTCTGGCCTCCTTGG | Chip strong | 10161 | 16.315468 | 2.7759731 | 286 |
| GCCAGCCTCCATCCTCCCTTG | Chip strong | 10191 | 21.391727 | 11.342846 | 149 |
| TCCCCTCTTGGCTTGGTCCAGA | Chip strong | 10285 | 8.0190945 | 16.142628 | 269 |
| GGTGCCCTCTGGCTCTACTCCC | Chip strong | 10302.5 | 7.4917507 | 16.076124 | 184 |
| AGGGAAGGACTGCTGGGTTGGC | Chip strong | 10310 | 6.749754 | 2.3204882 | 332 |
| GCTGAACGAGCTGGCCAAGTTC | Chip strong | 9451 | 6.6551905 | 19.321331 | 112 |
| CAGCCTCTATGCCCCCGTCACC | Chip strong | 9484 | 16.652414 | 11.957335 | 350 |
| ACCCCGCTCCTTGCAGCCTCTG | Chip strong | 9609 | 6.7912097 | 4.80404 | 321 |
| CTCTTTGGTTGGTTCCTGATGC | Chip strong | 9661 | 15.128378 | 18.743273 | 85 |
| AATGGTCTCTTTGTTCCCTGCT | Chip strong | 9183 | 7.6419687 | 3.2526188 | 315 |
| AGTGTTGGCTCGGCTGGCTGCC | Chip strong | 9220.5 | 15.521686 | 7.1320724 | 337 |
| ATTTACATACCCAGCAGCCTCC | Chip strong | 9344 | 14.651403 | 5.7202735 | 344 |
| ACCTTGTGATCCACCTGCTTTG | Chip strong | 9350 | 10.149202 | 4.1434402 | 322 |
| TGCCAGTATCCTTCTGAGACCC | Chip strong | 9374.5 | 18.697142 | 19.309006 | 284 |
| ATCTCAGCTCTGCCTCCTGGGT | Chip strong | 8963 | 12.361974 | 12.799247 | 33 |
| TCCTCCCTCACCTCAGTCTGGG | Chip strong | 8976.5 | 11.361602 | 9.0995693 | 213 |
| TAGCTGAGCCGCCTGGCTGGGG | Chip strong | 9026 | 6.8317003 | 8.4015751 | 193 |
| CCTCTTTCACCGTGCCTGTCCC | Chip strong | 8800 | 16.616077 | 5.438931 | 63 |
| TCCAGGCCCTCAATCCATTTCCA | Chip strong | 8934.5 | 13.815792 | 9.5553522 | 266 |
| CAGGCTGGCTCCCTGAAGGTTC | Chip strong | 8459.5 | 6.1472831 | 17.683357 | 353 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| TGCTCTGTTGGCTTCTTTTGTC | Chip strong | 8407 | 17.417171 | 17.734081 | 224 |
| CACTGTCTTCCTTTGGCTCCTC | Chip strong | 8497 | 10.860129 | 11.864268 | 48 |
| AGCACGGTGGGTTTGGCTGGCA | Chip strong | 8532 | 8.91047 | 7.0811062 | 18 |
| GTCCTCACTGGCCGACACGCTGA | Chip strong | 8536 | 7.1346483 | 19.281561 | 188 |
| CCAGGCTGGAGTGCAAGCAGCA | Chip strong | 8552.5 | 11.002619 | 19.600433 | 356 |
| CGGTGCCTCCTCCAGTGTTGCT | Chip strong | 8559 | 10.886886 | 9.833169 | 71 |
| GTCAGTCATTGAATGCTGGCCT | Chip strong | 8592.5 | 23.067156 | 11.230301 | 133 |
| CCTTTTATCCCCTAATTGGCCT | Chip strong | 8596 | 19.616385 | 9.8835402 | 67 |
| TGGTAGGTTGGGCAGTTC | Chip strong | 8731.5 | 31.377066 | 20.530041 | 301 |
| GTGTTCCTGTGCTGGATGGTCA | Chip strong | 2131 | 11.864914 | 6.3784571 | 191 |
| CCTCTGCACCAACCTGTCAAGA | Chip strong | 2057.5 | 11.429537 | 3.11975 | 62 |
| GGAGGTACTGTAGCTGGCGTT | Chip strong | 1877 | 10.634505 | 9.6884193 | 167 |
| GTGCTTTGCTGGAATCGAGGAA | Chip strong | 1710 | 10.403996 | 8.5636625 | 190 |
| AGCGTGTTGGGAGGAGCTGCAG | Chip strong | 1410 | 9.0065594 | 8.8227701 | 19 |
| TAGCATGGCTCTATGGAACA | Chip strong | 1393 | 10.196934 | 8.9662762 | 260 |
| GGCCAAGTGGATGCTGGTTTAGC | Chip strong | 1351 | 6.3048329 | 7.5876508 | 117 |
| AGGACCTGTAATCCCAGCACTT | Chip | 1119.5 | 4.0140038 | 5.6218853 | 23 |
| GTCTCGGACTCCTGATCTCAGG | Chip | 1380 | 4.1414785 | 3.9894354 | 189 |
| TCGCTCAGGCAGGAGTGCAGTG | Chip | 1902 | 5.7879028 | 8.7315207 | 271 |
| TGATCTCGTGATCTACCCGCCT | Chip | 1982 | 5.9927278 | 6.810081 | 280 |
| CACCTTGTGATCCACCCGCCTT | Chip | 2139 | 5.5668392 | 4.7121377 | 44 |
| AGTTCTCTTGCTTCAGCCTCCC | Chip | 8418 | 11.501246 | 1.3339518 | 31 |
| GCAGGGAACTGGCTGGGCTTTC | Chip | 9142.5 | 5.9037857 | 16.801399 | 148 |
| GCTCCCACTGCTGTCCTGCCAT | Chip | 9433 | 17.716768 | 1.6475885 | 110 |
| CCCCTCAGTTTGCTAGTATTTT | Chip | 11735 | 24.905746 | 1.1986766 | 56 |
| CTCGCCCCTCTCAGCCCTGCAA | Chip | 14248.5 | 19.352268 | 1.4588933 | 79 |
| GCCTGTCCTCTTCCGCCTGTCT | Chip | 14508 | 12.145576 | 1.6282115 | 105 |
| GGTTCTCAGCCTGAGCCGCCCC | Chip | 18192 | 21.105703 | 1.4826102 | 186 |
| CTGGCCTATCATAAGCATTTT | Chip | 65516 | 15.111923 | 1.4583727 | 88 |
| ACAGGCGATCCACCCGCCTCAG | Chip | 2228 | 5.9650521 | 8.9491081 | 318 |
| GAACTTGTGATCCGCCCACCTT | Chip | 2483 | 4.4610376 | 7.0900927 | 93 |
| GACCTTGTGATCCACCTGTTTT | Chip | 2612 | 4.8775668 | 12.335071 | 98 |
| CTCTGAGTCCTGCACTCACCCG | Chip | 2770 | 6.7869315 | 1.284364 | 82 |
| CTGCAGCCTCCACTTTCTGGGC | Chip | 2839 | 4.7054248 | 13.918253 | 380 |
| GTGTTGTCGCTGGGTTTTGAGGG | Chip | 3030 | 4.5279474 | 3.9595523 | 254 |
| TAGGAGGATTGCTTGTGGCCAG | Chip | 3154.5 | 4.6519237 | 4.9273152 | 194 |
| CGGTGGGTGCTTCAGGCGGTGG | Chip | 3999 | 5.0099111 | 5.715847 | 376 |
| GTGACTGTGGGTTTCTGGTTCC | Chip | 4025.5 | 5.8571658 | 7.4026732 | 136 |

-continued

| GAM RNA SEQUENCE | VALIDATION METHOD | SIGNAL | BACKGROUND Z-SCORE | MISMATCH Z-SCORE | GAM RNA SEQ-ID |
|---|---|---|---|---|---|
| GCTGCTGGGCCATTTGTTGG | Chip | 4101 | 7.7621112 | 1.3319389 | 114 |
| GCAGGCTCTGGCTTATTCTGGG | Chip | 4399 | 4.4706116 | 13.904231 | 101 |
| GCGGGCGGCTTCATCTTGCCCT | Chip | 5038 | 5.1213508 | 7.6892729 | 158 |
| TCCCAGCTCCTGGGCCCCACAG | Chip | 5372.5 | 4.9255114 | 7.1915674 | 267 |
| ATCTTTTATCACTCCCACTGCT | Chip | 5396 | 5.4679914 | 11.567021 | 340 |
| GATGGGTTTGTTGGAGAGGTC | Chip | 5425.5 | 4.8749881 | 17.533426 | 144 |
| GTGACCTGGCCGCCTAAACCCA | Chip | 5941.5 | 5.6531525 | 18.527802 | 135 |
| AAGACACCAGAGACTGGCCTCA | Chip | 6306 | 5.8909965 | 5.1631103 | 314 |
| TCCTCAGCTTGGCCACGGAGTT | Chip | 6478.5 | 5.8972673 | 17.989834 | 211 |
| TGTCTCCCCACTGGTCTTCCAG | Chip | 7039 | 5.6089306 | 15.167439 | 235 |
| AAACTGCTTCCTTGGCCT | Chip | 7436 | 5.6282043 | 5.6413546 | 312 |

| ROW# | INFECTION NAME | SEQ ID NOs OF GAMS ASSOCIATED WITH INFECTION |
|---|---|---|
| 2 | Bordetella pertussis | 1, 6, 10, 11, 12, 13, 16, 18, 19, 20, 21, 22, 23, 24, 25, 26, 27, 28, 29, 33, 34, 37, 41, 42, 43, 44, 47, 48, 49, 50, 52, 53, 54, 55, 57, 58, 59, 60, 63, 65, 66, 67, 68, 69, 70, 71, 75, 76, 77, 79, 84, 86, 87, 88, 89, 91, 94, 96, 97, 99, 100, 101, 102, 103, 104, 105, 106, 107, 108, 109, 110, 111, 112, 113, 114, 115, 117, 119, 120, 121, 122, 123, 125, 126, 127, 130, 131, 132, 133, 137, 138, 139, 140, 141, 142, 145, 147, 149, 150, 151, 154, 155, 156, 157, 158, 160, 161, 162, 164, 165, 166, 167, 168, 170, 171, 172, 173, 174, 175, 176, 177, 179, 180, 181, 183, 184, 185, 188, 191, 195, 196, 197, 204, 205, 211, 212, 214, 215, 216, 219, 220, 222, 225, 228, 230, 231, 233, 237, 239, 241, 242, 243, 244, 250, 251, 253, 262, 264, 265, 266, 268, 271, 272, 274, 276, 277, 280, 281, 282, 284, 285, 287, 288, 289, 290, 293, 294, 296, 297, 299, 300, 301, 302, 304, 306, 308, 310, 312, 317, 318, 321, 322, 324, 326, 327, 329, 330, 332, 333, 334, 335, 336, 339, 340, 342, 343, 345, 348, 349, 350, 351, 352, 353, 355, 356, 357, 358, 360, 361, 362, 364, 365, 366, 367, 368, 369, 370, 371, 372, 373, 374, 375, 376, 378, 380, 381, 382, 383, 384, 385 and 49788-55666. |
| 3 | Brucella suis 1330 | 1, 6, 10, 11, 12, 13, 14, 16, 18, 19, 21, 23, 27, 32, 35, 37, 39, 40, 42, 47, 48, 49, 50, 52, 53, 58, 62, 63, 65, 68, 70, 71, 77, 79, 80, 85, 86, 89, 90, 98, 102, 105, 107, 108, 109, 111, 112, 114, 115, 119, 120, 121, 122, 123, 124, 125, 126, 132, 138, 141, 142, 143, 150, 151, 152, 154, 155, 156, 157, 158, 160, 161, 162, 164, 166, 168, 171, 172, 173, 175, 176, 177, 180, 181, 183, 185, 186, 190, 195, 198, 199, 200, 201, 205, 207, 211, 212, 214, 215, 217, 218, 219, 220, 221, 222, 225, 229, 230, 231, 233, 236, 237, 240, 241, 243, 244, 250, 251, 256, 258, 263, 264, 265, 266, 270, 277, 279, 280, 281, 282, 285, 287, 289, 290, 293, 294, 295, 297, 300, 302, 303, 306, 308, 310, 312, 315, 318, 319, 320, 321, 330, 331, 333, 334, 335, 342, 343, 347, 348, 349, 353, 354, 356, 357, 360, 361, 364, 365, 366, 368, 369, 370, 371, 373, 374, 375, 377, 381, 382, 384 and 55667-60259. |
| 4 | Chlamydia trachomatis | 2, 3, 4, 6, 7, 8, 9, 10, 13, 14, 16, 18, 19, 20, 21, 22, 25, 26, 27, 30, 31, 32, 33, 36, 37, 38, 40, 45, 46, 47, 48, 49, 51, 52, 55, 62, 63, 64, 67, 73, 74, 75, 78, 81, 82, 84, 85, 86, 87, 88, 91, 94, 95, 98, 99, 104, 105, 106, 111, 113, 116, 122, 124, 126, 128, 132, 133, 136, 138, 146, 148, 149, 152, 154, 155, 156, 157, 160, 164, 166, 167, 177, 179, 180, 181, 187, 188, 190, 192, 194, 198, 199, 200, 205, 207, 208, 209, 210, 211, 213, 214, 217, 218, 222, 224, 225, 226, 229, 232, 233, 235, 236, 239, 241, 242, 243, 244, 245, 248, 251, 252, 253, 254, 256, 257, 259, 262, 264, 265, 269, 270, 271, 272, 273, 274, 278, 279, 287, 288, 289, 293, 295, 296, 297, 298, 299, 302, 303, 305, 306, 309, 311, 312, 316, 318, 319, 320, 322, 323, 324, 325, 326, 327, 328, 330, 332, 333, 335, 338, 340, 341, 343, 344, 345, 348, 349, 350, 353, 354, 356, 363, 373, 384 and 60260-67437. |
| 5 | Chlamydophila pneumoniae AR39 | 25, 27, 33, 46, 55, 62, 73, 105, 152, 160, 166, 177, 179, 180, 190, 205, 208, 213, 214, 218, 236, 242, 244, 262, 271, 274, 298, 323, 325, 327, 345, 353, 356 and 67438-68147. |
| 6 | Chlamydophila pneumoniae CWL029 | 3, 5, 6, 8, 9, 10, 13, 17, 20, 21, 22, 23, 25, 27, 28, 31, 32, 33, 37, 39, 45, 46, 47, 48, 50, 52, 55, 62, 63, 64, 66, 67, 69, 73, 74, 82, 84, 85, 88, 89, 90, 91, 92, 95, 101, 102, 104, 105, 111, 114, 124, 125, 126, 128, 143, 146, 148, 152, 159, 160, 161, 164, 165, 166, 168, 175, 176, 177, 178, 179, 180, 181, 187, 189, 190, 192, 194, 201, 203, 205, 207, 208, 209, 212, 213, 214, 217, 218, 221, 223, 224, 227, 232, 233, 234, 236, 238, 239, 241, 242, 243, 244, 245, 247, 248, |

| ROW# | INFECTION NAME | SEQ ID NOs OF GAMS ASSOCIATED WITH INFECTION |
|---|---|---|
|  |  | 252, 257, 258, 259, 260, 262, 263, 271, 272, 274, 275, 279, 281, 282, 283, 286, 289, 295, 297, 298, 299, 302, 305, 306, 309, 311, 312, 314, 319, 323, 324, 325, 326, 327, 330, 333, 338, 340, 343, 344, 345, 346, 348, 349, 350, 352, 353, 354, 356, 363, 377, 382, 383, 384 and 68148-75439. |
| 7 | Chlamydophila pneumoniae J138 | 3, 5, 6, 8, 9, 10, 17, 20, 21, 22, 23, 25, 27, 31, 32, 33, 37, 39, 45, 46, 47, 50, 52, 55, 62, 63, 64, 66, 67, 69, 73, 74, 82, 84, 85, 88, 89, 90, 92, 95, 101, 102, 104, 105, 111, 114, 125, 126, 128, 143, 146, 148, 152, 159, 160, 161, 164, 165, 166, 168, 175, 176, 177, 178, 179, 180, 181, 187, 189, 190, 192, 194, 201, 203, 205, 207, 208, 209, 212, 213, 214, 217, 218, 221, 223, 224, 227, 232, 233, 234, 236, 238, 239, 241, 242, 243, 244, 245, 247, 248, 252, 257, 259, 260, 262, 263, 271, 272, 274, 275, 279, 281, 282, 283, 286, 289, 295, 297, 298, 299, 302, 305, 306, 309, 311, 312, 314, 319, 323, 325, 326, 327, 330, 333, 338, 340, 343, 344, 345, 346, 348, 349, 350, 352, 353, 354, 356, 363, 377, 382, 383, 384 and 75440-82241. |
| 8 | Chlamydophila pneumoniae TW-183 | 20, 21, 22, 25, 27, 31, 33, 45, 46, 50, 55, 62, 64, 73, 82, 89, 92, 104, 105, 126, 143, 146, 152, 160, 161, 166, 175, 177, 178, 179, 180, 187, 190, 201, 205, 208, 209, 212, 213, 214, 217, 218, 221, 232, 236, 239, 242, 244, 248, 257, 262, 263, 271, 272, 274, 275, 279, 282, 289, 298, 299, 302, 306, 312, 323, 325, 327, 338, 340, 345, 346, 350, 352, 353, 356, 363, 382 and 82242-85213. |
| 9 | Coxiella burnetii RSA 493 | 1, 3, 5, 6, 7, 8, 10, 13, 22, 25, 27, 33, 36, 38, 40, 42, 45, 46, 48, 51, 52, 55, 62, 67, 73, 78, 80, 81, 84, 91, 105, 111, 116, 124, 126, 132, 141, 142, 146, 147, 152, 158, 160, 164, 166, 177, 179, 180, 186, 187, 190, 205, 208, 213, 214, 218, 227, 229, 232, 234, 236, 239, 241, 242, 244, 247, 248, 249, 252, 256, 259, 262, 268, 271, 272, 274, 279, 280, 281, 282, 285, 298, 299, 300, 303, 305, 306, 307, 312, 315, 316, 320, 323, 324, 325, 326, 327, 333, 340, 344, 345, 353, 354, 356, 365, 373, 374, 376, 379, 385 and 85214-90622. |
| 10 | Escherichia coli CFT 073 | 1, 2, 4, 5, 6, 7, 8, 9, 10, 11, 12, 13, 14, 16, 17, 18, 19, 21, 22, 23, 25, 26, 27, 28, 30, 31, 33, 34, 35, 36, 37, 39, 40, 42, 43, 45, 46, 47, 48, 49, 50, 51, 52, 53, 55, 56, 57, 58, 59, 62, 63, 64, 65, 66, 67, 68, 69, 70, 71, 72, 73, 75, 76, 78, 79, 80, 81, 82, 83, 84, 85, 86, 87, 88, 89, 90, 91, 92, 93, 94, 95, 96, 97, 99, 100, 101, 102, 103, 105, 106, 107, 108, 109, 110, 111, 112, 113, 114, 115, 116, 119, 120, 121, 122, 123, 124, 125, 126, 129, 131, 132, 133, 135, 136, 137, 138, 140, 141, 142, 143, 145, 146, 147, 148, 152, 154, 155, 156, 157, 158, 160, 161, 162, 163, 164, 165, 166, 167, 168, 171, 173, 174, 175, 176, 177, 179, 180, 181, 182, 184, 185, 186, 190, 191, 192, 193, 195, 196, 197, 203, 204, 205, 206, 207, 208, 209, 210, 211, 212, 213, 214, 215, 216, 217, 218, 220, 221, 222, 223, 224, 225, 229, 230, 231, 232, 233, 234, 235, 236, 237, 238, 239, 241, 242, 243, 244, 245, 246, 247, 248, 249, 250, 251, 252, 253, 254, 255, 256, 257, 258, 260, 261, 262, 265, 266, 267, 268, 270, 271, 272, 274, 276, 277, 278, 279, 280, 281, 282, 283, 284, 285, 287, 288, 289, 290, 291, 292, 293, 294, 295, 296, 297, 299, 300, 301, 302, 303, 305, 306, 307, 308, 309, 310, 311, 312, 314, 315, 316, 317, 318, 321, 322, 323, 324, 325, 326, 327, 329, 331, 332, 333, 334, 335, 336, 337, 338, 339, 340, 343, 344, 345, 347, 348, 349, 350, 351, 352, 353, 354, 355, 356, 357, 358, 359, 360, 361, 364, 365, 367, 368, 369, 370, 372, 373, 374, 375, 376, 378, 380, 381, 382, 383, 384, 385 and 90623-103607. |
| 11 | Haemophilus influenzae Rd | 2, 3, 5, 6, 7, 8, 9, 10, 13, 15, 19, 20, 21, 22, 25, 26, 27, 30, 31, 32, 33, 34, 37, 38, 40, 41, 45, 46, 48, 49, 50, 51, 52, 53, 55, 62, 63, 64, 66, 67, 68, 73, 78, 81, 83, 84, 85, 88, 90, 91, 92, 98, 101, 105, 106, 111, 116, 117, 119, 122, 123, 124, 125, 126, 134, 138, 144, 146, 149, 151, 152, 155, 156, 160, 161, 164, 165, 166, 169, 171, 172, 174, 176, 177, 179, 180, 183, 190, 197, 198, 199, 200, 201, 203, 205, 207, 208, 211, 213, 214, 218, 221, 223, 226, 228, 229, 234, 236, 239, 240, 242, 244, 247, 248, 251, 254, 255, 256, 259, 262, 263, 264, 271, 272, 274, 277, 279, 281, 282, 283, 295, 296, 299, 302, 305, 306, 308, 311, 312, 313, 316, 317, 318, 319, 322, 323, 324, 325, 326, 327, 329, 333, 335, 338, 339, 340, 343, 344, 345, 348, 351, 353, 354, 356, 365, 368, 371, 375, 377, 379, 380, 385 and 103608-111433. |
| 12 | Leptospira interrogans serovar lai str. 56601 | 1, 3, 5, 7, 8, 10, 13, 19, 22, 25, 32, 38, 39, 41, 48, 49, 52, 67, 71, 73, 84, 85, 90, 91, 93, 95, 117, 124, 128, 164, 174, 178, 179, 187, 190, 192, 193, 203, 207, 225, 226, 227, 229, 238, 244, 247, 250, 256, 257, 258, 259, 262, 272, 279, 295, 298, 299, 303, 306, 307, 316, 324, 327, 333, 338, 340, 344, 348, 376, 379, 384 and 111434-116384. |
| 13 | Listeria monocytogenes EGD-e | 5, 6, 7, 8, 9, 10, 13, 22, 36, 40, 48, 52, 67, 84, 90, 91, 95, 114, 116, 147, 185, 214, 244, 247, 248, 253, 254, 259, 262, 272, 276, 279, 299, 306, 308, 324, 333, 340, 355, 382 and 116385-119434. |
| 14 | Mycobacterium avium subsp. paratuberculosis | 1, 3, 4, 5, 6, 7, 10, 11, 12, 13, 14, 15, 16, 17, 18, 19, 20, 21, 22, 23, 24, 25, 26, 27, 29, 31, 32, 33, 34, 37, 42, 43, 44, 45, 46, 47, 50, 51, 53, 54, 55, 58, 59, 60, 61, 62, 64, 65, 66, 67, 68, 69, 70, 71, 72, 73, 75, 76, 77, 78, 79, 84, 86, 87, 88, 89, 90, 91, 94, 96, 97, 99, 100, 101, 102, 103, 105, 107, 108, 109, 110, 111, 112, 113, 114, 115, 116, 119, 120, 121, 122, 123, 125, 127, 130, 131, 132, 133, 135, 137, 138, 139, 140, 142, 143, 144, 146, 147, 148, 149, 150, 151, 152, 154, 155, 156, 157, 158, 160, 161, 162, 164, 165, 166, 167, 168, 170, 171, 172, 173, 174, 175, 176, 177, 179, 180, 181, 183, 184, 185, 188, 189, 190, 191, 195, 196, 197, 198, 199, 200, 201, 202, 203, 204, 207, 210, 211, 214, 215, 216, 218, 219, 220, 222, 225, 226, 230, 231, 233, 234, 236, 237, 239, 241, 242, 243, 244, 245, 248, 250, 251, 252, 253, 254, 257, 262, 263, 264, 265, 266, 268, 271, 272, 274, 277, 278, 280, 281, 282, 283, 285, 287, 288, 289, 290, 291, 292, 293, 294, 295, 296, 297, 298, 299, 300, 301, 302, 303, 305, 306, 310, 312, 313, 314, 318, 320, 321, 323, 324, 325, 327, 329, 331, 332, 333, 334, 335, 336, 337, |

-continued

| ROW# | INFECTION NAME | SEQ ID NOs OF GAMS ASSOCIATED WITH INFECTION |
|---|---|---|
| | | 341, 342, 345, 346, 347, 349, 351, 352, 353, 355, 356, 357, 358, 360, 361, 362, 364, 365, 366, 367, 368, 369, 370, 371, 372, 373, 374, 375, 376, 377, 378, 380, 381, 382, 383, 384 and 119435-127918. |
| 15 | Mycobacterium bovis subsp bovis AF2122/97 | 1, 3, 4, 5, 6, 7, 11, 12, 13, 14, 15, 16, 17, 18, 19, 20, 21, 22, 23, 24, 25, 26, 27, 28, 29, 31, 32, 33, 36, 37, 39, 41, 42, 43, 45, 46, 47, 48, 50, 51, 52, 53, 54, 55, 57, 58, 59, 60, 61, 62, 64, 65, 66, 67, 68, 69, 70, 71, 73, 75, 76, 77, 78, 79, 80, 83, 84, 86, 87, 88, 89, 90, 91, 93, 96, 97, 99, 100, 101, 102, 103, 104, 105, 106, 107, 108, 109, 110, 111, 112, 113, 114, 115, 116, 117, 118, 119, 120, 121, 122, 123, 125, 127, 130, 131, 132, 133, 134, 135, 137, 138, 139, 141, 142, 143, 144, 145, 146, 147, 148, 149, 150, 151, 152, 154, 155, 156, 157, 158, 159, 160, 161, 162, 163, 165, 166, 167, 168, 170, 171, 172, 173, 174, 175, 176, 177, 178, 179, 180, 181, 183, 184, 185, 188, 189, 190, 191, 193, 194, 195, 196, 197, 198, 199, 200, 201, 202, 203, 204, 205, 206, 207, 208, 210, 211, 212, 213, 214, 215, 216, 218, 219, 220, 222, 225, 230, 231, 233, 236, 237, 239, 240, 241, 242, 243, 244, 245, 246, 250, 251, 252, 253, 254, 255, 256, 257, 261, 262, 263, 264, 265, 266, 267, 268, 270, 271, 273, 276, 277, 278, 280, 281, 282, 283, 285, 286, 287, 288, 289, 290, 291, 292, 293, 294, 296, 297, 299, 300, 302, 303, 304, 305, 306, 308, 310, 312, 313, 314, 315, 318, 320, 321, 322, 323, 324, 325, 326, 327, 329, 330, 331, 332, 333, 334, 335, 336, 337, 341, 342, 345, 346, 347, 348, 349, 350, 351, 352, 353, 355, 356, 357, 358, 360, 361, 362, 364, 365, 366, 367, 369, 370, 371, 372, 373, 374, 375, 376, 378, 380, 381, 382, 383, 384, 385 and 127919-137561. |
| 16 | Mycobacterium leprae | 3, 4, 5, 6, 7, 12, 13, 14, 15, 18, 19, 21, 22, 23, 24, 26, 29, 31, 32, 33, 36, 37, 39, 41, 42, 43, 45, 46, 47, 48, 49, 50, 53, 54, 57, 59, 62, 65, 68, 69, 70, 71, 73, 74, 75, 76, 78, 81, 83, 84, 86, 90, 94, 96, 98, 101, 103, 106, 107, 109, 110, 111, 112, 113, 114, 115, 116, 118, 119, 120, 121, 123, 131, 133, 134, 135, 137, 142, 143, 144, 145, 146, 147, 149, 154, 156, 157, 158, 159, 161, 162, 163, 165, 166, 167, 171, 172, 173, 174, 175, 176, 179, 183, 184, 185, 187, 188, 189, 190, 193, 196, 197, 198, 199, 200, 201, 202, 204, 205, 206, 211, 212, 214, 215, 216, 218, 219, 220, 221, 223, 224, 225, 228, 230, 231, 232, 233, 234, 235, 236, 237, 241, 242, 243, 245, 249, 250, 251, 253, 254, 256, 258, 261, 263, 265, 267, 268, 269, 271, 274, 276, 277, 280, 281, 284, 288, 289, 290, 291, 293, 294, 295, 296, 297, 299, 300, 301, 302, 303, 305, 306, 307, 309, 310, 311, 312, 313, 314, 315, 318, 320, 321, 323, 324, 327, 329, 330, 331, 332, 333, 334, 335, 336, 337, 338, 339, 340, 341, 343, 345, 346, 347, 348, 349, 353, 355, 356, 357, 358, 360, 361, 364, 365, 368, 369, 370, 371, 372, 374, 375, 376, 377, 378, 380, 381, 382, 383 and 137562-144598. |
| 17 | Mycobacterium tuberculosis CDC1551 | 4, 5, 6, 7, 10, 13, 17, 20, 22, 23, 24, 25, 27, 31, 32, 33, 45, 46, 51, 53, 55, 62, 67, 69, 73, 84, 88, 90, 91, 99, 100, 102, 103, 105, 107, 113, 114, 116, 120, 137, 143, 146, 148, 149, 152, 155, 156, 160, 161, 165, 166, 168, 177, 179, 180, 185, 190, 198, 199, 200, 203, 205, 207, 208, 211, 213, 214, 215, 216, 218, 219, 225, 233, 236, 239, 242, 244, 257, 262, 264, 271, 272, 274, 281, 282, 289, 291, 292, 294, 299, 303, 305, 306, 312, 313, 323, 324, 325, 327, 329, 332, 333, 337, 341, 345, 346, 352, 353, 356, 381, 383 and 144599-146806. |
| 18 | Mycobacterium tuberculosis H37Rv | 1, 3, 4, 5, 6, 7, 10, 11, 12, 13, 14, 15, 16, 17, 18, 19, 20, 21, 22, 23, 24, 25, 26, 27, 28, 29, 31, 32, 33, 37, 39, 41, 42, 43, 45, 46, 47, 48, 50, 51, 52, 53, 54, 55, 57, 58, 59, 60, 61, 62, 63, 64, 65, 66, 67, 68, 69, 70, 71, 73, 75, 76, 77, 78, 79, 80, 83, 84, 86, 87, 88, 89, 90, 91, 93, 94, 96, 97, 99, 100, 101, 102, 103, 104, 105, 107, 108, 109, 110, 111, 112, 113, 114, 115, 116, 117, 118, 119, 120, 121, 122, 123, 125, 127, 130, 131, 132, 133, 134, 135, 137, 138, 139, 141, 142, 143, 144, 145, 146, 147, 148, 149, 150, 151, 152, 153, 154, 155, 156, 157, 158, 159, 160, 161, 162, 163, 165, 166, 167, 168, 170, 171, 172, 173, 174, 175, 176, 177, 178, 179, 180, 181, 183, 184, 185, 188, 189, 190, 191, 194, 195, 196, 197, 198, 199, 200, 201, 202, 203, 204, 205, 206, 207, 208, 210, 211, 212, 213, 214, 215, 216, 218, 219, 220, 222, 225, 230, 231, 233, 234, 236, 237, 239, 240, 241, 242, 243, 244, 245, 246, 250, 251, 252, 253, 254, 255, 256, 257, 261, 262, 263, 264, 265, 266, 267, 268, 270, 271, 272, 273, 274, 276, 277, 278, 280, 281, 282, 283, 284, 285, 286, 287, 288, 289, 290, 291, 292, 293, 294, 296, 297, 298, 299, 300, 302, 303, 304, 305, 306, 308, 310, 312, 313, 314, 315, 318, 320, 321, 323, 324, 325, 326, 327, 329, 330, 331, 332, 333, 334, 335, 336, 337, 341, 342, 345, 346, 347, 348, 349, 350, 351, 352, 353, 355, 356, 357, 358, 360, 361, 362, 364, 365, 366, 367, 368, 369, 370, 371, 372, 373, 374, 375, 376, 378, 380, 381, 382, 383, 384, 385 and 146807-155497. |
| 19 | Neisseria meningitidis MC58 | 56, 142, 218, 287, 316, 327, 351, 355, 365, 381 and 155498-155833. |
| 20 | Neisseria meningitidis Z2491 | 1, 6, 7, 8, 10, 12, 15, 17, 21, 22, 26, 28, 30, 37, 39, 40, 45, 49, 52, 56, 58, 60, 62, 63, 67, 70, 76, 86, 89, 90, 91, 96, 98, 102, 103, 105, 107, 108, 109, 111, 112, 113, 114, 115, 122, 123, 124, 125, 126, 127, 133, 138, 141, 142, 143, 145, 147, 148, 149, 152, 157, 158, 164, 165, 166, 170, 171, 175, 176, 178, 181, 183, 187, 189, 197, 203, 217, 218, 219, 220, 221, 222, 225, 229, 230, 231, 237, 239, 243, 245, 247, 248, 251, 253, 254, 256, 257, 258, 259, 264, 265, 268, 273, 281, 282, 283, 285, 287, 289, 290, 293, 294, 295, 297, 300, 302, 306, 308, 314, 315, 316, 319, 321, 322, 325, 327, 329, 332, 333, 334, 338, 340, 341, 344, 346, 348, 349, 350, 351, 354, 355, 356, 365, 371, 372, 375, 376, 380, 381, 382, 384 and 155834-160603. |
| 21 | Pseudomonas aeruginosa PA01 | 1, 2, 6, 10, 11, 12, 13, 14, 16, 17, 18, 19, 20, 21, 22, 23, 24, 25, 26, 27, 28, 29, 30, 31, 33, 34, 35, 36, 37, 41, 42, 43, 45, 46, 48, 49, 50, 52, 54, 55, 56, 57, 58, 59, 60, 62, 63, 64, 65, 66, 67, 68, 69, 70, 71, 73, 76, 77, 78, 79, 81, |

| ROW# | INFECTION NAME | SEQ ID NOs OF GAMS ASSOCIATED WITH INFECTION |
|---|---|---|
| | | 82, 83, 84, 86, 87, 88, 89, 90, 91, 94, 95, 96, 97, 99, 100, 101, 102, 103, 105, 106, 107, 108, 109, 110, 111, 112, 113, 114, 115, 116, 118, 119, 120, 121, 122, 123, 124, 125, 126, 127, 130, 131, 134, 137, 138, 139, 140, 141, 142, 144, 147, 149, 150, 151, 152, 154, 155, 156, 157, 158, 160, 161, 162, 163, 164, 165, 166, 167, 168, 169, 170, 171, 172, 173, 174, 175, 176, 177, 179, 180, 181, 183, 184, 185, 188, 190, 192, 193, 194, 195, 196, 197, 202, 204, 205, 208, 210, 211, 212, 213, 214, 215, 216, 218, 220, 222, 225, 228, 229, 230, 231, 232, 233, 236, 237, 241, 242, 243, 244, 250, 251, 253, 258, 262, 264, 265, 266, 267, 268, 270, 271, 272, 273, 274, 276, 277, 280, 281, 282, 283, 285, 286, 287, 288, 289, 290, 291, 292, 293, 294, 296, 297, 298, 299, 300, 301, 302, 306, 312, 314, 318, 319, 320, 321, 323, 324, 325, 327, 329, 330, 331, 333, 334, 335, 336, 339, 340, 341, 342, 343, 345, 347, 348, 349, 350, 351, 352, 353, 355, 356, 357, 358, 360, 361, 362, 364, 365, 366, 367, 368, 369, 370, 371, 372, 373, 374, 375, 376, 378, 380, 381, 382, 383, 384 and 160604-170274. |
| 22 | *Pseudomonas putida* KT2440 | 1, 5, 7, 9, 10, 11, 12, 13, 14, 16, 18, 19, 23, 24, 25, 26, 27, 28, 29, 31, 33, 34, 36, 37, 38, 39, 41, 42, 43, 44, 45, 46, 47, 49, 50, 51, 52, 53, 54, 55, 57, 58, 59, 61, 64, 65, 66, 68, 69, 70, 71, 73, 76, 84, 85, 86, 88, 89, 91, 94, 98, 99, 101, 102, 103, 105, 106, 107, 108, 109, 110, 111, 112, 113, 114, 115, 117, 118, 119, 120, 121, 122, 123, 125, 126, 131, 132, 133, 134, 135, 137, 138, 140, 141, 142, 143, 144, 145, 146, 147, 148, 149, 150, 151, 152, 153, 154, 155, 156, 157, 158, 159, 160, 161, 162, 163, 164, 166, 167, 168, 171, 172, 173, 174, 175, 176, 177, 179, 180, 181, 183, 184, 185, 187, 190, 191, 193, 195, 196, 197, 202, 204, 205, 207, 211, 212, 214, 215, 216, 220, 221, 222, 225, 228, 229, 230, 231, 232, 233, 234, 236, 237, 240, 241, 242, 243, 244, 248, 250, 251, 253, 255, 258, 264, 265, 266, 267, 270, 271, 272, 274, 276, 277, 280, 281, 282, 283, 284, 285, 287, 288, 289, 290, 291, 292, 293, 294, 295, 296, 297, 298, 299, 300, 301, 302, 303, 304, 305, 306, 308, 310, 312, 313, 314, 316, 317, 318, 320, 321, 322, 323, 324, 327, 329, 333, 334, 335, 336, 337, 342, 343, 345, 346, 347, 348, 349, 350, 351, 352, 353, 354, 355, 356, 357, 358, 360, 361, 364, 365, 366, 367, 368, 369, 370, 371, 373, 374, 375, 376, 377, 378, 380, 381, 382, 383, 384, 385 and 170275-178543. |
| 23 | *Rickettsia prowazekii* | 2, 10, 13, 25, 27, 31, 33, 45, 46, 48, 52, 55, 62, 67, 71, 73, 75, 81, 84, 91, 95, 99, 100, 105, 113, 124, 131, 152, 154, 155, 156, 157, 160, 162, 166, 177, 179, 180, 181, 190, 192, 204, 205, 208, 213, 214, 217, 218, 222, 231, 236, 239, 242, 244, 262, 265, 270, 271, 272, 274, 278, 287, 288, 289, 293, 294, 299, 305, 306, 323, 324, 325, 327, 333, 334, 340, 345, 353, 356, 373, 381 and 178544-179914. |
| 24 | *Salmonella enterica* enterica serovar Typhi | 1, 2, 3, 4, 6, 7, 8, 9, 10, 11, 12, 13, 16, 17, 18, 19, 20, 21, 22, 23, 25, 26, 27, 28, 30, 31, 32, 33, 35, 37, 38, 39, 40, 42, 43, 45, 46, 47, 48, 49, 50, 51, 52, 55, 56, 57, 58, 59, 60, 62, 63, 64, 65, 66, 67, 68, 69, 70, 72, 73, 75, 77, 79, 80, 81, 83, 84, 86, 88, 89, 90, 91, 92, 94, 95, 98, 99, 100, 101, 102, 105, 106, 107, 108, 109, 111, 112, 113, 114, 115, 116, 119, 120, 121, 122, 123, 124, 125, 126, 127, 129, 131, 132, 133, 135, 136, 137, 138, 142, 143, 144, 145, 146, 147, 148, 150, 152, 153, 154, 155, 156, 157, 158, 160, 161, 162, 163, 164, 165, 166, 167, 171, 172, 173, 174, 175, 176, 177, 179, 180, 181, 182, 183, 185, 187, 188, 189, 190, 191, 192, 193, 194, 195, 196, 197, 198, 199, 200, 201, 202, 203, 204, 205, 206, 208, 212, 213, 214, 215, 216, 217, 218, 219, 220, 221, 222, 223, 225, 226, 229, 230, 231, 232, 233, 234, 235, 236, 237, 238, 239, 240, 241, 242, 243, 244, 245, 247, 248, 250, 251, 252, 253, 254, 255, 256, 257, 260, 261, 262, 263, 265, 266, 269, 270, 271, 272, 274, 276, 277, 278, 280, 281, 282, 283, 284, 285, 287, 288, 289, 290, 291, 292, 293, 294, 295, 296, 297, 298, 299, 300, 301, 302, 303, 304, 305, 306, 308, 311, 312, 314, 315, 318, 319, 323, 324, 325, 327, 328, 329, 330, 331, 332, 333, 334, 335, 336, 337, 339, 340, 341, 342, 343, 344, 345, 346, 347, 348, 349, 351, 352, 353, 354, 355, 356, 357, 358, 360, 361, 364, 365, 366, 367, 369, 370, 371, 373, 374, 375, 376, 378, 379, 380, 381, 382, 383, 384, 385 and 179915-190940. |
| 25 | *Salmonella enterica* enterica serovar Typhi Ty2 | 1, 2, 3, 4, 6, 7, 8, 9, 10, 11, 12, 13, 14, 16, 17, 18, 19, 20, 21, 22, 23, 25, 26, 27, 28, 30, 31, 32, 33, 35, 37, 38, 39, 40, 42, 43, 45, 46, 47, 48, 49, 50, 51, 52, 55, 56, 57, 58, 59, 60, 62, 63, 64, 65, 66, 67, 68, 69, 70, 71, 72, 73, 75, 77, 79, 80, 81, 83, 84, 85, 86, 88, 89, 90, 91, 94, 95, 98, 99, 100, 101, 102, 105, 106, 107, 108, 109, 111, 112, 113, 114, 115, 116, 119, 120, 121, 122, 123, 124, 125, 126, 127, 129, 131, 132, 133, 135, 136, 137, 138, 142, 143, 144, 145, 146, 147, 148, 150, 152, 153, 154, 155, 156, 157, 158, 160, 161, 162, 163, 164, 165, 166, 167, 171, 172, 173, 174, 175, 176, 177, 179, 180, 181, 182, 183, 185, 187, 188, 189, 190, 191, 192, 193, 194, 195, 196, 197, 198, 199, 200, 201, 202, 203, 204, 205, 206, 208, 212, 213, 214, 215, 216, 217, 218, 219, 220, 221, 222, 223, 225, 226, 229, 230, 231, 232, 233, 234, 235, 236, 237, 238, 239, 240, 241, 242, 243, 244, 245, 247, 248, 250, 251, 252, 253, 254, 255, 256, 257, 260, 261, 262, 263, 265, 266, 269, 270, 271, 272, 274, 276, 277, 278, 280, 281, 282, 283, 284, 285, 287, 288, 289, 290, 291, 292, 293, 294, 295, 296, 297, 298, 299, 300, 301, 302, 303, 304, 305, 306, 308, 311, 312, 314, 315, 318, 319, 323, 324, 325, 327, 328, 329, 330, 331, 332, 333, 334, 335, 336, 337, 338, 339, 340, 341, 342, 343, 344, 345, 346, 347, 348, 349, 351, 352, 353, 354, 355, 356, 357, 358, 360, 361, 364, 365, 366, 367, 369, 370, 371, 373, 374, 375, 376, 378, 379, 380, 381, 382, 383, 384, 385 and 190941-201927. |
| 26 | *Salmonella typhimurium* LT2 | 1, 2, 3, 5, 6, 7, 8, 9, 10, 11, 12, 13, 14, 16, 17, 18, 19, 20, 21, 22, 23, 24, 25, 26, 27, 28, 29, 30, 31, 32, 33, 36, 37, 38, 39, 42, 43, 45, 46, 47, 48, 49, 50, 51, 52, 54, 55, 56, 57, 58, 59, 60, 62, 63, 64, 65, 66, 67, 68, 69, 70, 71, |

-continued

| ROW# | INFECTION NAME | SEQ ID NOs OF GAMS ASSOCIATED WITH INFECTION |
|---|---|---|
| | | 72, 73, 75, 77, 79, 82, 83, 84, 86, 88, 89, 90, 91, 94, 95, 96, 100, 101, 102, 103, 104, 105, 107, 108, 109, 111, 112, 113, 114, 115, 116, 119, 120, 121, 122, 123, 124, 125, 126, 127, 129, 131, 132, 133, 135, 137, 138, 142, 143, 144, 145, 146, 147, 148, 149, 150, 151, 152, 154, 155, 156, 157, 158, 160, 161, 162, 163, 164, 165, 166, 167, 168, 170, 171, 172, 173, 174, 175, 176, 177, 179, 180, 181, 182, 183, 185, 187, 188, 189, 190, 192, 193, 194, 195, 196, 197, 198, 199, 200, 201, 202, 203, 204, 205, 206, 207, 208, 211, 212, 213, 214, 215, 216, 217, 218, 219, 220, 221, 222, 225, 226, 227, 228, 229, 230, 231, 232, 233, 234, 235, 236, 237, 238, 239, 240, 241, 242, 243, 244, 245, 247, 248, 249, 250, 251, 252, 253, 255, 256, 257, 258, 260, 261, 262, 263, 266, 267, 268, 270, 271, 272, 273, 274, 275, 276, 279, 280, 281, 282, 283, 285, 287, 288, 289, 290, 291, 292, 293, 294, 296, 297, 298, 299, 300, 302, 303, 306, 307, 308, 309, 310, 311, 312, 314, 315, 317, 318, 319, 323, 324, 325, 326, 327, 328, 329, 330, 331, 332, 333, 334, 335, 336, 337, 338, 340, 341, 342, 343, 344, 345, 347, 348, 349, 350, 351, 352, 353, 354, 355, 356, 357, 358, 359, 360, 361, 362, 363, 364, 365, 366, 368, 369, 370, 371, 373, 374, 375, 376, 379, 380, 381, 382, 383, 384, 385 and 201928-215605. |
| 27 | *Shigella flexneri* 2a str. 2457T | 1, 2, 5, 6, 9, 10, 11, 12, 13, 14, 16, 17, 18, 19, 21, 22, 23, 24, 25, 26, 27, 28, 29, 30, 32, 33, 35, 36, 37, 38, 39, 40, 41, 42, 43, 46, 47, 48, 49, 50, 51, 52, 54, 55, 56, 57, 58, 59, 62, 63, 65, 66, 67, 68, 69, 70, 71, 73, 76, 78, 80, 83, 84, 85, 86, 87, 88, 89, 90, 91, 93, 94, 95, 97, 99, 101, 102, 103, 104, 105, 107, 108, 109, 110, 111, 112, 113, 114, 115, 116, 117, 119, 120, 121, 122, 123, 124, 125, 126, 129, 131, 132, 133, 134, 135, 136, 137, 138, 139, 141, 142, 143, 145, 146, 147, 148, 149, 150, 151, 152, 154, 155, 156, 157, 158, 160, 161, 162, 163, 164, 165, 166, 167, 171, 172, 173, 174, 175, 176, 177, 179, 180, 181, 182, 184, 185, 187, 190, 191, 195, 196, 197, 198, 199, 200, 201, 202, 203, 204, 205, 207, 208, 212, 213, 214, 216, 218, 220, 221, 222, 223, 224, 225, 229, 230, 231, 232, 233, 234, 236, 237, 238, 239, 240, 241, 242, 243, 244, 245, 247, 248, 250, 251, 252, 253, 254, 255, 256, 257, 260, 261, 262, 263, 265, 268, 270, 271, 272, 274, 276, 277, 278, 279, 280, 281, 282, 283, 284, 285, 287, 288, 289, 290, 291, 292, 293, 295, 296, 297, 298, 299, 300, 301, 302, 304, 306, 307, 308, 309, 310, 311, 312, 314, 315, 316, 317, 318, 320, 321, 322, 323, 324, 325, 327, 328, 329, 331, 332, 333, 334, 335, 336, 337, 338, 339, 340, 341, 343, 344, 345, 346, 347, 348, 349, 350, 351, 352, 353, 354, 356, 357, 358, 359, 360, 361, 362, 364, 365, 366, 367, 368, 369, 371, 373, 374, 375, 376, 379, 380, 381, 382, 383, 384, 385 and 215606-226197. |
| 28 | *Shigella flexneri* 2a str. 301 | 1, 2, 5, 6, 9, 10, 11, 12, 13, 14, 16, 17, 18, 19, 21, 22, 23, 24, 25, 26, 27, 28, 29, 30, 32, 33, 35, 36, 37, 39, 40, 41, 42, 43, 46, 47, 48, 49, 50, 51, 52, 54, 55, 56, 57, 58, 59, 62, 63, 64, 65, 66, 67, 68, 69, 70, 71, 73, 76, 77, 78, 80, 83, 84, 85, 86, 87, 88, 89, 90, 91, 92, 93, 94, 95, 97, 99, 101, 102, 103, 104, 105, 107, 108, 109, 110, 111, 112, 113, 114, 115, 116, 119, 120, 121, 122, 123, 124, 125, 126, 129, 132, 133, 134, 135, 136, 137, 138, 141, 142, 143, 144, 145, 146, 147, 148, 149, 150, 151, 152, 154, 155, 156, 157, 158, 159, 160, 161, 162, 163, 164, 165, 166, 167, 168, 171, 172, 173, 174, 175, 176, 177, 179, 180, 181, 182, 184, 185, 187, 190, 191, 195, 196, 197, 198, 199, 200, 201, 202, 203, 205, 207, 208, 210, 212, 213, 214, 216, 217, 218, 220, 221, 222, 223, 224, 225, 229, 230, 231, 232, 233, 234, 236, 237, 238, 239, 240, 241, 242, 243, 244, 245, 247, 248, 250, 251, 252, 253, 254, 255, 256, 257, 260, 262, 263, 264, 265, 266, 268, 269, 270, 271, 272, 274, 276, 277, 278, 279, 280, 281, 282, 283, 284, 285, 287, 288, 289, 290, 291, 292, 293, 295, 296, 297, 298, 299, 300, 301, 302, 304, 306, 308, 309, 311, 312, 314, 315, 316, 317, 318, 320, 321, 323, 324, 325, 327, 328, 329, 331, 333, 334, 335, 336, 337, 338, 339, 340, 341, 343, 344, 345, 346, 347, 348, 349, 350, 351, 352, 353, 354, 356, 357, 358, 359, 360, 361, 362, 364, 365, 366, 367, 368, 369, 371, 373, 374, 375, 376, 378, 379, 380, 381, 382, 383, 384, 385 and 226198-237003. |
| 29 | *Staphylococcus aureus* subsp. *aureus* Mu50 | 2, 5, 7, 8, 9, 10, 13, 16, 19, 22, 25, 27, 31, 32, 33, 35, 36, 38, 39, 40, 41, 45, 46, 47, 48, 50, 51, 52, 55, 62, 63, 67, 71, 73, 81, 83, 84, 85, 90, 91, 92, 93, 95, 98, 100, 101, 105, 106, 111, 113, 116, 119, 120, 124, 131, 133, 138, 139, 146, 147, 149, 152, 153, 156, 160, 161, 162, 165, 166, 169, 171, 172, 174, 177, 179, 180, 181, 190, 192, 203, 204, 205, 207, 208, 213, 214, 217, 218, 222, 228, 231, 232, 236, 238, 240, 242, 244, 245, 247, 248, 252, 254, 256, 259, 261, 262, 270, 271, 272, 274, 275, 287, 293, 294, 299, 301, 302, 305, 306, 308, 309, 311, 316, 317, 323, 324, 325, 326, 327, 332, 333, 334, 335, 337, 339, 340, 342, 343, 344, 345, 346, 348, 349, 351, 353, 354, 356, 363, 365, 368, 371, 375, 379, 381 and 237004-244310. |
| 30 | *Staphylococcus aureus* subsp. *aureus* MW2 | 2, 5, 7, 8, 10, 13, 16, 19, 22, 25, 27, 30, 31, 32, 33, 38, 39, 40, 41, 45, 46, 47, 48, 50, 51, 52, 55, 62, 63, 67, 71, 72, 73, 78, 81, 83, 84, 90, 91, 92, 93, 95, 98, 100, 101, 105, 106, 109, 111, 113, 117, 119, 120, 124, 126, 128, 130, 131, 133, 134, 138, 139, 143, 149, 152, 153, 156, 160, 161, 162, 166, 169, 171, 172, 174, 177, 179, 180, 181, 182, 190, 192, 203, 204, 205, 207, 208, 213, 214, 217, 218, 222, 228, 231, 232, 236, 238, 242, 244, 247, 248, 252, 254, 256, 257, 259, 261, 262, 271, 272, 274, 279, 287, 293, 294, 295, 299, 301, 302, 306, 307, 308, 309, 315, 316, 323, 324, 325, 326, 327, 332, 333, 334, 335, 337, 338, 339, 342, 343, 344, 345, 346, 348, 350, 351, 353, 356, 363, 365, 368, 371, 375, 379, 381 and 244311-250683. |
| 31 | *Staphylococcus aureus* subsp. *aureus* N315 | 2, 5, 7, 8, 9, 10, 13, 16, 19, 22, 25, 27, 31, 32, 33, 35, 36, 38, 39, 40, 41, 45, 46, 47, 48, 50, 51, 52, 55, 62, 63, 67, 71, 73, 81, 83, 84, 85, 90, 91, 92, 93, 95, 98, 100, 101, 105, 106, 111, 113, 117, 119, 120, 124, 131, 133, 134, 138, 139, 143, 146, 147, 149, 152, 153, 156, 160, 161, 162, 166, 169, 171, 172, |

-continued

| ROW# | INFECTION NAME | SEQ ID NOs OF GAMS ASSOCIATED WITH INFECTION |
|---|---|---|
|  |  | 174, 177, 179, 180, 181, 190, 192, 203, 204, 205, 207, 208, 213, 214, 217, 218, 222, 226, 228, 231, 232, 236, 238, 240, 242, 244, 245, 247, 248, 252, 254, 256, 259, 260, 261, 262, 270, 271, 272, 274, 275, 279, 287, 293, 294, 299, 301, 302, 305, 306, 307, 308, 309, 311, 316, 317, 323, 324, 325, 326, 327, 332, 333, 334, 335, 337, 339, 340, 342, 343, 344, 345, 346, 348, 349, 351, 353, 354, 356, 363, 365, 368, 371, 375, 379, 381 and 250684-257140. |
| 32 | *Streptococcus pneumoniae* R6 | 2, 3, 5, 6, 10, 13, 14, 17, 20, 21, 22, 23, 25, 26, 27, 30, 31, 32, 33, 35, 36, 37, 38, 39, 40, 41, 46, 47, 48, 49, 50, 52, 55, 56, 62, 63, 67, 73, 77, 81, 83, 84, 85, 87, 90, 91, 92, 94, 95, 100, 101, 102, 105, 106, 111, 112, 114, 115, 116, 117, 119, 123, 124, 126, 133, 136, 138, 143, 145, 146, 147, 149, 152, 156, 160, 161, 164, 166, 168, 169, 171, 172, 174, 175, 176, 177, 179, 180, 190, 192, 203, 204, 205, 208, 209, 213, 214, 217, 218, 223, 226, 228, 229, 232, 233, 235, 236, 238, 239, 242, 244, 245, 246, 247, 248, 249, 252, 255, 256, 257, 258, 259, 260, 261, 262, 264, 268, 271, 272, 274, 279, 282, 283, 284, 287, 295, 296, 297, 298, 299, 300, 302, 303, 305, 306, 307, 309, 311, 312, 314, 315, 316, 320, 321, 323, 324, 325, 326, 327, 329, 333, 335, 338, 340, 341, 344, 345, 348, 350, 351, 352, 353, 356, 357, 359, 365, 368, 371, 372, 373, 375, 377, 379, 380, 382, 384, 385 and 257141-265301. |
| 33 | *Streptococcus pneumoniae* TIGR4 | 2, 10, 13, 25, 27, 33, 46, 48, 50, 52, 55, 62, 63, 67, 73, 81, 84, 91, 101, 105, 106, 111, 119, 149, 152, 160, 161, 164, 166, 168, 169, 171, 172, 175, 176, 177, 179, 180, 190, 205, 208, 213, 214, 218, 228, 236, 242, 244, 246, 262, 268, 271, 272, 274, 297, 299, 306, 321, 323, 324, 325, 327, 329, 333, 340, 345, 348, 351, 353, 356, 359, 365, 368, 371, 372, 375, 380 and 265302-266788. |
| 34 | *Streptococcus pyogenes* M1 GAS | 3, 5, 8, 10, 21, 22, 25, 27, 32, 37, 38, 39, 40, 43, 49, 90, 95, 96, 106, 116, 126, 129, 138, 163, 164, 168, 175, 176, 180, 226, 232, 244, 246, 259, 261, 262, 268, 283, 295, 296, 297, 299, 306, 309, 316, 321, 329, 330, 333, 348, 349, 359, 372, 379, 380 and 266789-269521. |
| 35 | *Streptococcus pyogenes* MGAS315 | 3, 8, 10, 13, 20, 22, 25, 27, 31, 32, 33, 37, 38, 40, 46, 48, 52, 55, 62, 67, 73, 84, 90, 91, 105, 106, 113, 116, 129, 138, 152, 160, 164, 166, 168, 175, 176, 177, 179, 180, 186, 190, 192, 205, 208, 211, 213, 214, 218, 226, 229, 232, 236, 242, 244, 246, 262, 268, 271, 272, 274, 282, 283, 295, 296, 297, 299, 306, 309, 312, 321, 323, 324, 325, 327, 329, 333, 340, 345, 348, 349, 353, 356, 359, 372, 379, 380, 381 and 269522-272357. |
| 36 | *Streptococcus pyogenes* MGAS8232 | 3, 4, 8, 10, 13, 21, 22, 25, 27, 31, 33, 37, 38, 39, 40, 46, 48, 52, 55, 62, 67, 73, 84, 90, 91, 95, 105, 106, 113, 116, 129, 138, 152, 160, 163, 164, 166, 168, 175, 176, 177, 179, 180, 190, 205, 208, 213, 214, 218, 226, 232, 236, 242, 244, 246, 247, 259, 260, 261, 262, 268, 271, 272, 274, 295, 296, 297, 299, 306, 307, 309, 316, 321, 323, 324, 325, 327, 329, 330, 333, 337, 340, 344, 345, 348, 349, 353, 356, 359, 363, 372, 379, 380, 381 and 272358-275553. |
| 37 | *Streptococcus pyogenes* SSI-1 | 10, 13, 25, 27, 31, 33, 46, 48, 52, 55, 62, 67, 73, 84, 91, 105, 113, 152, 160, 164, 166, 168, 175, 176, 177, 179, 180, 190, 205, 208, 213, 214, 218, 236, 242, 244, 246, 262, 268, 271, 272, 274, 297, 299, 306, 321, 323, 324, 325, 327, 329, 333, 340, 345, 348, 353, 356, 359, 372, 380, 381 and 275554-276703. |
| 38 | *Treponema pallidum* subsp. *pallidum* str. Nichols | 3, 10, 13, 48, 52, 57, 59, 67, 81, 84, 86, 90, 91, 121, 131, 134, 174, 175, 176, 184, 218, 228, 231, 235, 236, 243, 261, 262, 269, 272, 289, 291, 295, 299, 306, 312, 324, 329, 332, 333, 340, 345, 356, 358 and 276704-277654. |
| 39 | *Yersinia pestis* | 1, 2, 3, 4, 5, 6, 7, 8, 9, 10, 12, 13, 16, 18, 19, 21, 22, 25, 26, 27, 28, 29, 30, 31, 32, 33, 34, 36, 37, 39, 40, 41, 42, 43, 45, 46, 47, 48, 51, 52, 53, 54, 55, 57, 58, 61, 62, 63, 67, 68, 70, 71, 73, 75, 76, 78, 82, 84, 85, 87, 88, 89, 90, 91, 93, 94, 95, 98, 99, 101, 102, 103, 105, 106, 107, 108, 111, 112, 113, 114, 115, 116, 117, 120, 121, 122, 123, 124, 125, 126, 129, 130, 131, 132, 133, 134, 135, 136, 138, 140, 141, 142, 143, 146, 148, 149, 151, 152, 153, 154, 155, 156, 160, 164, 165, 166, 167, 169, 171, 172, 174, 175, 176, 177, 178, 179, 180, 182, 184, 186, 187, 188, 190, 191, 192, 193, 196, 197, 198, 199, 200, 201, 202, 203, 205, 206, 208, 209, 211, 213, 214, 215, 217, 218, 219, 220, 221, 222, 224, 225, 226, 227, 229, 230, 232, 233, 234, 236, 237, 238, 239, 240, 241, 242, 243, 244, 245, 250, 251, 252, 253, 255, 256, 257, 258, 259, 260, 262, 263, 264, 270, 271, 272, 274, 276, 279, 280, 281, 282, 283, 286, 287, 289, 291, 292, 293, 295, 296, 298, 299, 300, 301, 302, 304, 306, 307, 308, 309, 311, 314, 315, 317, 319, 321, 322, 323, 324, 325, 326, 327, 329, 330, 331, 333, 334, 335, 336, 337, 340, 341, 342, 343, 344, 345, 346, 348, 349, 350, 351, 352, 353, 354, 355, 356, 357, 358, 359, 363, 364, 365, 367, 368, 370, 372, 373, 374, 376, 377, 378, 379, 380, 381, 382, 383, 384 and 277655-287825. |
| 40 | *Yersinia pestis* KIM | 1, 2, 3, 4, 5, 6, 7, 8, 9, 10, 12, 13, 16, 18, 19, 20, 21, 22, 25, 26, 27, 28, 29, 31, 32, 33, 34, 36, 37, 39, 40, 41, 42, 43, 45, 46, 47, 48, 51, 52, 53, 54, 55, 57, 58, 61, 62, 63, 65, 67, 68, 70, 71, 72, 73, 75, 76, 78, 84, 85, 87, 88, 89, 90, 91, 93, 94, 95, 97, 99, 101, 102, 103, 105, 106, 107, 108, 111, 112, 113, 114, 115, 117, 118, 120, 121, 122, 123, 124, 125, 126, 129, 130, 131, 132, 133, 134, 135, 136, 138, 140, 142, 143, 146, 147, 148, 149, 151, 152, 153, 154, 156, 158, 160, 164, 165, 166, 169, 171, 172, 174, 175, 176, 177, 178, 179, 180, 182, 186, 187, 188, 190, 191, 192, 193, 196, 197, 198, 199, 200, 201, 202, 203, 205, 206, 207, 208, 209, 211, 213, 214, 215, 217, 218, 220, 221, 222, 224, 225, 226, 227, 229, 230, 232, 233, 234, 235, 236, 237, 238, 239, 240, 241, 242, 243, 244, 247, 248, 250, 251, 252, 253, 255, 256, 257, 258, 260, 262, 263, 264, 270, 271, 272, 274, 276, 279, 281, 282, 283, 284, 286, 287, 288, 289, 291, 292, 293, 294, 295, 296, 298, 299, 300, 302, 303, 305, 306, 307, 308, 309, 311, 314, 315, |

| ROW# | INFECTION NAME | SEQ ID NOs OF GAMS ASSOCIATED WITH INFECTION |
|---|---|---|
| | | 317, 318, 319, 321, 322, 323, 324, 325, 327, 329, 330, 331, 333, 334, 335, 336, 337, 340, 341, 342, 343, 344, 345, 346, 348, 349, 350, 351, 352, 353, 354, 355, 356, 357, 358, 359, 362, 363, 364, 365, 367, 368, 370, 373, 374, 375, 376, 377, 378, 379, 380, 381, 382, 383, 384, 385 and 287826-298021. |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07943754B2). An electronic copy of the "Sequence Listing" will also be available from the USPTO upon request and payment of the fee set forth in 37 CFR 1.19(b)(3).

The invention claimed is:

1. An isolated nucleic acid, wherein the sequence of the nucleic acid is selected from the group consisting of:
   (a) a sequence consisting of SEQ ID NO: 348;
   (b) a sequence consisting of nucleotides 14-34 of SEQ ID NO: 4233864;
   (c) a sequence consisting of nucleotides 14-36 of SEQ ID NO: 4233864;
   (d) a sequence consisting of nucleotides 14-37 of SEQ ID NO: 4233864;
   (e) a DNA encoding the nucleic acid of any one of (a)-(d), wherein the DNA is identical in length to (a)-(d), respectively; and
   (f) the complement of any one of (a)-(e), wherein the complement is identical in length to (a)-(e), respectively.

2. An isolated nucleic acid, wherein the sequence of the nucleic acid is selected from the group consisting of:
   (a) SEQ ID NO: 4233864;
   (b) a DNA encoding the nucleic acid of (a), wherein the DNA is identical in length to (a); and
   (c) the complement of (a) or (b), wherein the complement is identical in length to (a) or (b).

3. A vector comprising a human insert, wherein the human insert consists of the sequence of the nucleic acid of claim 1, and wherein the vector comprises no other inserts but the nucleic acid of claim 1.

4. A vector comprising a human insert, wherein the human insert consists of the sequence of the nucleic acid of claim 2, and wherein the vector comprises no other inserts but the nucleic acid of claim 2.

5. A probe consisting of a human insert, wherein the human insert consists of the sequence of the nucleic acid of claim 1.

6. A probe consisting of a human insert, wherein the human insert consists of the sequence of the nucleic acid of claim 2.

* * * * *